United States Patent
Ruddock et al.

(10) Patent No.: US 10,168,331 B2
(45) Date of Patent: Jan. 1, 2019

(54) DIAGNOSIS OF UROTHELIAL CANCER

(71) Applicant: Randox Laboratories Ltd., Northern Ireland (GB)

(72) Inventors: Mark Ruddock, Northern Ireland (GB); Cherith Reid, Northern Ireland (GB); John Lamont, Northern Ireland (GB); Stephen Fitzgerald, Northern Ireland (GB); Ricardo De Matos Simoes, Northern Ireland (GB); Kathleen Williamson, Northern Ireland (GB)

(73) Assignee: RANDOX LABORATORIES LTD., Northern Ireleand (GB)

( * ) Notice: Subject to any disclaimer, the term of this patent is extended or adjusted under 35 U.S.C. 154(b) by 0 days.

(21) Appl. No.: 15/304,473

(22) PCT Filed: Apr. 2, 2015

(86) PCT No.: PCT/GB2015/051053
§ 371 (c)(1),
(2) Date: Oct. 14, 2016

(87) PCT Pub. No.: WO2015/150834
PCT Pub. Date: Oct. 8, 2015

(65) Prior Publication Data
US 2017/0089900 A1   Mar. 30, 2017

(30) Foreign Application Priority Data

Apr. 4, 2014 (GB) .................................. 1406178.2
Apr. 9, 2014 (GB) .................................. 1406399.4

(51) Int. Cl.
| G01N 33/574 | (2006.01) |
| G01N 33/68  | (2006.01) |
| G01N 33/543 | (2006.01) |
| G01N 33/577 | (2006.01) |

(52) U.S. Cl.
CPC ..... *G01N 33/57407* (2013.01); *G01N 33/543* (2013.01); *G01N 33/577* (2013.01); *G01N 33/57488* (2013.01); *G01N 33/6869* (2013.01); *G01N 2333/485* (2013.01); *G01N 2333/545* (2013.01); *G01N 2333/5412* (2013.01); *G01N 2333/5421* (2013.01)

(58) Field of Classification Search
CPC ........... G01N 33/574; G01N 33/57407; G01N 33/57488; G01N 33/6869; G01N 33/577; G01N 33/485; G01N 2333/5421; G01N 2333/5412; G01N 2333/545

See application file for complete search history.

(56) References Cited

U.S. PATENT DOCUMENTS

2014/0072987 A1   3/2014 Ruddock et al.

FOREIGN PATENT DOCUMENTS

| WO | 2011012901 A1 | 2/2011 |
| WO | 2014060753 A1 | 4/2014 |

OTHER PUBLICATIONS

Abogunrin, F., et al., "The impact of biomarkers in multivariate algorithms for bladder cancer diagnosis in patients with hematuria," Cancer, vol. 118, No. 10, 2012, pp. 2641-2650.
Gunster, Marco, International Search Report and Written Opinion, International Application No. PCT/GB2015/051053, dated Sep. 8, 2015.
Knowlton, N. et al., "Template-driven gene selection procedure," IEE Proc.—Syst. Biol., vol. 153, No. 1, 2006, pp. 4-12.
Nickitas-Etienne, Athina, International Preliminary Report on Patentability, International Application No. PCT/GB2015/051053, dated Oct. 4, 2016.

*Primary Examiner* — Tracy Vivlemore
*Assistant Examiner* — Carmencita M Belei
(74) *Attorney, Agent, or Firm* — Gavrilovich, Dodd & Lindsey LLP

(57) ABSTRACT

The present invention provides a method and a solid state device for identifying the presence of urothelial cancer in a patient comprising assigning the subject to a sub-population according to smoking habits, measuring the level of each biomarker of a panel of biomarkers in one or more samples obtained from the subject; and correlating the measured levels of the panel of biomarkers with the likelihood of the subject having urothelial cancer such that the subject can be classified as having urothelial cancer or as being a control.

3 Claims, 9 Drawing Sheets

DIAGNOSIS OF UROTHELIAL CANCER

CROSS REFERENCE TO RELATED APPLICATION

This application is a U.S. National Stage Application filed under 35 U.S.C. § 371 and claims priority to International Application No. PCT/GB2015/051053, filed Apr. 2, 2015, which application claims priority to Great Britain Application Nos. 1406399.4, filed Apr. 9, 2014 and 1406178.2 filed Apr. 4, 2014, the disclosures of which are incorporated herein by reference in their entireties.

FIELD OF INVENTION

The invention relates to methods for identification of biomarker panels for diagnosis of urothelial cancer and improved methods for diagnosing and identifying the likelihood of developing urothelial cancer.

BACKGROUND OF THE INVENTION

Urothelial cancer (UC) or bladder cancer is a leading cause of death worldwide. Most of the patients who present with superficial UC tumours will experience a recurrence within 5 years and almost 90% of these patients will have a recurrence within 15 years.

Haematuria, which refers to the presence of blood in urine, is a presenting symptom for a variety of diseases, including UC. The number of patients presenting with haematuria is progressively increasing in our aging population and the diagnosis of serious diseases in some of these patients can be delayed when triage is ineffective. Therefore new risk stratification approaches are needed.

Diagnosis of the underlying cause of hematuria is a significant healthcare challenge. Hematuria can indicate the presence of UC, but it is also a symptom of a wide range of other pathologies including urolithiasis, benign prostate enlargement (BPE), renal disease and other urinary tract cancers. The final diagnosis for haematuria patients ranges from no diagnosis, through benign conditions including urinary infection, stone disease, BPE to renal diseases and malignant causes. UC is the most common malignancy in haematuric patients and is the fourth most common cancer in men. UC was the estimated cause of death in 150,200 people, worldwide in 2008.

UC is associated with many risk factors, for example its development is three times more common in men than in women. However, this gender disparity is largely historical and is related to smoking habits. Smoking increases the risk of UC four-fold and cessation of smoking is associated with a decreased risk. Although UC is associated with smoking and carcinogen exposure, urothelial cancers that arise following chronic inflammation are usually squamous cell carcinomas.

At the time of diagnosis, approximately 70% of patients diagnosed with UC have tumours that are pathologically staged as pTa, pT1 or carcinoma in situ (CIS) i.e., non-muscle invasive (NMI) disease and these patients can have a good prognosis. When a patient's tumour is pathologically defined as ≥T1G3 UC, the patient is deemed to have a high risk of progression to a more life threatening disease. Muscle invasive UC (MI UC) encompasses all pathological stages≥pT2. The risk parameters that are currently used to tailor follow-up for patients diagnosed with UC, include pathological parameters i.e., grade, stage and associated CIS, together with resistance to Bacille Calmette-Guerin treatment. However, it is not always possible to correctly predict the outcome for patients. This is largely attributable to the molecular heterogeneity within tumours which means that a spectrum of outcomes, spanning from negligible risk to life threatening prognosis, exists within the same pathologically classified groups. For this reason, all patients with NMI disease have frequent surveillance cystoscopies and those with MI have radiological surveillance for lymph node recurrence or distant metastasis.

Cystoscopy is the gold standard for the detection and surveillance of NMI UC. However, this procedure is costly for health services and invasive for the patient. Furthermore, it requires a significant clinical input and has its own shortcomings. Cytology, another diagnostic test for urothelial cancer, detects the presence of malignant cells in urine. Although cytology has high specificity, it has insufficient sensitivity to stand alone as a diagnostic test for UC in patients presenting with haematuria. Despite their approval by the Food and Drug Administration (FDA), three diagnostic urothelial cancer biomarkers, Nuclear Matrix Protein 22, Bladder Tumour Antigen (BTA) and Fibrinogen Degradation Product, are not in use in routine practise as diagnostic biomarkers for UC because of their limited specificity. There is therefore a strong clinical need for tests which can at least stratify risk of UC, and if possible, be diagnostic in haematuric patients.

Researchers often combine multiple tests, genes or biomarkers. However, it is not possible to intuitively predict how multiple measurements, will collectively reflect the underlying biological heterogeneity in complex diseases, such as UC. Complex diseases consist of multiple components which interact to produce emergent properties that the individual components do not possess.

Smoking and occupational carcinogen exposure are risk factors in approximately 60% of UCs; other known risk factors include increased age, male gender, recurrent urinary infections and bladder stones. However, the factors which confound diagnosis of UC and the characteristics of incorrectly classified patients have not been systematically investigated. Identification of patient characteristics associated with misclassification or misdiagnosis can be useful because this information allows meaningful application of diagnostic classifiers for risk stratification.

Therefore, there is a need for new approaches to identifying factors that confound diagnosis of serious disease. Identification of such factors would enable clinicians to interpret risk classifiers alongside other clinical information at the time of triage, in order to make more accurate diagnoses. In the case of patients presenting with haematuria this would reduce the number of cystoscopies and enable priority diagnosis of aggressive UC and other serious diseases, resulting in improved patient outcomes at reduced costs.

SUMMARY OF THE INVENTION

According to a first aspect, the present invention provides a method of identifying a panel of biomarkers for diagnosis of serious disease, the method comprising the steps of: measuring the level of each biomarker in a biomarker panel in a sample obtained from each subject in a test population; stratifying the test population into sub-populations defined by variables that individually divide the test population into groups containing at least 35% of the total test population; and assessing combinations of biomarkers that allow accurate classification of disease in subjects in the sub-populations of the test population.

According to a second aspect, the present invention provides a method of classifying the urothelial cancer status of a subject, comprising the steps of: assigning the subject to a sub-population according to one or more factors selected from smoking habits, age, gender, alcohol consumption, anti-cholesterol medication, anti-hypertensive medication, occupational risks, exposure to hazardous chemicals, cytological detection of inflammatory cells and measurable urinary dipstick protein; measuring the level of each biomarker of a panel of biomarkers in one or more samples obtained from the subject; and correlating the measured levels of the panel of biomarkers with the likelihood of the subject having urothelial cancer such that the subject can be classified as having urothelial cancer or as being a control.

According to further aspects of the invention, a solid state device according to the second aspect can be used to define the likelihood of a subject having urothelial cancer or to stratify the risk of a subject having a serious underlying pathology, wherein combination of antibodies present on the solid state device are selected according to a sub-population group that is appropriate to the subject. The sub-population group is selected according to one or more factors selected from smoking habits, age, gender, alcohol consumption, anti-cholesterol medication, anti-hypertensive medication, occupational risks, exposure to hazardous chemicals, cytological detection of inflammatory cells and measurable urinary dipstick protein.

DESCRIPTION OF THE INVENTION

Figure 1:
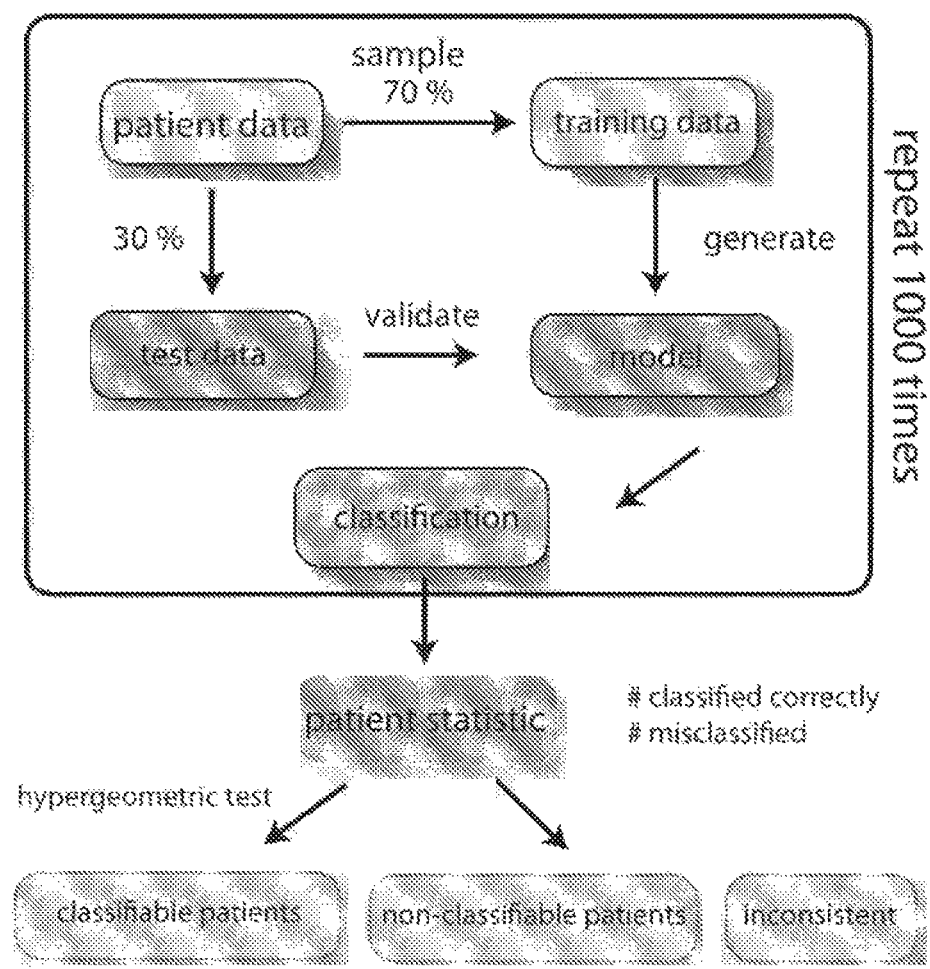
FIG. 1 shows implementation of the supervised patient classification analysis. For each training data set a random forest UC classifier was generated using all biomarker measurements (Table 3) and subsequently validated using the corresponding test dataset. Hypergeometric testing was then used to determine the probabilities that each patient was correctly, incorrectly or inconsistently classified.

The present invention provides both a method of defining biomarker panels useful in diagnosing a serious disease such as urothelial cancer and methods of diagnosing urothelial cancer and identifying the likelihood of developing urothelial cancer. The methods provided are advantageous as they provide clinicians with information concerning risk factors that confound traditional diagnostic methods and that can be used at the time of triage. Using the method of the invention, each patient can be assigned to a relevant sub-population so that appropriate testing can be carried out so as to permit accurate diagnosis and patient classification. As a result, patients can be followed up more effectively, further investigational and therapeutic intervention can be directed more appropriately, and resources in the healthcare system can be better managed. Furthermore, the invention enables priority diagnosis of aggressive urothelial cancer and other serious diseases, leading to improved patient outcomes at reduced costs.

The method of identifying a panel of biomarkers for diagnosis of serious disease involves three steps: a first 'data gathering' step that involves measurement of biomarker levels in samples obtained from subjects in a test population; a second 'population stratification' step that involves subdividing the test population according to risk factors that are under investigation; and a third 'classification' step that involves identification of biomarkers and panels of biomarkers that permit accurate identification of the disease within subdivided sections of the test population from the 'population stratification' step.

The first 'data gathering' step involves measurement of a panel of biomarker candidates in samples from subjects in the test population. The panel of biomarker candidates should include those biomarkers that are being investigated for usefulness in diagnosing the disease, and in the case of urothelial cancer this panel includes Bladder Tumour Antigen (BTA), Carcino-embryonic antigen (CEA), Human cytokeratin 18 (CK18), C-reactive protein (CRP), Creatinine, d Dimer, Epidermal growth factor (EGF), FAS, Hyaluronidase (HA), IL1α, IL1β, IL2, IL4, IL6, IL8, IL10, Interferon gamma (IFNγ), Monocyte Chemoattractant Protein 1 (MCP1), matrix metalloproteinase 9 (MMP9), Neutrophil gelatinase-associated lipocalin (NGAL), MMP9NGAL complex MMP9NGAL), Neuron specific enolase (NSE), Free Prostate Specific Antigen (FPSA), Total Prostate Specific Antigen (TPSA), Thrombomodulin (TM), Tumour necrosis factor α (TNFα), sTNFR1, sTNFR2, Vascular endothelial growth factor (VEGF) and von Willebrand factor (vWF). The test population for this method should include subjects suffering from the disease being investigated and subjects not suffering form that disease, and the disease status of each subject in the test population should be confirmed or be able to be confirmed independently of the method of the invention.

The second 'population stratification' step of the method involves subdividing the test population based on the presence or absence of known disease risk factors or other factors that are known to confound diagnosis of the disease using known biomarkers. In the case of urothelial cancer such factors include history of smoking, age, gender, alcohol consumption, history of anti-cholesterol medication, history of anti-hypertensive medication, occupational exposure to hazardous chemicals, cytological detection of inflammatory cells and presence of measurable dipstick protein in urine. Subdivision of the total test population according to each of these factors should yield two groups of subjects, and each group should comprise no less than 33% of the total test population.

The third 'classification' step of the method involves association of measured levels of individual biomarkers or panels of biomarkers with the correct classification of subjects within a subpopulation as suffering from or nor suffering from the disease being investigated. For each subpopulation an exhaustive search of sets of biomarkers is conducted, using a logistic regression classification to define diagnostic sets of biomarkers. The performance of each set of biomarkers was assessed using the average Area Under the Curve (AUC) measure and standard deviation (sd) from a repeated random sub-sampling analyses. Top performing sets of biomarkers are then identified on the basis of their hypergeometric distribution:

$$P(x=a) = \frac{\binom{k}{a}\binom{N-k}{b}}{\binom{N}{m}} \quad (1)$$

For the stratified analysis the variable "a" denotes the count frequency of a biomarker i being present among the top-ranked 50 sets of biomarkers and "b" in the remaining sets of biomarkers. "m" is the total count frequency of a biomarker i among all sets of biomarkers. "k" denotes the total count frequency of all biomarkers in the 50 top-ranked sets of biomarkers. "N" denotes the total count frequency of all biomarkers among all sets of biomarkers.

The method of diagnosing urothelial cancer in a subject involves three steps: a first 'assigning' step that involves identification of factors present in the subject that are likely to confound diagnosis of urothelial cancer using available biomarkers; a second 'data gathering' step that involves measuring the level of the appropriate panel of biomarkers in one or more samples obtained from the subject; and a third 'correlating' step that involves classification of the subject as suffering from or not suffering from urothelial cancer based on the confounding factors identified and the measured levels of the panel of biomarkers.

In the context of the present invention the term "urothelial cancer" is understood to include urothelial carcinoma (UC), bladder squamous cell carcinoma or bladder adenocarcinoma. Preferably, the urothelial cancer is urothelial carcinoma.

The terms "diagnose" and "diagnosing" as used herein relate to the confirmation that a subject is suffering or is likely to suffer from that disease. The terms "classify" and "classifier" as used herein relate to classification of a subject as suffering from (or likely to suffer from) or not suffering from (or not likely to suffer from) a specified disease such as urothelial cancer.

The terms "subject" and "patient" are used interchangeably herein and refer to a mammal including a non-primate (e.g. a cow, pig, horse, dog, cat, rat and mouse) and a primate (e.g. a monkey and human). Preferably the subject or patient is a human.

Preferably, the subject is a patient a presenting with haematuria. For the avoidance of doubt, the term "haematuria" refers to the presence of red blood cells in the urine. Haematuria may be caused by a number of conditions, such as urothelial cancer, BPE, kidney stones and infection, prostate cancer, renal cell carcinoma or urinary tract infections.

Preferably, the biomarkers are detected in at least one sample obtained from the subject selected from a urine sample, blood sample, serum sample or plasma sample.

The terms "serious disease" and "serious underlying pathology" are used interchangeably herein, and refer to life-threatening conditions such as kidney disease, aggressive bladder cancer or other aggressive cancers.

The term "has a history of smoking" refers herein to whether or not the subject smokes or has smoked. The term "smoking" includes all forms of tobacco smoking, including cigarettes, cigars and pipe tobacco. An individual subject is either classified as positive (i.e. has a history of smoking) or negative (i.e. no history of smoking) for smoking habits.

The term "gender" refers to whether the subject is male or female.

The phrases "history of prescribed anti-hypertensive medication" and "history of anti-cholesterol medication" refers herein to whether or not the subject is prescribed, or has a history of being prescribed, one or more of these medications. For the purpose of the method of the invention, medication is considered separately. Therefore an individual subject could be positive for one or more medication but negative for the other. For the avoidance of doubt, anti-hypertensives are a class of drugs used to treat hypertension (high blood pressure). The most widely used include thiazide diuretics, ACE inhibitors, calcium channel blockers, beta-blockers, and angiotensin II receptor antagonists or ARBs. Anti-cholesterol medications are a class of drugs that reduce the level of circulating low density lipoprotein cholesterol, reduce the level of circulating triglycerides and/or increase the level of circulating high density lipoprotein cholesterol. These drugs include Statins, Bile acid binding resins and agents, Cholesterol absorption inhibitors, Combination cholesterol absorption inhibitor and statin, Fibrates, Niacin, Combination statin and niacin, and Omega-3 fatty acids.

The phrase "history of alcohol consumption" refers herein to whether or not the subject consumes or has consumed alcohol including all forms of alcohol, including spirits, wine and beer. An individual subject is either classified as positive (i.e. has a history of consuming alcohol) or negative (i.e. no history of consuming alcohol).

The phrase "history of exposure to occupational risks or hazardous chemicals" refers herein to whether or not the subject is known to have been exposed to known occupational risks or hazardous chemicals. Each subject's occupational risk score can be classified and scored as low, moderate or high. An individual subject is either classified as positive (i.e. has a history of exposure to occupational risks or hazardous chemicals) if this factor is scored as moderate or high, or classified as negative (i.e. no history of exposure to occupational risks or hazardous chemicals) if this factor is scored as low.

The term "proteinuria" refers herein to whether or not a urine sample obtained from a subject contains an abnormal level of protein as measured using a standard "dipstick" assay. Levels of urinary protein less than 30 mg/dL are considered normal, while levels above that concentration are detectable by the dipstick test and constitute proteinuria. An individual subject is either classified as positive (i.e. has proteinuria) if protein is detected by the dipstick test, or classified as negative (i.e. does not have proteinuria) if no protein is detected by the dipstick test.

The phrase "cytological detection of inflammatory cells" refers herein to whether or not a sample obtained from the subject subjected to cytological examination provides evidence of the presence of inflammatory cells. An individual subject is either classified as positive (i.e. has cytological detection of inflammatory cells) if inflammatory cells are detectable on cytology examination, or classified as negative (i.e. does not have cytological detection of inflammatory cells) if no inflammatory cells are detectable on cytology examination.

The word "history" is sometimes abbreviated herein to "Hx".

The biomarkers are selected from the list comprising: Bladder Tumour Antigen (BTA), Carcino-embryonic antigen (CEA), Human cytokeratin 18 (CK18), C-reactive protein (CRP), Creatinine, d Dimer, Epidermal growth factor (EGF), FAS, Hyaluronidase (HA), IL1α, IL1β, IL2, IL4, IL6, IL8, IL10, Interferon gamma (IFNγ), Monocyte Chemoattractant Protein 1 (MCP1), matrix metalloproteinase 9 (MMP9), Neutrophil gelatinase-associated lipocalin (NGAL), MMP9NGAL complex (MMP9NGAL), Neuron specific enolase (NSE), Free Prostate Specific Antigen (FPSA), Total Prostate Specific Antigen (TPSA), Thrombomodulin (TM), Tumour necrosis factor α (TNFα), sTNFR1, sTNFR2, Vascular endothelial growth factor (VEGF) and von Willebrand factor (vWF).

Diagnosis may be made on the basis of the level of expression of the biomarker in the patient. The biomarker combinations of the present invention are preferably those which are expressed in the urine of a patient. Particular biomarkers may be expressed in the patient's blood.

The level of expression of the biomarker combination in the patient is detected in one or more samples that are isolated from the patient. In a preferred embodiment, the sample isolated from the patient is a urine sample or a blood sample.

Concentrations or expression levels of the biomarkers within the combination may be determined either sequentially or simultaneously in one or more samples isolated from the patient. The biomarker concentrations within the isolated sample may be determined by routine methods, which are known in the art.

In the method of the present invention an individual biomarker within the combination of biomarkers tested may be found at a different level or a similar level compared to the corresponding biomarker in a normal control sample. In some embodiments, the concentration of biomarkers are found at a significantly higher level than in a control sample. The determination of a "higher concentration" and a "lower concentration" is relative and determined with respect to a control subject known not to have cancer, preferably bladder cancer. Significant levels of biomarkers will be apparent to the skilled person.

Osmolarity, total urinary protein (TUP) and/or creatinine levels in the sample may also be measured and the resulting value(s) included in the statistical analysis. Creatinine levels (μmol/L) can be measured using a Daytona RX Series Clinical Analyser (Randox). Osmolarity (mOsm) can be measured using a Löser Micro-Osmometer (Type 15) (Löser Messtechnik, Germany). TUP levels (mg/ml) can be measured in a urine sample by Bradford assay $A_{595}$ nm (Hitachi U2800 spectrophotometer) using bovine serum albumin as the standard.

If the subject has a history of smoking the levels of urinary EGF, urinary IL6, urinary VEGF and urinary CK18; urinary EGF, serum IL8, urinary vWF and urinary FAS; or urinary EGF, urinary IL1α, plasma MMP9NGAL and urinary vWF are measured.

If the subject has a history of smoking the levels of EGF, IL1β, sTNFR, VEGF and CK18; BTA, EGF, IL1β, vWF and FAS; EGF, IL1β, IL8, TM, and vWF; dDimer, EGF, IL1β, IL8, VEGF and vWF; EGF, IL1β, NSE, sTNFR2, VEGF and vWF; EGF, IL2, TM, sTNFR2, VEGF and CK18; EGF, IL1α, MMP9, MMP9NGAL, NSE, VEGF and vWF; EGF, IL1β, NGAL, NSE, sTNFR1, VEGF and vWF; or dDimer, EGF, IL1α, IL8, NSE, vWF and FAS are measured in a urine sample obtained from the subject.

If the subject has a history of smoking the levels of d-Dimer, EGF, IL1α, IL8 and NGAL; IL1α, IL2, IL8, NGAL and sTNFR1; IL1α, IL10, NGAL, NSE and TNФα; d-Dimer, IL2, IL10, MMP9NGAL, NGAL and sTNFR1; EGF, FPSA, IL10, NGAL, TNFα and TPSA; CEA, IL1α, IL4, IL8, IL10 and NGAL; EGF, CRP, IL10, MMP9NGAL, NGAL, TM and VEGF; CEA, CRP, IL10, MMP9NGAL, NGAL, TM and TNFα; or CEA, d-Dimer, IL2, IL8, IL10, IFNγ and NSE are measured in a serum sample obtained from the subject.

If the subject has a history of smoking the levels of IL4, IFNγ, MCP1, MMP9NGAL and TM; IL1α, IL4, IFNγ, MCP1 and MMP9NGAL; EGF, IL1α, IL4, MCP1, MMP9NGAL; d-Dimer, IL1α, IL4, IL10, MMP9NGAL and sTNFR1; IL4, IL10, MMP9NGAL, TM, sTNFR1 and TNFα; IL1β, IL4, IL8, MCP1, MMP9NGAL and TNFα; IL1α, IL1β, IL2, IL4, IL10, MMP9NGAL and TNFα; d-Dimer, IL1α, IL4, IFNγ, MCP1, MMP9NGAL and TM; or d-Dimer, EGF, IL1α, IL4, IL10, IFNγ, and MMP9NGAL are measured in a plasma sample obtained from the subject.

If the subject does not have a history of smoking the levels of serum CEA, urinary EGF, plasma IL8 and urinary CK18;

serum CEA, plasma IL8, serum NGAL and serum TM; or serum CEA, plasma IL8, serum NGAL and plasma NSE are measured.

If the subject does not have a history of smoking the levels of BTA, MMP9NGAL, TM, sTNFR2 and VEGF; BTA, IL4, MMP9, NSE and FAS; BTA, MMP9NGAL, TNFα, sTNFR2 and VEGF; BTA, MCP1, MMP9, sTNFR2, vWF and FAS; d-Dimer, IL6, IL8, NGAL, NSE and TNFα; BTA, IL6, MCP1, TNFα, sTNFR2 and FAS; EGF, CRP, IL8, NGAL, NSE, TM and HA; BTA, EGF, IL8, MCP1, NGAL, NSE, sTNFR1; or BTA, IL4, MCP1, TM, sTNFR2, vWF and FAS are measured in a urine sample obtained from the subject.

If the subject does not have a history of smoking the levels of CEA, EGF, IL4, NGAL and TNFα; CEA, EGF, IL8, NGAL and TPSA; CEA, IL8, MCP1, NGAL and TPSA; CEA, IL6, IL8, MMP9NGAL, NGAL and VEGF; CEA, d-Dimer, CRP, MMP9NGAL, NGAL and NSE; CEA, CRP, IL2, MMP9NGAL, NGAL and TM; CEA, EGF, CRP, IL4, IL8, NGAL and NSE; CEA, IL6, IL8, IFNγ, NGAL, TM and VEGF; or CEA, FPSA, CRP, IL4, MMP9NGAL, NGAL and TM are measured in a serum sample obtained from the subject.

If the subject does not have a history of smoking the levels of IL1α, MMP9NGAL, NSE, sTNFR1 and VEGF; IFNγ, MCP1, MMP9NGAL, NGAL and NSE; IFNγ, MMP9NGAL, NGAL, NSE and TNFα; IL6, IFNγ, MMP9NGAL, NGAL, NSE and TNFα; d-Dimer, IL1α, IL4, MMP9NGAL, NSE and VEGF; d-Dimer, EGF, IL1α, IL8, MMP9NGA and NSE; d-Dimer, EGF, IL1α, IFNγ, MMP9NGAL, TNFα and VEGF; EGF, IL1α, IL2, MMP9NGAL, NGAL, NSE and TM; or IL1α, IFNγ, MMP9NGAL, NGAL, NSE, TM and TNFα are measured in a plasma sample obtained from the subject.

If the subject is aged 65 years or older the levels of serum IL2, serum MMP9NGAL, serum NGAL and plasma sTNFR1; urinary MMP9NGAL, serum NGAL, plasma NGAL and urinary vWF; or serum CEA, serum d-Dimer, plasma d-Dimer and serum IFN-J are measured.

If the subject is aged 65 years or older the levels of BTA, IL1β, VEGF, vWF and HA; d-Dimer, IL1α, NSE, vWF and HA; BTA, d-Dimer, IL1β, vWF and HA; BTA, IL1β, IL4, VEGF, vWF and HA; BTA, IL1β, IL8, sTNFR2, vWF and HA; BTA, EGF, IL1α, NSE, vWF and HA; d-Dimer, CRP, IL1α, IL2, NSE, vWF and HA; BTA, IL1α, IL8, MMP9NGAL, vWF, HA and CK18; or d-Dimer, IL1α, MCP1, NSE, TNFα, vWF and HA are measured in a urine sample obtained from the subject.

If the subject is aged 65 years or older the levels of CEA, d-Dimer, IL4, NGAL and TM; IL1α, MMP9NGAL, NGAL, sTNFR1 and TNFα; IL2, MMP9NGAL, NGAL, sTNFR1 and VEGF; CEA, d-Dimer, IL1α, NGAL, NSE and TM; CEA, EGF, IL1α, MMP9NGAL, NGAL and TPSA; CEA, d-Dimer, CRP, IL1β, NGAL and TM; CEA, d-Dimer, FPSA, CRP, IL10, NGAL and TM; CEA, d-Dimer, CRP, NGAL, NSE, TM and TPSA; or d-Dimer, IL1α, IL8, IFNγ, MMP9NGAL, NGAL and TM are measured in a serum sample obtained from the subject.

If the subject is aged 65 years or older the levels of CRP, IL1α, MMP9NGAL, TM and VEGF; CRP, IL1α, IL1β, MMP9NGAL and NGAL; CRP, IL1α, IL4, MMP9NGAL and TM; CRP, IL1α, IL2, IL4, MMP9NGAL and TM; EGF, CRP, IL1α, IL1β, MMP9NGAL and VEGF; EGF, IL1α, IL6, MMP9NGAL, TM and TNFα; CRP, IL1α, IL10, MMP9NGAL, TM, TNFα and VEGF; IL1α, IL6, IL10, MMP9NGAL, TM, TNFα and VEGF; or CRP, IL1α, IL4, IL6, MMP9NGAL, TM and TNFα are measured in a plasma sample obtained from the subject.

If the subject is aged less than 65 years old the levels of serum CEA, urinary EGF, serum IL1α, and urinary VEGF; serum CEA, urinary CRP, serum IL1α and urinary VEGF; or serum CEA, serum-IL1α, plasma IFNγ and urinary VEGF are measured.

If the subject is aged less than 65 years old the levels of EGF, IL2, HA, FAS and CK18; EGF, IL2, MMP9NGAL, HA and CK18; EGF, vWF, HA, FAS and CK18; EGF, IL2, IL8, MMP9, HA and CK18; BTA, EGF, IL1β, IL8, HA and CK18; d-Dimer, EGF, NSE, vWF, HA and CK18; EGF, CRP, IL1β, IL2, IL8, HA and CK18; EGF, IL1β, IL4, IL8, vWF, HA and CK18; or EGF, IL1β, IL6, IL8, MMP9, HA and CK18 are measured in a urine sample obtained from the subject.

If the subject is aged less than 65 years old the levels of CEA, IL1α, IL4, TM and TNFα; CEA, IL1α, IL2, IL4 and IL8; CEA, IL1α, IL1β, IL4 and VEGF; CEA, IL1α, IL4, IL8, MMP9NGAL and sTNFR1; CEA, IL1α, IL2, IL4, NSE and sTNFR1; CEA, EGF, IL1α, IL4, IL8 and TM; CEA, IL1α, IL2, IL4, IL8, IFNγ and MMP9NGAL; CEA, EGF, FPSA, IL1α, IL4, IL8 and VEGF; and CEA, IL1α, IL2, IL8, IFNγ, MCP1 and sTNFR1 are measured in a serum sample obtained from the subject.

If the subject is aged less than 65 years old the levels of d-Dimer, IL8, IL10, NSE and VEGF; d-Dimer, IL8, MMP9NGAL, TNFα and VEGF; EGF, IL8, IL10, MMP9NGAL and sTNFR1; EGF, CRP, IL6, IL8, IL10 and sTNFR1; CRP, IL6, IL8, IL10, IFNγ and sTNFR1; d-Dimer, IL4, IL8, MMP9NGAL, NGAL and TNFα; CRP, IL4, IL6, IL8, IL10, MMP9NGAL and TNFα; EGF, CRP, IL1β, IL8, IFNγ, NGAL and sTNFR1; or d-Dimer, EGF, CRP, IL8, IL10, IFNγ and MMP9NGAL are measured in a plasma sample obtained from the subject.

If the subject has a history of anti-hypertensive medication the levels of urinary EGF, urinary IL1α, serum IL10 and urinary vWF; urinary EGF, plasma IL10, urinary VEGF and urinary vWF; or serum sTNFR1, plasma sTNFR1, serum TNFα and urinary vWF are measured.

If the subject has a history of anti-hypertensive medication the levels of CRP, IL2, IL8, sTNFR2 and vWF; EGF, IL8, NSE, TNFα and vWF; BTA, EGF, IL4, vWF and HA; BTA, EGF, IL1β, IL8, VEGF and vWF; d-Dimer, CRP, IL8, sTNFR2, vWF and CK18; d-Dimer, EGF, IL2, VEGF, vWF and FAS; CRP, IL1β, IL6, IL8, MMP9, NGAL and vWF; d-Dimer, IL8, MMP9, NSE, TM, sTNFR2 and vWF; or BTA, d-Dimer, EGF, IL4, NGAL, NSE and vWF are measured in a urine sample obtained from the subject.

If the subject has a history of anti-hypertensive medication the levels of CEA, NGAL, NSE, TNFα and TPSA; CEA, MMP9NGAL, NGAL, TM and TNFα; CEA, IL1β, NGAL, sTNFR1 and TPSA; CEA, IL1β, IL10, NGAL, TM and VEGF; CEA, d-Dimer, IL1β, MMP9NGAL, NGAL and TM; CEA, EGF, IL1α, IL1β, NGAL and TNFα; CEA, IL1α, IL1β, IL10, NGAL, sTNFR1 and TNFα; CEA, IL1α, NGAL, NSE, TM, TNFα and TPSA; or CEA, IL1β, IL4, IL10, MMP9NGAL, NGAL and TM are measured in a serum sample obtained from the subject.

If the subject has a history of anti-hypertensive medication the levels of IL1α, IL1β, IL4, IFNγ and VEGF; EGF, CRP, IL2, IL4 and IL8; EGF, CRP, IL2, IL10 and NGAL; EGF, IL6, IL10, IFNγ, MCP1 and MMP9NGAL; d-Dimer, EGF, IL1β, IL4, IL6 and MCP1; EGF, CRP, IL1β, IL2, MMP9NGAL and NGAL; d-Dimer, EGF, CRP, IL2, IL10, MMP9NGAL and TM; CRP, IL1α, IL1β, IL4, IL6, IFNγ and sTNFR1; or EGF, CRP, IL4, IL6, IL10, IFNγ and MMP9NGAL are measured in a plasma sample obtained from the subject.

If the subject does not have a history of anti-hypertensive medication the levels of serum CEA, urinary CRP, urinary NSE and serum TNFα; serum CEA, urinary CRP, serum IL4 and urinary sTNFR1; or urinary Creatinine, serum IL6, plasma MMP9NGAL and urinary VEGF are measured.

If the subject does not have a history of anti-hypertensive medication the levels of CRP, NGAL, VEGF, HA and CK18; d-Dimer, TNFα, VEGF, HA and CK18; MMP9, NSE, TM, VEGF and FAS; EGF, NGAL, VEGF, vWF, HA and CK18; CRP, IL1β, IL6, sTNFR1, VEGF and vWF; d-Dimer, EGF, IL4, VEGF, HA and CK18; CRP, IL1β, IL6, IL8, MMP9, NGAL and vWF; d-Dimer, IL8, MMP9, NSE, TM, sTNFR2 and vWF; or BTA, d-Dimer, EGF, IL4, NGAL, NSE and vWF are measured in a urine sample obtained from the subject.

If the subject does not have a history of anti-hypertensive medication the levels of CEA, d-Dimer, IL4, MMP9NGAL and sTNFR1; CEA, EGF, IL10, MMP9NGAL and TNFα; CEA, d-Dimer, CRP, IL4 and IL10; CEA, d-Dimer, CRP, IL4, IL10 and TM; CEA, d-Dimer, CRP, IL4, IL6 and MMP9NGAL; CEA, d-Dimer, IL2, IL4, IL8 and MMP9NGAL; CEA, d-Dimer, EGF, IL4, IL8, IL10 and NSE; CEA, d-Dimer, CRP, IL4, MCP1, MMP9NGAL and TNFα; and CEA, d-Dimer, CRP, IL4, IL6, TM and TNFα are measured in a serum sample obtained from the subject.

If the subject does not have a history of anti-hypertensive medication the levels of EGF, IL1α, IL8, MMP9NGAL and VEGF; IL1α, IL8, IFNγ, MMP9NGAL and VEGF; CRP, IL1α, IL8, MMP9NGAL and NGAL; EGF, CRP, IL1β, IL8, MMP9NGAL and VEGF; CRP, IL1α, IL6, IL8, IL10, MMP9NGAL; EGF, IL1β, IL4, IL8, MMP9NGAL and VEGF; EGF, CRP, IL1α, IL8, MMP9NGAL, TNFα and VEGF; EGF, CRP, IL1β, IL8, MMP9NGAL, sTNFR1 and VEGF; and d-Dimer, EGF, IL1β, IL6, IL8, MMP9NGAL and VEGF are measured in a plasma sample obtained from the subject.

If the subject has cytological detection of inflammatory cells the levels of urinary BTA, serum CEA, plasma IL10 and urinary CK18; urinary BTA, plasma IL6, serum NSE and plasma NSE; or urinary dipstick protein, urinary BTA, plasma IL6 and serum NGAL are measured.

If the subject has cytological detection of inflammatory cells the levels of BTA, IL1α, NGAL, sTNFR1 and vWF; BTA, IL8, MMP9NGAL, VEGF and CK18; BTA, IL6, MMP9NGAL, NSE and CK18; BTA, IL2, MMP9NGAL, sTNFR1, TNFα and VEGF; BTA, IL2, MMP9NGAL, NGAL, TNFα and CK18; BTA, IL2, MMP9NGAL, NSE, VEGF and CK18; BTA, IL2, MMP9NGAL, NGAL, sTNFR1, TNFα and VEGF; BTA, IL2, MMP9NGAL, TM, sTNFR1, vWF and FAS; or BTA, IL2, MMP9NGAL, sTNFR1, VEGF, vWF and CK18 are measured in a urine sample obtained from the subject.

If the subject has cytological detection of inflammatory cells the levels of CEA, IL1α, NGAL, NSE and TPSA; IL1α, MMP9NGAL, NGAL, TPSA and VEGF; CEA, IL1α, IL10, NGAL and VEGF; CEA, IL10, MMP9NGAL, NGAL, TNFα and VEGF; IL1α, IL10, MMP9NGAL, NGAL, NSE and VEGF; CRP, IL10, MMP9NGAL, NGAL, TPSA and VEGF; CEA, CRP, IL1β, IL2, TM, sTNFR1 and TPSA; CRP, IL1β, IL2, IL6, MMP9NGAL, NGAL and TNFα; or CRP, IL1β, IL2, MMP9NGAL, NGAL, NSE and TNFα are measured in a serum sample obtained from the subject.

If the subject has cytological detection of inflammatory cells the levels of IL1α, IL6, IL8, MMP9NGAL and NSE; IL6, IFNγ, MMP9NGAL, NSE and sTNFR1; IL1α, IL1β, IL8, IL10 and MMP9NGAL; IL6, IL8, IFNγ, MMP9NGAL, NGAL and NSE; IL1α, IL6, MMP9NGAL, NSE, TM and TNFα; d-Dimer, IL4, IL8, IFNγ, MMP9NGAL and VEGF; IL1α, IL8, IL10, MCP1, MMP9NGAL, NSE and TM; d-Dimer, IL2, IL6, IL8, MMP9NGAL, TM and sTNFR1; or IL1α, IL2, IL6, IL8, MCP1, MMP9NGAL and NSE are measured in a plasma sample obtained from the subject.

If the subject does not have cytological detection of inflammatory cells the levels of serum CEA, plasma IL8, serum TNFα and urinary FAS; urinary EGF, serum EGF, serum FPSA and serum IL4; or urinary EGF, urinary CRP, urinary IL4 and urinary NSE are measured.

If the subject does not have cytological detection of inflammatory cells the levels of EGF, CRP, IL4, TM and vWF; BTA, d-Dimer, EGF, CRP and IL4; EGF, CRP, IL4, IL6 and vWF; d-Dimer, EGF, CRP, IL4, sTNFR1 and vWF; d-Dimer, EGF, CRP, IL4, sTNFR1 and sTNFR2; EGF, IL2, IL4, sTNFR2, VEGF and vWF; EGF, CRP, IL4, MCP1, VEGF, FAS and CK18; d-Dimer, EGF, CRP, IL4, IL6, sTNFR2 and vWF; or d-Dimer, EGF, CRP, IL4, IL6, sTNFR2 and CK18 are measured in a urine sample obtained from the subject.

If the subject does not have cytological detection of inflammatory cells the levels of CEA, EGF, CRP, IL4 and IFNγ; d-Dimer, FPSA, IL6, IFNγ and NGAL; IL1α, IL4, MMP9NGAL, NGAL and TM; IL4, MMP9NGAL, NGAL, NSE, sTNFR1 and TPSA; CEA, EGF, FPSA, IL4, NSE and sTNFR1; CEA, EGF, FPSA, IL4, MCP1 and VEGF; FPSA, IL2, IL4, IL6, MMP9NGAL, NGAL and sTNFR1; CEA, EGF, FPSA, CRP, IL4, IL6 and MMP9NGAL; or d-Dimer, IL1β, IL4, IL8, MCP1, NGAL and TM are measured in a serum sample obtained from the subject.

If the subject does not have cytological detection of inflammatory cells the levels of d-Dimer, IL1β, IL8, MMP9NGAL and TM; d-Dimer, IL8, TM, TNFα and VEGF; IL2, IL8, MMP9NGAL, TM and TNFα; d-Dimer, IL8, MMP9NGAL, NSE, TM and TNFα; d-Dimer, IL2, IL8, MMP9NGAL, NSE and TNFα; d-Dimer, IL8, IFNγ, MMP9NGAL, sTNFR1 and TNFα; d-Dimer, IL1α, IL8, MMP9NGAL, TM, TNFα and VEGF; d-Dimer, CRP, IL2, IL6, IL8, MMP9NGAL and TNFα; or d-Dimer, IL1α, IL1β, IL8, MMP9NGAL, TM and VEGF are measured in a plasma sample obtained from the subject.

If the subject has a history of alcohol consumption the levels of urinary EGF, urinary IL1β, plasma MMP9NGAL and urinary vWF; serum CEA, urinary EGF, urinary vWF and urinary CK18; or serum CEA, urinary EGF, plasma NSE and urinary vWF are measured.

If the subject has a history of alcohol consumption the levels of EGF, MMP9, sTNFR2, VEGF and vWF; EGF, IL1α, IL4, vWF and FAS; EGF, IL1α, MMP9, vWF and HA; d-Dimer, EGF, CRP, IL1α, IL6 and vWF; EGF, CRP, IL1α, sTNFR, vWF and CK18; BTA, EGF, CRP, IL1α, vWF and FAS; EGF, IL1α, IL6, NGAL, sTNFR2, vWF and FAS; EGF, IL1α, IL2, IL6, NGAL, VEGF and vWF; or u-EGF, u-IL1α, u-NGAL, u-NSE, sTNFR2, u-vWF and u-CK18 are measured in a urine sample obtained from the subject.

If the subject has a history of alcohol consumption the levels of CRP, IL1β, IL6, IL8 and NGAL; d-Dimer, IL1β, IL4, IFNγ and NGAL; CRP, IL1β, IL4, MCP1 and NGAL; EGF, CRP, IL1α, IL1β, NGAL and TPSA; CEA, CRP, IL1β, IL2, NGAL and NSE; CEA, d-Dimer, CRP, IL1α, IL6 and NGAL; EGF, CRP, IL8, MCP1, MMP9NGAL, NGAL and sTNFR1; CEA, EGF, CRP, IL1β, MMP9NGAL, NGAL and TM; or CEA, d-Dimer, IL1α, IL2, IL4, IL10 and NGAL are measured in a serum sample obtained from the subject.

If the subject has a history of alcohol consumption the levels of d-Dimer, IL4, MMP9NGAL, NSE and TM; IL1β, IL4, MMP9NGAL, NSE and TNFα; EGF, CRP, IL4, MMP9NGAL and sTNFR1; IL1α, IL2, IL4, MMP9NGAL, NSE and TNFα; IL2, IL4, IL6, MMP9NGAL, NSE and TM; CRP, IL1α, IL1β, IL4, MMP9NGAL and TNFα; d-Dimer, IL1β, IL4, MMP9NGAL, NGAL, NSE and VEGF; d-Dimer, IL1α, IL2, MMP9NGAL, NSE, sTNFR and TNFα; or d-Dimer, CRP, IL1α, IL4, IL10, NSE and sTNFR are measured in a plasma sample obtained from the subject.

If the subject does not have a history of alcohol consumption the levels of serum MMP9NGAL, serum sTNFR1, serum TNFα and urinary VEGF; serum CEA, urinary EGF, serum IL10 and serum NGAL; or urinary IL6, plasma MMP9NGAL, urinary VEGF and urinary CK18 are measured.

If the subject does not have a history of alcohol consumption the levels of IL2, IL8, NGAL, HA and CK18; IL2, IL4, VEGF, HA and CK18; IL1β, IL2, IL8, NGAL and CK18; IL2, IL4, IL8, NGAL, HA and CK18; BTA, d-Dimer, IL2, IL8, MMP9NGAL and CK18; IL2, IL4, IL8, sTNFR2, HA and CK18; IL1β, IL2, IL6, IL8, NGAL, NSE and CK18; IL1α, IL2, IL6, IL8, NGAL, HA and CK18; or BTA, IL1α, IL2, IL8, NGAL, VEGF and CK18 are measured in a urine sample obtained from the subject.

If the subject does not have a history of alcohol consumption the levels of CEA, IL1α, IL8, TM and sTNFR1; CEA, IL1α, IL6, NGAL and TM; CEA, IL1α, IL2, TM and sTNFR1; CEA, IL2, IL8, NSE, TM and sTNFR1; CEA, IL10, MMP9NGAL, NSE, TM and sTNFR1; CEA, CRP, IL2, IL10, NGAL and TM; CEA, CRP, IL4, IL6, IL10, sTNFR1 and TPSA; CEA, d-Dimer, EGF, IL1α, IL10, NSE and sTNFR1; or CEA, d-Dimer, IL1α, IL1β, IL4, TM and sTNFR1 are measured in a serum sample obtained from the subject.

If the subject does not have a history of alcohol consumption the levels of IL1α, IFNγ, MMP9NGAL, sTNFR1 and TNFα; EGF, IL4, MCP1, MMP9NGAL and sTNFR1; IL1α, IL8, IL10, MMP9NGAL and VEGF; IL1α, IL1β, IL10, IFNγ, MMP9NGAL and VEGF; EGF, CRP, IL1α, MMP9NGAL, TNFα and VEGF; IL1α, IL6, IL8, IFNγ, MMP9NGAL and sTNFR1; IL1α, IL2, IL8, IFNγ, MMP9NGAL, sTNFR1 and TNFα; IL1α, IL2, IL6, IL10, MMP9NGAL, TNFα and VEGF; or IL1α, IL4, IL6, IL10, MMP9NGAL, NGAL and VEGF are measured in a plasma sample obtained from the subject.

If the subject has a history of exposure to occupational risks or hazardous chemicals the levels of serum CEA, urinary EGF, urinary VEGF and urinary vWF; urinary EGF, serum IL8, urinary vWF and urinary HA; or serum IL4, plasma IL8, serum MCP1 and urinary VEGF are measured.

If the subject has a history of exposure to occupational risks or hazardous chemicals the levels of BTA, IL2, IL4, MMP9NGAL and VEGF; BTA, IL1α, IL8, NGAL and NSE; BTA, CRP, IL4, NSE and CK18; BTA, d-Dimer, CRP, IL4, sTNFR1 and vWF; IL4, IL8, NGAL, NSE, TM and sTNFR1; CRP, IL2, IL8, MCP1, MMP9NGAL and TNFα; EGF, IL1α, IL8, MMP9NGAL, NSE, vWF and CK18; EGF, IL6, IL8, MMP9NGAL, NSE, VEGF and vWF; or CRP, IL1α, IL6, IL8, MMP9NGAL, NSE and VEGF are measured in a urine sample obtained from the subject.

If the subject has a history of exposure to occupational risks or hazardous chemicals the levels of IL2, IL10, NGAL, NSE and VEGF; CEA, IL4, IL8, NGAL and TM; CEA, CRP, NGAL, NSE and sTNFR1; d-Dimer, CRP, IL6, IL8, NSE and sTNFR1; CEA, IL4, IL10, IFNγ, MCP1 and NGAL; FPSA, IL4, IL8, MMP9NGAL, NSE and sTNFR1; FPSA, IL1β, IL2, IL4, IL8, MMP9NGAL and NGAL; CEA, d-Dimer, IL8, IL10, IFNγ, NGAL and NSE; and CEA, EGF, CRP, IL10, MCP1, NGAL and NSE VEGF are measured in a serum sample obtained from the subject.

If the subject has a history of exposure to occupational risks or hazardous chemicals the levels of IL1α, IL6, MMP9NGAL, TM and sTNFR1; IL1α, IL1β, IL6, IL8 and TNFα; IL8, MMP9NGAL, NGAL, NSE and TNFα; IL1β, IL2, IL8, MMP9NGAL, NGAL and NSE; IL1β, IL8, IL10, MCP1, NGAL and TM; IL8, IFNγ, MMP9NGAL, TM, sTNFR1 and TNFα; IL1β, IL8, IFNγ, MCP1, MMP9NGAL, TM and sTNFR1; IL1α, IL4, IL8, IL10, MCP1, TM and sTNFR1; or IL1α, IL1β, IL6, IL8, NGAL, NSE and VEGF are measured in a plasma sample obtained from the subject.

If the subject does not have a history of exposure to occupational risks or hazardous chemicals the levels of serum CEA, serum d-Dimer, urinary EGF and serum IL1α; serum CEA, serum d-Dimer, serum IL6 and serum MCP1; or urinary BTA, serum CEA, urinary TNFα and urinary CK18 are measured.

If the subject does not have a history of exposure to occupational risks or hazardous chemicals the levels of BTA, TM, TNFα, sTNFR2 and vWF; BTA, TM, TNFα, vWF and FAS; EGF, NSE, TNFα, vWF and HA; IL6, MCP1, TNFα, vWF, FAS and CK18; BTA, d-Dimer, CRP, TNFα, vWF and HA; BTA, IL1α, TNFα, vWF, HA and FAS; BTA, d-Dimer, MMP9NGAL, TM, TNFα, vWF and HA; IL6, NGAL, sTNFR, TNFα, vWF, FAS and CK18; or BTA, IL1α, IL1β, IL6, NGAL, TNFα and CK18 are measured in a urine sample obtained from the subject.

If the subject does not have a history of exposure to occupational risks or hazardous chemicals the levels of CEA, d-Dimer, NSE, TM and TPSA; CEA, EGF, IL10, MCP1 and sTNFR1; CEA, d-Dimer, CRP, MCP1 and NGAL; CEA, d-Dimer, EGF, IL8, IL10 and TM; CEA, d-Dimer, IL4, MCP1, MMP9NGAL and sTNFR1; CEA, d-Dimer, EGF, IL6, NGAL and TM; CEA, d-Dimer, IL4, IL10, MCP1, MMP9NGAL and NSE; CEA, d-Dimer, IFNγ, MCP1, MMP9NGAL, TM and TPSA; or CEA, d-Dimer, EGF, IL6, IL10, MMP9NGAL and TM are measured in a serum sample obtained from the subject.

If the subject does not have a history of exposure to occupational risks or hazardous chemicals the levels of IL4, IL6, IFNγ, MMP9NGAL and NGAL; IL1β, IL4, IL10, MMP9NGAL and TM; IL2, IL4, IL6, IFNγ and MMP9NGAL; IL2, IL4, IL10, MMP9NGAL, TNFα and VEGF; CRP, IL4, IL10, MMP9NGAL, TNFα and VEGF; IL1α, IL4, IL10, IFNγ, MMP9NGAL and NSE; IL4, IL6, IL10, MMP9NGAL, NGAL, sTNFR1 and VEGF; d-Dimer, CRP, IL1α, IL1β, IL2, IL4 and MMP9NGAL; or d-Dimer, CRP, IL1β, IL4, IL6, IL10 and MMP9NGAL are measured in a plasma sample obtained from the subject.

If the subject has a history of anti-cholesterol medication the levels of serum MCP1, plasma MCP1, serum NGAL and plasma NGAL; urinary CRP, serum IL2, serum NGAL and plasma NGAL; or urinary Creatinine, serum NGAL, plasma NGAL and plasma VEGF are measured.

If the subject has a history of anti-cholesterol medication the levels of CRP, MCP1, sTNFR2, vWF and FAS; d-Dimer, IL6, MMP9NGAL, NSE and VEGF; BTA, MCP1, sTNFR2, vWF and FAS; d-Dimer, IL6, NGAL, NSE, VEGF and HA; IL1β, IL6, IL8, MMP9NGAL, NSE and VEGF; BTA, d-Dimer, IL6, NGAL, NSE and VEGF; BTA, CRP, IL1β, IL8, sTNFR2, vWF and FAS; d-Dimer, IL4, IL6, MMP9, NSE, VEGF and CK18; or BTA, CRP, IL1α, IL2, sTNFR2, vWF and FAS are measured in a urine sample obtained from the subject.

If the subject has a history of anti-cholesterol medication the levels of IL6, IL8, NGAL, TPSA and VEGF; FPSA, NGAL, TM, TNFα and VEGF; IL1β, IL2, NGAL, TM and VEGF; IL1α, MCP1, MMP9NGAL, NGAL, TM and TNFα; CEA, FPSA, IL8, NGAL, TM and VEGF; FPSA, IL4, NGAL, NSE, TNFα and VEGF; FPSA, IL1β, IL10, NGAL, TM, TNFα and VEGF; CEA, IL1β, IL4, NGAL, TM, TPSA and VEGF; or FPSA, IL1β, IL4, IL10, NGAL, TM and VEGF are measured in a serum sample obtained from the subject.

If the subject has a history of anti-cholesterol medication the levels of IL2, IFNγ, MCP1, MMP9NGAL and TM; IL1α, IL1β, IL6, TNFα and VEGF; IL4, IL6, IFNγ, MCP1 and TNFα; d-Dimer, IL2, IL6, MMP9NGAL, TM and TNFα; IL2, IL10, IFNγ, MCP1, MMP9NGAL and TNFα; IL6, MCP1, NGAL, NSE, TM and TNFα; d-Dimer, EGF, IL6, IL10, IFNγ, MCP1 and TNFα; d-Dimer, IL10, IFNγ, MCP1, NGAL, sTNFR and VEGF; or d-Dimer, IL6, IL8, IL10, NSE, TM and TNFα are measured in a plasma sample obtained from the subject.

If the subject does not have a history of anti-cholesterol medication the levels of serum CEA, urinary EGF, urinary HA and urinary CK18; serum CEA, urinary EGF, urinary IL8 and urinary CK18; or serum CEA, urinary EGF, plasma IL6 and urinary MMP9NGAL are measured.

If the subject does not have a history of anti-cholesterol medication the levels of BTA, CRP, IL2, IL4 and CK18; EGF, IL1β, NGAL, VEGF and CK18; BTA, IL4, IL8, HA and CK18; EGF, CRP, IL4, VEGF, HA and CK18; EGF, IL4, IL6, IL8, vWF and CK18; BTA, EGF, IL4, IL8, HA and CK18; BTA, EGF, CRP, IL4, sTNFR1, HA and CK18; EGF, IL1α, IL1β, IL4, sTNFR1, VEGF and CK18; or EGF, CRP, IL4, MMP9NGAL, NGAL, HA and CK18 are measured in a urine sample obtained from the subject.

If the subject does not have a history of anti-cholesterol medication the levels of CEA, FPSA, IL10, IFNγ and NGAL; CEA, IL1α, IL1β, MMP9NGAL and sTNFR1; CEA, IL1α, MMP9NGAL, TM and TNFα; CEA, IL1α, IL1β, IL6, NGAL and NSE; CEA, IL4, IL6, IL8, MMP9NGAL and TNFα; CEA, d-Dimer, IL1α, IL4, IL6 and sTNFR1; CEA, IL1α, IL4, IL6, IL8, TM and sTNFR1; CEA, IL1α, IL1β, IL4, IL8, MMP9NGAL and VEGF; or CEA, IL1α, IL4, IL10, MMP9NGAL, TM and TNFα are measured in a serum sample obtained from the subject.

If the subject does not have a history of anti-cholesterol medication the levels of IL1α, IL8, MMP9NGAL, NGAL and sTNFR1; IL1α, IL1β, IL4, IFNγ and psTNFR1; IL1α, IL1β, IL8, TM and psTNFR1; d-Dimer, IL1α, IL4, IL10, MMP9NGAL and TNFα; CRP, IL8, IL10, MMP9NGAL, TM and sTNFR1; d-Dimer, IL1α, IL1β, IL4, TM and sTNFR1; IL1β, IL6, IL8, MMP9NGAL, sTNFR1, TNFα and VEGF; d-Dimer, IL1α, IL4, IL8, NGAL, TM and sTNFR1; or IL1α, IL1β, IL4, IL6, IL8, MMP9NGAL and sTNFR1 are measured in a plasma sample obtained from the subject.

If the subject has proteinuria the levels of serum CEA, plasma CRP, urinary IL8 and plasma TNFα; urinary EGF, urinary IL1β, serum IL6 and urinary vWF; or serum CEA, plasma IL1α, urinary NSE and serum NSE are measured.

If the subject has proteinuria the levels of EGF, IL2, NSE, TM and CK18; EGF, IL6, sTNFR1, HA and CK18; EGF, NGAL, vWF, HA and CK18; EGF, IL8, sTNFR2, VEGF, uvWF and HA; EGF, IL1α, MMP9, NSE, uvWF and HA; EGF, CRP, IL2, IL4, TM and CK18; EGF, IL1β, IL2, NSE, TM, VEGF and vWF; EGF, IL1β, MMP9, MMP9NGAL, TNFα, vWF and HA; or EGF, IL2, IL4, NGAL, NSE, TM and CK18 are measured in a urine sample obtained from the subject.

If the subject has proteinuria the levels of CEA, IL8, IL10, NSE and TNFα; CEA, IL2, IL8, MMP9NGAL and NSE; CEA, IL2, IL6, IL10 and NSE; CEA, IL1β, IL2, IL8, IL10 and NSE; CEA, IL1β, IL2, IL8, NSE and TPSA; CEA, CRP, IL10, MMP9NGAL, NGAL and VEGF; CEA, IL1β, IL2, IL4, IL8, NSE and TNFα; CEA, EGF, IL4, IL8, IL10, TPSA and VEGF; or CEA, IL1β, IL2, IL4, IL10, MMP9NGAL and TM are measured in a serum sample obtained from the subject.

If the subject has proteinuria the levels of CRP, IL1α, IL8, IFNγ, TM; CRP, IL1α, IL8, IFNγ, NGAL; IL1α, IL2, IL8, MCP1, TM; EGF, IL1α, IL4, IL8, IFNγ, TM; d-Dimer, IL1α, IL8, IFNγ, MCP1, TM; IL1α, IL8, IFNγ, MCP1, TM, TNFα; IL1α, IL2, IL8, IL10, IFNγ, MCP1, TM; IL1α, IL2, IL8, IFNγ, MCP1, MMP9NGAL, TM; or EGF, CRP, IL1α, IL4, IL8, IFNγ, TNFα are measured in a plasma sample obtained from the subject.

If the subject does not have proteinuria the levels of urinary BTA, urinary NGAL, serum NGAL and urinary TNFα; urinary d-Dimer, urinary CRP, urinary NGAL and serum TNFα; or serum CEA, urinary CRP, plasma MMP9NGAL and urinary NGAL are measured.

If the subject does not have proteinuria the levels of d-Dimer, CRP, IL4, NGAL and sTNFR2; CRP, MMP9NGAL, NGAL, sTNFR2 and VEGF; BTA, CRP, IL4, NGAL and sTNFR2; CRP, MCP1, MMP9, NGAL, sTNFR2 and VEGF; d-Dimer, CRP, IL2, IL4, NGAL and sTNFR; BTA, CRP, IL2, NGAL, sTNFR2 and vWF; d-Dimer, CRP, IL1α, IL4, MMP9NGAL, TM and CK18; BTA, EGF, CRP, MMP9, NGAL, vWF and FAS; or BTA, CRP, NGAL, NSE, TM, sTNFR2 and vWF are measured in a urine sample obtained from the subject.

If the subject does not have proteinuria the levels of FPSA, IL1α, IL4, IFNγ and NGAL; d-Dimer, IL2, IL4, NGAL and TM; d-Dimer, IL6, NGAL, TM and sTNFR1; d-Dimer, IL1β, IL8, NGAL, TM and TNFα; CEA, IL4, IL8, NGAL, TNFα and TPSA; d-Dimer, FPSA, IL2, IL6, IL8 and NGAL; FPSA, CRP, IL2, IL6, NGAL, TNFα and VEGF; CEA, FPSA, CRP, IL6, IL10, NGAL and VEGF; or d-Dimer, FPSA, IL1β, IFNγ, MMP9NGAL, NGAL and TM are measured in a serum sample obtained from the subject.

If the subject does not have proteinuria the levels of d-Dimer, IL4, MCP1, MMP9NGAL and TNFα; EGF, IL1α, IL2, MMP9NGAL and NGAL; d-Dimer, IL4, MCP1, MMP9NGAL and sTNFR1; d-Dimer, IL1β, IL4, IL8, IL10 and MMP9NGAL; d-Dimer, EGF, IL8, IL10, MMP9NGAL and TM; d-Dimer, EGF, IFNγ, MMP9NGAL, NSE and VEGF; EGF, IL1α, IL2, IL4, MCP1, MMP9NGAL and NGAL; d-Dimer, EGF, CRP, IL8, MMP9NGAL, NSE and VEGF; and d-Dimer, EGF, IL1β, IL8, IL10, MMP9NGAL and VEGF are measured in a plasma sample obtained from the subject.

The "level" of a combination of biomarkers refers to the amount, the level or concentration of each biomarker of the combination of biomarkers within the sample.

The accuracy of the methods which are the subject of the invention is often described by their receiver-operating characteristics (ROC).

The ROC graph is a plot of all of the sensitivity/specificity pairs resulting from continuously varying the decision threshold over the entire range of data observed. To construct a ROC curve for multiple biomarkers, a logistic regression equation is derived for the biomarker combination of interest, by inputting measured protein concentration value of each of the biomarkers in a patient's sample into the equation.

Although a logistic regression equation is the preferred statistical method for the current invention, other conventional statistical methods can be used.

The combinations of biomarkers used to diagnose urothelial cancer in the present invention have a sensitivity and specificity of at least 70%. This means that out of 100 patients which have urothelial cancer, 70% of them will be correctly identified from the determination of the presence of a particular combination of biomarkers as positive for urothelial cancer while out of 100 patients who do not have urothelial cancer 70% will accurately test negative for the disease.

A ROC plot depicts the overlap between the two distributions by plotting the sensitivity versus 1—specificity for the complete range of decision thresholds. On the y-axis is sensitivity, or the true-positive fraction defined as [(number of true-positive test results)/(number of true-positive+number of false-negative test results)]. This has also been referred to as positivity in the presence of a disease or condition. It is calculated solely from the affected subgroup. On the x-axis is the false-positive fraction, or 1—specificity [defined as (number of false-positive results)/(number of true-negative+number of false-positive results)]. It is an index of specificity and is calculated entirely from the unaffected subgroup. Because the true- and false-positive fractions are calculated entirely separately, by using the test results from two different subgroups, the ROC plot is independent of the prevalence of disease in the sample. Each point on the ROC plot represents a sensitivity/specificity pair corresponding to a particular decision threshold. A test with perfect discrimination (no overlap in the two distributions of results) has an ROC plot that passes through the upper left corner, where the true-positive fraction is 1.0, or 100% (perfect sensitivity), and the false-positive fraction is 0 (perfect specificity). The theoretical plot for a test with no discrimination (identical distributions of results for the two groups) is a 45° diagonal line from the lower left corner to the upper right corner. Most plots fall in between these two extremes. Qualitatively, the closer the plot is to the upper left corner, the higher the overall accuracy of the test.

One convenient goal to quantify the diagnostic accuracy of a laboratory test is to express its performance by a single number. The most common global measure is the area under the curve (AUC) of the ROC plot. The area under the ROC curve is a measure of the probability that the perceived measurement will allow correct identification of a condition. By convention, this area is always 0.5. Values range between 1.0 (perfect separation of the test values of the two groups) and 0.5 (no apparent distributional difference between the two groups of test values). The area does not depend only on a particular portion of the plot such as the point closest to the diagonal or the sensitivity at 90% specificity, but on the entire plot. This is a quantitative, descriptive the level of how close the ROC plot is to the perfect one (area=1.0).

Scores between 0 and 1 make it possible to assign a subject as a "low-risk control" (i.e. requiring primary care monitoring), a "high-risk control" (i.e. requiring close evaluation and further investigation), a "low-risk bladder cancer" (i.e. requiring urgent cystoscopy) or a "high-risk bladder cancer" (i.e. requiring immediate cystoscopy). Scores<0.4 indicate that the risk of serious disease is low, or if the initial diagnostic step has also been carried out and produces a score<0.4, it is unlikely that the subject has UC. A score>0.6 indicates a high risk of serious disease, or that the patient could have UC if the score is based on the initial diagnostic step. Scores between 0.4 and 0.6 can be interpreted as indicative of potential risk and the possibility of UC. Subjects with scores of 0.2 from the method of the invention (and the initial diagnostic step if that is carried out) and no clinical risk factors are identified as low-risk controls. Such subjects could be monitored in primary care.

The individual biomarkers identified by the present inventors as having an altered level in subjects suffering form or having increased risk of urothelial cancer compared to a control value are Bladder Tumour Antigen (BTA), Carcino-embryonic antigen (CEA), Human cytokeratin 18 (CK18), C-reactive protein (CRP), Creatinine, d Dimer, Epidermal growth factor (EGF), FAS, Hyaluronidase (HA), IL1α, IL1β, IL2, IL4, IL6, IL8, IL10, Interferon gamma (IFNγ), Monocyte Chemoattractant Protein 1 (MCP1), matrix metalloproteinase 9 (MMP9), Neutrophil gelatinase-associated lipocalin (NGAL), MMP9NGAL complex, Neuron specific enolase (NSE), Free Prostate Specific Antigen (FPSA), Total Prostate Specific Antigen (TPSA), Thrombomodulin (TM), Tumour necrosis factor α (TNFα), sTNFR1, sTNFR2, Vascular endothelial growth factor (VEGF) and von Willebrand factor (vWF). These biomarkers were identified by statistical analysis based on a diagnostic algorithm of demographic variables which include one or more of the patient's smoking history, age, history of anti-hypertension medication, history of anti-cholesterol medication, history of alcohol consumption, history of exposure to occupational risks or hazardous chemicals, proteinuria and cytological detection of inflammatory cells. Each of these demographic variables may be assigned a notional value which can be used in Forward Wald binary logistic regression analyses to create a diagnostic algorithm designated as PPP. PPP represents, in a single measure, the intrinsic contribution toward group membership with which each subject commences screening. The contribution that each biomarker makes to the area under the curve (AUC) values for the PPP algorithm can be assessed to determine whether a combination of biomarkers increases the statistical significance of the PPP algorithm.

A second aspect of the present invention provides a solid state device for diagnosis of urothelial cancer, the device comprising a substrate comprising an antibody that specifically binds one or more biomarkers selected from Bladder Tumour Antigen (BTA), Carcino-embryonic antigen (CEA), Human cytokeratin 18 (CK18), C-reactive protein (CRP), Creatinine, d Dimer, Epidermal growth factor (EGF), FAS, Hyaluronidase (HA), IL1α, IL1β, IL2, IL4, IL6, IL8, IL10, Interferon gamma (IFNγ), Monocyte Chemoattractant Protein 1 (MCP1), matrix metalloproteinase 9 (MMP9), Neutrophil gelatinase-associated lipocalin (NGAL), MMP9NGAL complex, Neuron specific enolase (NSE), Free Prostate Specific Antigen (FPSA), Total Prostate Specific Antigen (TPSA), Thrombomodulin (TM), Tumour necrosis factor α (TNFα), tumour necrosis factor Receptor 1 (sTNFR1), tumour necrosis factor Receptor 2 (sTNFR2), Vascular endothelial growth factor (VEGF) and von Willebrand factor (vWF).

The antibodies used in the present invention can be of any conventional type. Polyclonal and monoclonal antibodies are preferred, with monoclonal antibodies being most preferred.

A device that may be used in the invention may be prepared by activating the surface of a suitable substrate, and applying an array of antibodies on to discrete sites on the surface. If desired, the other active areas may be blocked. The ligands may be bound to the substrate via a linker. In particular, it is preferred that the activated surface is reacted successively with an organosilane, a bifunctional linker and the antibody. The solid state device used in the methods of the present invention may be manufactured according to the method disclosed in, for example, GB-A-2324866 the content of which is incorporated herein in its entirety. Preferably, the solid state device used in the methods of the present invention is the Biochip Array Technology system (BAT) (available from Randox Laboratories Limited). More preferably, the Evidence Evolution and Evidence Investigator apparatus (available from Randox Laboratories) may be used to determine the levels of biomarkers in the sample.

The solid state device is used in combination with other clinical indicators including the risk factors that might confound diagnosis of urothelial cancer using biomarkers, to assess the risk of a subject having urothelial cancer and/or stratify the level of risk of serious disease, wherein combination of antibodies present on the solid state device are selected according to a sub-population group that is appropriate to the subject.

At least one, but optionally two or more different solid state devices according to the invention may be used for each individual subject in order to assess their risk of having urothelial cancer. If multiple devices are used, each will comprise a combination of antibodies selected according to sub-population groups that are appropriate to the subject.

The solid state devices comprise antibodies that specifically bind to biomarkers that allow diagnosis of urothelial cancer in subpopulations of subjects according the invention. Such solid state devices for diagnosis of urothelial cancer in subjects that have a history of smoking comprise antibodies that bind specifically to urinary EGF, urinary IL6, urinary VEGF and urinary CK18; urinary EGF, serum IL8, urinary vWF and urinary FAS; urinary EGF, urinary IL1α, plasma MMP9NGAL and urinary vWF; EGF, IL1β, sTNFR, VEGF and CK18; BTA, EGF, IL1β, vWF and FAS; EGF, IL1β, IL8, TM, and vWF; d-Dimer, EGF, IL1β, IL8, VEGF and vWF; EGF, IL1β, NSE, sTNFR2, VEGF and vWF; EGF, IL2, TM, sTNFR2, VEGF and CK18; EGF, IL1α, MMP9, MMP9NGAL, NSE, VEGF and vWF; EGF, IL1β, NGAL, NSE, sTNFR1, VEGF and vWF; d-Dimer, EGF, IL1α, IL8, NSE, vWF and FAS; d-Dimer, EGF, IL1α, IL8 and NGAL; IL1α, IL2, IL8, NGAL and sTNFR1; IL1α, IL10, NGAL, NSE and TNFα; d-Dimer, IL2, IL10, MMP9NGAL, NGAL and sTNFR1; EGF, FPSA, IL10, NGAL, TNFα and TPSA; CEA, IL1α, IL4, IL8, IL10 and NGAL; EGF, CRP, IL10, MMP9NGAL, NGAL, TM and VEGF; CEA, CRP, IL10, MMP9NGAL, NGAL, TM and TNFα; CEA, d-Dimer, IL2, IL8, IL10, IFNγ and NSE; IL4, IFNγ, MCP1, MMP9NGAL and TM; IL1α, IL4, IFNγ, MCP1 and MMP9NGAL; EGF, IL1α, IL4, MCP1, MMP9NGAL; dDimer, IL1α, IL4, IL10, MMP9NGAL and sTNFR1; IL4, IL10, MMP9NGAL, TM, sTNFR1 and TNFα; IL1β, IL4, IL8, MCP1, MMP9NGAL and TNFα; IL1α, IL1β, IL2, IL4, IL10, MMP9NGAL and TNFα d-Dimer, IL1α, IL4, IFNγ, MCP1, MMP9NGAL and TM; or d-Dimer, EGF, IL1α, IL4, IL10, IFNγ, and MMP9NGAL.

The solid state devices for diagnosis of urothelial cancer in subjects that do not have a history of smoking comprise comprises antibodies that bind specifically to serum CEA, urinary EGF, plasma IL8 and urinary CK18; serum CEA, plasma IL8, serum NGAL and serum TM; serum CEA, plasma IL8, serum NGAL and plasma NSE; BTA, MMP9NGAL, TM, sTNFR2 and VEGF; BTA, IL4, MMP9, NSE and FAS; BTA, MMP9NGAL, TNFα, sTNFR2 and VEGF; BTA, MCP1, MMP9, sTNFR2, vWF and FAS; d-Dimer, IL6, IL8, NGAL, NSE and TNFα; BTA, IL6, MCP1, TNFα, sTNFR2 and FAS; EGF, CRP, IL8, NGAL, NSE, TM and HA; BTA, EGF, IL8, MCP1, NGAL, NSE, sTNFR1; BTA, IL4, MCP1, TM, sTNFR2, vWF and FAS; CEA, EGF, IL4, NGAL and TNFα; CEA, EGF, IL8, NGAL and TPSA; CEA, IL8, MCP1, NGAL and TPSA; CEA, IL6, IL8, MMP9NGAL, NGAL and VEGF; CEA, d-Dimer, CRP, MMP9NGAL, NGAL and NSE; CEA, CRP, IL2, MMP9NGAL, NGAL and TM; CEA, EGF, CRP, IL4, IL8, NGAL and NSE; CEA, IL6, IL8, IFNγ, NGAL, TM and VEGF; CEA, FPSA, CRP, IL4, MMP9NGAL, NGAL and TM; IL1α, MMP9NGAL, NSE, sTNFR1 and VEGF; IFNγ, MCP1, MMP9NGAL, NGAL and NSE; IFNγ, MMP9NGAL, NGAL, NSE and TNFα; IL6, IFNγ, MMP9NGAL, NGAL, NSE and TNFα; d-Dimer, IL1α, IL4, MMP9NGAL, NSE and VEGF; d-Dimer, EGF, IL1α, IL8, MMP9NGAL and NSE; d-Dimer, EGF, IL1α, IFNγ, MMP9NGAL, TNFα and VEGF; EGF, IL1α, IL2, MMP9NGAL, NGAL, NSE and TM; or IL1α, IFNγ, MMP9NGAL, NGAL, NSE, TM and TNFα.

The solid state devices for diagnosis of urothelial cancer in subjects that are aged 65 years or older comprise comprises antibodies that bind specifically to serum IL2, serum MMP9NGAL, serum NGAL and plasma sTNFR1; urinary MMP9NGAL, serum NGAL, plasma NGAL and urinary vWF; serum CEA, serum d-Dimer, plasma d-Dimer and serum IFNγ; BTA, IL1β, VEGF, vWF and HA; d-Dimer, IL1α, NSE, vWF and HA; BTA, d-Dimer, IL1β, vWF and HA; BTA, IL1β, IL4, VEGF, vWF and HA; BTA, IL1β, IL8, sTNFR2, vWF and HA; BTA, EGF, IL1α, NSE, vWF and HA; d-Dimer, CRP, IL1α, IL2, NSE, vWF and HA; BTA, IL1α, IL8, MMP9NGAL, vWF, HA and CK18; d-Dimer, IL1α, MCP1, NSE, TNFα, vWF and HA; CEA, d-Dimer, IL4, NGAL and TM; IL1α, MMP9NGAL, NGAL, sTNFR1 and TNFα; IL2, MMP9NGAL, NGAL, sTNFR1 and VEGF; CEA, d-Dimer, IL1α, NGAL, NSE and TM; CEA, EGF, IL1α, MMP9NGAL, NGAL and TPSA; CEA, d-Dimer, CRP, IL1β, NGAL and TM; CEA, d-Dimer, FPSA, CRP, IL10, NGAL and TM; CEA, d-Dimer, CRP, NGAL, NSE, TM and TPSA; d-Dimer, IL1α, IL8, IFNγ, MMP9NGAL, NGAL and TM; CRP, IL1α, MMP9NGAL, TM and VEGF; CRP, IL1α, IL1β, MMP9NGAL and NGAL; CRP, IL1α, IL4, MMP9NGAL and TM; CRP, IL1α, IL2, IL4, MMP9NGAL and TM; EGF, CRP, IL1α, IL1β, MMP9NGAL and VEGF; EGF, IL1α, IL6, MMP9NGAL, TM and TNFα; CRP, IL1α, IL10, MMP9NGAL, TM, TNFα and VEGF; IL1α, IL6, IL10, MMP9NGAL, TM, TNFα and VEGF; or CRP, IL1α, IL4, IL6, MMP9NGAL, TM and TNFα.

The solid state devices for diagnosis of urothelial cancer in subjects that are less than 65 years old comprise antibodies that bind specifically to serum CEA, urinary EGF, serum IL1α and urinary VEGF; serum CEA, urinary CRP, serum IL1α and urinary VEGF; serum CEA, serum-IL1α, plasma IFNγ and urinary VEGF; EGF, IL2, HA, FAS and CK18; EGF, IL2, MMP9NGAL, HA and CK18; EGF, vWF, HA, FAS and CK18; EGF, IL2, IL8, MMP9, HA and CK18; BTA, EGF, IL1β, IL8, HA and CK18; d-Dimer, EGF, NSE, vWF, HA and CK18; EGF, CRP, IL1β, IL2, IL8, HA and CK18; EGF, IL1β, IL4, IL8, vWF, HA and CK18; EGF, IL1β, IL6, IL8, MMP9, HA and CK18; CEA, IL1α, IL4, TM and TNFα; CEA, IL1α, IL2, IL4 and IL8; CEA, IL1α, IL1β, IL4 and VEGF; CEA, IL1α, IL4, IL8, MMP9NGAL and sTNFR1; CEA, IL1α, IL2, IL4, NSE and sTNFR1; CEA, EGF, IL1α, IL4, IL8 and TM; CEA, IL1α, IL2, IL4, IL8, IFNγ and MMP9NGAL; CEA, EGF, FPSA, IL1α, IL4, IL8 and VEGF; CEA, IL1α, IL2, IL8, IFNγ, MCP1 and sTNFR1; d-Dimer, IL8, IL10, NSE and VEGF; d-Dimer, IL8, MMP9NGAL, TNFα and VEGF; EGF, IL8, IL10, MMP9NGAL and sTNFR1; EGF, CRP, IL6, IL8, IL10 and sTNFR1; CRP, IL6, IL8, IL10, IFNγ and sTNFR1; d-Dimer, IL4, IL8, MMP9NGAL, NGAL and TNFα; CRP, IL4, IL6, IL8, IL10, MMP9NGAL and TNFα; EGF, CRP, IL1β, IL8, IFNγ, NGAL and sTNFR1; or d-Dimer, EGF, CRP, IL8, IL10, IFNγ and MMP9NGAL.

The solid state devices for diagnosis of urothelial cancer in a subject that has a history of anti-hypertensive medication comprises antibodies that bind specifically to urinary EGF, urinary SERUM-IL1α, IL1α, serum IL10 and urinary vWF; urinary EGF, plasma IL10, urinary VEGF and urinary vWF; serum sTNFR1, plasma sTNFR1, serum TNFα and urinary vWF; CRP, IL2, IL8, sTNFR2 and vWF; EGF, IL8, NSE, TNFα and vWF; BTA, EGF, IL4, vWF and HA; BTA, EGF, IL1β, IL8, VEGF and vWF; d-Dimer, CRP, IL8, sTNFR2, vWF and CK18; d-Dimer, EGF, IL2, VEGF, vWF and FAS; CRP, IL1β, IL6, IL8, MMP9, NGAL and vWF; d-Dimer, IL8, MMP9, NSE, TM, sTNFR2 and vWF; BTA, d-Dimer, EGF, IL4, NGAL, NSE and vWF; CEA, NGAL, NSE, TNFα and TPSA; CEA, MMP9NGAL, NGAL, TM and TNFα; CEA, IL1β, NGAL, sTNFR1 and TPSA; CEA, IL1β, IL10, NGAL, TM and VEGF; CEA, d-Dimer, IL1β, MMP9NGAL, NGAL and TM; CEA, EGF, IL1α, IL1β, NGAL and TNFα; CEA, IL1α, IL1β, IL10, NGAL, sTNFR1 and TNFα; CEA, IL1α, NGAL, NSE, TM, TNFα and TPSA; CEA, IL1β, IL4, IL10, MMP9NGAL, NGAL and TM; IL1α, IL1β, IL4, IFNγ and VEGF; EGF, CRP, IL2, IL4 and IL8; EGF, CRP, IL2, IL10 and NGAL; EGF, IL6, IL10, IFNγ, MCP1 and MMP9NGAL; d-Dimer, EGF, IL1β, IL4, IL6 and MCP1; EGF, CRP, IL1β, IL2, MMP9NGAL and NGAL; d-Dimer, EGF, CRP, IL2, IL10, MMP9NGAL and TM; CRP, IL1α, IL1β, IL4, IL6, IFNγ and sTNFR1; or EGF, CRP, IL4, IL6, IL10, IFNγ and MMP9NGAL.

The solid state devices for diagnosis of urothelial cancer in a subject that does not have a history of anti-hypertensive medication comprises antibodies that bind specifically to serum CEA, urinary CRP, urinary NSE and serum TNFα; serum CEA, urinary CRP, serum IL4 and urinary sTNFR1; urinary Creatinine, serum IL6, plasma MMP9NGAL and urinary VEGF; CRP, NGAL, VEGF, HA and CK18; d-Dimer, TNFα, VEGF, HA and CK18; MMP9, NSE, TM, VEGF and FAS; EGF, NGAL, VEGF, vWF, HA and CK18; CRP, IL1β, IL6, sTNFR1, VEGF and vWF; d-Dimer, EGF, IL4, VEGF, HA and CK18; CRP, IL1β, IL6, IL8, MMP9, NGAL and vWF; d-Dimer, IL8, MMP9, NSE, TM, sTNFR2 and vWF; BTA, d-Dimer, EGF, IL4, NGAL, NSE and vWF; CEA, d-Dimer, IL4, MMP9NGAL and sTNFR1; CEA, EGF, IL10, MMP9NGAL and TNFα; CEA, d-Dimer, CRP, IL4 and IL10; CEA, d-Dimer, CRP, IL4, IL10 and TM; CEA, d-Dimer, CRP, IL4, IL6 and MMP9NGAL; CEA, d-Dimer, IL2, IL4, IL8 and MMP9NGAL; CEA, d-Dimer, EGF, IL4, IL8, IL10 and NSE; CEA, d-Dimer, CRP, IL4, MCP1, MMP9NGAL and TNFα; CEA, d-Dimer, CRP, IL4, IL6, TM and TNFα; EGF, IL1α, IL8, MMP9NGAL and VEGF; IL1α, IL8, IFNγ, MMP9NGAL and VEGF; CRP, IL1α, IL8, MMP9NGAL and NGAL; EGF, CRP, IL1β, IL8, MMP9NGAL and VEGF; CRP, IL1α, IL6, IL8, IL10, MMP9NGAL; EGF, IL1β, IL4, IL8, MMP9NGAL and VEGF; EGF, CRP, IL1α, IL8, MMP9NGAL, TNFα and VEGF; EGF, CRP, IL1β, IL8, MMP9NGAL, sTNFR1 and VEGF; or d-Dimer, EGF, IL1β, IL6, IL8, MMP9NGAL and VEGF.

The solid state devices for diagnosis of urothelial cancer in a subject that has cytological detection of inflammatory cells comprises antibodies that bind specifically to urinary BTA, serum CEA, plasma IL10 and urinary CK18; urinary BTA, plasma IL6, serum NSE and plasma NSE; urinary dipstick protein, urinary BTA, plasma IL6 and serum NGAL; BTA, IL1α, NGAL, sTNFR1 and vWF; BTA, IL8, MMP9NGAL, VEGF and CK18; BTA, IL6, MMP9NGAL, NSE and CK18; BTA, IL2, MMP9NGAL, sTNFR1, TNFα and VEGF; BTA, IL2, MMP9NGAL, NGAL, TNFα and CK18; BTA, IL2, MMP9NGAL, NSE, VEGF and CK18; BTA, IL2, MMP9NGAL, NGAL, sTNFR1, TNFα and VEGF; BTA, IL2, MMP9NGAL, TM, sTNFR1, vWF and FAS; BTA, IL2, MMP9NGAL, sTNFR1, VEGF, vWF and CK18; CEA, IL1α, NGAL, NSE and TPSA; IL1α, MMP9NGAL, NGAL, TPSA and VEGF; CEA, IL1α, IL10, NGAL and VEGF; CEA, IL10, MMP9NGAL, NGAL, TNFα and VEGF; IL1α, IL10, MMP9NGAL, NGAL, NSE and VEGF; CRP, IL10, MMP9NGAL, NGAL, TPSA and VEGF; CEA, CRP, IL1β, IL2, TM, sTNFR1 and TPSA; CRP, IL1β, IL2, IL6, MMP9NGAL, NGAL and TNFα; CRP, IL1β, IL2, MMP9NGAL, NGAL, NSE and TNFα; IL1α, IL6, IL8, MMP9NGAL and NSE; IL6, IFNγ, MMP9NGAL, NSE and sTNFR1; IL1α, IL1β, IL8, IL10 and MMP9NGAL; IL6, IL8, IFNγ, MMP9NGAL, NGAL and NSE; IL1α, IL6, MMP9NGAL, NSE, TM and TNFα; d-Dimer, IL4, IL8, IFNγ, MMP9NGAL and VEGF; IL1α, IL8, IL10, MCP1, MMP9NGAL, NSE and TM; d-Dimer, IL2, IL6, IL8, MMP9NGAL, TM and sTNFR1; or IL1α, IL2, IL6, IL8, MCP1, MMP9NGAL and NSE.

The solid state devices for diagnosis of urothelial cancer in a subject that does not have cytological detection of inflammatory cells comprises antibodies that bind specifically to serum CEA, plasma IL8, serum TNFα and urinary FAS; urinary EGF, serum EGF, serum FPSA and serum IL4; urinary EGF, urinary CRP, urinary IL4 and urinary NSE; EGF, CRP, IL4, TM and vWF; BTA, d-Dimer, EGF, CRP and IL4; EGF, CRP, IL4, IL6 and vWF; d-Dimer, EGF, CRP, IL4, sTNFR1 and vWF; d-Dimer, EGF, CRP, IL4, sTNFR1 and sTNFR2; EGF, IL2, IL4, sTNFR2, VEGF and vWF; EGF, CRP, IL4, MCP1, VEGF, FAS and CK18; d-Dimer, EGF, CRP, IL4, IL6, sTNFR2 and vWF; d-Dimer, EGF, CRP, IL4, IL6, sTNFR2 and CK18; CEA, EGF, CRP, IL4 and IFNγ; d-Dimer, FPSA, IL6, IFNγ and NGAL; IL1α, IL4, MMP9NGAL, NGAL and TM; IL4, MMP9NGAL, NGAL, NSE, sTNFR1 and TPSA; CEA, EGF, FPSA, IL4, NSE and sTNFR1; CEA, EGF, FPSA, IL4, MCP1 and VEGF; FPSA, IL2, IL4, IL6, MMP9NGAL, NGAL and sTNFR1; CEA, EGF, FPSA, CRP, IL4, IL6 and MMP9NGAL; d-Dimer, IL1β, IL4, IL8, MCP1, NGAL and TM; d-Dimer, IL1β, IL8, MMP9NGAL and TM; d-Dimer, IL8, TM, TNFα and VEGF; IL2, IL8, MMP9NGAL, TM and TNFα; d-Dimer, IL8, MMP9NGAL, NSE, TM and TNFα; d-Dimer, IL2, IL8, MMP9NGAL, NSE and TNFα; d-Dimer, IL8, IFNγ, MMP9NGAL, sTNFR1 and TNFα; d-Dimer, IL1α, IL8, MMP9NGAL, TM, TNFα and VEGF; d-Dimer, CRP, IL2, IL6, IL8, MMP9NGAL and TNFα; or d-Dimer, IL1α, IL1β, IL8, MMP9NGAL, TM and VEGF.

The solid state devices for diagnosis of urothelial cancer in a subject that has a history of alcohol consumption comprises antibodies that bind specifically to urinary EGF, urinary IL1β, plasma MMP9NGAL and urinary vWF; serum CEA, urinary EGF, urinary vWF and urinary CK18; serum CEA, urinary EGF, plasma NSE and urinary vWF; EGF, MMP9, sTNFR2, VEGF and vWF; EGF, IL1α, IL4, vWF and FAS; EGF, IL1α, MMP9, vWF and HA; d-Dimer, EGF, CRP, IL1α, IL6 and vWF; EGF, CRP, IL1α, sTNFR, vWF and CK18; BTA, EGF, CRP, IL1α, vWF and FAS; EGF, IL1α, IL6, NGAL, sTNFR2, vWF and FAS; EGF, IL1α, IL2, IL6, NGAL, VEGF and vWF; EGF, IL1α, NGAL, NSE, sTNFR2, vWF and CK18; CRP, IL1β, IL6, IL8 and NGAL; d-Dimer, IL1β, IL4, IFNγ and NGAL; CRP, IL1β, IL4, MCP1 and NGAL; EGF, CRP, IL1α, IL1β, NGAL and TPSA; CEA, CRP, IL1β, IL2, NGAL and NSE; CEA, d-Dimer, CRP, IL1α, IL6 and NGAL; EGF, CRP, IL8, MCP1, MMP9NGAL, NGAL and sTNFR1; CEA, EGF, CRP, IL1β, MMP9NGAL, NGAL and TM; CEA, d-Dimer, IL1α, IL2, IL4, IL10 and NGAL; d-Dimer, IL4, MMP9NGAL, NSE and TM; IL1β, IL4, MMP9NGAL, NSE and TNFα; EGF, CRP, IL4, MMP9NGAL and sTNFR1; IL1α, IL2, IL4, MMP9NGAL, NSE and TNFα; IL2, IL4, IL6, MMP9NGAL, NSE and TM; CRP, IL1α, IL1β, IL4, MMP9NGAL and TNFα; d-Dimer, IL1β, IL4, MMP9NGAL, NGAL, NSE and VEGF; d-Dimer, IL1α, IL2, MMP9NGAL, NSE, sTNFR and TNFα; or d-Dimer, CRP, IL1α, IL4, IL10, NSE and sTNFR.

The solid state devices for diagnosis of urothelial cancer in a subject that does not have a history of alcohol consumption comprises antibodies that bind specifically to serum MMP9NGAL, serum sTNFR1, serum TNFα and urinary VEGF; serum CEA, urinary EGF, serum IL10 and serum NGAL; urinary IL6, plasma MMP9NGAL, urinary VEGF and urinary CK18; IL2, IL8, NGAL, HA and CK18; IL2, IL4, VEGF, HA and CK18; IL1β, IL2, IL8, NGAL and CK18; IL2, IL4, IL8, NGAL, HA and CK18; BTA, d-Dimer, IL2, IL8, MMP9NGAL and CK18; IL2, IL4, IL8, sTNFR2, HA and CK18; IL1β, IL2, IL6, IL8, NGAL, NSE and CK18; IL1α, IL2, IL6, IL8, NGAL, HA and CK18; BTA, IL1α, IL2, IL8, NGAL, VEGF and CK18; CEA, IL1α, IL8, TM and sTNFR1; CEA, IL1α, IL6, NGAL and TM; CEA, IL1α, IL2, TM and sTNFR1; CEA, IL2, IL8, NSE, TM and sTNFR1; CEA, IL10, MMP9NGAL, NSE, TM and sTNFR1; CEA, CRP, IL2, IL10, NGAL and TM; CEA, CRP, IL4, IL6, IL10, sTNFR1 and TPSA; CEA, d-Dimer, EGF, IL1α, IL10, NSE and sTNFR1; CEA, d-Dimer, IL1α, IL1β, IL4, TM and sTNFR1; IL1α, IFNγ, MMP9NGAL, sTNFR1 and TNFα; EGF, IL4, MCP1, MMP9NGAL and sTNFR1; IL1α, IL8, IL10, MMP9NGAL and VEGF; IL1α, IL1β, IL10, IFNγ, MMP9NGAL and VEGF; EGF, CRP, IL1α, MMP9NGAL, TNFα and VEGF; IL1α, IL6, IL8, IFNγ, MMP9NGAL and sTNFR1; L1α, IL2, IL8, IFNγ, MMP9NGAL, sTNFR1 and TNFα; IL1α, IL2, IL6, IL10, MMP9NGAL, TNFα and VEGF; or IL1α, IL4, IL6, IL10, MMP9NGAL, NGAL and VEGF.

The solid state devices for diagnosis of urothelial cancer in a subject that has a history of exposure to occupational risk or hazardous chemicals comprises antibodies that bind specifically to serum CEA, urinary EGF, urinary VEGF and urinary vWF; urinary EGF, serum IL8, urinary vWF and urinary HA; serum IL4, plasma IL8, serum MCP1 and urinary VEGF; BTA, IL2, IL4, MMP9NGAL and VEGF; BTA, IL1α, IL8, NGAL and NSE; BTA, CRP, IL4, NSE and CK18; BTA, d-Dimer, CRP, IL4, sTNFR1 and vWF; IL4, IL8, NGAL, NSE, TM and sTNFR1; CRP, IL2, IL8, MCP1, MMP9NGAL and TNFα; EGF, IL1α, IL8, MMP9NGAL, NSE, vWF and CK18; EGF, IL6, IL8, MMP9NGAL, NSE, VEGF and vWF; CRP, IL1α, IL6, IL8, MMP9NGAL, NSE and VEGF; IL2, IL10, NGAL, NSE and VEGF; CEA, IL4, IL8, NGAL and TM; CEA, CRP, NGAL, NSE and sTNFR1; d-Dimer, CRP, IL6, IL8, NSE and sTNFR1; CEA, IL4, IL10, IFNγ, MCP1 and NGAL; FPSA, IL4, IL8, MMP9NGAL, NSE and sTNFR1; FPSA, IL1β, IL2, IL4, IL8, MMP9NGAL and NGAL; CEA, d-Dimer, IL8, IL10, IFNγ, NGAL and NSE; CEA, EGF, CRP, IL10, MCP1, NGAL and NSE; IL1α, IL6, MMP9NGAL, TM and sTNFR1; IL1α, IL1β, IL6, IL8 and TNFα; IL8, MMP9NGAL, NGAL, NSE and TNFα; IL1β, IL2, IL8, MMP9NGAL, NGAL and NSE; IL1β, IL8, IL10, MCP1, NGAL and TM; IL8, IFNγ, MMP9NGAL, TM, sTNFR1 and TNFα; IL1β, IL8, IFNγ, MCP1, MMP9NGAL, TM and sTNFR1; IL1α, IL4, IL8, IL10, MCP1, TM and sTNFR1; or IL1α, IL1β, IL6, IL8, NGAL, NSE and VEGF.

The solid state devices for diagnosis of urothelial cancer in a subject that does not have a history of exposure to occupational risk or hazardous chemicals comprises antibodies that bind specifically to serum CEA, serum d-Dimer, urinary EGF and serum IL1α; serum CEA, serum d-Dimer, serum IL6 and serum MCP1; urinary BTA, serum CEA, urinary TNFα and urinary CK18; BTA, TM, TNFα, sTNFR2 and vWF; BTA, TM, TNFα, vWF and FAS; EGF, NSE, TNFα, vWF and HA; IL6, MCP1, TNFα, vWF, FAS and CK18; BTA, d-Dimer, CRP, TNFα, vWF and HA; BTA, IL1α, TNFα, vWF, HA and FAS; BTA, d-Dimer, MMP9NGAL, TM, TNFα, vWF and HA; IL6, NGAL, sTNFR, TNFα, vWF, FAS and CK18; BTA, IL1α, IL1β, IL6, NGAL, TNFα and CK18; CEA, d-Dimer, NSE, TM and TPSA; CEA, EGF, IL10, MCP1 and sTNFR1; CEA, d-Dimer, CRP, MCP1 and NGAL; CEA, d-Dimer, EGF, IL8, IL10 and TM; CEA, d-Dimer, IL4, MCP1, MMP9NGAL and sTNFR1; CEA, d-Dimer, EGF, IL6, NGAL and TM; CEA, d-Dimer, IL4, IL10, MCP1, MMP9NGAL and NSE; CEA, d-Dimer, IFNγ, MCP1, MMP9NGAL, TM and TPSA; CEA, d-Dimer, EGF, IL6, IL10, MMP9NGAL and TM; IL4, IL6, IFNγ, MMP9NGAL and NGAL; IL1β, IL4, IL10, MMP9NGAL and TM; IL2, IL4, IL6, IFNγ and MMP9NGAL; IL2, IL4, IL10, MMP9NGAL, TNFα and VEGF; CRP, IL4, IL10, MMP9NGAL, TNFα and VEGF; IL1α, IL4, IL10, IFNγ, MMP9NGAL and NSE; IL4, IL6, IL10, MMP9NGAL, NGAL, sTNFR1 and VEGF; d-Dimer, CRP, IL1α, IL1β, IL2, IL4 and MMP9NGAL; or d-Dimer, CRP, IL1β, IL4, IL6, IL10 and MMP9NGAL.

The solid state devices for diagnosis of urothelial cancer in a subject that has a history of anti-cholesterol medication comprises antibodies that bind specifically to serum MCP1, plasma MCP1, serum NGAL and plasma NGAL; urinary CRP, serum IL2, serum NGAL and plasma NGAL; urinary Creatinine, serum NGAL, plasma NGAL and plasma VEGF; CRP, MCP1, sTNFR2, vWF and FAS; d-Dimer, IL6, MMP9NGAL, NSE and VEGF; BTA, MCP1, sTNFR2, vWF and FAS; d-Dimer, IL6, NGAL, NSE, VEGF and HA; IL1β, IL6, IL8, MMP9NGAL, NSE and VEGF; BTA, d-Dimer, IL6, NGAL, NSE and VEGF; BTA, CRP, IL1β, IL8, sTNFR2, vWF and FAS; d-Dimer, IL4, IL6, MMP9, NSE, VEGF and CK18; BTA, CRP, IL1α, IL2, sTNFR2, vWF and FAS; IL6, IL8, NGAL, TPSA and VEGF; FPSA, NGAL, TM, TNFα and VEGF; IL1β, IL2, NGAL, TM and VEGF; IL1α, MCP1, MMP9NGAL, NGAL, TM and TNFα; CEA, FPSA, IL8, NGAL, TM and VEGF; FPSA, IL4, NGAL, NSE, TNFα and VEGF; FPSA, IL1β, IL10, NGAL, TM, TNFα and VEGF; CEA, IL1β, IL4, NGAL, TM, TPSA and VEGF; FPSA, IL1β, IL4, IL10, NGAL, TM and VEGF; IL2, IFNγ, MCP1, MMP9NGAL and TM; IL1α, IL1β, IL6, TNFα and VEGF; IL4, IL6, IFNγ, MCP1 and TNFα; d-Dimer, IL2, IL6, MMP9NGAL, TM and TNFα; IL2, IL10, IFNγ, MCP1, MMP9NGAL and TNFα; IL6, MCP1, NGAL, NSE, TM and TNFα; d-Dimer, EGF, IL6, IL10, IFNγ, MCP1 and TNFα; d-Dimer, IL10, IFNγ, MCP1, NGAL, sTNFR1 and VEGF; or d-Dimer, IL6, IL8, IL10, NSE, TM and TNFα.

The solid state devices for diagnosis of urothelial cancer in a subject that does not have a history of anti-cholesterol medication comprises antibodies that bind specifically to serum CEA, urinary EGF, urinary HA and urinary CK18; serum CEA, urinary EGF, urinary IL8 and urinary CK18; serum CEA, urinary EGF, plasma IL6 and urinary MMP9NGAL; BTA, CRP, IL2, IL4 and CK18; EGF, IL1β, NGAL, VEGF and CK18; BTA, IL4, IL8, HA and CK18; EGF, CRP, IL4, VEGF, HA and CK18; EGF, IL4, IL6, IL8, vWF and CK18; BTA, EGF, IL4, IL8, HA and CK18; BTA, EGF, CRP, IL4, sTNFR1, HA and CK18; EGF, IL1α, IL1β, IL4, sTNFR1, VEGF and CK18; EGF, CRP, IL4, MMP9NGAL, NGAL, HA and CK18; CEA, FPSA, IL10, IFNγ and NGAL; CEA, IL1α, IL1β, MMP9NGAL and sTNFR1; CEA, IL1α, MMP9NGAL, TM and TNFα; CEA, IL1α, IL1β, IL6, NGAL and NSE; CEA, IL4, IL6, IL8, MMP9NGAL and TNFα; CEA, d-Dimer, IL1α, IL4, IL6 and sTNFR1; CEA, IL1α, IL4, IL6, IL8, TM and sTNFR1; CEA, IL1α, IL1β, IL4, IL8, MMP9NGAL and VEGF; CEA, IL1α, IL4, IL10, MMP9NGAL, TM and TNFα; IL1α, IL8, MMP9NGAL, NGAL and sTNFR1; IL1α, IL1β, IL4, IFNγ and psTNFR1; IL1α, IL1β, IL8, TM and psTNFR1; d-Dimer, IL1α, IL4, IL10, MMP9NGAL and TNFα; CRP, IL8, IL10, MMP9NGAL, TM and sTNFR1; d-Dimer, IL1α, IL1β, IL4, TM and sTNFR1; IL1β, IL6, IL8, MMP9NGAL, sTNFR1, TNFα and VEGF; d-Dimer, IL1α, IL4, IL8, NGAL, TM and sTNFR1; or IL1α, IL1β, IL4, IL6, IL8, MMP9NGAL and sTNFR1.

The solid state devices for diagnosis of urothelial cancer in a subject that has proteinuria comprises antibodies that bind specifically to serum CEA, plasma CRP, urinary IL8 and plasma TNFα; urinary EGF, urinary IL1β, serum IL6 and urinary vWF; serum CEA, plasma IL1α, urinary NSE and serum NSE; EGF, IL2, NSE, TM and CK18; EGF, IL6, sTNFR1, HA and CK18; EGF, NGAL, vWF, HA and CK18; EGF, IL8, sTNFR2, VEGF, uvWF and HA; EGF, IL1α, MMP9, NSE, uvWF and HA; EGF, CRP, IL2, IL4, TM and CK18; EGF, IL1β, IL2, NSE, TM, VEGF and vWF; EGF, IL1β, MMP9, MMP9NGAL, TNFα, vWF and HA; EGF, IL2, IL4, NGAL, NSE, TM and CK18; CEA, IL8, IL10, NSE and TNFα; CEA, IL2, IL8, MMP9NGAL and NSE; CEA, IL2, IL6, IL10 and NSE; CEA, IL1β, IL2, IL8, IL10 and NSE; CEA, IL1β, IL2, IL8, NSE and TPSA; CEA, CRP, IL10, MMP9NGAL, NGAL and VEGF; CEA, IL1β, IL2, IL4, IL8, NSE and TNFα; CEA, EGF, IL4, IL8, IL10, TPSA and VEGF; CEA, IL1β, IL2, IL4, IL10, MMP9NGAL and TM; CRP, IL1α, IL8, IFNγ, TM; CRP, IL1α, IL8, IFNγ, NGAL; IL1α, IL2, IL8, MCP1, TM; EGF, IL1α, IL4, IL8, IFNγ, TM; d-Dimer, IL1α, IL8, IFNγ, MCP1, TM; IL1α, IL8, IFNγ, MCP1, TM, TNFα; IL1α, IL2, IL8, IL10, IFNγ, MCP1, TM; IL1α, IL2, IL8, IFNγ, MCP1, MMP9NGAL, TM; or EGF, CRP, IL1α, IL4, IL8, IFNγ, TNFα.

The solid state devices for diagnosis of urothelial cancer in a subject that does not have proteinuria comprises antibodies that bind specifically to urinary BTA, urinary NGAL, serum NGAL and urinary TNFα; urinary d-Dimer, urinary CRP, urinary NGAL and serum TNFα; serum CEA, urinary CRP, plasma MMP9NGAL and urinary NGAL; d-Dimer, CRP, IL4, NGAL and sTNFR2; CRP, MMP9NGAL, NGAL, sTNFR2 and VEGF; BTA, CRP, IL4, NGAL and sTNFR2; CRP, MCP1, MMP9, NGAL, sTNFR2 and VEGF; d-Dimer, CRP, IL2, IL4, NGAL and sTNFR; BTA, CRP, IL2, NGAL, sTNFR2 and vWF; d-Dimer, CRP, IL1α, IL4, MMP9NGAL, TM and CK18; BTA, EGF, CRP, MMP9, NGAL, vWF and FAS; BTA, CRP, NGAL, NSE, TM, sTNFR2 and vWF; FPSA, IL1α, IL4, IFNγ and NGAL; d-Dimer, IL2, IL4, NGAL and TM; d-Dimer, IL6, NGAL, TM and sTNFR1; d-Dimer, IL1β, IL8, NGAL, TM and TNFα; CEA, IL4, IL8, NGAL, TNFα and TPSA; d-Dimer, FPSA, IL2, IL6, IL8 and NGAL; FPSA, CRP, IL2, IL6, NGAL, TNFα and VEGF; CEA, FPSA, CRP, IL6, IL10, NGAL and VEGF; d-Dimer, FPSA, IL1β, IFNγ, MMP9NGAL, NGAL and TM; d-Dimer, IL4, MCP1, MMP9NGAL and TNFα; EGF, IL1α, IL2, MMP9NGAL and NGAL; d-Dimer, IL4, MCP1, MMP9NGAL and sTNFR1; d-Dimer, IL1β, IL4, IL8, IL10 and MMP9NGAL; d-Dimer, EGF, IL8, IL10, MMP9NGAL and TM; d-Dimer, EGF, IFNγ, MMP9NGAL, NSE and VEGF; EGF, IL1α, IL2, IL4, MCP1, MMP9NGAL and NGAL; d-Dimer, EGF, CRP, IL8, MMP9NGAL, NSE and VEGF; or d-Dimer, EGF, IL1β, IL8, IL10, MMP9NGAL and VEGF.

The method of the invention may be carried out two or more times for each individual subject by selecting two or more sub-population groups appropriate to the subject and determining the level of one or more biomarkers selected according to the sub-population groups.

In the context of the methods of the invention, a "control" or "control value" is understood to mean the level of a particular biomarker typically found in patients who do not have urothelial cancer. The control level of a biomarker may be determined by analysis of a sample isolated from a person with haematuria but who does not have urothelial cancer or may be the level of the biomarker understood by the skilled person to be typical for such a person. The control value of a biomarker may be determined by methods known in the art and normal values for a biomarker may be referenced from the literature from the manufacturer of an assay used to determine the biomarker level.

A number of biomarkers present in a sample isolated from a patient having urothelial cancer may have levels which are different to that of a control. However, the levels of some of the biomarkers that are different compared to a control may not show a strong enough correlation with urothelial cancer such that they may be used to diagnose urothelial cancer with an acceptable accuracy.

The invention is further described with reference to the following non-limiting examples:

EXAMPLES

The present inventors analysed data from 156 patients recruited to a case control study to identify characteristics associated with misclassification of diagnosis of urothelial cancer (UC). First, UC diagnostic classifiers for 16 stratified subpopulations were defined. Second, based on 29 biomarkers measured in urine, serum and plasma, a random forest classification was undertaken. Using random sub-sampling to generate 1000 training and test patient datasets, the probabilities of correct, incorrect and inconsistent classification for each patient were estimated. Third, the distribution of patient characteristics was explored by using Fisher's exact tests and by defining classifiers for control and UC classified subpopulations.

Patient Information and Samples

Patients

One hundred and eighty-one patients were recruited to a case control study between November 2006 and October 2008 following written informed consent. The study had ethical approval from the Office for Research Ethics Committees Northern Ireland (ORECNI 80/04) and hospital review boards and was conducted according to STARD guidelines [2]. We adopted a case control study design in order to recruit sufficient numbers of UCs to ensure that the classifier did not generate a large number of false positives; and similarly, we recruited sufficient numbers of control patients to ensure that the classifier had high sensitivity. At the time of recruitment, demographic details, medications and occupations were recorded from each patient. We classified each patient's occupational risk score as low, moderate or high [2]. Patients with low occupational risk scores who had no known exposure to chemicals were compared to patients with moderate or high occupational risk scores or past exposure to chemicals. Final diagnosis for each patient was determined approximately six months after recruitment following review of each patient's notes. We excluded 19 patients with a history of UC who were disease-free at the time of recruitment, one with adenocarcinoma, one with squamous cell carcinoma, three aged>85 years, and one with insufficient samples prior to our statistical analyses. A cohort of 156 patients remained for our analyses; 80 patients with pathologically proven UC and 76 controls. Cytology reports were available for 64 controls and 75 UCs.

Biomarkers and Analyses

Twenty-six protein biomarkers were measured in triplicate in urine (u), serum (s) and plasma (p) for each patient; three additional biomarkers were measured in urine as single measures. We also measured creatinine, total protein and osmolality in triplicate in urine from each patient. Scientists, blinded to all patient information, analyzed the anonymized samples using biochip array technology [14] or ELISAs as previously described [2]. Missing values were imputed using the median value from the available measurements for each individual biomarker (Table 3).

Statistical Analyses—Stratified Subpopulation Classifiers

It was hypothesized that a stratified subpopulation with low inter-patient heterogeneity, concomitant with a low level of confounding variables could achieve a UC diagnostic classifier with higher accuracy than a subpopulation with high inter-patient heterogeneity.

The 156 patients were stratified into 16 subpopulations using variables which, when split into two subpopulations, each contained >50 patients. For each subpopulation we conducted an exhaustive search of sets of four biomarkers (814,385 classifiers based on 68 measurements), using a logistic regression classification to define UC diagnostic classifiers [15]. The performance of each classifier was assessed using the average Area Under the Curve (AUC) measure [16] and standard deviation (sd) from a repeated random sub-sampling analyses.

Identification of Top Ranked Biomarkers/Variables in Diagnostic Classifiers

Because we performed exhaustive searches, we identified multiple classifiers with a similar accuracy. The top-ranked biomarkers or categorical variables following each classification analysis were identified on the basis of their hypergeometric distribution:

$$P(x=a) = \frac{\binom{k}{a}\binom{N-k}{b}}{\binom{N}{m}} \quad (1)$$

For the stratified analysis the variable "a" denotes the count frequency of a biomarker i being present among the top-ranked 50 classifiers and "b" in the remaining classifiers. "m" is the total count frequency of a biomarker i among all classifiers. "k" denotes the total count frequency of all biomarkers in the 50 top-ranked classifiers. "N" denotes the total count frequency of all biomarkers among all classifiers. For the enrichment test we used a significance level of $\alpha=0.05$ and considered multiple testing using Bonferroni.

Statistical Analyses—Supervised Patient Classification Analysis

For the patient dataset $L=L_1, \ldots, L_w$ with "w" patients and "m" biomarker measurements we used a repeated random sub-sampling for the generation of n=1000 pairs of training and test datasets. For each training dataset, which comprised 70% of the 156 patients, a random forest UC diagnostic classifier was generated using all the biomarker measurements (Table 3). This classifier was subsequently validated using the corresponding test dataset based on the remaining 30% of the 156 patients (FIG. 1). The random forest classification was performed using the R package random forest [17].

For each patient $L_i$ we determined the count frequencies that they were correctly, incorrectly or inconsistently classified across all test datasets. For each patient we tested two null-hypotheses: (1) that they were not more often correctly classified than expected by random chance $H_0^1$); and (2) not more often incorrectly classified than expected by random chance ($H_0^2$). The probability to reject the null hypothesis was estimated by the hypergeometric distribution (eq. 1).

For the n=1000 random sub-sampled test datasets each consisting of 30% of the patients (47 patients), a total of N=47,000 predictions were performed. For testing $H_0^1$, "a" denotes the frequency that a patient $L_i$ was classified correctly, "k" the total number of correct classifications for all patients, "m" the frequency a patient $L_i$ was sampled in "n" test datasets and b=m−a. For testing $H_0^2$, "a" denotes the frequency how often a patient $L_i$ was classified falsely, "k" the total number of false classifications for all patients. For both tests we used a significance level $\alpha=0.05$ and applied multiple hypothesis testing adjustments using the false discovery rate (FDR)[18]. We designated the subpopulation that rejected $H_0^1$ as classifiable, the subpopulation that rejected $H_0^2$ as non-classifiable, and a subpopulation that rejected neither $H_0^1$ and $H_0^2$ as inconsistent.

We then performed exhaustive searches of sets of five categorical variables (575,757 classifiers based on 39 variables) to determine UC diagnostic classifiers for the classifiable and non-classifiable subpopulations as previously described for the stratified subpopulation diagnostic classifiers.

Comparison of Characteristics Across Classifiable and Non-Classifiable Subpopulations We performed a Fisher's exact test to compare the distribution of characteristics across the following classifiable and non-classifiable patient subpopulations: classifiable and non-classifiable control patients; classifiable and non-classifiable UC patients; classifiable controls and non-classifiable UC patients and; classifiable UC and non-classifiable control patients, applying multiple hypotheses testing adjustments using the FDR as appropriate [18].

Results and Discussion

UC Diagnostic Classifiers for Stratified Sub-Populations

Figure 2A:
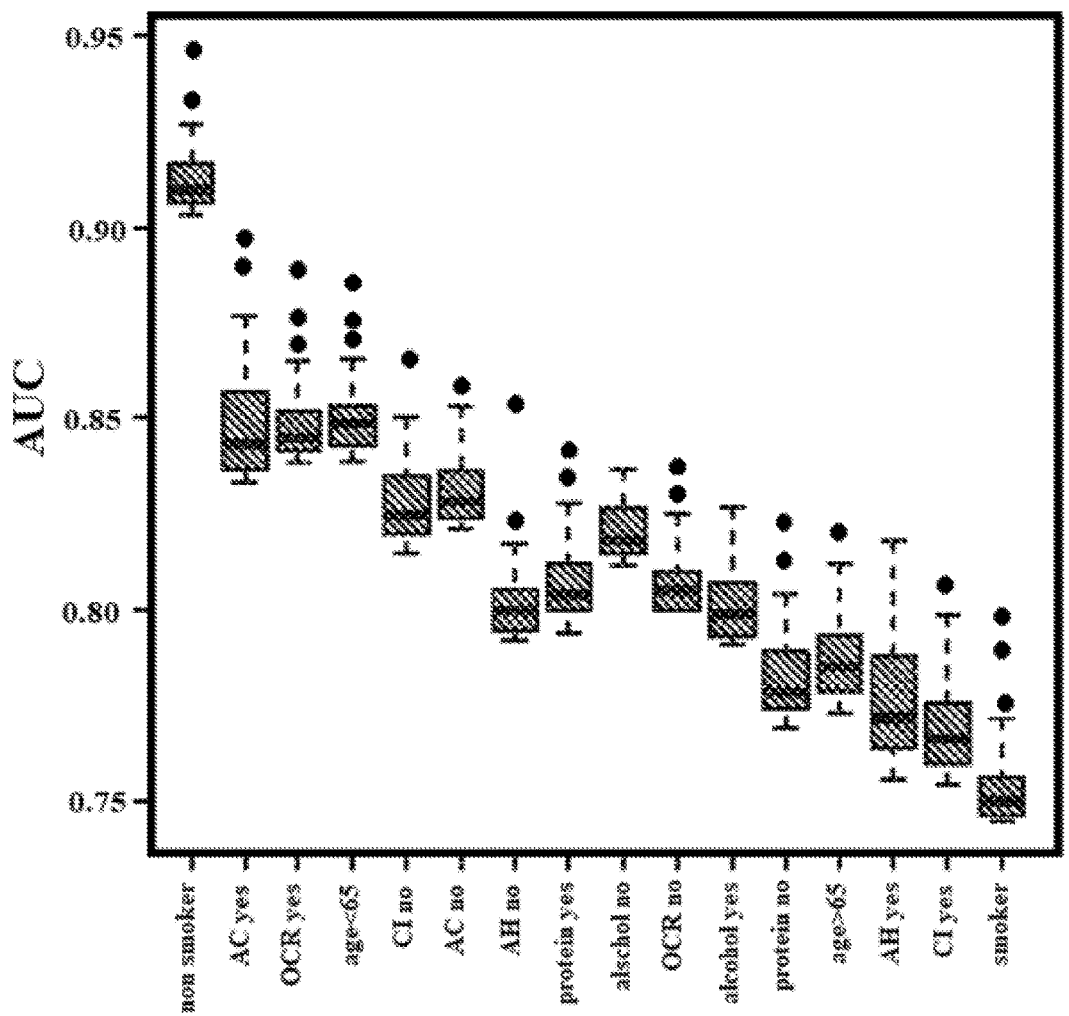
FIG. 2 shows UC diagnostic classifiers for stratified patient subpopulations. We performed an exhaustive search to identify sets of four biomarkers that accurately classified stratified patient subpopulations. A) Boxplots illustrating the medians and interquartile range of the 10 top-ranked UC diagnostic classifiers for each stratified patient subpopulation. B) The number of UCs and control patients in each patient subpopulation. C) A map illustrating the links between the enriched biomarkers of the 50 top-ranked UC diagnostic classifiers for each stratified patient subpopulation. Yellow circles (urine biomarkers); pink (serum biomarkers); green (plasma biomarkers). AC, anti-cholesterol; CI, cytology inflammation; AH, anti-hypertensives.
Figure 2B:
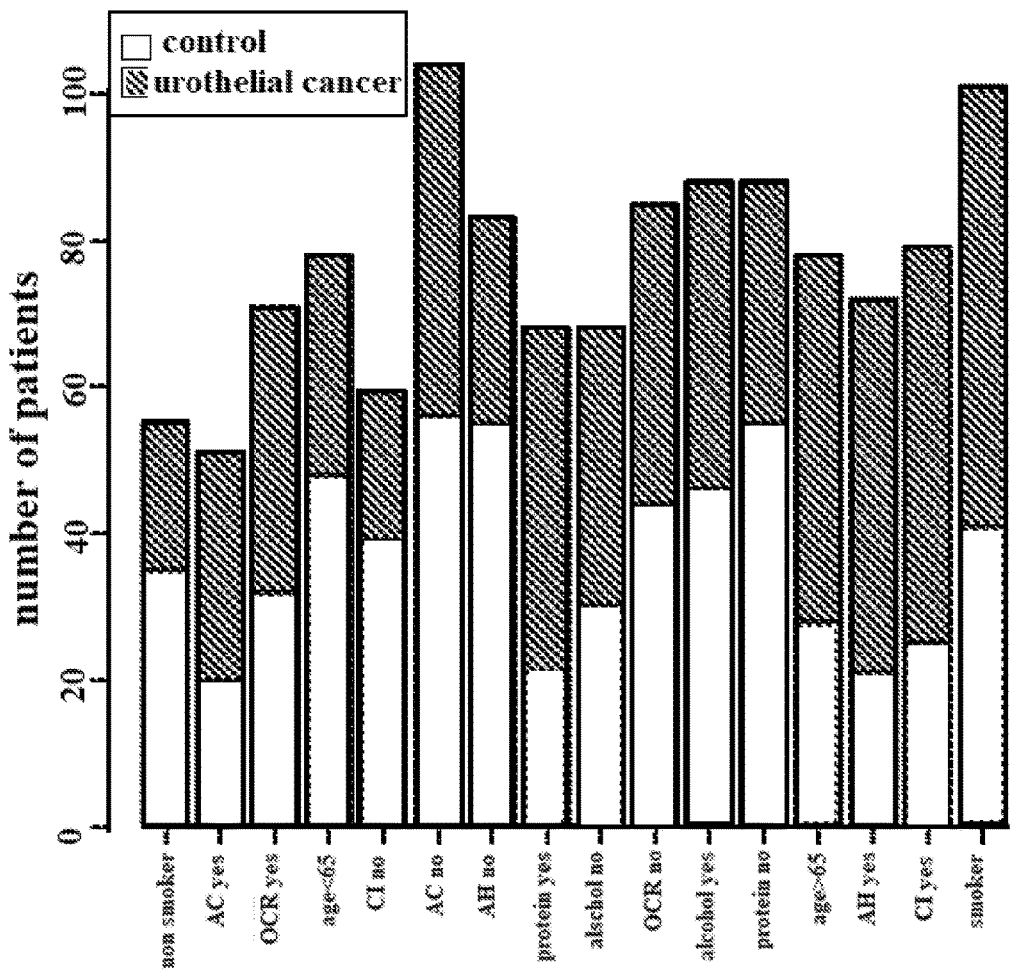
Figure 2C:
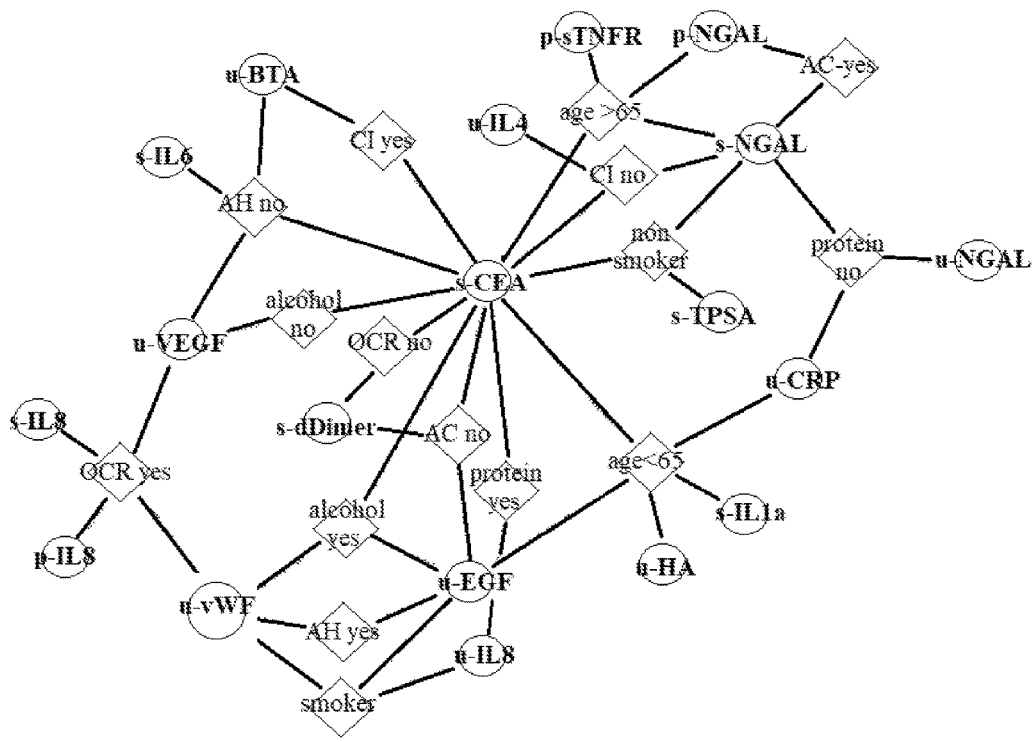

The classifier for the non-smoker subpopulation significantly outperformed the classification performance of all other subpopulations achieving AUC>0.95 (sd=0.10). Carcino-embryonic antigen (CEA) acted as a central protein biomarker with links to 11 stratified subpopulations (FIG. 2; Table 1).

The poor performances of the classifiers for the smoking and >65 years stratified patient subpopulations (Table 1), indicate that smoking and increased age confound UC diagnostic classifiers. The best classification performances across stratified subpopulations were achieved for the subpopulation composed of non-smokers (FIG. 2) suggesting that non-smokers were the most homogeneous subpopulation.

We observed that biomarkers in diagnostic classifiers were highly redundant resulting in multiple classifiers that achieved similar accuracies. Urine biomarkers were omnipresent in the best performing diagnostic classifiers supporting the concept that protein secretions from tumor and urothelial cells into urine, accurately reflect the status of the urothelium, both in the absence and/or presence of UC, in a way that captures the complexities of the disease status of individual patients [19]. Contrary to commonly applied heuristic approaches, we applied an exhaustive search of all biomarker measurements, meaning that every possible combination of biomarkers was assessed, in comparison to a feature selection method that searches only a subspace thereof.

The top performing combinations of 5, 6 and 7 biomarkers in urine, serum and plasma were identified for each subpopulation of the test population. These combinations (classifiers) are presented below in Tables 4 to 12. Table 4 provides the best performing combinations of 5 biomarkers measured in urine for each of the subpopulations based on subjects history of smoking, age, history of anti-hypertensive medication, history of anti-cholesterol medication, history of exposure to occupational risks or hazardous chemicals, history of alcohol consumption, cytological detection of inflammatory cells and proteinuria. Tables 7 and 10 respectively provide the best performing combinations of 6 and 7 biomarkers measured in urine for each of the same subpopulations. Tables 5, 8 and 11 respectively provide the best performing combinations of 5, 6 and 7 biomarkers measured in serum for each of the same subpopulations. Tables 6, 9 and 12 respectively provide the best performing combinations of 5, 6 and 7 biomarkers measured in plasma for each of the same subpopulations.

For each combination of 5, 6 or 7 biomarkers identified in tables 4 to 12, the skilled person would appreciate that the level of each individual biomarker can be altered in a sample independently of the other biomarkers in the same combination. The individual biomarkers identified by the present inventors as having an altered level in subjects suffering from or having increased risk of urothelial cancer compared to a control value are BTA, CEA, CK18, CRP, Creatinine, d Dimer, EGF, FAS, HA, IL1α, IL1β, IL2, IL4, IL6, IL8, IL10, IFNγ, MCP1, MMP9, NGAL, MMP9NGAL complex, NSE, FPSA, TPSA, TM, TNFα, sTNFR1, sTNFR2, VEGF and vWF. These biomarkers were identified by statistical analysis based on diagnostic algorithms across demographic variables which include one or more of the patient's smoking history, age, history of anti-hypertension medication, history of anti-cholesterol medication, history of alcohol consumption, history of exposure to occupational risks or hazardous chemicals, proteinuria and cytological detection of inflammatory cells. Relevant demographic variables for each patient may be assigned a notional value on the basis of predicted probability (PP) on the basis of Forward Wald binary logistic regression analyses. PP represents, in a single measure, the intrinsic contribution toward group membership (urothelial cancer or control) with which each subject commences screening. The contribution that each biomarker makes to the area under the curve (AUC) values for each PP can be assessed to determine whether a combination of biomarkers increases PP for that patient.

For exemplary purposes the alterations in the levels of biomarkers in the combinations of 7 biomarkers in samples from healthy subjects relative to those from urothelial cancer patients are indicated in Tables 13 to 15. In Table 13 it can be seen how individual biomarker levels in 7 biomarker combinations are altered in urine from healthy subjects compared to urine from UC patients. In Table 14 it can be seen how individual biomarker levels in 7 biomarker combinations are altered in serum from healthy subjects compared to serum from UC patients. In Table 15 it can be seen how individual biomarker levels in 7 biomarker combinations are altered in plasma from healthy subjects compared to plasma from UC patients.

For exemplary purposes the alterations in the levels of biomarkers in the combinations of 7 biomarkers in samples from UC patients relative to those from healthy subjects are indicated in Tables 16 to 18. In Table 16 it can be seen how individual biomarker levels in 7 biomarker combinations are altered in urine from UC patients compared to urine from healthy subjects. In Table 17 it can be seen how individual biomarker levels in 7 biomarker combinations are altered in serum from UC patients compared to serum from healthy subjects. In Table 18 it can be seen how individual biomarker levels in 7 biomarker combinations are altered in plasma from UC patients compared to plasma from healthy subjects.

Supervised Classification Analyses

Figure 3A:
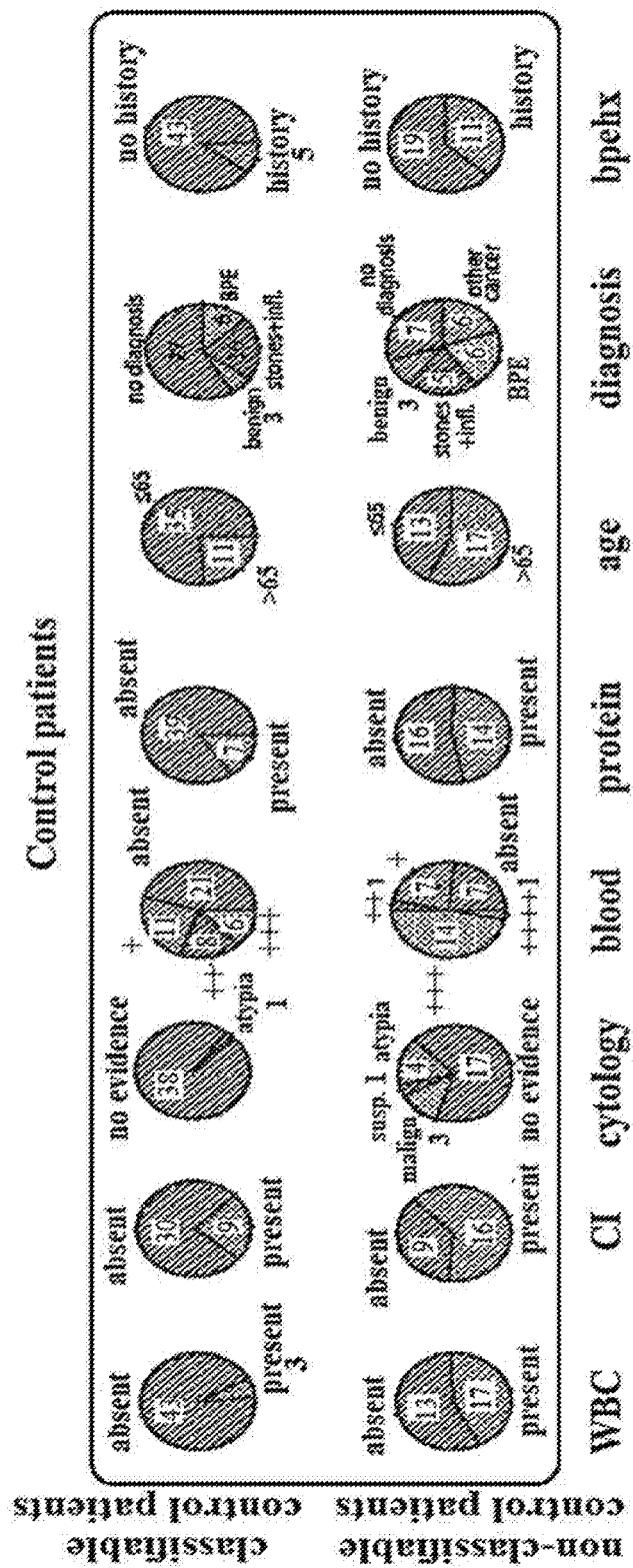
FIG. 3 shows comparative characteristics across classifiable and non-classifiable patient subpopulations. We performed Fisher's exact test to identify confounding variables, i.e., variables with significant heterogeneity across classifiable and non-classifiable patient groupings. In this figure the inconsistently classified patients (n=10) are included with the non-classifiable patients (n=46). The heterogeneity is reflected in the pie charts which demonstrate the numbers of patients in each category within each relevant subpopulation. A) Control patients misclassified as UC were more likely to be dipstick positive for white blood cells (wbc) (p=0.002), to have cytology inflammation (CI) (p=0.017), abnormal cytology (p=0.019); visible hematuria (p=0.019), proteinuria (p=0.019), to be >65 years old (p=0.028), to have high risk final diagnoses (p=0.028), and to have a history of benign prostate enlargement (bpehx) (p=0.036) than classifiable controls. B) UC patients misclassified as controls tended to have less severe hematuria (p<0.001), to have proteinuria (p=0.002), non-muscle invasive tumors (p=0.004), stage pTa UC (p=0.005), to have no evidence of malignancy in cytology preparations (p=0.009), to be lower grade UC (p=0.017), and to have an absence of inflammatory cells in cytology preparations (CI) (p=0.017) when compared to classifiable controls. C) When classifiable controls were compared with non-classifiable UC patients, non-classifiable UC patients had greater proportions of patients who had smoked for >10 years (p=0.001); greater proportions of patients taking AH medication (p=0.001); greater proportions of patients taking beta blockers (p=0.004), and greater proportions of patients who were smokers (p=0.019). Variables in A, B and C are illustrated in decreasing order of significance from left to right. p-values were adjusted by false discovery rate (FDR); α<0.05. wbc dipstick white blood cells; CI cytology inflammation; bpehx history of benign prostate enlargement; AH anti-hypertensive medication; betabl beta blocker medication.

One hundred of the 156 (64%) patients were classified correctly (controls (n=46) (FIG. 3A), UC (n=54) (FIG. 3B)); 46/156 (30%) were non-classifiable (controls (n=23), UC (n=23)); and 10/156 (6%) were inconsistently classified (controls (n=7), UC (n=3)) (FIGS. 3A and B). The 54 patients with UC who were correctly classified had CIS (n=1), pTaG1 (n=2), pTaG2 (n=17), pTaG3 (n=5), pT1G2 (n=3), pT1G3 (n=8), pT2aG2 (n=1), pT2aG3 (n=9), pT2bG3 (n=2), pT3aG3 (n=1), pT3bG3 (n=3), and pT4aG3 (n=2); the 23 who were non-classifiable had pTaG1 (n=2), pTaG2 (n=16), pTaG3 (n=3), pT1 G3 (n=1), and CIS (n=1). Two patients with pTaG3 disease and one with pT1 G3 were inconsistently classified. Three patients with renal cancer and two with prostate cancer were classified as UC; one patient with prostate cancer was inconsistently classified (FIG. 3A).

Characteristics of Classifiable and Non-Classifiable Patient Subpopulations

Interestingly, age, smoking years and anti-hypertensive medication were the top-ranked contributors to the most accurate diagnostic classifiers for the subpopulation of patients classified as controls (Table 2A). In comparison to classifiable control patients, non-classifiable control patients were more likely to be dipstick positive for white blood cells, to have inflammatory cells in their urine, to have abnormal cytology and to be dipstick positive for blood (FIG. 3A). Interestingly, 65/80 (81%) patients with pathologically proven UC and 48/76 (61%) of the controls had visible hematuria [2].

The patients misclassified as "controls" could have had unidentified UC. Nine of the 36 patients with a final diagnosis "no diagnosis" were non-classifiable or inconsistently classified (FIG. 3A). Undetected UC is now an accepted challenge [20], but, because we do not yet know the proportion of anticipatory controls, it is not possible to introduce methodologies to adjust for their existence when we are measuring the accuracy of diagnostic classifiers [21]. This highlights that accurate clinical final diagnoses may only be possible after several years follow-up.

Figure 3B:
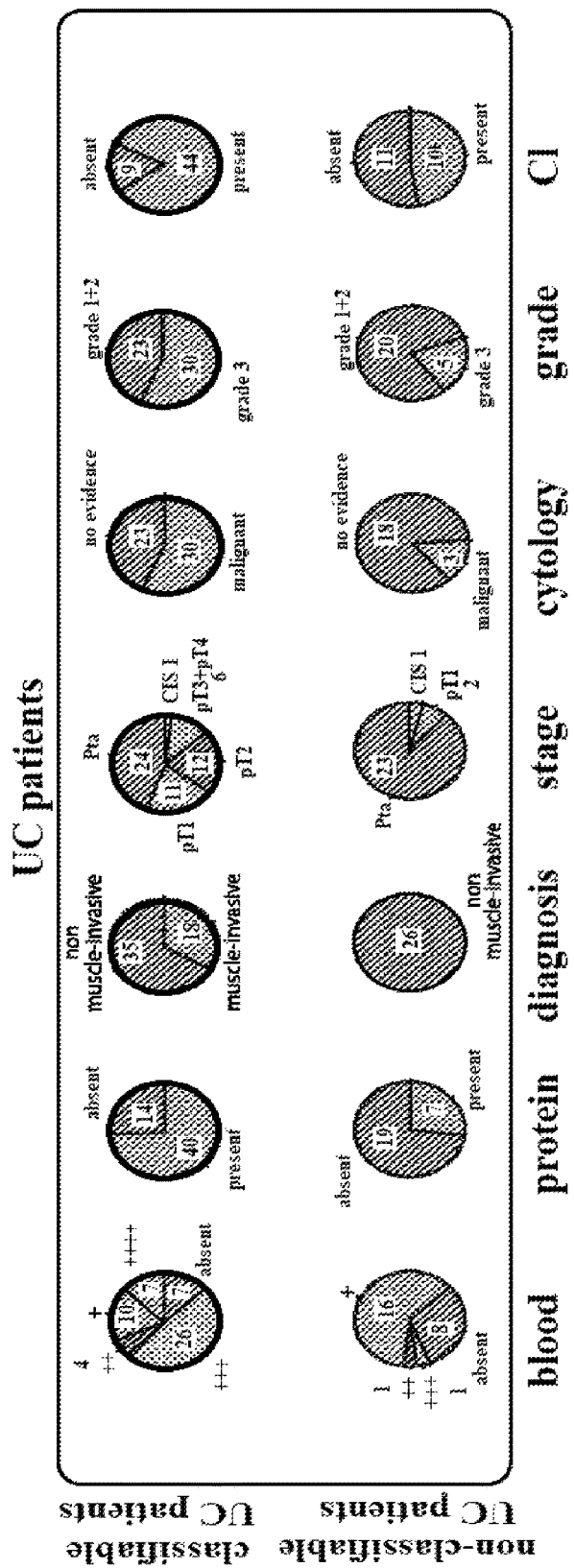
Figure 3C:
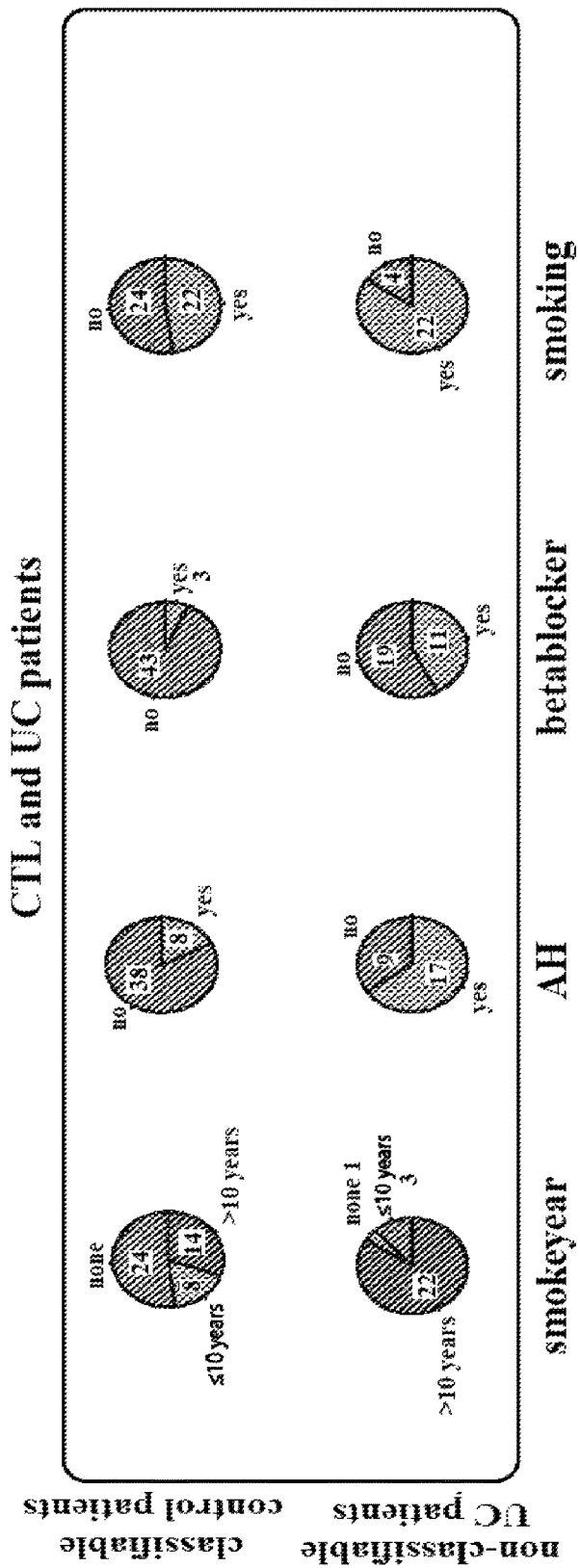
Figure 4A:
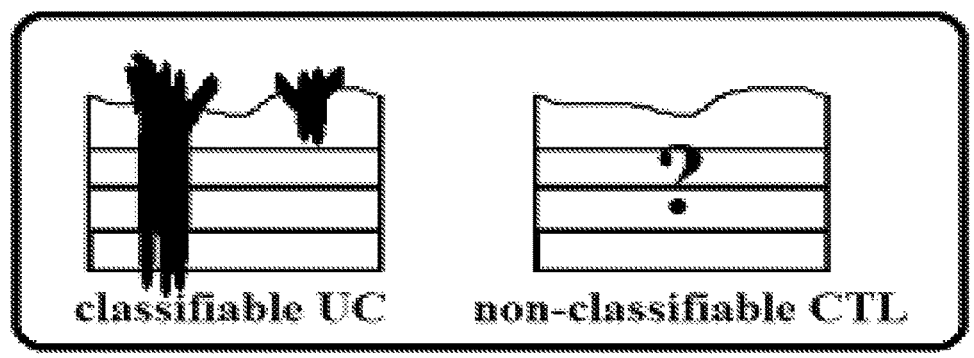
FIG. 4 shows characteristics of the patients classified as controls and patients classified as urothelial cancers. Patients with hematuria were classified into urothelial cancers (UC) or controls (CTL) using a biochip [14] formatted with the antibodies against the proteins of a UC diagnostic classifier for all patients. A) Patients classified as UC were predominantly high grade/stage UCs or controls (CTL), a proportion of whom may had serious diagnoses. B) Patients classified as controls included 21 patients with pTa tumors, one with a pT1 tumor and one who had carcinoma in situ. Twenty-two of these 23 patients with transitional cell carcinoma of the bladder (TCCB) were either smokers or aged>65 years. The 18 patients classified as controls who did not smoke and were aged 65 years were low risk. TCC=transitional cell carcinoma, BPE=benign prostate enlargement, RCC=renal cell carcinoma, UTI=urinary tract infection.
Figure 4A:
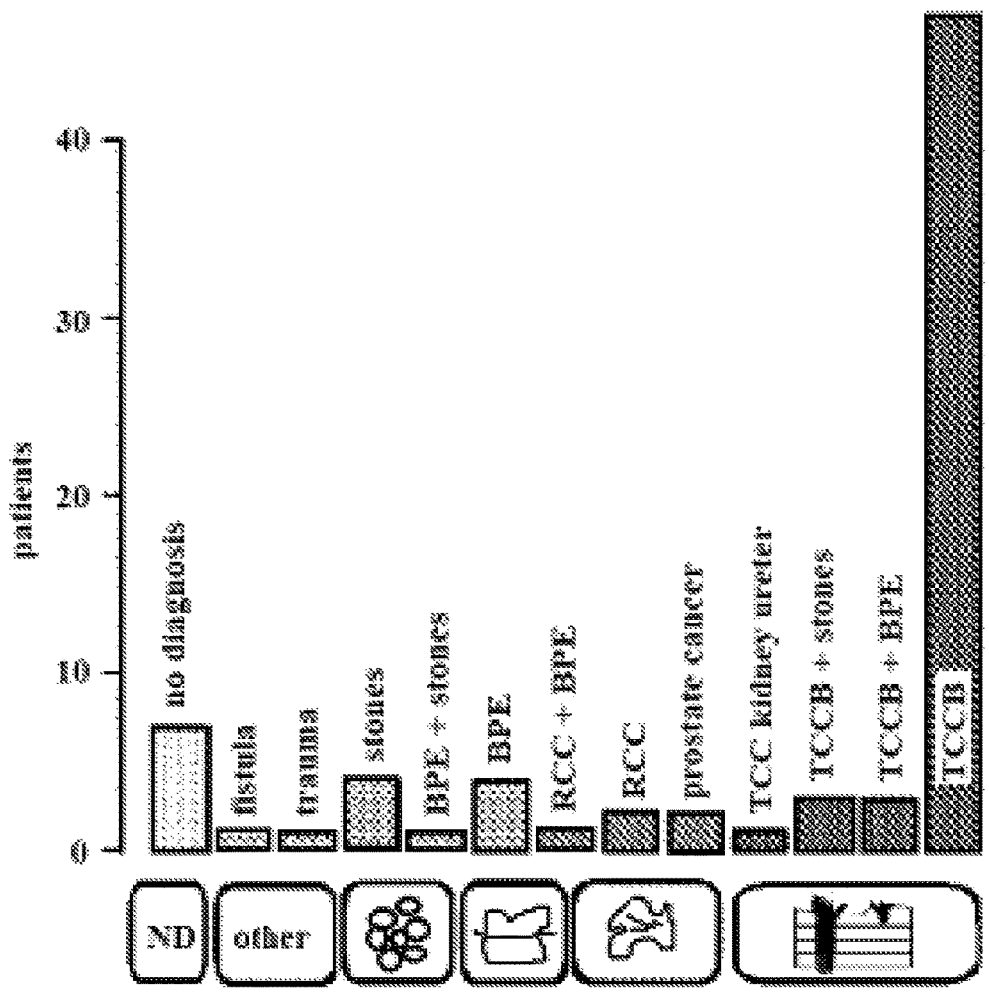

Non-classifiable UC patients were more likely than classifiable UC patients to be dipstick negative for blood and protein, to have low stage UC (FIG. 3B). Non classifiable UC patients were more likely than classifiable controls to be taking anti-hypertensives (AH) and to be heavy smokers (FIG. 3C). Patients correctly classified as UC were predominantly high grade/stage UCs; a proportion of the controls, classified as UC, had serious diagnoses, including cancers other than bladder cancer (FIG. 4A). Age, cigarettes/day, history of BPE, diuretic medication and anti-hypertensive medication frequently contributed to the diagnostic classifier for the subpopulation classified as UC (Table 2B). The latter variables thus discriminated the misclassified controls from the classifiable UCs.

There was no significant heterogeneity across the classifiable UC and non-classifiable control patients.

Figure 4B:
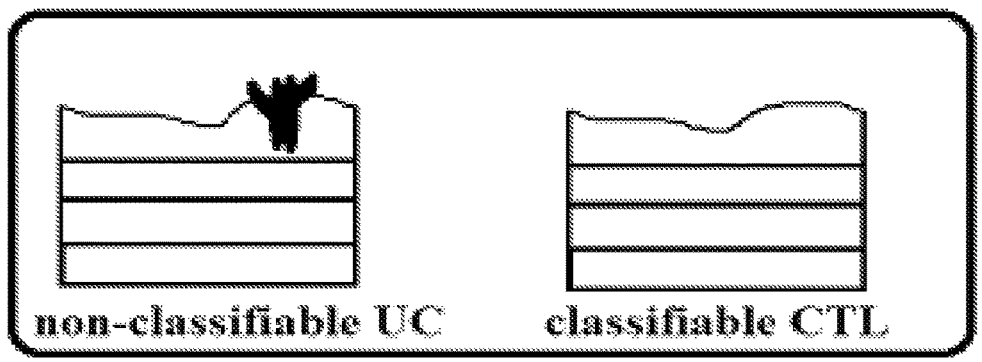
Figure 4B:
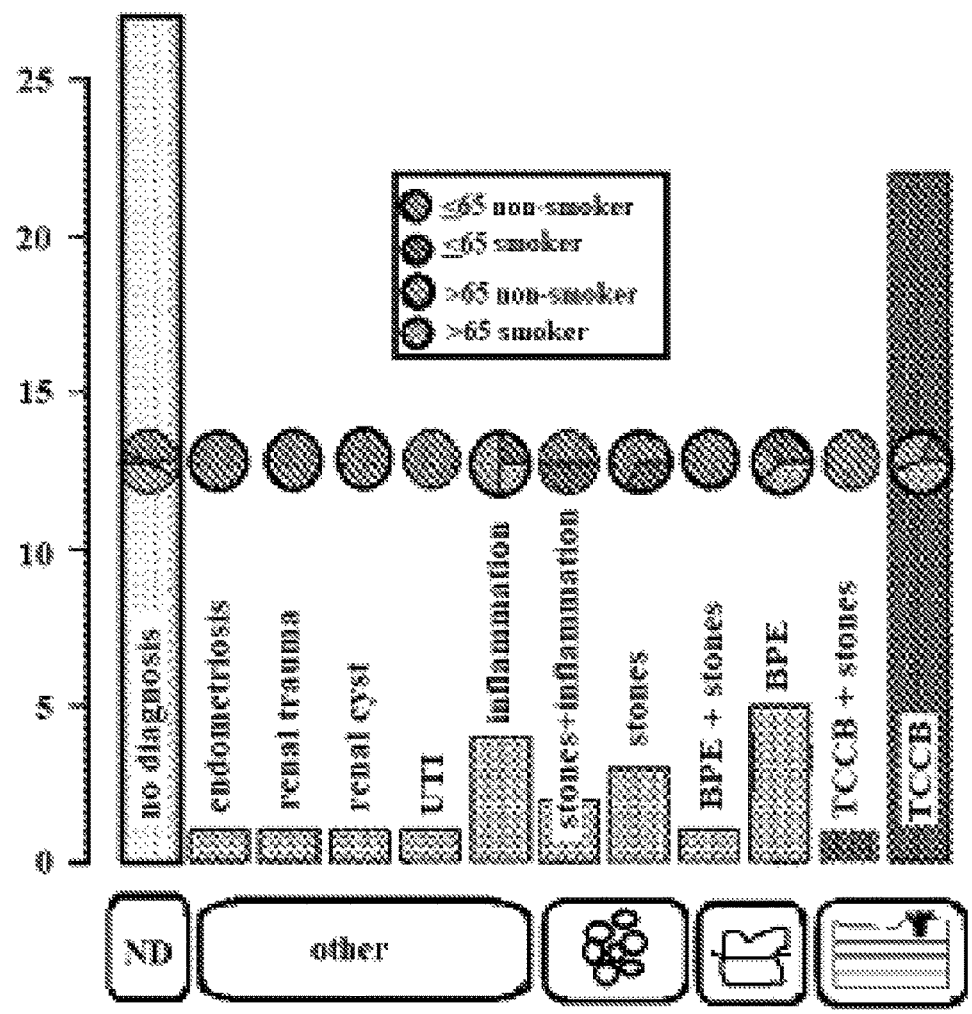

From our finding that age and smoking years were the top-ranked variables which contributed to the UC diagnostic classifiers for patients classified as controls, we extrapolated that smoking and age>65 years might discriminate the misclassified UC from the classifiable controls. Indeed, 22 of the 23 non-classifiable UC patients were smokers, >65 years or smokers>65 years (FIG. 4B). The remaining patient had pTa disease concomitant with stone disease which may have confounded classification (FIG. 4B). Eighteen of the 46 patients who were classified as controls did not smoke and were aged≤65 years. These patients had low risk diagnoses; no diagnosis (n=12), renal trauma (n=1), stones (n=3), urinary tract infection (n=1), BPE and stone (n=1) (FIG. 4B).

Diagnostic Classifiers for the Identification of Low Risk Subpopulations

We have demonstrated that the most accurate classification was achieved for younger non-smokers. Young smokers with micro hematuria could be prioritised for screening using biochips formatted with antibodies to the proteins contributing to diagnostic classifiers [14]. Once validated, biochip screening could replace cystoscopy for these low-risk patients, thus reducing healthcare costs.

We have conducted the first systematic investigation of the pathologies and patient characteristics underlying the failure of diagnostic classifiers for patients with hematuria. Although the biomarkers and patients are specific to our study, our novel approach and analyses could be applied to identify confounding factors for diagnostic classifiers in other complex diseases.

TABLE 1

UC diagnostic classifiers for stratified subpopulations.

| Population | set | Biomarker | TP | FP | FN | TN | AUC |
|---|---|---|---|---|---|---|---|
| non smoker | 1 | s-CEA, u-EGF, p-IL8, u-CK18 | 1.84 (0.37) | 0.08 (0.28) | 0.16 (0.37) | 2.92 (0.28) | 0.95 (0.1) |
| non smoker | 2 | s-CEA, p-IL8, s-NGAL, s-TM | 1.76 (0.44) | 0.04 (0.20) | 0.24 (0.44) | 2.96 (0.20) | 0.93 (0.11) |
| non smoker | 3 | s-CEA, p-IL8, s-NGAL, p-NSE | 1.84 (0.37) | 0.20 (0.41) | 0.16 (0.37) | 2.80 (0.41) | 0.93 (0.12) |
| AC yes | 1 | s-MCP1, p-MCP1, s-NGAL, p-NGAL | 2.56 (0.65) | 0.12 (0.33) | 0.44 (0.65) | 1.88 (0.33) | 0.9 (0.14) |
| AC yes | 2 | u-CRP, s-IL2, s-NGAL, p-NGAL | 2.64 (0.49) | 0.20 (0.50) | 0.36 (0.49) | 1.80 (0.50) | 0.89 (0.16) |
| AC yes | 3 | u-Creat, s-NGAL, p-NGAL, p-VEGF | 2.80 (0.41) | 0.36 (0.57) | 0.20 (0.41) | 1.64 (0.57) | 0.88 (0.16) |
| OCR yes | 1 | s-CEA, u-EGF, u-VEGF, u-vWF | 3.52 (0.59) | 0.32 (0.48) | 0.48 (0.59) | 2.68 (0.48) | 0.89 (0.1) |
| OCR yes | 2 | u-EGF, s-IL8, u-vWF, u-HA | 3.48 (0.65) | 0.36 (0.57) | 0.52 (0.65) | 2.64 (0.57) | 0.88 (0.14) |
| OCR yes | 3 | s-IL4, p-IL8, s-MCP1, u-VEGF | 3.08 (0.91) | 0.08 (0.28) | 0.92 (0.91) | 2.92 (0.28) | 0.87 (0.12) |
| age ≤ 65 | 1 | s-CEA, u-EGF, s-IL1α, u-VEGF | 2.48 (0.65) | 0.28 (0.46) | 0.52 (0.65) | 4.72 (0.46) | 0.89 (0.12) |
| age ≤ 65 | 2 | s-CEA, u-CRP, s-IL1α, u-VEGF | 2.40 (0.87) | 0.28 (0.46) | 0.60 (0.87) | 4.72 (0.46) | 0.87 (0.14) |
| age ≤ 65 | 3 | s-CEA, s-IL1α, p-IFN-γ, u-VEGF | 2.32 (0.85) | 0.16 (0.37) | 0.68 (0.85) | 4.84 (0.37) | 0.87 (0.14) |
| CI no | 1 | s-CEA, p-IL8, s-TNFα, u-FAS | 1.68 (0.56) | 0.44 (0.85) | 0.32 (0.56) | 3.56 (0.65) | 0.86 (0.17) |
| CI no | 2 | u-EGF, s-EGF, s-FPSA, s-IL4 | 1.68 (0.63) | 0.56 (0.82) | 0.32 (0.63) | 3.44 (0.82) | 0.85 (0.15) |
| CI no | 3 | u-EGF, u-CRP, u-IL4, u-NSE | 1.52 (0.65) | 0.24 (0.52) | 0.48 (0.65) | 3.76 (0.52) | 0.85 (0.18) |
| AC no | 1 | s-CEA, u-EGF, u-HA, u-CK18 | 4.28 (0.74) | 0.84 (0.94) | 0.72 (0.74) | 5.16 (0.94) | 0.86 (0.12) |
| AC no | 2 | s-CEA, u-EGF, u-IL8, u-CK18 | 4.20 (0.76) | 0.80 (0.87) | 0.80 (0.76) | 5.20 (0.87) | 0.85 (0.11) |
| AC no | 3 | s-CEA, u-EGF, p-IL6, u-MMP9NGAL | 4.04 (0.89) | 0.68 (0.90) | 0.96 (0.89) | 5.32 (0.90) | 0.85 (0.11) |
| AH no | 1 | s-CEA, u-CRP, u-NSE, s-TNFα | 2.32 (0.69) | 0.32 (0.56) | 0.68 (0.69) | 4.68 (0.56) | 0.85 (0.13) |
| AH no | 2 | s-CEA, u-CRP, s-IL4, u-sTNFR | 2.32 (0.69) | 0.64 (0.7) | 0.68 (0.69) | 4.36 (0.70) | 0.82 (0.12) |
| AH no | 3 | u-Creat, s-IL6, p-MMP9NGAL, u-VEGF | 2.00 (0.87) | 0.12 (0.33) | 1.00 (0.87) | 4.88 (0.33) | 0.82 (0.14) |
| OCR no | 1 | s-CEA, s-dDimer, u-EGF, s-IL1α | 3.16 (0.9) | 0.48 (0.59) | 0.84 (0.9) | 3.52 (0.59) | 0.84 (0.14) |
| OCR no | 2 | s-CEA, s-dDimer, s-IL6, s-MCP1 | 3.00 (0.71) | 0.36 (0.57) | 1.00 (0.71) | 3.64 (0.57) | 0.83 (0.11) |
| OCR no | 3 | u-BTA, s-CEA, u-TNFα, u-CK18 | 3.12 (0.88) | 0.52 (0.71) | 0.88 (0.88) | 3.48 (0.71) | 0.82 (0.10) |
| protein yes | 1 | s-CEA, p-CRP, u-IL8, p-TNFα | 4.80 (0.41) | 0.56 (0.58) | 0.20 (0.41) | 1.44 (0.58) | 0.84 (0.15) |
| protein yes | 2 | u-EGF, u-IL1β, s-IL6, u-vWF | 4.44 (0.71) | 0.44 (0.51) | 0.56 (0.71) | 1.56 (0.51) | 0.83 (0.14) |
| protein yes | 3 | s-CEA, p-IL1α, u-NSE, s-NSE | 4.68 (0.56) | 0.56 (0.51) | 0.32 (0.56) | 1.44 (0.51) | 0.83 (0.13) |
| alcohol no | 1 | s-MMPNG, s-sTNFR, s-TNFα, u-VEGF | 3.44 (0.71) | 0.56 (0.58) | 0.56 (0.71) | 2.44 (0.58) | 0.84 (0.13) |
| alcohol no | 2 | s-CEA, u-EGF, s-IL10, s-NGAL | 3.36 (0.64) | 0.52 (0.59) | 0.64 (0.64) | 2.48 (0.59) | 0.83 (0.15) |
| alcohol no | 3 | u-IL6, p-MMP9NGAL, u-VEGF, u-CK18 | 3.52 (0.51) | 0.64 (0.76) | 0.48 (0.51) | 2.36 (0.76) | 0.83 (0.14) |
| alcohol yes | 1 | u-EGF, u-IL1β, s-MMP9NGAL, u-vWF | 3.48 (0.82) | 1.08 (0.95) | 0.52 (0.82) | 3.92 (0.95) | 0.83 (0.11) |
| alcohol yes | 2 | s-CEA, u-EGF, u-vWF, u-CK18 | 3.16 (1.03) | 0.72 (0.61) | 0.84 (1.03) | 4.28 (0.61) | 0.82 (0.13) |
| alcohol yes | 3 | s-CEA, u-EGF, p-NSE, u-vWF | 3.28 (074) | 0.92 (0.95) | 0.72 (0.74) | 4.08 (0.95) | 0.82 (0.13) |
| protein no | 1 | u-BTA, u-NGAL, s-NGAL, u-TNFα | 2.12 (0.67) | 0.32 (0.56) | 0.88 (0.67) | 4.68 (0.56) | 0.82 (0.11) |
| protein no | 2 | u-dDimer, u-CRP, u-NGAL, s-TNFα | 2.24 (0.78) | 0.6 (0.87) | 0.76 (0.78) | 4.4 (0.87) | 0.81 (0.14) |
| protein no | 3 | s-CEA, u-CRP, P-MMP9NGAL, u-NGAL | 2.28 (0.74) | 0.76 (0.72) | 0.72 (0.74) | 4.24 (0.72) | 0.8 (0.14) |
| age > 65 | 1 | s-IL2, s-MMP9NGAL, s-NGAL, p-sTNFR | 4.40 (0.87) | 0.72 (0.68) | 0.6 (0.87) | 2.28 (0.68) | 0.82 (0.16) |
| age > 65 | 2 | u-MMP9NGAL, s-NGAL, p-NGAL, u-vWF | 4.32 (0.75) | 0.72 (0.79) | 0.68 (0.75) | 2.28 (0.79) | 0.81 (0.15) |
| age > 65 | 3 | s-CEA, s-dDimer, p-dDimer, s-Ifn-γ | 4.40 (0.82) | 0.80 (0.76) | 0.60 (0.82) | 2.20 (0.76) | 0.81 (0.15) |
| AH yes | 1 | u-EGF, u-IL1α, s-IL10, u-vWF | 4.88 (0.33) | 0.68 (0.63) | 0.12 (0.33) | 1.32 (0.63) | 0.82 (0.16) |
| AH yes | 2 | u-EGF, p-IL10, u-VEGF, u-vWF | 4.84 (0.37) | 0.68 (0.69) | 0.16 (0.37) | 1.32 (0.69) | 0.81 (0.17) |
| AH yes | 3 | s-sTNFR, p-sTNFR, s-TNFα, u-vWF | 4.40 (0.65) | 0.52 (0.65) | 0.6 (0.65) | 1.48 (0.65) | 0.81 (0.19) |
| CI yes | 1 | u-BTA, s-CEA, p-IL10, u-CK18 | 4.72 (0.46) | 1.00 (0.76) | 0.28 (0.46) | 2.00 (0.76) | 0.81 (0.13) |
| CI yes | 2 | u-BTA, p-IL6, s-NSE, p-NSE | 4.72 (0.46) | 1.04 (0.84) | 0.28 (0.46) | 1.96 (0.84) | 0.80 (0.15) |
| CI yes | 3 | u-protein, u-BTA, p-IL6, s-NGAL | 4.44 (0.82) | 0.92 (0.57) | 0.56 (0.82) | 2.08 (0.57) | 0.79 (0.13) |
| smoker | 1 | u-EGF, u-IL6, u-VEGF, u-CK18 | 5.52 (0.65) | 1.32 (0.75) | 0.48 (0.65) | 2.68 (0.75) | 0.80 (0.10) |

TABLE 1-continued

UC diagnostic classifiers for stratified subpopulations.

| Population | set | Biomarker | TP | FP | FN | TN | AUC |
|---|---|---|---|---|---|---|---|
| smoker | 2 | u-EGF, s-IL8, u-vWF, u-FAS | 5.40 (0.76) | 1.28 (0.98) | 0.60 (0.760) | 2.72 (0.98) | 0.79 (0.13) |
| smoker | 3 | u-EGF, u-IL1α, p-MMP9NGAL, u-vWF | 5.44 (0.65) | 1.44 (0.92) | 0.56 (0.65) | 2.56 (0.92) | 0.77 (0.13) |

Table 1: UC diagnostic classifiers for stratified subpopulations. Patients were stratified into subpopulations when variables contained >50 patients in each subpopulation. Patients were split according to smoking, anti cholesterol (AC) medication, occupational risk or chemical exposure (OCC), age, cytology with inflammatory cells (CI), anti-hypertensive (AH) medication, dip stick protein and alcohol. The diagnostic classifiers with the three highest AUCs are shown. TP = total positives, FP = false positives, FN = false negatives, TN = true negatives, u- = urine, s- = serum, p- = plasma, BTA = Bladder Tumor Antigen, CEA = Carcinoembryonic antigen, CK18 = Human cytokeratin 18, CRP = C-reactive protein, EGF = Epidermal Growth Factor, HA = Hyaluronidase, Ifn-γ = Interferon-γ, MCP-1 = Monocyte chemoattractant protein 1, MMP9 = Matrix metalloproteinase 9, MMP9NGAL complex, NGAL = Neutrophil gelatinase-associated lipocalin, NSE = Neurone Specific Enolase, PSA = Prostate specific antigen, TM = Thrombomodulin, TNFα = Tumor necrosis factor α, VEGF = Vascular endothelial growth factor, vWF = von Willebrand Factor.

TABLE 2

UC diagnostic classifiers based on categorical variables for the control and UC classified subpopulations.

| | Variables | TP | FP | FN | TN | AUC |
|---|---|---|---|---|---|---|
| A) | | | | | | |
| 1 | age, smoking years, history stone disease, alpha blockers, beta | 2.52 (0.59) | 0.52 (0.71) | 0.48 (0.59) | 4.48 (0.71) | 0.87 (0.15) |
| 2 | age, smoking, alpha blockers, anti-cholesterol, | 2.52 (0.59) | 0.72 (0.89) | 0.48 (0.59) | 4.28 (0.89) | 0.85 (0.13) |
| 3 | age, smoking, alpha blockers, antidepressants, dipstick protein | 2.32 (0.8) | 0.40 (0.58) | 0.68 (0.8) | 4.60 (0.58) | 0.85 (0.14) |
| B) | | | | | | |
| 1 | age, cigarettes/day, history benign prostate enlargement, diuretic medication, anti-hypertensive medications | 4.56 (0.58) | 0.96 (0.89) | 0.44 (0.58) | 2.04 (0.89) | 0.80 (0.14) |
| 2 | age, cigarettes per day, history benign prostate enlargement, history of malignancy, anti-hypertensive medications | 4.60 (0.58) | 1.04 (0.68) | 0.40 (0.58) | 1.96 (0.68) | 0.79 (0.1) |
| 3 | age, cigarettes/day, history BPE, diuretic medication, anti-inflammatories | 4.60 (0.5) | 1.04 (0.98) | 0.40 (0.5) | 1.96 (0.98) | 0.79 (0.18) |

Table 2: UC diagnostic classifiers based on categorical variables for the control and UC classified subpopulations. Diagnostic classifiers for the control classified (A) and UC classified (B) subpopulations, TP = total positives, FP = false positives, FN = false negatives, TN = true negatives, AUC = area under the curve.

TABLE 3

Overview of protein biomarkers. The missing data column shows the number of patients with missing values.

| Biomarker | Sensitivity | Missing data |
|---|---|---|
| Bladder Tumor Antigen (BTA) | 0.65 U/ml | u (0) |
| Carcino-embryonic antigen (CEA) | 0.29 ng/mL | s (0) |
| Human cytokeratin 18 (CK18) | 0.12 ng/mL | u (2) |
| C-reactive protein (CRP) | 0.67 ng/mL | u (0), s (25), p (21) |
| d-Dimer | 2.10 ng/mL | u (0), s (21), p (0) |
| Epidermal Growth Factor (EGF) | 2.90 ng/mL | u (2), s (28), p (0) |
| FAS | 5.00 ng/mL | u (2) |
| Hyaluronidase (HA) | 25.00 ng/mL | u (2) |
| IL1α | 0.80 pg/mL | u (1), s (8), p (0) |
| IL1β | 1.60 pg/mL | u (1), s (8), p (0) |
| IL2 | 4.80 pg/mL | u (1), s (8), p (0) |
| IL4 | 6.60 pg/mL | u (0), s (30), p (42) |
| IL6 | 1.20 pg/mL | u (0), s (8), p (0) |

TABLE 3-continued

Overview of protein biomarkers. The missing data column shows the number of patients with missing values.

| Biomarker | Sensitivity | Missing data |
|---|---|---|
| IL8 | 7.90 pg/mL | u (1), s (47), p (0) |
| IL10 | 1.10 pg/mL | s (8), p (0) |
| Interferon-γ (Inf-γ) | 0.44 pg/ml | s (8), p (0) |
| Monocyte chemoattractant protein 1/(MCP-1) | 13.20 pg/mL | u (1), s (8), p (0) |
| Matrix metalloproteinase 9 (MMP9) | 3.03 ng/mL | u (1) |
| MMP9-NGAL complex | N/A | u (5), s(2), p(3) |
| NGAL (Neutrophil gelatinase-associated lipocalin) | 17.80 ng/mL | u (0), s (21), p (0) |
| Neurone Specific Enolase (NSE), γ-enolase | 0.26 ng/mL | u (0), s (21), p (0) |
| Prostate specific antigen (PSA) (free) | 0.02 ng/ml | s (0) |
| Prostate specific antigen (PSA) (total) | 0.45 ng/ml | s (0) |
| Thrombomodulin (TM) | 0.50 ng/mL | u (0), s (21), p (0) |
| Tumor necrosis factor α (TNFα) | 4.40 pg/mL | u (1), s (8), p (0) |
| sTNFR1 | 0.24 ng/ml | u (0), s (21), p(0) |
| sTNFR2 | 0.20 ng/ml | u (1) |
| Vascular endothelial growth factor (VEGF) | 14.60 pg/mL | u (1), s (8), p (0) |
| von Willebrand Factor (vWF) | 1 U/ml | u (8) |
| protein | N/A | u (0) |
| creatinine | N/A | u (0) |
| osmolality | N/A | u (0) |

TABLE 4

Urine 5 biomarker classifiers

| name | num | Biomarker | TP | FP | FN | TN | AUC |
|---|---|---|---|---|---|---|---|
| smoking no | 1 | u-BTA, u-MMP9NG, u-TM, u-sTNFR2, u-VEGF | 1.6 (0.65) | 0.12 (0.33) | 0.4 (0.65) | 2.88 (0.33) | 0.88 (0.17) |
| smoking no | 2 | u-BTA, u-IL4, u-MMP9, u-NSE, u-FAS | 1.64 (0.49) | 0.2 (0.41) | 0.36 (0.49) | 2.8 (0.41) | 0.88 (0.14) |
| smoking no | 3 | u-BTA, u-MMP9NG, u-TNFa, u-sTNFR2, u-VEGF | 1.56 (0.65) | 0.12 (0.33) | 0.44 (0.65) | 2.88 (0.33) | 0.87 (0.17) |
| CI no | 1 | u-EGF, u-CRP, u-IL4, u-TM, u-vWF | 1.6 (0.5) | 0.2 (0.41) | 0.4 (0.5) | 3.8 (0.41) | 0.88 (0.12) |
| CI no | 2 | u-BTA, u-dDimer, u-EGF, u-CRP, u-IL4 | 1.52 (0.65) | 0.2 (0.5) | 0.48 (0.65) | 3.8 (0.5) | 0.86 (0.16) |
| CI no | 3 | u-EGF, u-CRP, u-IL4, u-IL6, u-vWF | 1.64 (0.57) | 0.48 (0.65) | 0.36 (0.57) | 3.52 (0.65) | 0.85 (0.18) |
| age < 65 | 1 | u-EGF, u-IL2, u-HA, u-FAS, u-CK18 | 2.36 (0.86) | 0.4 (0.58) | 0.64 (0.86) | 4.6 (0.58) | 0.85 (0.17) |
| age < 65 | 2 | u-EGF, u-IL2, u-MMP9NG, u-HA, u-CK18 | 2.4 (0.71) | 0.48 (0.65) | 0.6 (0.71) | 4.52 (0.65) | 0.85 (0.15) |
| age < 65 | 3 | u-EGF, u-vWF, u-HA, u-FAS, u-CK18 | 2.24 (0.83) | 0.28 (0.54) | 0.76 (0.83) | 4.72 (0.54) | 0.85 (0.16) |
| OCR yes | 1 | u-BTA, u-IL2, u-IL4, u-MMP9NG, u-VEGF | 2.96 (1.06) | 0.12 (0.33) | 1.04 (1.06) | 2.88 (0.33) | 0.85 (0.14) |
| OCR yes | 2 | u-BTA, u-IL1a, u-IL8, u-NGAL, u-NSE | 3 (1.04) | 0.16 (0.47) | 1 (1.04) | 2.84 (0.47) | 0.85 (0.14) |
| OCR yes | 3 | u-BTA, u-CRP, u-IL4, u-NSE, u-CK18 | 3.4 (0.76) | 0.48 (0.65) | 0.6 (0.76) | 2.52 (0.65) | 0.84 (0.16) |
| alcohol no | 1 | u-IL2, u-IL8, u-NGAL, u-HA, u-CK18 | 3.36 (0.76) | 0.6 (0.58) | 0.64 (0.76) | 2.4 (0.58) | 0.82 (0.12) |
| alcohol no | 2 | u-IL2, u-IL4, u-VEGF, u-HA, u-CK18 | 3.28 (0.74) | 0.56 (0.65) | 0.72 (0.74) | 2.44 (0.65) | 0.82 (0.12) |
| alcohol no | 3 | u-IL1b, u-IL2, u-IL8, u-NGAL, u-CK18 | 3.24 (0.72) | 0.64 (0.61) | 0.76 (0.72) | 2.36 (0.81) | 0.8 (0.16) |
| alcohol yes | 1 | u-EGF, u-MMP9, u-sTNFR2, u-VEGF, u-vWF | 3.2 (0.76) | 0.8 (0.71) | 0.8 (0.76) | 4.2 (0.71) | 0.82 (0.1) |
| alcohol yes | 2 | u-EGF, u-IL1a, u-IL4, u-vWF, u-FAS | 3.48 (0.51) | 1.24 (1.05) | 0.52 (0.51) | 3.76 (1.05) | 0.81 (0.11) |
| alcohol yes | 3 | u-EGF, u-IL1a, u-MMP9, u-vWF, u-HA | 3.44 (0.65) | 1.2 (0.87) | 0.56 (0.65) | 3.8 (0.87) | 0.81 (0.12) |
| AC no | 1 | u-BTA, u-CRP, u-IL2, u-IL4, u-CK18 | 3.64 (1.11) | 0.56 (0.77) | 1.36 (1.11) | 5.44 (0.77) | 0.82 (0.11) |
| AC no | 2 | u-EGF, u-IL1b, u-NGAL, u-VEGF, u-CK18 | 3.84 (0.94) | 0.84 (0.75) | 1.16 (0.94) | 5.16 (0.75) | 0.81 (0.09) |
| AC no | 3 | u-BTA, u-IL4, u-IL8, u-HA, u-CK18 | 3.36 (1.32) | 0.28 (0.54) | 1.64 (1.32) | 5.72 (0.54) | 0.81 (0.13) |
| AC yes | 1 | u-CRP, u-MCP1, u-sTNFR2, u-vWF, u-FAS | 2.92 (0.28) | 0.68 (0.63) | 0.08 (0.28) | 1.32 (0.63) | 0.82 (0.15) |
| AC yes | 2 | u-dDimer, u-IL6, u-MMP9NG, u-NSE, u-VEGF | 2.24 (0.88) | 0.24 (0.52) | 0.76 (0.88) | 1.76 (0.52) | 0.81 (0.17) |

TABLE 4-continued

Urine 5 biomarker classifiers

| name | num | Biomarker | TP | FP | FN | TN | AUC |
|---|---|---|---|---|---|---|---|
| AC yes | 3 | u-BTA, u-MCP1, u-sTNFR2, u-vWF, u-FAS | 2.8 (0.41) | 0.64 (0.76) | 0.2 (0.41) | 1.36 (0.76) | 0.81 (0.18) |
| AH no | 1 | u-CRP, u-NGAL, u-VEGF, u-HA, u-CK18 | 2.04 (0.89) | 0.28 (0.54) | 0.96 (0.89) | 4.72 (0.54) | 0.81 (0.16) |
| AH no | 2 | u-dDimer, u-TNFa, u-VEGF, u-HA, u-CK18 | 1.92 (0.64) | 0.28 (0.46) | 1.08 (0.64) | 4.72 (0.46) | 0.79 (0.12) |
| AH no | 3 | u-MMP9, u-NSE, u-TM, u-VEGF, u-FAS | 1.8 (0.71) | 0.12 (0.33) | 1.2 (0.71) | 4.88 (0.33) | 0.79 (0.11) |
| age > 65 | 1 | u-BTA, u-IL1b, u-VEGF, u-vWF, u-HA | 4.56 (0.58) | 0.88 (0.73) | 0.44 (0.58) | 2.12 (0.73) | 0.81 (0.14) |
| age > 65 | 2 | u-dDimer, u-IL1a, u-NSE, u-vWF, u-HA | 4.4 (0.76) | 1 (0.82) | 0.6 (0.76) | 2 (0.82) | 0.77 (0.17) |
| age > 65 | 3 | u-BTA, u-dDimer, u-IL1b, u-vWF, u-HA | 4.48 (0.71) | 1.08 (0.95) | 0.52 (0.71) | 1.92 (0.95) | 0.77 (0.18) |
| protein yes | 1 | u-EGF, u-IL2, u-NSE, u-TM, u-CK18 | 4.56 (0.58) | 0.6 (0.71) | 0.44 (0.58) | 1.4 (0.71) | 0.81 (0.18) |
| protein yes | 2 | u-EGF, u-IL6, u-sTNFR, u-HA, u-CK18 | 4.36 (0.7) | 0.52 (0.51) | 0.64 (0.7) | 1.48 (0.51) | 0.81 (0.14) |
| protein yes | 3 | u-EGF, u-NGAL, u-vWF, u-HA, u-CK18 | 4.44 (0.77) | 0.64 (0.7) | 0.56 (0.77) | 1.36 (0.7) | 0.78 (0.2) |
| protein no | 1 | u-dDimer, u-CRP, u-IL4, u-NGAL, u-sTNFR2 | 2.24 (0.6) | 0.76 (0.78) | 0.76 (0.6) | 4.24 (0.78) | 0.8 (0.12) |
| protein no | 2 | u-CRP, u-MMP9NG, u-NGAL, u-sTNFR2, u-VEGF | 2.08 (0.64) | 0.52 (0.51) | 0.92 (0.64) | 4.48 (0.51) | 0.79 (0.12) |
| protein no | 3 | u-BTA, u-CRP, u-IL4, u-NGAL, u-sTNFR2 | 2 (0.82) | 0.4 (0.71) | 1 (0.82) | 4.6 (0.71) | 0.79 (0.15) |
| smoking yes | 1 | u-EGF, u-IL1b, u-sTNFR, u-VEGF, u-CK18 | 5.48 (0.59) | 1.4 (0.87) | 0.52 (0.59) | 2.6 (0.87) | 0.78 (0.13) |
| smoking yes | 2 | u-BTA, u-EGF, u-IL1b, u-vWF, u-FAS | 5.32 (0.75) | 1.32 (0.95) | 0.68 (0.75) | 2.68 (0.95) | 0.78 (0.12) |
| smoking yes | 3 | u-EGF, u-IL1b, u-IL8, u-TM, u-vWF | 5.56 (0.65) | 1.48 (0.87) | 0.44 (0.65) | 2.52 (0.87) | 0.78 (0.11) |
| AH yes | 1 | u-CRP, u-IL2, u-IL8, u-sTNFR2, u-vWF | 4.8 (0.41) | 0.8 (0.58) | 0.2 (0.41) | 1.2 (0.58) | 0.78 (0.14) |
| AH yes | 2 | u-EGF, u-IL8, u-NSE, u-TNFa, u-vWF | 4.72 (0.68) | 0.8 (0.58) | 0.28 (0.68) | 1.2 (0.58) | 0.77 (0.16) |
| AH yes | 3 | u-BTA, u-EGF, u-IL4, u-vWF, u-HA | 5 (0) | 0.92 (0.7) | 0 (0) | 1.08 (0.7) | 0.77 (0.18) |
| OCR no | 1 | u-BTA, u-TM, u-TNFa, u-sTNFR2, u-vWF | 2.76 (0.93) | 0.6 (0.82) | 1.24 (0.93) | 3.4 (0.82) | 0.77 (0.18) |
| OCR no | 2 | u-BTA, u-TM, u-TNFa, u-vWF, u-FAS | 2.72 (0.94) | 0.56 (0.71) | 1.28 (0.94) | 3.44 (0.71) | 0.77 (0.13) |
| OCR no | 3 | u-EGF, u-NSE, u-TNFa, u-vWF, u-HA | 3.08 (0.7) | 0.92 (0.76) | 0.92 (0.7) | 3.08 (0.76) | 0.77 (0.11) |
| CI yes | 1 | u-BTA, u-IL1a, u-NGAL, u-sTNFR, u-vWF | 4.56 (0.51) | 1.24 (0.83) | 0.44 (0.51) | 1.76 (0.83) | 0.75 (0.16) |
| CI yes | 2 | u-BTA, u-IL8, u-MMP9NG, u-VEGF, u-CK18 | 4.32 (0.69) | 1.12 (0.78) | 0.68 (0.69) | 1.88 (0.78) | 0.75 (0.14) |
| CI yes | 3 | u-BTA, u-IL6, u-MMP9NG, u-NSE, u-CK18 | 4.64 (0.64) | 1.36 (0.81) | 0.36 (0.64) | 1.64 (0.81) | 0.74 (0.15) |

TABLE 5

Serum 5 biomarker classifiers

| name | num | Biomarker | TP | FP | FN | TN | AUC |
|---|---|---|---|---|---|---|---|
| smoking no | 1 | s-CEA, s-EGF, s-IL4, s-NGAL, s-TNFa | 1.8 (0.41) | 0.16 (0.47) | 0.2 (0.41) | 2.84 (0.47) | 0.92 (0.12) |
| smoking no | 2 | s-CEA, s-EGF, s-IL8, s-NGAL, s-TPSA | 1.8 (0.41) | 0.16 (0.37) | 0.2 (0.41) | 2.84 (0.37) | 0.92 (0.12) |
| smoking no | 3 | s-CEA, s-IL8, s-MCP1, s-NGAL, s-TPSA | 1.8 (0.5) | 0.16 (0.37) | 0.2 (0.5) | 2.84 (0.37) | 0.92 (0.13) |
| age < 65 | 1 | s-CEA, s-IL1a, s-IL4, s-TM, s-TNFa | 2.28 (0.89) | 0.28 (0.54) | 0.72 (0.89) | 4.72 (0.54) | 0.85 (0.16) |
| age < 65 | 2 | s-CEA, s-IL1a, s-IL2, s-IL4, s-IL8 | 2.4 (0.71) | 0.56 (0.65) | 0.6 (0.71) | 4.44 (0.65) | 0.84 (0.14) |
| age < 65 | 3 | s-CEA, s-IL1a, s-IL1b, s-IL4, s-VEGF | 2.36 (0.49) | 0.76 (0.72) | 0.64 (0.49) | 4.24 (0.72) | 0.82 (0.13) |
| AC no | 1 | s-CEA, s-FPSA, s-IL10, s-Ifngg, s-NGAL | 3.88 (1.05) | 0.68 (0.63) | 1.12 (1.05) | 5.32 (0.63) | 0.83 (0.1) |
| AC no | 2 | s-CEA, s-IL1a, s-IL1b, s-MMPNG, s-sTNFR | 3.92 (1.08) | 0.84 (0.8) | 1.08 (1.08) | 5.16 (0.8) | 0.82 (0.12) |

TABLE 5-continued

Serum 5 biomarker classifiers

| name | num | Biomarker | TP | FP | FN | TN | AUC |
|---|---|---|---|---|---|---|---|
| AC no | 3 | s-CEA, s-IL1a, s-MMPNG, s-TM, s-TNFa | 4 (0.96) | 1.08 (0.81) | 1 (0.96) | 4.92 (0.81) | 0.81 (0.11) |
| OCR yes | 1 | s-IL2, s-IL10, s-NGAL, s-NSE, s-VEGF | 3.16 (0.85) | 0.4 (0.5) | 0.84 (0.85) | 2.6 (0.5) | 0.83 (0.13) |
| OCR yes | 2 | s-CEA, s-IL4, s-IL8, s-NGAL, s-TM | 3.24 (0.83) | 0.56 (0.71) | 0.76 (0.83) | 2.44 (0.71) | 0.81 (0.17) |
| OCR yes | 3 | s-CEA, s-CRP, s-NGAL, s-NSE, s-sTNFR | 3.28 (0.84) | 0.6 (0.65) | 0.72 (0.84) | 2.4 (0.65) | 0.81 (0.13) |
| alcohol no | 1 | s-CEA, s-IL1a, s-IL8, s-TM, s-sTNFR | 3.36 (0.76) | 0.56 (0.65) | 0.64 (0.76) | 2.44 (0.65) | 0.83 (0.12) |
| alcohol no | 2 | s-CEA, s-IL1a, s-IL6, s-NGAL, s-TM | 3.28 (0.74) | 0.52 (0.65) | 0.72 (0.74) | 2.48 (0.65) | 0.82 (0.13) |
| alcohol no | 3 | s-CEA, s-IL1a, s-IL2, s-TM, s-sTNFR | 3.24 (0.72) | 0.52 (0.65) | 0.76 (0.72) | 2.48 (0.65) | 0.82 (0.15) |
| protein yes | 1 | s-CEA, s-IL8, s-IL10, s-NSE, s-TNFa | 4.36 (0.7) | 0.44 (0.51) | 0.64 (0.7) | 1.56 (0.51) | 0.83 (0.12) |
| protein yes | 2 | s-CEA, s-IL2, s-IL8, s-MMPNG, s-NSE | 4.4 (0.65) | 0.52 (0.51) | 0.6 (0.65) | 1.48 (0.51) | 0.81 (0.14) |
| protein yes | 3 | s-CEA, s-IL2, s-IL6, s-IL10, s-NSE | 4.4 (0.65) | 0.6 (0.58) | 0.6 (0.65) | 1.4 (0.58) | 0.79 (0.17) |
| alcohol yes | 1 | s-CRP, s-IL1b, s-IL6, s-IL8, s-NGAL | 3.12 (0.67) | 0.72 (0.84) | 0.88 (0.67) | 4.28 (0.84) | 0.82 (0.13) |
| alcohol yes | 2 | s-dDimer, s-IL1b, s-IL4, s-Ifngg, s-NGAL | 2.8 (0.76) | 0.36 (0.57) | 1.2 (0.76) | 4.64 (0.57) | 0.81 (0.1) |
| alcohol yes | 3 | s-CRP, s-IL1b, s-IL4, s-MCP1, s-NGAL | 3.12 (0.73) | 0.76 (0.66) | 0.88 (0.73) | 4.24 (0.66) | 0.81 (0.13) |
| CI no | 1 | s-CEA, s-EGF, s-CRP, s-IL4, s-Ifngg | 1.4 (0.65) | 0.28 (0.46) | 0.6 (0.65) | 3.72 (0.46) | 0.82 (0.17) |
| CI no | 2 | s-dDimer, s-FPSA, s-IL6, s-Ifngg, s-NGAL | 1.32 (0.75) | 0.12 (0.33) | 0.68 (0.75) | 3.88 (0.33) | 0.82 (0.18) |
| CI no | 3 | s-IL1a, s-IL4, s-MMPNG, s-NGAL, s-TM | 1.48 (0.59) | 0.52 (0.82) | 0.52 (0.59) | 3.48 (0.82) | 0.8 (0.19) |
| OCR no | 1 | s-CEA, s-dDimer, s-NSE, s-TM, s-TPSA | 3.08 (0.7) | 0.56 (0.82) | 0.92 (0.7) | 3.44 (0.82) | 0.82 (0.13) |
| OCR no | 2 | s-CEA, s-EGF, s-IL10, s-MCP1, s-sTNFR | 2.92 (0.86) | 0.4 (0.58) | 1.08 (0.86) | 3.6 (0.58) | 0.82 (0.15) |
| OCR no | 3 | s-CEA, s-dDimer, s-CRP, s-MCP1, s-NGAL | 2.96 (0.93) | 0.48 (0.65) | 1.04 (0.93) | 3.52 (0.65) | 0.81 (0.14) |
| AC yes | 1 | s-IL6, s-IL8, s-NGAL, s-TPSA, s-VEGF | 2.52 (0.59) | 0.48 (0.51) | 0.48 (0.59) | 1.52 (0.51) | 0.8 (0.15) |
| AC yes | 2 | s-FPSA, s-NGAL, s-TM, s-TNFa, s-VEGF | 2.52 (0.71) | 0.52 (0.71) | 0.48 (0.71) | 1.48 (0.71) | 0.79 (0.22) |
| AC yes | 3 | s-IL1b, s-IL2, s-NGAL, s-TM, s-VEGF | 2.48 (0.77) | 0.56 (0.71) | 0.52 (0.77) | 1.44 (0.71) | 0.77 (0.23) |
| age > 65 | 1 | s-CEA, s-dDimer, s-IL4, s-NGAL, s-TM | 4.56 (0.58) | 1.04 (0.68) | 0.44 (0.58) | 1.96 (0.68) | 0.78 (0.13) |
| age > 65 | 2 | s-IL1a, s-MMPNG, s-NGAL, s-sTNFR, s-TNFa | 4.04 (0.84) | 0.76 (0.6) | 0.96 (0.84) | 2.24 (0.6) | 0.78 (0.13) |
| age > 65 | 3 | s-IL2, s-MMPNG, s-NGAL, s-sTNFR, s-VEGF | 4.12 (0.93) | 0.88 (0.6) | 0.88 (0.93) | 2.12 (0.6) | 0.77 (0.14) |
| AH no | 1 | s-CEA, s-dDimer, s-IL4, s-MMPNG, s-sTNFR | 1.96 (0.73) | 0.44 (0.65) | 1.04 (0.73) | 4.56 (0.65) | 0.78 (0.11) |
| AH no | 2 | s-CEA, s-EGF, s-IL10, s-MMPNG, s-TNFa | 1.76 (0.88) | 0.24 (0.44) | 1.24 (0.88) | 4.76 (0.44) | 0.77 (0.14) |
| AH no | 3 | s-CEA, s-dDimer, s-CRP, s-IL4, s-IL10 | 1.8 (1) | 0.4 (0.5) | 1.2 (1) | 4.6 (0.5) | 0.76 (0.18) |
| protein no | 1 | s-FPSA, s-IL1a, s-IL4, s-Ifngg, s-NGAL | 1.84 (0.75) | 0.44 (0.65) | 1.16 (0.75) | 4.56 (0.65) | 0.76 (0.14) |
| protein no | 2 | s-dDimer, s-IL2, s-IL4, s-NGAL, s-TM | 1.72 (0.79) | 0.28 (0.46) | 1.28 (0.79) | 4.72 (0.46) | 0.76 (0.13) |
| protein no | 3 | s-dDimer, s-IL6, s-NGAL, s-TM, s-sTNFR | 1.72 (0.74) | 0.28 (0.61) | 1.28 (0.74) | 4.72 (0.61) | 0.76 (0.15) |
| AH yes | 1 | s-CEA, s-NGAL, s-NSE, s-TNFa, s-TPSA | 4.52 (0.77) | 0.88 (0.73) | 0.48 (0.77) | 1.12 (0.73) | 0.73 (0.19) |
| AH yes | 2 | s-CEA, s-MMPNG, s-NGAL, s-TM, s-TNFa | 4.56 (0.58) | 0.92 (0.7) | 0.44 (0.58) | 1.08 (0.7) | 0.73 (0.17) |
| AH yes | 3 | s-CEA, s-IL1b, s-NGAL, s-sTNFR, s-TPSA | 4.64 (0.7) | 0.96 (0.61) | 0.36 (0.7) | 1.04 (0.61) | 0.72 (0.18) |
| CI yes | 1 | s-CEA, s-IL1a, s-NGAL, s-NSE, s-TPSA | 4.6 (0.65) | 1.4 (0.71) | 0.4 (0.65) | 1.6 (0.71) | 0.73 (0.14) |
| CI yes | 2 | s-IL1a, s-MMPNG, s-NGAL, s-TPSA, s-VEGF | 4.72 (0.68) | 1.48 (0.96) | 0.28 (0.68) | 1.52 (0.96) | 0.73 (0.17) |
| CI yes | 3 | s-CEA, s-IL1a, s-IL10, s-NGAL, s-VEGF | 4.56 (0.65) | 1.48 (0.71) | 0.44 (0.65) | 1.52 (0.71) | 0.71 (0.14) |
| smoking yes | 1 | s-dDimer, s-EGF, s-IL1a, s-IL8, s-NGAL | 5.04 (1.02) | 1.76 (1.05) | 0.96 (1.02) | 2.24 (1.05) | 0.7 (0.17) |

TABLE 5-continued

Serum 5 biomarker classifiers

| name | num | Biomarker | TP | FP | FN | TN | AUC |
|---|---|---|---|---|---|---|---|
| smoking yes | 2 | s-IL1a, s-IL2, s-IL8, s-NGAL, s-sTNFR | 4.8 (1.08) | 1.64 (0.99) | 1.2 (1.08) | 2.36 (0.99) | 0.7 (0.13) |
| smoking yes | 3 | s-IL1a, s-IL10, s-NGAL, s-NSE, s-TNFa | 4.92 (1) | 1.72 (0.79) | 1.08 (1) | 2.28 (0.79) | 0.7 (0.13) |

TABLE 6

Plasma 5 biomarker classifiers

| name | num | Biomarker | TP | FP | FN | TN | AUC |
|---|---|---|---|---|---|---|---|
| OCR no | 1 | p-IL4, p-IL6, p-Ifng, p-MMPNG, p-NGAL | 3.64 (0.49) | 1.2 (0.91) | 0.36 (0.49) | 2.8 (0.91) | 0.8 (0.11) |
| OCR no | 2 | p-IL1b, p-IL4, p-IL10, p-MMPNG, p-TM | 3.64 (0.57) | 1.28 (0.94) | 0.36 (0.57) | 2.72 (0.94) | 0.8 (0.11) |
| OCR no | 3 | p-IL2, p-IL4, p-IL6, p-Ifng, p-MMPNG | 3.6 (0.65) | 1.28 (0.89) | 0.4 (0.65) | 2.72 (0.89) | 0.79 (0.11) |
| OCR yes | 1 | p-IL1a, p-IL6, p-MMPNG, p-TM, p-sTNFR | 3.28 (0.61) | 0.88 (0.78) | 0.72 (0.61) | 2.12 (0.78) | 0.76 (0.17) |
| OCR yes | 2 | p-IL1a, p-IL1b, p-IL6, p-IL8, p-TNFa | 2.84 (0.85) | 0.6 (0.5) | 1.16 (0.85) | 2.4 (0.5) | 0.76 (0.14) |
| OCR yes | 3 | p-IL8, p-MMPNG, p-NGAL, p-NSE, p-TNFa | 2.68 (0.9) | 0.48 (0.65) | 1.32 (0.9) | 2.52 (0.65) | 0.76 (0.17) |
| AC yes | 1 | p-IL2, p-Ifng, p-MCP1, p-MMPNG, p-TM | 2.56 (0.65) | 0.72 (0.68) | 0.44 (0.65) | 1.28 (0.68) | 0.75 (0.19) |
| AC yes | 2 | p-IL1a, p-IL1b, p-IL6, p-TNFa, p-VEGF | 3 (0) | 1.24 (0.6) | 0 (0) | 0.76 (0.6) | 0.69 (0.15) |
| AC yes | 3 | p-IL4, p-IL6, p-Ifng, p-MCP1, p-TNFa | 2.4 (0.5) | 0.88 (0.73) | 0.6 (0.5) | 1.12 (0.73) | 0.68 (0.19) |
| CI no | 1 | p-dDimer, p-IL1b, p-IL8, p-MMPNG, p-TM | 1.32 (0.69) | 0.72 (0.94) | 0.68 (0.69) | 3.28 (0.94) | 0.74 (0.2) |
| CI no | 2 | p-dDimer, p-IL8, p-TM, p-TNFa, p-VEGF | 1.16 (0.75) | 0.4 (0.65) | 0.84 (0.75) | 3.6 (0.65) | 0.74 (0.2) |
| CI no | 3 | p-IL2, p-IL8, p-MMPNG, p-TM, p-TNFa | 1.24 (0.66) | 0.64 (0.64) | 0.76 (0.66) | 3.36 (0.64) | 0.73 (0.18) |
| smoking no | 1 | p-IL1a, p-MMPNG, p-NSE, p-sTNFR, p-VEGF | 1.2 (0.71) | 0.36 (0.64) | 0.8 (0.71) | 2.64 (0.64) | 0.74 (0.18) |
| smoking no | 2 | p-Ifng, p-MCP1, p-MMPNG, p-NGAL, p-NSE | 1.2 (0.71) | 0.44 (0.71) | 0.8 (0.71) | 2.56 (0.71) | 0.73 (0.21) |
| smoking no | 3 | p-Ifng, p-MMPNG, p-NGAL, p-NSE, p-TNFa | 1.2 (0.76) | 0.44 (0.51) | 0.8 (0.76) | 2.56 (0.51) | 0.73 (0.21) |
| age < 65 | 1 | p-dDimer, p-IL8, p-IL10, p-NSE, p-VEGF | 1.72 (0.94) | 0.56 (0.71) | 1.28 (0.94) | 4.44 (0.71) | 0.73 (0.17) |
| age < 65 | 2 | p-dDimer, p-IL8, p-MMPNG, p-TNFa, p-VEGF | 1.56 (1.08) | 0.36 (0.76) | 1.44 (1.08) | 4.64 (0.76) | 0.72 (0.18) |
| age < 65 | 3 | p-EGF, p-IL8, p-IL10, p-MMPNG, p-sTNFR | 1.56 (0.87) | 0.36 (0.57) | 1.44 (0.87) | 4.64 (0.57) | 0.72 (0.16) |
| protein no | 1 | p-dDimer, p-IL4, p-MCP1, p-MMPNG, p-TNFa | 1.6 (0.96) | 0.6 (0.87) | 1.4 (0.96) | 4.4 (0.87) | 0.71 (0.19) |
| protein no | 2 | p-EGF, p-IL1a, p-IL2, p-MMPNG, p-NGAL | 1.6 (0.76) | 0.8 (0.76) | 1.4 (0.76) | 4.2 (0.76) | 0.69 (0.15) |
| protein no | 3 | p-dDimer, p-IL4, p-MCP1, p-MMPNG, p-sTNFR | 1.52 (0.96) | 0.68 (0.75) | 1.48 (0.96) | 4.32 (0.75) | 0.69 (0.19) |
| AC no | 1 | p-IL1a, p-IL8, p-MMPNG, p-NGAL, p-sTNFR | 2.96 (0.93) | 1.12 (1.05) | 2.04 (0.93) | 4.88 (1.05) | 0.7 (0.14) |
| AC no | 2 | p-IL1a, p-IL1b, p-IL4, p-Ifng, p-sTNFR | 3 (0.76) | 1.2 (0.96) | 2 (0.76) | 4.8 (0.96) | 0.7 (0.11) |
| AC no | 3 | p-IL1a, p-IL1b, p-IL8, p-TM, p-sTNFR | 2.36 (1.15) | 0.44 (0.65) | 2.64 (1.15) | 5.56 (0.65) | 0.7 (0.12) |
| alcohol no | 1 | p-IL1a, p-Ifng, p-MMPNG, p-sTNFR, p-TNFa | 3.48 (0.82) | 1.4 (0.96) | 0.52 (0.82) | 1.6 (0.96) | 0.7 (0.21) |
| alcohol no | 2 | p-EGF, p-IL4, p-MCP1, p-MMPNG, p-sTNFR | 3.48 (0.59) | 1.44 (0.92) | 0.52 (0.59) | 1.56 (0.92) | 0.7 (0.16) |
| alcohol no | 3 | p-IL1a, p-IL8, p-IL10, p-MMPNG, p-VEGF | 3.8 (0.41) | 1.68 (0.8) | 0.2 (0.41) | 1.32 (0.8) | 0.7 (0.15) |
| age > 65 | 1 | p-CRP, p-IL1a, p-MMPNG, p-TM, p-VEGF | 4.8 (0.41) | 1.68 (0.85) | 0.2 (0.41) | 1.32 (0.85) | 0.7 (0.16) |
| age > 65 | 2 | p-CRP, p-IL1a, p-IL1b, p-MMPNG, p-NGAL | 4.76 (0.52) | 1.76 (0.93) | 0.24 (0.52) | 1.24 (0.93) | 0.68 (0.16) |
| age > 65 | 3 | p-CRP, p-IL1a, p-IL4, p-MMPNG, p-TM | 4.76 (0.44) | 1.8 (0.65) | 0.24 (0.44) | 1.2 (0.65) | 0.68 (0.1) |
| alcohol yes | 1 | p-dDimer, p-IL4, p-MMPNG, p-NSE, p-TM | 2.84 (1.07) | 1.64 (1.04) | 1.16 (1.07) | 3.36 (1.04) | 0.69 (0.14) |

TABLE 6-continued

Plasma 5 biomarker classifiers

| name | num | Biomarker | TP | FP | FN | TN | AUC |
|---|---|---|---|---|---|---|---|
| alcohol yes | 2 | p-IL1b, p-IL4, p-MMPNG, p-NSE, p-TNFa | 2.96 (0.89) | 1.92 (1) | 1.04 (0.89) | 3.08 (1) | 0.68 (0.13) |
| alcohol yes | 3 | p-EGF, p-CRP, p-IL4, p-MMPNG, p-sTNFR | 2.96 (0.93) | 1.96 (1.17) | 1.04 (0.93) | 3.04 (1.17) | 0.67 (0.15) |
| AH no | 1 | p-EGF, p-IL1a, p-IL8, p-MMPNG, p-VEGF | 1.68 (0.95) | 0.92 (0.7) | 1.32 (0.95) | 4.08 (0.7) | 0.69 (0.15) |
| AH no | 2 | p-IL1a, p-IL8, p-Ifng, p-MMPNG, p-VEGF | 1.36 (0.99) | 0.48 (0.71) | 1.64 (0.99) | 4.52 (0.71) | 0.68 (0.19) |
| AH no | 3 | p-CRP, p-IL1a, p-IL8, p-MMPNG, p-NGAL | 1.48 (0.65) | 0.8 (0.71) | 1.52 (0.65) | 4.2 (0.71) | 0.67 (0.16) |
| smoking yes | 1 | p-IL4, p-Ifng, p-MCP1, p-MMPNG, p-TM | 5.6 (0.65) | 2.4 (0.71) | 0.4 (0.65) | 1.6 (0.71) | 0.67 (0.09) |
| smoking yes | 2 | p-IL1a, p-IL4, p-Ifng, p-MCP1, p-MMPNG | 5.48 (0.77) | 2.36 (0.95) | 0.52 (0.77) | 1.64 (0.95) | 0.66 (0.13) |
| smoking yes | 3 | p-EGF, p-IL1a, p-IL4, p-MCP1, p-MMPNG | 5.64 (0.57) | 2.48 (1.05) | 0.36 (0.57) | 1.52 (1.05) | 0.66 (0.12) |
| protein yes | 1 | p-CRP, p-IL1a, p-IL8, p-Ifng, p-TM | 4.56 (0.65) | 1.16 (0.47) | 0.44 (0.65) | 0.84 (0.47) | 0.67 (0.13) |
| protein yes | 2 | p-CRP, p-IL1a, p-IL8, p-Ifng, p-NGAL | 4.72 (0.61) | 1.24 (0.6) | 0.28 (0.61) | 0.76 (0.6) | 0.66 (0.17) |
| protein yes | 3 | p-IL1a, p-IL2, p-IL8, p-MCP1, p-TM | 4.8 (0.41) | 1.28 (0.61) | 0.2 (0.41) | 0.72 (0.61) | 0.66 (0.16) |
| AH yes | 1 | p-IL1a, p-IL1b, p-IL4, p-Ifng, p-VEGF | 4.96 (0.2) | 1.52 (0.51) | 0.04 (0.2) | 0.48 (0.51) | 0.62 (0.12) |
| AH yes | 2 | p-EGF, p-CRP, p-IL2, p-IL4, p-IL8 | 4.8 (0.41) | 1.48 (0.51) | 0.2 (0.41) | 0.52 (0.51) | 0.61 (0.13) |
| AH yes | 3 | p-EGF, p-CRP, p-IL2, p-IL10, p-NGAL | 5 (0) | 1.56 (0.51) | 0 (0) | 0.44 (0.51) | 0.61 (0.13) |
| CI yes | 1 | p-IL1a, p-IL6, p-IL8, p-MMPNG, p-NSE | 4.48 (0.51) | 2.12 (0.78) | 0.52 (0.51) | 0.88 (0.78) | 0.59 (0.15) |
| CI yes | 2 | p-IL6, p-Ifng, p-MMPNG, p-NSE, p-sTNFR | 4.52 (0.65) | 2.2 (0.71) | 0.48 (0.65) | 0.8 (0.71) | 0.59 (0.11) |
| CI yes | 3 | p-IL1a, p-IL1b, p-IL8, p-IL10, p-MMPNG | 4.96 (0.2) | 2.52 (0.51) | 0.04 (0.2) | 0.48 (0.51) | 0.58 (0.08) |

TABLE 7

Urine 6 biomarker classifiers

| name | num | Biomarker | TP | FP | FN | TN | AUC |
|---|---|---|---|---|---|---|---|
| smoking no | 1 | u-BTA, u-MCP1, u-MMP9, u-sTNFR2, u-vWF, u-FAS | 1.72 (0.46) | 0.16 (0.37) | 0.28 (0.46) | 2.84 (0.37) | 0.9 (0.15) |
| smoking no | 2 | u-dDimer, u-IL6, u-IL8, u-NGAL, u-NSE, u-TNFa | 1.64 (0.57) | 0.08 (0.28) | 0.36 (0.57) | 2.92 (0.28) | 0.9 (0.15) |
| smoking no | 3 | u-BTA, u-IL6, u-MCP1, u-TNFa, u-sTNFR2, u-FAS | 1.68 (0.56) | 0.16 (0.37) | 0.32 (0.56) | 2.84 (0.37) | 0.89 (0.15) |
| age < 65 | 1 | u-EGF, u-IL2, u-IL8, u-MMP9, u-HA, u-CK18 | 2.48 (0.71) | 0.32 (0.63) | 0.52 (0.71) | 4.68 (0.63) | 0.88 (0.13) |
| age < 65 | 2 | u-BTA, u-EGF, u-IL1b, u-IL8, u-HA, u-CK18 | 2.36 (0.64) | 0.36 (0.64) | 0.64 (0.64) | 4.64 (0.64) | 0.86 (0.13) |
| age < 65 | 3 | u-dDimer, u-EGF, u-NSE, u-vWF, u-HA, u-CK18 | 2.36 (0.7) | 0.36 (0.49) | 0.64 (0.7) | 4.64 (0.49) | 0.86 (0.13) |
| OCR yes | 1 | u-BTA, u-dDimer, u-CRP, u-IL4, u-sTNFR, u-vWF | 3.6 (0.65) | 0.44 (0.58) | 0.4 (0.65) | 2.56 (0.58) | 0.88 (0.14) |
| OCR yes | 2 | u-IL4, u-IL8, u-NGAL, u-NSE, u-TM, u-sTNFR | 3.2 (0.82) | 0.2 (0.5) | 0.8 (0.82) | 2.8 (0.5) | 0.87 (0.12) |
| OCR yes | 3 | u-CRP, u-IL2, u-IL8, u-MCP1, u-MMP9NG, u-TNFa | 3.4 (0.82) | 0.36 (0.57) | 0.6 (0.82) | 2.64 (0.57) | 0.86 (0.16) |
| CI no | 1 | u-dDimer, u-EGF, u-CRP, u-IL4, u-sTNFR, u-vWF | 1.8 (0.41) | 0.64 (0.81) | 0.2 (0.41) | 3.36 (0.81) | 0.87 (0.12) |
| CI no | 2 | u-dDimer, u-EGF, u-CRP, u-IL4, u-sTNFR, u-sTNFR2 | 1.56 (0.51) | 0.2 (0.5) | 0.44 (0.51) | 3.8 (0.5) | 0.86 (0.14) |
| CI no | 3 | u-EGF, u-IL2, u-IL4, u-sTNFR2, u-VEGF, u-vWF | 1.6 (0.65) | 0.32 (0.48) | 0.4 (0.65) | 3.68 (0.48) | 0.86 (0.19) |
| AC no | 1 | u-EGF, u-CRP, u-IL4, u-VEGF, u-HA, u-CK18 | 3.92 (0.7) | 0.44 (0.77) | 1.08 (0.7) | 5.56 (0.77) | 0.86 (0.08) |
| AC no | 2 | u-EGF, u-IL4, u-IL6, u-IL8, u-vWF, u-CK18 | 3.88 (0.83) | 0.48 (0.77) | 1.12 (0.83) | 5.52 (0.77) | 0.85 (0.12) |
| AC no | 3 | u-BTA, u-EGF, u-IL4, u-IL8, u-HA, u-CK18 | 3.8 (0.91) | 0.48 (0.51) | 1.2 (0.91) | 5.52 (0.51) | 0.84 (0.09) |
| AC yes | 1 | u-dDimer, u-IL6, u-NGAL, u-NSE, u-VEGF, u-HA | 2.4 (0.71) | 0.24 (0.6) | 0.6 (0.71) | 1.76 (0.6) | 0.84 (0.2) |

TABLE 7-continued

Urine 6 biomarker classifiers

| name | num | Biomarker | TP | FP | FN | TN | AUC |
|---|---|---|---|---|---|---|---|
| AC yes | 2 | u-IL1b, u-IL6, u-IL8, u-MMP9NG, u-NSE, u-VEGF | 2.44 (0.58) | 0.28 (0.46) | 0.56 (0.58) | 1.72 (0.46) | 0.84 (0.14) |
| AC yes | 3 | u-BTA, u-dDimer, u-IL6, u-NGAL, u-NSE, u-VEGF | 2.36 (0.64) | 0.24 (0.52) | 0.64 (0.64) | 1.76 (0.52) | 0.83 (0.19) |
| alcohol yes | 1 | u-dDimer, u-EGF, u-CRP, u-IL1a, u-IL6, u-vWF | 3.48 (0.71) | 0.96 (0.89) | 0.52 (0.71) | 4.04 (0.89) | 0.84 (0.12) |
| alcohol yes | 2 | u-EGF, u-CRP, u-IL1a, u-sTNFR, u-vWF, u-CK18 | 3.56 (0.65) | 1.08 (0.95) | 0.44 (0.65) | 3.92 (0.95) | 0.84 (0.11) |
| alcohol yes | 3 | u-BTA, u-EGF, u-CRP, u-IL1a, u-vWF, u-FAS | 3.6 (0.65) | 1.16 (1.11) | 0.4 (0.65) | 3.84 (1.11) | 0.83 (0.13) |
| age > 65 | 1 | u-BTA, u-IL1b, u-IL4, u-VEGF, u-vWF, u-HA | 4.72 (0.46) | 0.8 (0.82) | 0.28 (0.46) | 2.2 (0.82) | 0.84 (0.15) |
| age > 65 | 2 | u-BTA, u-IL1b, u-IL8, u-sTNFR2, u-vWF, u-HA | 4.64 (0.49) | 0.96 (0.84) | 0.36 (0.49) | 2.04 (0.84) | 0.8 (0.16) |
| age > 65 | 3 | u-BTA, u-EGF, u-IL1a, u-NSE, u-vWF, u-HA | 4.68 (0.48) | 1 (0.65) | 0.32 (0.48) | 2 (0.65) | 0.8 (0.12) |
| alcohol no | 1 | u-IL2, u-IL4, u-IL8, u-NGAL, u-HA, u-CK18 | 3.28 (0.74) | 0.48 (0.65) | 0.72 (0.74) | 2.52 (0.65) | 0.83 (0.14) |
| alcohol no | 2 | u-BTA, u-dDimer, u-IL2, u-IL8, u-MMP9NG, u-CK18 | 3.12 (0.78) | 0.4 (0.65) | 0.88 (0.78) | 2.6 (0.65) | 0.82 (0.11) |
| alcohol no | 3 | u-IL2, u-IL4, u-IL8, u-sTNFR2, u-HA, u-CK18 | 3.28 (0.84) | 0.6 (0.71) | 0.72 (0.84) | 2.4 (0.71) | 0.81 (0.15) |
| protein yes | 1 | u-EGF, u-IL8, u-sTNFR2, u-VEGF, u-vWF, u-HA | 4.4 (0.65) | 0.48 (0.51) | 0.6 (0.65) | 1.52 (0.51) | 0.82 (0.12) |
| protein yes | 2 | u-EGF, u-IL1a, u-MMP9, u-NSE, u-vWF, u-HA | 4.36 (0.91) | 0.48 (0.71) | 0.64 (0.91) | 1.52 (0.71) | 0.82 (0.19) |
| protein yes | 3 | u-EGF, u-CRP, u-IL2, u-IL4, u-TM, u-CK18 | 4.8 (0.41) | 0.68 (0.63) | 0.2 (0.41) | 1.32 (0.63) | 0.81 (0.17) |
| protein no | 1 | u-CRP, u-MCP1, u-MMP9, u-NGAL, u-sTNFR2, u-VEGF | 2.2 (0.65) | 0.52 (0.65) | 0.8 (0.65) | 4.48 (0.65) | 0.81 (0.12) |
| protein no | 2 | u-dDimer, u-CRP, u-IL2, u-IL4, u-NGAL, u-sTNFR | 2.2 (0.91) | 0.68 (0.85) | 0.8 (0.91) | 4.32 (0.85) | 0.8 (0.14) |
| protein no | 3 | u-BTA, u-CRP, u-IL2, u-NGAL, u-sTNFR2, u-vWF | 2.24 (0.66) | 0.76 (0.88) | 0.76 (0.66) | 4.24 (0.88) | 0.8 (0.13) |
| smoking yes | 1 | u-dDimer, u-EGF, u-IL1b, u-IL8, u-VEGF, u-vWF | 5.8 (0.41) | 1.36 (0.95) | 0.2 (0.41) | 2.64 (0.95) | 0.81 (0.12) |
| smoking yes | 2 | u-EGF, u-IL1b, u-NSE, u-sTNFR2, u-VEGF, u-vWF | 5.56 (0.58) | 1.24 (0.83) | 0.44 (0.58) | 2.76 (0.83) | 0.81 (0.13) |
| smoking yes | 3 | u-EGF, u-IL2, u-TM, u-sTNFR2, u-VEGF, u-CK18 | 5.4 (0.87) | 1.24 (0.83) | 0.6 (0.87) | 2.76 (0.83) | 0.8 (0.12) |
| AH no | 1 | u-EGF, u-NGAL, u-VEGF, u-vWF, u-HA, u-CK18 | 2.16 (0.75) | 0.52 (0.71) | 0.84 (0.75) | 4.48 (0.71) | 0.81 (0.14) |
| AH no | 2 | u-CRP, u-IL1b, u-IL6, u-sTNFR, u-VEGF, u-vWF | 1.88 (0.73) | 0.08 (0.28) | 1.12 (0.73) | 4.92 (0.28) | 0.81 (0.12) |
| AH no | 3 | u-dDimer, u-EGF, u-IL4, u-VEGF, u-HA, u-CK18 | 2.04 (0.79) | 0.36 (0.76) | 0.96 (0.79) | 4.64 (0.76) | 0.8 (0.13) |
| AH yes | 1 | u-BTA, u-EGF, u-IL1b, u-IL8, u-VEGF, u-vWF | 4.88 (0.44) | 0.76 (0.66) | 0.12 (0.44) | 1.24 (0.66) | 0.8 (0.18) |
| AH yes | 2 | u-dDimer, u-CRP, u-IL8, u-sTNFR2, u-vWF, u-CK18 | 4.68 (0.48) | 0.68 (0.69) | 0.32 (0.48) | 1.32 (0.69) | 0.8 (0.16) |
| AH yes | 3 | u-dDimer, u-EGF, u-IL2, u-VEGF, u-vWF, u-FAS | 4.88 (0.33) | 0.8 (0.65) | 0.12 (0.33) | 1.2 (0.65) | 0.79 (0.16) |
| OCR no | 1 | u-IL6, u-MCP1, u-TNFa, u-vWF, u-FAS, u-CK18 | 3.08 (0.64) | 0.76 (0.78) | 0.92 (0.64) | 3.24 (0.78) | 0.79 (0.12) |
| OCR no | 2 | u-BTA, u-dDimer, u-CRP, u-TNFa, u-vWF, u-HA | 2.76 (1.01) | 0.52 (0.71) | 1.24 (1.01) | 3.48 (0.71) | 0.78 (0.15) |
| OCR no | 3 | u-BTA, u-IL1a, u-TNFa, u-vWF, u-HA, u-FAS | 2.8 (0.71) | 0.56 (0.71) | 1.2 (0.71) | 3.44 (0.71) | 0.78 (0.14) |
| CI yes | 1 | u-BTA, u-IL2, u-MMP9NG, u-sTNFR, u-TNFa, u-VEGF | 4.48 (0.59) | 1.04 (0.93) | 0.52 (0.59) | 1.96 (0.93) | 0.77 (0.16) |
| CI yes | 2 | u-BTA, u-IL2, u-MMP9NG, u-NGAL, u-TNFa, u-CK18 | 4.72 (0.46) | 1.2 (0.58) | 0.28 (0.46) | 1.8 (0.58) | 0.77 (0.1) |
| CI yes | 3 | u-BTA, u-IL2, u-MMP9NG, u-NSE, u-VEGF, u-CK18 | 4.32 (0.75) | 1 (0.91) | 0.68 (0.75) | 2 (0.91) | 0.77 (0.18) |

TABLE 8

Serum 6 biomarker classifiers

| name | num | Biomarker | TP | FP | FN | TN | AUC |
|---|---|---|---|---|---|---|---|
| smoking no | 1 | s-CEA, s-IL6, s-IL8, s-MMPNG, s-NGAL, s-VEGF | 1.84 (0.37) | 0.04 (0.2) | 0.16 (0.37) | 2.96 (0.2) | 0.95 (0.1) |

TABLE 8-continued

Serum 6 biomarker classifiers

| name | num | Biomarker | TP | FP | FN | TN | AUC |
|---|---|---|---|---|---|---|---|
| smoking no | 2 | s-CEA, s-dDimer, s-CRP, s-MMPNG, s-NGAL, s-NSE | 1.8 (0.41) | 0.08 (0.28) | 0.2 (0.41) | 2.92 (0.28) | 0.94 (0.11) |
| smoking no | 3 | s-CEA, s-CRP, s-IL2, s-MMPNG, s-NGAL, s-TM | 1.8 (0.41) | 0.12 (0.33) | 0.2 (0.41) | 2.88 (0.33) | 0.93 (0.12) |
| protein yes | 1 | s-CEA, s-IL1b, s-IL2, s-IL8, s-IL10, s-NSE | 4.44 (0.87) | 0.36 (0.57) | 0.56 (0.87) | 1.64 (0.57) | 0.85 (0.18) |
| protein yes | 2 | s-CEA, s-IL1b, s-IL2, s-IL8, s-NSE, s-TPSA | 4.8 (0.5) | 0.64 (0.57) | 0.2 (0.5) | 1.36 (0.57) | 0.82 (0.15) |
| protein yes | 3 | s-CEA, s-CRP, s-IL10, s-MMPNG, s-NGAL, s-VEGF | 4.64 (0.49) | 0.6 (0.65) | 0.36 (0.49) | 1.4 (0.65) | 0.81 (0.15) |
| age < 65 | 1 | s-CEA, s-IL1a, s-IL4, s-IL8, s-MMPNG, s-sTNFR | 2.4 (0.58) | 0.56 (0.82) | 0.6 (0.58) | 4.44 (0.82) | 0.84 (0.11) |
| age < 65 | 2 | s-CEA, s-IL1a, s-IL2, s-IL4, s-NSE, s-sTNFR | 2.32 (0.85) | 0.6 (0.71) | 0.68 (0.85) | 4.4 (0.71) | 0.83 (0.16) |
| age < 65 | 3 | s-CEA, s-EGF, s-IL1a, s-IL4, s-IL8, s-TM | 2.24 (0.83) | 0.48 (0.51) | 0.76 (0.83) | 4.52 (0.51) | 0.83 (0.16) |
| alcohol no | 1 | s-CEA, s-IL2, s-IL8, s-NSE, s-TM, s-sTNFR | 3.52 (0.65) | 0.6 (0.65) | 0.48 (0.65) | 2.4 (0.65) | 0.84 (0.14) |
| alcohol no | 2 | s-CEA, s-IL10, s-MMPNG, s-NSE, s-TM, s-sTNFR | 3.32 (0.69) | 0.52 (0.65) | 0.68 (0.69) | 2.48 (0.65) | 0.83 (0.15) |
| alcohol no | 3 | s-CEA, s-CRP, s-IL2, s-IL10, s-NGAL, s-TM | 3.36 (0.76) | 0.56 (0.58) | 0.64 (0.76) | 2.44 (0.58) | 0.83 (0.13) |
| OCR no | 1 | s-CEA, s-dDimer, s-EGF, s-IL8, s-IL10, s-TM | 3.04 (0.84) | 0.36 (0.57) | 0.96 (0.84) | 3.64 (0.57) | 0.84 (0.12) |
| OCR no | 2 | s-CEA, s-dDimer, s-IL4, s-MCP1, s-MMPNG, s-sTNFR | 3.24 (0.88) | 0.56 (0.65) | 0.76 (0.88) | 3.44 (0.65) | 0.84 (0.14) |
| OCR no | 3 | s-CEA, s-dDimer, s-EGF, s-IL6, s-NGAL, s-TM | 3.04 (0.79) | 0.4 (0.58) | 0.96 (0.79) | 3.6 (0.58) | 0.83 (0.12) |
| OCR yes | 1 | s-dDimer, s-CRP, s-IL6, s-IL8, s-NSE, s-sTNFR | 3.24 (0.83) | 0.44 (0.58) | 0.76 (0.83) | 2.56 (0.58) | 0.83 (0.13) |
| OCR yes | 2 | s-CEA, s-IL4, s-IL10, s-Ifngg, s-MCP1, s-NGAL | 3.32 (0.56) | 0.52 (0.77) | 0.68 (0.56) | 2.48 (0.77) | 0.83 (0.12) |
| OCR yes | 3 | s-FPSA, s-IL4, s-IL8, s-MMPNG, s-NSE, s-sTNFR | 3.28 (1.02) | 0.52 (0.77) | 0.72 (1.02) | 2.48 (0.77) | 0.82 (0.14) |
| CI no | 1 | s-IL4, s-MMPNG, s-NGAL, s-NSE, s-sTNFR, s-TPSA | 1.52 (0.65) | 0.4 (0.5) | 0.48 (0.65) | 3.6 (0.5) | 0.83 (0.2) |
| CI no | 2 | s-CEA, s-EGF, s-FPSA, s-IL4, s-NSE, s-sTNFR | 1.68 (0.48) | 0.76 (0.78) | 0.32 (0.48) | 3.24 (0.78) | 0.82 (0.16) |
| CI no | 3 | s-CEA, s-EGF, s-FPSA, s-IL4, s-MCP1, s-VEGF | 1.44 (0.71) | 0.32 (0.56) | 0.56 (0.71) | 3.68 (0.56) | 0.82 (0.2) |
| AC no | 1 | s-CEA, s-IL1a, s-IL1b, s-IL6, s-NGAL, s-NSE | 3.76 (1.01) | 0.6 (0.71) | 1.24 (1.01) | 5.4 (0.71) | 0.83 (0.12) |
| AC no | 2 | s-CEA, s-IL4, s-IL6, s-IL8, s-MMPNG, s-TNFa | 3.96 (0.89) | 0.84 (0.75) | 1.04 (0.89) | 5.16 (0.75) | 0.83 (0.11) |
| AC no | 3 | s-CEA, s-dDimer, s-IL1a, s-IL4, s-IL6, s-sTNFR | 3.84 (0.94) | 0.72 (0.84) | 1.16 (0.94) | 5.28 (0.84) | 0.82 (0.11) |
| AH no | 1 | s-CEA, s-dDimer, s-CRP, s-IL4, s-IL10, s-TM | 2.16 (0.8) | 0.36 (0.49) | 0.84 (0.8) | 4.64 (0.49) | 0.82 (0.12) |
| AH no | 2 | s-CEA, s-dDimer, s-CRP, s-IL4, s-IL6, s-MMPNG | 2.08 (0.76) | 0.36 (0.57) | 0.92 (0.76) | 4.64 (0.57) | 0.81 (0.14) |
| AH no | 3 | s-CEA, s-dDimer, s-IL2, s-IL4, s-IL8, s-MMPNG | 1.96 (0.98) | 0.44 (0.58) | 1.04 (0.98) | 4.56 (0.58) | 0.78 (0.16) |
| alcohol yes | 1 | s-EGF, s-CRP, s-IL1a, s-IL1b, s-NGAL, s-TPSA | 3.24 (0.72) | 0.84 (0.94) | 0.76 (0.72) | 4.16 (0.94) | 0.82 (0.13) |
| alcohol yes | 2 | s-CEA, s-CRP, s-IL1b, s-IL2, s-NGAL, s-NSE | 2.88 (1.09) | 0.4 (0.58) | 1.12 (1.09) | 4.6 (0.58) | 0.82 (0.16) |
| alcohol yes | 3 | s-CEA, s-dDimer, s-CRP, s-IL1a, s-IL6, s-NGAL | 3.08 (0.86) | 0.8 (0.87) | 0.92 (0.86) | 4.2 (0.87) | 0.8 (0.14) |
| AC yes | 1 | s-IL1a, s-MCP1, s-MMPNG, s-NGAL, s-TM, s-TNFa | 2.8 (0.41) | 0.64 (0.76) | 0.2 (0.41) | 1.36 (0.76) | 0.81 (0.18) |
| AC yes | 2 | s-CEA, s-FPSA, s-IL8, s-NGAL, s-TM, s-VEGF | 2.48 (0.59) | 0.52 (0.65) | 0.52 (0.59) | 1.48 (0.65) | 0.78 (0.19) |
| AC yes | 3 | s-FPSA, s-IL4, s-NGAL, s-NSE, s-TNFa, s-VEGF | 2.4 (0.65) | 0.48 (0.59) | 0.6 (0.65) | 1.52 (0.59) | 0.78 (0.16) |
| age > 65 | 1 | s-CEA, s-dDimer, s-IL1a, s-NGAL, s-NSE, s-TM | 4.08 (0.95) | 0.68 (0.8) | 0.92 (0.95) | 2.32 (0.8) | 0.79 (0.15) |
| age > 65 | 2 | s-CEA, s-EGF, s-IL1a, s-MMPNG, s-NGAL, s-TPSA | 4.32 (0.8) | 0.88 (0.83) | 0.68 (0.8) | 2.12 (0.83) | 0.79 (0.15) |
| age > 65 | 3 | s-CEA, s-dDimer, s-CRP, s-IL1b, s-NGAL, s-TM | 4.36 (0.7) | 0.96 (0.73) | 0.64 (0.7) | 2.04 (0.73) | 0.78 (0.13) |
| protein no | 1 | s-dDimer, s-IL1b, s-IL8, s-NGAL, s-TM, s-TNFa | 1.88 (0.73) | 0.24 (0.52) | 1.12 (0.73) | 4.76 (0.52) | 0.79 (0.14) |
| protein no | 2 | s-CEA, s-IL4, s-IL8, s-NGAL, s-TNFa, s-TPSA | 1.96 (0.79) | 0.52 (0.59) | 1.04 (0.79) | 4.48 (0.59) | 0.77 (0.15) |
| protein no | 3 | s-dDimer, s-FPSA, s-IL2, s-IL6, s-IL8, s-NGAL | 1.8 (0.76) | 0.32 (0.56) | 1.2 (0.76) | 4.68 (0.56) | 0.77 (0.13) |

TABLE 8-continued

Serum 6 biomarker classifiers

| name | num | Biomarker | TP | FP | FN | TN | AUC |
|---|---|---|---|---|---|---|---|
| AH yes | 1 | s-CEA, s-IL1b, s-IL10, s-NGAL, s-TM, s-VEGF | 4.32 (0.85) | 0.64 (0.7) | 0.68 (0.85) | 1.36 (0.7) | 0.77 (0.19) |
| AH yes | 2 | s-CEA, s-dDimer, s-IL1b, s-MMPNG, s-NGAL, s-TM | 4.32 (0.8) | 0.76 (0.6) | 0.68 (0.8) | 1.24 (0.6) | 0.74 (0.17) |
| AH yes | 3 | s-CEA, s-EGF, s-IL1a, s-IL1b, s-NGAL, s-TNFa | 4.64 (0.57) | 0.92 (0.64) | 0.36 (0.57) | 1.08 (0.64) | 0.73 (0.16) |
| CI yes | 1 | s-CEA, s-IL10, s-MMPNG, s-NGAL, s-TNFa, s-VEGF | 4.64 (0.57) | 1.4 (0.91) | 0.36 (0.57) | 1.6 (0.91) | 0.73 (0.17) |
| CI yes | 2 | s-IL1a, s-IL10, s-MMPNG, s-NGAL, s-NSE, s-VEGF | 4.68 (0.63) | 1.44 (0.92) | 0.32 (0.63) | 1.56 (0.92) | 0.73 (0.15) |
| CI yes | 3 | s-CRP, s-IL10, s-MMPNG, s-NGAL, s-TPSA, s-VEGF | 4.76 (0.44) | 1.52 (0.96) | 0.24 (0.44) | 1.48 (0.96) | 0.72 (0.17) |
| smoking yes | 1 | s-dDimer, s-IL2, s-IL10, s-MMPNG, s-NGAL, s-sTNFR | 5.24 (0.93) | 1.76 (1.01) | 0.76 (0.93) | 2.24 (1.01) | 0.72 (0.16) |
| smoking yes | 2 | s-EGF, s-FPSA, s-IL10, s-NGAL, s-TNFa, s-TPSA | 5.12 (1.09) | 1.76 (0.83) | 0.88 (1.09) | 2.24 (0.83) | 0.71 (0.16) |
| smoking yes | 3 | s-CEA, s-IL1a, s-IL4, s-IL8, s-IL10, s-NGAL | 4.68 (0.75) | 1.52 (0.77) | 1.32 (0.75) | 2.48 (0.77) | 0.7 (0.12) |

TABLE 9

Plasma 6 biomarker classifiers

| name | num | Biomarker | TP | FP | FN | TN | AUC |
|---|---|---|---|---|---|---|---|
| OCR no | 1 | p-IL2, p-IL4, p-IL10, p-MMPNG, p-TNFa, p-VEGF | 3.52 (0.96) | 1.12 (0.67) | 0.48 (0.96) | 2.88 (0.67) | 0.8 (0.13) |
| OCR no | 2 | p-CRP, p-IL4, p-IL10, p-MMPNG, p-TNFa, p-VEGF | 3.48 (0.71) | 1.24 (0.97) | 0.52 (0.71) | 2.76 (0.97) | 0.78 (0.14) |
| OCR no | 3 | p-IL1a, p-IL4, p-IL10, p-Ifng, p-MMPNG, p-NSE | 3.48 (0.65) | 1.28 (0.68) | 0.52 (0.65) | 2.72 (0.68) | 0.78 (0.11) |
| smoking no | 1 | p-IL6, p-Ifng, p-MMPNG, p-NGAL, p-NSE, p-TNFa | 1.36 (0.64) | 0.24 (0.52) | 0.64 (0.64) | 2.76 (0.52) | 0.8 (0.2) |
| smoking no | 2 | p-dDimer, p-IL1a, p-IL4, p-MMPNG, p-NSE, p-VEGF | 1.36 (0.57) | 0.36 (0.57) | 0.64 (0.57) | 2.64 (0.57) | 0.78 (0.18) |
| smoking no | 3 | p-dDimer, p-EGF, p-IL1a, p-IL8, p-MMPNG, p-NSE | 1.24 (0.78) | 0.32 (0.48) | 0.76 (0.78) | 2.68 (0.48) | 0.76 (0.23) |
| OCR yes | 1 | p-IL1b, p-IL2, p-IL8, p-MMPNG, p-NGAL, p-NSE | 3.04 (0.89) | 0.64 (0.7) | 0.96 (0.89) | 2.36 (0.7) | 0.77 (0.16) |
| OCR yes | 2 | p-IL1b, p-IL8, p-IL10, p-MCP1, p-NGAL, p-TM | 2.88 (1.01) | 0.52 (0.77) | 1.12 (1.01) | 2.48 (0.77) | 0.77 (0.19) |
| OCR yes | 3 | p-IL8, p-Ifng, p-MMPNG, p-TM, p-sTNFR, p-TNFa | 2.88 (0.83) | 0.52 (0.51) | 1.12 (0.83) | 2.48 (0.51) | 0.77 (0.14) |
| CI no | 1 | p-dDimer, p-IL8, p-MMPNG, p-NSE, p-TM, p-TNFa | 1.28 (0.74) | 0.44 (0.65) | 0.72 (0.74) | 3.56 (0.65) | 0.76 (0.21) |
| CI no | 2 | p-dDimer, p-IL2, p-IL8, p-MMPNG, p-NSE, p-TNFa | 1.28 (0.68) | 0.52 (0.65) | 0.72 (0.68) | 3.48 (0.65) | 0.76 (0.18) |
| CI no | 3 | p-dDimer, p-IL8, p-Ifng, p-MMPNG, p-sTNFR, p-TNFa | 1.2 (0.71) | 0.36 (0.49) | 0.8 (0.71) | 3.64 (0.49) | 0.76 (0.2) |
| alcohol no | 1 | p-IL1a, p-IL1b, p-IL10, p-Ifng, p-MMPNG, p-VEGF | 3.92 (0.28) | 1.48 (0.96) | 0.08 (0.28) | 1.52 (0.96) | 0.74 (0.17) |
| alcohol no | 2 | p-EGF, p-CRP, p-IL1a, p-MMPNG, p-TNFa, p-VEGF | 3.8 (0.41) | 1.56 (0.92) | 0.2 (0.41) | 1.44 (0.92) | 0.72 (0.17) |
| alcohol no | 3 | p-IL1a, p-IL6, p-IL8, p-Ifng, p-MMPNG, p-sTNFR | 3.4 (0.65) | 1.28 (0.79) | 0.6 (0.65) | 1.72 (0.79) | 0.71 (0.14) |
| AC no | 1 | p-dDimer, p-IL1a, p-IL4, p-IL10, p-MMPNG, p-TNFa | 3.72 (1.1) | 1.64 (1.04) | 1.28 (1.1) | 4.36 (1.04) | 0.74 (0.14) |
| AC no | 2 | p-CRP, p-IL8, p-IL10, p-MMPNG, p-TM, p-sTNFR | 3.2 (1.22) | 1.36 (1.22) | 1.8 (1.22) | 4.64 (1.22) | 0.71 (0.18) |
| AC no | 3 | p-dDimer, p-IL1a, p-IL1b, p-IL4, p-TM, p-sTNFR | 2.92 (1.22) | 1.04 (0.93) | 2.08 (1.22) | 4.96 (0.93) | 0.71 (0.13) |
| age < 65 | 1 | p-EGF, p-CRP, p-IL6, p-IL8, p-IL10, p-sTNFR | 1.6 (0.71) | 0.32 (0.75) | 1.4 (0.71) | 4.68 (0.75) | 0.73 (0.11) |
| age < 65 | 2 | p-CRP, p-IL6, p-IL8, p-IL10, p-Ifng, p-sTNFR | 1.64 (0.86) | 0.4 (0.65) | 1.36 (0.86) | 4.6 (0.65) | 0.73 (0.16) |
| age < 65 | 3 | p-dDimer, p-IL4, p-IL8, p-MMPNG, p-NGAL, p-TNFa | 1.72 (0.74) | 0.56 (0.77) | 1.28 (0.74) | 4.44 (0.77) | 0.73 (0.14) |
| protein no | 1 | p-dDimer, p-IL1b, p-IL4, p-IL8, p-IL10, p-MMPNG | 1.8 (0.82) | 0.76 (0.6) | 1.2 (0.82) | 4.24 (0.6) | 0.72 (0.16) |
| protein no | 2 | p-dDimer, p-EGF, p-IL8, p-IL10, p-MMPNG, p-TM | 1.72 (0.74) | 0.88 (1.27) | 1.28 (0.74) | 4.12 (1.27) | 0.7 (0.16) |
| protein no | 3 | p-dDimer, p-EGF, p-Ifng, p-MMPNG, p-NSE, p-VEGF | 1.56 (0.92) | 0.64 (0.64) | 1.44 (0.92) | 4.36 (0.64) | 0.7 (0.15) |

TABLE 9-continued

Plasma 6 biomarker classifiers

| name | num | Biomarker | TP | FP | FN | TN | AUC |
|---|---|---|---|---|---|---|---|
| AH no | 1 | p-EGF, p-CRP, p-IL1b, p-IL8, p-MMPNG, p-VEGF | 1.84 (0.8) | 0.84 (0.8) | 1.16 (0.8) | 4.16 (0.8) | 0.72 (0.13) |
| AH no | 2 | p-CRP, p-IL1a, p-IL6, p-IL8, p-IL10, p-MMPNG | 1.28 (0.89) | 0.2 (0.41) | 1.72 (0.89) | 4.8 (0.41) | 0.69 (0.16) |
| AH no | 3 | p-EGF, p-IL1b, p-IL4, p-IL8, p-MMPNG, p-VEGF | 1.6 (0.87) | 0.88 (1.01) | 1.4 (0.87) | 4.12 (1.01) | 0.68 (0.16) |
| alcohol yes | 1 | p-IL1a, p-IL2, p-IL4, p-MMPNG, p-NSE, p-TNFa | 2.76 (0.97) | 1.36 (1.15) | 1.24 (0.97) | 3.64 (1.15) | 0.71 (0.14) |
| alcohol yes | 2 | p-IL2, p-IL4, p-IL6, p-MMPNG, p-NSE, p-TM | 2.8 (0.76) | 1.76 (1.3) | 1.2 (0.76) | 3.24 (1.3) | 0.67 (0.18) |
| alcohol yes | 3 | p-CRP, p-IL1a, p-IL1b, p-IL4, p-MMPNG, p-TNFa | 2.72 (0.79) | 1.68 (0.9) | 1.28 (0.79) | 3.32 (0.9) | 0.67 (0.12) |
| age > 65 | 1 | p-CRP, p-IL1a, p-IL2, p-IL4, p-MMPNG, p-TM | 4.8 (0.5) | 1.64 (0.7) | 0.2 (0.5) | 1.36 (0.7) | 0.71 (0.1) |
| age > 65 | 2 | p-EGF, p-CRP, p-IL1a, p-IL1b, p-MMPNG, p-VEGF | 4.92 (0.28) | 1.76 (0.72) | 0.08 (0.28) | 1.24 (0.72) | 0.7 (0.13) |
| age > 65 | 3 | p-EGF, p-IL1a, p-IL6, p-MMPNG, p-TM, p-TNFa | 4.8 (0.41) | 1.72 (0.94) | 0.2 (0.41) | 1.28 (0.94) | 0.69 (0.15) |
| AC yes | 1 | p-dDimer, p-IL2, p-IL6, p-MMPNG, p-TM, p-TNFa | 2.24 (0.52) | 0.68 (0.56) | 0.76 (0.52) | 1.32 (0.56) | 0.7 (0.15) |
| AC yes | 2 | p-IL2, p-IL10, p-Ifng, p-MCP1, p-MMPNG, p-TNFa | 2.36 (0.64) | 0.76 (0.6) | 0.64 (0.64) | 1.24 (0.6) | 0.7 (0.16) |
| AC yes | 3 | p-IL6, p-MCP1, p-NGAL, p-NSE, p-TM, p-TNFa | 2.48 (0.71) | 0.84 (0.62) | 0.52 (0.71) | 1.16 (0.62) | 0.7 (0.18) |
| smoking yes | 1 | p-dDimer, p-IL1a, p-IL4, p-IL10, p-MMPNG, p-sTNFR | 5.48 (0.71) | 2.16 (0.99) | 0.52 (0.71) | 1.84 (0.99) | 0.69 (0.13) |
| smoking yes | 2 | p-IL4, p-IL10, p-MMPNG, p-TM, p-sTNFR, p-TNFa | 5.48 (0.87) | 2.16 (0.69) | 0.52 (0.87) | 1.84 (0.69) | 0.69 (0.1) |
| smoking yes | 3 | p-IL1b, p-IL4, p-IL8, p-MCP1, p-MMPNG, p-TNFa | 5.52 (0.71) | 2.32 (0.8) | 0.48 (0.71) | 1.68 (0.8) | 0.67 (0.12) |
| protein yes | 1 | p-EGF, p-IL1a, p-IL4, p-IL8, p-Ifng, p-TM | 4.64 (0.57) | 1.12 (0.78) | 0.36 (0.57) | 0.88 (0.78) | 0.68 (0.21) |
| protein yes | 2 | p-dDimer, p-IL1a, p-IL8, p-Ifng, p-MCP1, p-TM | 4.76 (0.44) | 1.24 (0.72) | 0.24 (0.44) | 0.76 (0.72) | 0.67 (0.18) |
| protein yes | 3 | p-IL1a, p-IL8, p-Ifng, p-MCP1, p-TM, p-TNFa | 4.56 (0.77) | 1.16 (0.69) | 0.44 (0.77) | 0.84 (0.69) | 0.67 (0.21) |
| AH yes | 1 | p-EGF, p-IL6, p-IL10, p-Ifng, p-MCP1, p-MMPNG | 4.8 (0.41) | 1.44 (0.65) | 0.2 (0.41) | 0.56 (0.65) | 0.62 (0.13) |
| AH yes | 2 | p-dDimer, p-EGF, p-IL1b, p-IL4, p-IL6, p-MCP1 | 4.56 (0.58) | 1.4 (0.58) | 0.44 (0.58) | 0.6 (0.58) | 0.61 (0.14) |
| AH yes | 3 | p-EGF, p-CRP, p-IL1b, p-IL2, p-MMPNG, p-NGAL | 4.56 (0.71) | 1.4 (0.58) | 0.44 (0.71) | 0.6 (0.58) | 0.61 (0.14) |
| CI yes | 1 | p-IL6, p-IL8, p-Ifng, p-MMPNG, p-NGAL, p-NSE | 4.48 (0.71) | 2.12 (0.73) | 0.52 (0.71) | 0.88 (0.73) | 0.59 (0.12) |
| CI yes | 2 | p-IL1a, p-IL6, p-MMPNG, p-NSE, p-TM, p-TNFa | 4.52 (0.59) | 2.16 (0.62) | 0.48 (0.59) | 0.84 (0.62) | 0.59 (0.14) |
| CI yes | 3 | p-dDimer, p-IL4, p-IL8, p-Ifng, p-MMPNG, p-VEGF | 4.8 (0.41) | 2.36 (0.64) | 0.2 (0.41) | 0.64 (0.64) | 0.59 (0.1) |

TABLE 10

Urine 7 biomarker classifiers

| name | num | Biomarker | TP | FP | FN | TN | AUC |
|---|---|---|---|---|---|---|---|
| smoking no | 1 | u-EGF, u-CRP, u-IL8, u-NGAL, u-NSE, u-TM, u-HA | 1.84 (0.37) | 0.24 (0.44) | 0.16 (0.37) | 2.76 (0.44) | 0.92 (0.1) |
| smoking no | 2 | u-BTA, u-EGF, u-IL8, u-MCP1, u-NGAL, u-NSE, u-sTNFR | 1.68 (0.48) | 0.16 (0.37) | 0.32 (0.48) | 2.84 (0.37) | 0.89 (0.14) |
| smoking no | 3 | u-BTA, u-IL4, u-MCP1, u-TM, u-sTNFR2, u-vWF, u-FAS | 1.6 (0.5) | 0.04 (0.2) | 0.4 (0.5) | 2.96 (0.2) | 0.89 (0.12) |
| OCR yes | 1 | u-EGF, u-IL1a, u-IL8, u-MMP9NG, u-NSE, u-vWF, u-CK18 | 3.72 (0.46) | 0.4 (0.5) | 0.28 (0.46) | 2.6 (0.5) | 0.9 (0.1) |
| OCR yes | 2 | u-EGF, u-IL6, u-IL8, u-MMP9NG, u-NSE, u-VEGF, u-vWF | 3.68 (0.48) | 0.48 (0.65) | 0.32 (0.48) | 2.52 (0.65) | 0.88 (0.13) |
| OCR yes | 3 | u-CRP, u-IL1a, u-IL6, u-IL8, u-MMP9NG, u-NSE, u-VEGF | 3.36 (0.76) | 0.28 (0.46) | 0.64 (0.76) | 2.72 (0.46) | 0.87 (0.13) |
| age < 65 | 1 | u-EGF, u-CRP, u-IL1b, u-IL2, u-IL8, u-HA, u-CK18 | 2.56 (0.58) | 0.36 (0.49) | 0.44 (0.58) | 4.64 (0.49) | 0.89 (0.12) |
| age < 65 | 2 | u-EGF, u-IL1b, u-IL4, u-IL8, u-vWF, u-HA, u-CK18 | 2.44 (0.58) | 0.24 (0.44) | 0.56 (0.58) | 4.76 (0.44) | 0.88 (0.11) |
| age < 65 | 3 | u-EGF, u-IL1b, u-IL6, u-IL8, u-MMP9, u-HA, u-CK18 | 2.44 (0.65) | 0.36 (0.57) | 0.56 (0.65) | 4.64 (0.57) | 0.87 (0.13) |

TABLE 10-continued

Urine 7 biomarker classifiers

| name | num | Biomarker | TP | FP | FN | TN | AUC |
|---|---|---|---|---|---|---|---|
| CI no | 1 | u-EGF, u-CRP, u-IL4, u-MCP1, u-VEGF, u-FAS, u-CK18 | 1.72 (0.54) | 0.36 (0.64) | 0.28 (0.54) | 3.64 (0.64) | 0.88 (0.15) |
| CI no | 2 | u-dDimer, u-EGF, u-CRP, u-IL4, u-IL6, u-sTNFR2, u-vWF | 1.76 (0.44) | 0.48 (0.59) | 0.24 (0.44) | 3.52 (0.59) | 0.88 (0.14) |
| CI no | 3 | u-dDimer, u-EGF, u-CRP, u-IL4, u-IL6, u-sTNFR2, u-CK18 | 1.6 (0.65) | 0.2 (0.5) | 0.4 (0.65) | 3.8 (0.5) | 0.88 (0.21) |
| AC no | 1 | u-BTA, u-EGF, u-CRP, u-IL4, u-sTNFR, u-HA, u-CK18 | 4.28 (0.89) | 0.76 (0.93) | 0.72 (0.89) | 5.24 (0.93) | 0.86 (0.11) |
| AC no | 2 | u-EGF, u-IL1a, u-IL1b, u-IL4, u-sTNFR, u-VEGF, u-CK18 | 3.96 (1.14) | 0.56 (0.77) | 1.04 (1.14) | 5.44 (0.77) | 0.85 (0.14) |
| AC no | 3 | u-EGF, u-CRP, u-IL4, u-MMP9NG, u-NGAL, u-HA, u-CK18 | 3.92 (0.76) | 0.52 (0.59) | 1.08 (0.76) | 5.48 (0.59) | 0.85 (0.09) |
| alcohol yes | 1 | u-EGF, u-IL1a, u-IL6, u-NGAL, u-sTNFR2, u-vWF, u-FAS | 3.52 (0.77) | 1 (1) | 0.48 (0.77) | 4 (1) | 0.84 (0.13) |
| alcohol yes | 2 | u-EGF, u-IL1a, u-IL2, u-IL6, u-NGAL, u-VEGF, u-vWF | 3.36 (0.76) | 0.84 (0.8) | 0.64 (0.76) | 4.16 (0.8) | 0.84 (0.11) |
| alcohol yes | 3 | u-EGF, u-IL1a, u-NGAL, u-NSE, u-sTNFR2, u-vWF, u-CK18 | 3.52 (0.82) | 1.04 (0.89) | 0.48 (0.82) | 3.96 (0.89) | 0.84 (0.12) |
| AC yes | 1 | u-BTA, u-CRP, u-IL1b, u-IL8, u-sTNFR2, u-vWF, u-FAS | 2.72 (0.46) | 0.48 (0.65) | 0.28 (0.46) | 1.52 (0.65) | 0.83 (0.19) |
| AC yes | 2 | u-dDimer, u-IL4, u-IL6, u-MMP9, u-NSE, u-VEGF, u-CK18 | 2.36 (0.76) | 0.24 (0.44) | 0.64 (0.76) | 1.76 (0.44) | 0.83 (0.15) |
| AC yes | 3 | u-BTA, u-CRP, u-IL1a, u-IL2, u-sTNFR2, u-vWF, u-FAS | 2.88 (0.33) | 0.6 (0.65) | 0.12 (0.33) | 1.4 (0.65) | 0.83 (0.18) |
| AH no | 1 | u-dDimer, u-CRP, u-IL2, u-NSE, u-VEGF, u-vWF, u-CK18 | 2.2 (0.71) | 0.36 (0.49) | 0.8 (0.71) | 4.64 (0.49) | 0.83 (0.12) |
| AH no | 2 | u-dDimer, u-CRP, u-IL2, u-NSE, u-TNFa, u-VEGF, u-HA | 2.08 (0.81) | 0.28 (0.61) | 0.92 (0.81) | 4.72 (0.61) | 0.82 (0.14) |
| AH no | 3 | u-EGF, u-CRP, u-IL1a, u-IL1b, u-NGAL, u-VEGF, u-HA | 2.04 (0.73) | 0.28 (0.46) | 0.96 (0.73) | 4.72 (0.46) | 0.81 (0.14) |
| CI yes | 1 | u-BTA, u-IL2, u-MMP9NG, u-NGAL, u-sTNFR, u-TNFa, u-VEGF | 4.64 (0.57) | 0.84 (0.85) | 0.36 (0.57) | 2.16 (0.85) | 0.82 (0.14) |
| CI yes | 2 | u-BTA, u-IL2, u-MMP9NG, u-TM, u-sTNFR, u-vWF, u-FAS | 4.4 (0.82) | 0.88 (0.88) | 0.6 (0.82) | 2.12 (0.88) | 0.79 (0.14) |
| CI yes | 3 | u-BTA, u-IL2, u-MMP9NG, u-sTNFR, u-VEGF, u-vWF, u-CK18 | 4.36 (0.64) | 0.88 (0.83) | 0.64 (0.64) | 2.12 (0.83) | 0.79 (0.13) |
| protein no | 1 | u-dDimer, u-CRP, u-IL1a, u-IL4, u-MMP9NG, u-TM, u-CK18 | 2.28 (0.79) | 0.56 (0.65) | 0.72 (0.79) | 4.44 (0.65) | 0.82 (0.15) |
| protein no | 2 | u-BTA, u-EGF, u-CRP, u-MMP9, u-NGAL, u-vWF, u-FAS | 2.28 (0.84) | 0.68 (0.85) | 0.72 (0.84) | 4.32 (0.85) | 0.81 (0.15) |
| protein no | 3 | u-BTA, u-CRP, u-NGAL, u-NSE, u-TM, u-sTNFR2, u-vWF | 2.16 (0.9) | 0.48 (0.59) | 0.84 (0.9) | 4.52 (0.59) | 0.81 (0.16) |
| protein yes | 1 | u-EGF, u-IL1b, u-IL2, u-NSE, u-TM, u-VEGF, u-vWF | 4.64 (0.57) | 0.56 (0.65) | 0.36 (0.57) | 1.44 (0.65) | 0.82 (0.16) |
| protein yes | 2 | u-EGF, u-IL1b, u-MMP9, u-MMP9NG, u-TNFa, u-vWF, u-HA | 4.56 (0.58) | 0.56 (0.65) | 0.44 (0.58) | 1.44 (0.65) | 0.82 (0.17) |
| protein yes | 3 | u-EGF, u-IL2, u-IL4, u-NGAL, u-NSE, u-TM, u-CK18 | 4.6 (0.5) | 0.6 (0.76) | 0.4 (0.5) | 1.4 (0.76) | 0.81 (0.19) |
| alcohol no | 1 | u-IL1b, u-IL2, u-IL6, u-IL8, u-NGAL, u-NSE, u-CK18 | 3.04 (0.73) | 0.4 (0.58) | 0.96 (0.73) | 2.6 (0.58) | 0.81 (0.13) |
| alcohol no | 2 | u-IL1a, u-IL2, u-IL6, u-IL8, u-NGAL, u-HA, u-CK18 | 3.16 (0.8) | 0.52 (0.71) | 0.84 (0.8) | 2.48 (0.71) | 0.81 (0.16) |
| alcohol no | 3 | u-BTA, u-IL1a, u-IL2, u-IL8, u-NGAL, u-VEGF, u-CK18 | 3.16 (0.85) | 0.52 (0.65) | 0.84 (0.85) | 2.48 (0.65) | 0.81 (0.15) |
| AH yes | 1 | u-CRP, u-IL1b, u-IL6, u-IL8, u-MMP9, u-NGAL, u-vWF | 4.8 (0.41) | 0.68 (0.69) | 0.2 (0.41) | 1.32 (0.69) | 0.81 (0.18) |
| AH yes | 2 | u-dDimer, u-IL8, u-MMP9, u-NSE, u-TM, u-sTNFR2, u-vWF | 4.4 (0.87) | 0.56 (0.71) | 0.6 (0.87) | 1.44 (0.71) | 0.8 (0.18) |
| AH yes | 3 | u-BTA, u-dDimer, u-EGF, u-IL4, u-NGAL, u-NSE, u-vWF | 4.6 (0.5) | 0.64 (0.49) | 0.4 (0.5) | 1.36 (0.49) | 0.8 (0.14) |
| age > 65 | 1 | u-dDimer, u-CRP, u-IL1a, u-IL2, u- u-NSE, u-vWF, u-vWF, u-HA | 4.36 (0.81) | 0.76 (0.97) | 0.64 (0.81) | 2.24 (0.97) | 0.81 (0.19) |
| age > 65 | 2 | u-BTA, u-IL1a, u-IL8, u-MMP9NG, u-vWF, u-HA, u-CK18 | 4.56 (0.65) | 0.92 (1) | 0.44 (0.65) | 2.08 (1) | 0.8 (0.18) |
| age > 65 | 3 | u-dDimer, u-IL1a, u-MCP1, u-NSE, u-TNFa, u-vWF, u-HA | 4.4 (0.71) | 0.84 (0.9) | 0.6 (0.71) | 2.16 (0.9) | 0.8 (0.18) |
| smoking yes | 1 | u-EGF, u-IL1a, u-MMP9, u-MMP9NG, u-NSE, u-VEGF, u-vWF | 5.28 (0.98) | 1.12 (0.88) | 0.72 (0.98) | 2.88 (0.88) | 0.8 (0.12) |
| smoking yes | 2 | u-EGF, u-IL1b, u-NGAL, u-NSE, u-sTNFR, u-VEGF, u-vWF | 5.36 (0.81) | 1.2 (1) | 0.64 (0.81) | 2.8 (1) | 0.8 (0.13) |
| smoking yes | 3 | u-dDimer, u-EGF, u-IL1a, u-IL8, u-NSE, u-vWF, u-FAS | 5.08 (0.76) | 1.04 (0.89) | 0.92 (0.76) | 2.96 (0.89) | 0.79 (0.12) |
| OCR no | 1 | u-BTA, u-dDimer, u-MMP9NG, u-TM, u-TNFa, u-vWF, u-HA | 2.88 (0.93) | 0.52 (0.65) | 1.12 (0.93) | 3.48 (0.65) | 0.8 (0.13) |
| OCR no | 2 | u-IL6, u-NGAL, u-sTNFR, u-TNFa, u-vWF, u-FAS, u-CK18 | 3.04 (0.84) | 0.68 (0.75) | 0.96 (0.84) | 3.32 (0.75) | 0.8 (0.13) |

TABLE 10-continued

Urine 7 biomarker classifiers

| name | num | Biomarker | TP | FP | FN | TN | AUC |
|---|---|---|---|---|---|---|---|
| OCR no | 3 | u-BTA, u-IL1a, u-IL1b, u-IL6, u-NGAL, u-TNFa, u-CK18 | 2.88 (0.83) | 0.56 (0.92) | 1.12 (0.83) | 3.44 (0.92) | 0.79 (0.16) |

TABLE 11

Serum 7 biomarker classifiers

| name | num | Biomarker | TP | FP | FN | TN | AUC |
|---|---|---|---|---|---|---|---|
| smoking no | 1 | s-CEA, s-EGF, s-CRP, s-IL4, s-IL8, s-NGAL, s-NSE | 1.88 (0.33) | 0.16 (0.37) | 0.12 (0.33) | 2.84 (0.37) | 0.94 (0.13) |
| smoking no | 2 | s-CEA, s-IL6, s-IL8, s-Ifngg, s-NGAL, s-TM, s-VEGF | 1.8 (0.41) | 0.04 (0.2) | 0.2 (0.41) | 2.96 (0.2) | 0.94 (0.1) |
| smoking no | 3 | s-CEA, s-FPSA, s-CRP, s-IL4, s-MMPNG, s-NGAL, s-TM | 1.88 (0.44) | 0.2 (0.41) | 0.12 (0.44) | 2.8 (0.41) | 0.94 (0.12) |
| age < 65 | 1 | s-CEA, s-IL1a, s-IL2, s-IL4, s-IL8, s-Ifngg, s-MMPNG | 2.48 (0.65) | 0.48 (0.59) | 0.52 (0.65) | 4.52 (0.59) | 0.87 (0.09) |
| age < 65 | 2 | s-CEA, s-EGF, s-FPSA, s-IL1a, s-IL4, | 2.44 (0.58) | 0.48 (0.65) | 0.56 (0.58) | 4.52 (0.65) | 0.86 (0.12) |
| age < 65 | 3 | s-IL8, s-VEGF s-CEA, s-IL1a, s-IL2, s-IL8, s-Ifngg, s-MCP1, s-sTNFR | 2.36 (0.91) | 0.52 (0.71) | 0.64 (0.91) | 4.48 (0.71) | 0.84 (0.17) |
| OCR no | 1 | s-CEA, s-dDimer, s-IL4, s-IL10, s-MCP1, s-MMPNG, s-NSE | 3.52 (0.65) | 0.72 (0.74) | 0.48 (0.65) | 3.28 (0.74) | 0.85 (0.11) |
| OCR no | 2 | s-CEA, s-dDimer, s-Ifngg, s-MCP1, s-MMPNG, s-TM, s-TPSA | 3.2 (0.76) | 0.44 (0.51) | 0.8 (0.76) | 3.56 (0.51) | 0.84 (0.12) |
| OCR no | 3 | s-CEA, s-dDimer, s-EGF, s-IL6, s-IL10, s-MMPNG, s-TM | 3.6 (0.5) | 0.88 (1.01) | 0.4 (0.5) | 3.12 (1.01) | 0.84 (0.12) |
| CI no | 1 | s-FPSA, s-IL2, s-IL4, s-IL6, s-MMPNG, s-NGAL, s-sTNFR | 1.56 (0.58) | 0.36 (0.49) | 0.44 (0.58) | 3.64 (0.49) | 0.84 (0.18) |
| CI no | 2 | s-CEA, s-EGF, s-FPSA, s-CRP, s-IL4, s-IL6, s-MMPNG | 1.64 (0.49) | 0.56 (0.71) | 0.36 (0.49) | 3.44 (0.71) | 0.84 (0.15) |
| CI no | 3 | s-dDimer, s-IL1b, s-IL4, s-IL8, s-MCP1, s-NGAL, s-TM | 1.44 (0.51) | 0.2 (0.41) | 0.56 (0.51) | 3.8 (0.41) | 0.84 (0.14) |
| alcohol no | 1 | s-CEA, s-CRP, s-IL4, s-IL6, s-IL10, s-sTNFR, s-TPSA | 3.36 (0.95) | 0.48 (0.71) | 0.64 (0.95) | 2.52 (0.71) | 0.84 (0.18) |
| alcohol no | 2 | s-CEA, s-dDimer, s-EGF, s-IL1a, s-IL10, s-NSE, s-sTNFR | 3.28 (0.79) | 0.48 (0.59) | 0.72 (0.79) | 2.52 (0.59) | 0.83 (0.12) |
| alcohol no | 3 | s-CEA, s-dDimer, s-IL1a, s-IL1b, s-IL4, s-TM, s-sTNFR | 3.6 (0.58) | 0.72 (0.68) | 0.4 (0.58) | 2.28 (0.68) | 0.83 (0.13) |
| AC yes | 1 | s-FPSA, s-IL1b, s-IL10, s-NGAL, s-TM, s-TNFa, s-VEGF | 2.52 (0.59) | 0.32 (0.48) | 0.48 (0.59) | 1.68 (0.48) | 0.84 (0.13) |
| AC yes | 2 | s-CEA, s-IL1b, s-IL4, s-NGAL, s-TM, s-TPSA, s-VEGF | 2.4 (0.5) | 0.4 (0.5) | 0.6 (0.5) | 1.6 (0.5) | 0.8 (0.12) |
| AC yes | 3 | s-FPSA, s-IL1b, s-IL4, s-IL10, s-NGAL, s-TM, s-VEGF | 2.68 (0.56) | 0.6 (0.65) | 0.32 (0.56) | 1.4 (0.65) | 0.8 (0.22) |
| OCR yes | 1 | s-FPSA, s-IL1b, s-IL2, s-IL4, s-IL8, s-MMPNG, s-NGAL | 3.12 (0.73) | 0.32 (0.56) | 0.88 (0.73) | 2.68 (0.56) | 0.84 (0.13) |
| OCR yes | 2 | s-CEA, s-dDimer, s-IL8, s-IL10, s-Ifngg, s-NGAL, s-NSE | 3.16 (0.9) | 0.4 (0.65) | 0.84 (0.9) | 2.6 (0.65) | 0.83 (0.16) |
| OCR yes | 3 | s-CEA, s-EGF, s-CRP, s-IL10, s-MCP1, s-NGAL, s-NSE | 3.24 (0.78) | 0.48 (0.71) | 0.76 (0.78) | 2.52 (0.71) | 0.82 (0.15) |
| AC no | 1 | s-CEA, s-IL1a, s-IL4, s-IL6, s-IL8, s-TM, s-sTNFR | 4 (0.71) | 0.8 (0.87) | 1 (0.71) | 5.2 (0.87) | 0.83 (0.11) |
| AC no | 2 | s-CEA, s-IL1a, s-IL1b, s-IL4, s-IL8, s-MMPNG, s-VEGF | 4.08 (0.7) | 1 (0.91) | 0.92 (0.7) | 5 (0.91) | 0.82 (0.11) |
| AC no | 3 | s-CEA, s-IL1a, s-IL4, s-IL10, s-MMPNG, s-TM, s-TNFa | 3.88 (0.88) | 0.76 (0.97) | 1.12 (0.88) | 5.24 (0.97) | 0.82 (0.1) |
| alcohol yes | 1 | s-EGF, s-CRP, s-IL8, s-MCP1, s-MMPNG, s-NGAL, s-sTNFR | 3.24 (0.78) | 0.76 (0.66) | 0.76 (0.78) | 4.24 (0.66) | 0.83 (0.12) |
| alcohol yes | 2 | s-CEA, s-EGF, s-CRP, s-IL1b, s-MMPNG, s-NGAL, s-TM | 3.16 (0.8) | 0.72 (0.89) | 0.84 (0.8) | 4.28 (0.89) | 0.82 (0.11) |
| alcohol yes | 3 | s-CEA, s-dDimer, s-IL1a, s-IL2, s-IL4, s-IL10, s-NGAL | 3.16 (0.8) | 0.76 (0.78) | 0.84 (0.8) | 4.24 (0.78) | 0.82 (0.11) |
| protein yes | 1 | s-CEA, s-IL1b, s-IL2, s-IL4, s-IL8, s-NSE, s-TNFa | 4.52 (0.65) | 0.52 (0.65) | 0.48 (0.65) | 1.48 (0.65) | 0.82 (0.18) |
| protein yes | 2 | s-CEA, s-EGF, s-IL4, s-IL8, s-IL10, s-TPSA, s-VEGF | 4.2 (0.87) | 0.4 (0.5) | 0.8 (0.87) | 1.6 (0.5) | 0.82 (0.17) |
| protein yes | 3 | s-CEA, s-IL1b, s-IL2, s-IL4, s-IL10, s-MMPNG, s-TM | 4.48 (0.65) | 0.52 (0.51) | 0.52 (0.65) | 1.48 (0.51) | 0.82 (0.17) |
| age > 65 | 1 | s-CEA, s-dDimer, s-FPSA, s-CRP, s-IL10, s-NGAL, s-TM | 4.44 (0.87) | 0.8 (0.76) | 0.56 (0.87) | 2.2 (0.76) | 0.81 (0.15) |

TABLE 11-continued

Serum 7 biomarker classifiers

| name | num | Biomarker | TP | FP | FN | TN | AUC |
|---|---|---|---|---|---|---|---|
| age > 65 | 2 | s-CEA, s-dDimer, s-CRP, s-NGAL, s-NSE, s-TM, s-TPSA | 4.6 (0.58) | 0.96 (0.79) | 0.4 (0.58) | 2.04 (0.79) | 0.8 (0.13) |
| age > 65 | 3 | s-dDimer, s-IL1a, s-IL8, s-Ifngg, s-MMPNG, s-NGAL, s-TM | 4.28 (0.98) | 0.8 (0.76) | 0.72 (0.98) | 2.2 (0.76) | 0.79 (0.12) |
| AH no | 1 | s-CEA, s-dDimer, s-EGF, s-IL4, s-IL8, s-IL10, s-NSE | 2.16 (0.75) | 0.56 (0.65) | 0.84 (0.75) | 4.44 (0.65) | 0.8 (0.11) |
| AH no | 2 | s-CEA, s-dDimer, s-CRP, s-IL4, s-MCP1, s-MMPNG, s-TNFa | 2.16 (0.69) | 0.56 (0.77) | 0.84 (0.69) | 4.44 (0.77) | 0.8 (0.13) |
| AH no | 3 | s-CEA, s-dDimer, s-CRP, s-IL4, s-IL6, s-TM, s-TNFa | 1.96 (1.06) | 0.24 (0.44) | 1.04 (1.06) | 4.76 (0.44) | 0.8 (0.18) |
| protein no | 1 | s-FPSA, s-CRP, s-IL2, s-IL6, s-NGAL, s-TNFa, s-VEGF | 2.08 (0.76) | 0.48 (0.71) | 0.92 (0.76) | 4.52 (0.71) | 0.8 (0.12) |
| protein no | 2 | s-CEA, s-FPSA, s-CRP, s-IL6, s-IL10, s-NGAL, s-VEGF | 1.96 (0.68) | 0.44 (0.71) | 1.04 (0.68) | 4.56 (0.71) | 0.78 (0.13) |
| protein no | 3 | s-dDimer, s-FPSA, s-IL1b, s-Ifngg, s-MMPNG, s-NGAL, s-TM | 1.96 (0.89) | 0.44 (0.58) | 1.04 (0.89) | 4.56 (0.58) | 0.78 (0.14) |
| AH yes | 1 | s-CEA, s-IL1a, s-IL1b, s-IL10, s-NGAL, s-sTNFR, s-TNFa | 4.08 (1.08) | 0.6 (0.65) | 0.92 (1.08) | 1.4 (0.65) | 0.76 (0.22) |
| AH yes | 2 | s-CEA, s-IL1a, s-NGAL, s-NSE, s-TM, s-TNFa, s-TPSA | 4.44 (0.77) | 0.76 (0.6) | 0.56 (0.77) | 1.24 (0.6) | 0.75 (0.16) |
| AH ys | 3 | s-CEA, s-IL1b, s-IL4, s-IL10, s-MMPNG, s-NGAL, s-TM | 4.4 (0.96) | 0.76 (0.83) | 0.6 (0.96) | 1.24 (0.83) | 0.75 (0.2) |
| smoking yes | 1 | s-EGF, s-CRP, s-IL10, s-MMPNG, s-NGAL, s-TM, s-VEGF | 5.08 (0.76) | 1.44 (0.92) | 0.92 (0.76) | 2.56 (0.92) | 0.74 (0.13) |
| smoking yes | 2 | s-CEA, s-CRP, s-IL10, s-MMPNG, s-NGAL, s-TM, s-TNFa | 5.16 (0.9) | 1.68 (0.99) | 0.84 (0.9) | 2.32 (0.99) | 0.72 (0.14) |
| smoking yes | 3 | s-CEA, s-dDimer, s-IL2, s-IL8, s-IL10, s-Ifngg, s-NSE | 5.08 (1.15) | 1.68 (0.85) | 0.92 (1.15) | 2.32 (0.85) | 0.71 (0.16) |
| CI yes | 1 | s-CEA, s-CRP, s-IL1b, s-IL2, s-TM, s-sTNFR, s-TPSA | 4.76 (0.44) | 1.4 (0.87) | 0.24 (0.44) | 1.6 (0.87) | 0.74 (0.16) |
| CI yes | 2 | s-CRP, s-IL1b, s-IL2, s-IL6, s-MMPNG, s-NGAL, s-TNFa | 4.68 (0.56) | 1.36 (0.81) | 0.32 (0.56) | 1.64 (0.81) | 0.74 (0.16) |
| CI yes | 3 | s-CRP, s-IL1b, s-IL2, s-MMPNG, s-NGAL, s-NSE, s-TNFa | 4.64 (0.57) | 1.36 (0.86) | 0.36 (0.57) | 1.64 (0.86) | 0.74 (0.14) |

TABLE 12

Plasma 7 biomarker classifiers

| name | num | Biomarker | TP | FP | FN | TN | AUC |
|---|---|---|---|---|---|---|---|
| smoking no | 1 | p-dDimer, p-EGF, p-IL1a, p-Ifng, p-MMPNG, p-TNFa, p-VEGF | 1.4 (0.58) | 0.28 (0.54) | 0.6 (0.58) | 2.72 (0.54) | 0.8 (0.19) |
| smoking no | 2 | p-EGF, p-IL1a, p-IL2, p-MMPNG, p-NGAL, p-NSE, p-TM | 1.48 (0.59) | 0.48 (0.71) | 0.52 (0.59) | 2.52 (0.71) | 0.79 (0.2) |
| smoking no | 3 | p-IL1a, p-Ifng, p-MMPNG, p-NGAL, p-NSE, p-TM, p-TNFa | 1.24 (0.66) | 0.2 (0.41) | 0.76 (0.66) | 2.8 (0.41) | 0.78 (0.18) |
| OCR yes | 1 | p-IL1b, p-IL8, p-Ifng, p-MCP1, p-MMPNG, p-TM, p-sTNFR | 3.12 (0.83) | 0.6 (0.71) | 0.88 (0.83) | 2.4 (0.71) | 0.79 (0.16) |
| OCR yes | 2 | p-IL1a, p-IL4, p-IL8, p-IL10, p-MCP1, p-TM, p-sTNFR | 2.8 (1) | 0.48 (0.59) | 1.2 (1) | 2.52 (0.59) | 0.77 (0.18) |
| OCR yes | 3 | p-IL1a, p-IL1b, p-IL6, p-IL8, p-NGAL, p-NSE, p-VEGF | 2.88 (1.01) | 0.56 (0.71) | 1.12 (1.01) | 2.44 (0.71) | 0.77 (0.13) |
| OCR no | 1 | p-IL4, p-IL6, p-IL10, p-MMPNG, p-NGAL, p-sTNFR, p-VEGF | 3.6 (0.65) | 1.32 (0.75) | 0.4 (0.65) | 2.68 (0.75) | 0.78 (0.09) |
| OCR no | 2 | p-dDimer, p-CRP, p-IL1a, p-IL1b, p-IL2, p-IL4, p-MMPNG | 3.48 (0.59) | 1.24 (0.93) | 0.52 (0.59) | 2.76 (0.93) | 0.78 (0.13) |
| OCR no | 3 | p-dDimer, p-CRP, p-IL1b, p-IL4, p-IL6, p-IL10, p-MMPNG | 3.44 (0.71) | 1.2 (0.96) | 0.56 (0.71) | 2.8 (0.96) | 0.78 (0.13) |
| CI no | 1 | p-dDimer, p-IL1a, p-IL8, p-MMPNG, p-TM, p-TNFa, p-VEGF | 1.2 (0.58) | 0.32 (0.48) | 0.8 (0.58) | 3.68 (0.48) | 0.76 (0.16) |
| CI no | 2 | p-dDimer, p-CRP, p-IL2, p-IL6, p-IL8, p-MMPNG, p-TNFa | 1.28 (0.68) | 0.52 (0.82) | 0.72 (0.68) | 3.48 (0.82) | 0.76 (0.22) |
| CI no | 3 | p-dDimer, p-IL1a, p-IL1b, p-IL8, p-MMPNG, p-TM, p-VEGF | 1.24 (0.72) | 0.44 (0.71) | 0.76 (0.72) | 3.56 (0.71) | 0.76 (0.19) |
| AC yes | 1 | p-dDimer, p-EGF, p-IL6, p-IL1b, p-Ifng, p-MCP1, p-TNFa | 2.36 (0.57) | 0.6 (0.65) | 0.64 (0.57) | 1.4 (0.65) | 0.74 (0.19) |
| AC yes | 2 | p-dDimer, p-IL10, p-Ifng, p-MCP1, p-NGAL, p-sTNFR, p-VEGF | 2.16 (0.85) | 0.52 (0.59) | 0.84 (0.85) | 1.48 (0.59) | 0.73 (0.2) |
| AC yes | 3 | p-dDimer, p-IL6, p-IL8, p-IL10, p-NSE, p-TM, p-TNFa | 2.24 (0.66) | 0.6 (0.65) | 0.76 (0.66) | 1.4 (0.65) | 0.72 (0.2) |
| age < 65 | 1 | p-CRP, p-IL4, p-IL6, p-IL8, p-IL10, p-MMPNG, p-TNFa | 1.8 (0.96) | 0.6 (0.58) | 1.2 (0.96) | 4.4 (0.58) | 0.74 (0.19) |

TABLE 12-continued

Plasma 7 biomarker classifiers

| name | num | Biomarker | TP | FP | FN | TN | AUC |
|---|---|---|---|---|---|---|---|
| age < 65 | 2 | p-EGF, p-CRP, p-IL1b, p-IL8, p-Ifng, p-NGAL, p-sTNFR | 1.88 (0.97) | 0.76 (0.83) | 1.12 (0.97) | 4.24 (0.83) | 0.74 (0.16) |
| age < 65 | 3 | p-dDimer, p-EGF, p-CRP, p-IL8, p-IL10, p-Ifng, p-MMPNG | 1.84 (0.9) | 0.76 (0.78) | 1.16 (0.9) | 4.24 (0.78) | 0.73 (0.16) |
| alcohol no | 1 | p-IL1a, p-IL2, p-IL8, p-Ifng, p-MMPNG, p-sTNFR, p-TNFa | 3.52 (0.65) | 1.2 (1) | 0.48 (0.65) | 1.8 (1) | 0.74 (0.16) |
| alcohol no | 2 | p-IL1a, p-IL2, p-IL6, p-IL10, p-MMPNG, p-TNFa, p-VEGF | 3.28 (0.84) | 1.08 (0.86) | 0.72 (0.84) | 1.92 (0.86) | 0.73 (0.17) |
| alcohol no | 3 | p-IL1a, p-IL4, p-IL6, p-IL10, p-MMPNG, p-NGAL, p-VEGF | 3.44 (0.87) | 1.2 (0.71) | 0.56 (0.87) | 1.8 (0.71) | 0.73 (0.19) |
| AH no | 1 | p-EGF, p-CRP, p-IL1a, p-IL8, p-MMPNG, p-TNFa, p-VEGF | 1.6 (0.76) | 0.28 (0.46) | 1.4 (0.76) | 4.72 (0.46) | 0.74 (0.13) |
| AH no | 2 | p-EGF, p-CRP, p-IL1b, p-IL8, p-MMPNG, p-sTNFR, p-VEGF | 1.72 (0.79) | 0.6 (0.65) | 1.28 (0.79) | 4.4 (0.65) | 0.73 (0.15) |
| AH no | 3 | p-dDimer, p-EGF, p-IL1b, p-IL6, p-IL8, p-MMPNG, p-VEGF | 1.8 (0.82) | 0.8 (0.76) | 1.2 (0.82) | 4.2 (0.76) | 0.72 (0.14) |
| AC no | 1 | p-IL1b, p-IL6, p-IL8, p-MMPNG, p-sTNFR, p-TNFa, p-VEGF | 3.44 (0.87) | 1.28 (0.94) | 1.56 (0.87) | 4.72 (0.94) | 0.74 (0.11) |
| AC no | 2 | p-dDimer, p-IL1a, p-IL4, p-IL8, p-NGAL, p-TM, p-sTNFR | 3 (1.19) | 0.88 (0.88) | 2 (1.19) | 5.12 (0.88) | 0.73 (0.12) |
| AC no | 3 | p-IL1a, p-IL1b, p-IL4, p-IL6, p-IL8, p-MMPNG, p-sTNFR | 3.76 (0.72) | 1.88 (1.05) | 1.24 (0.72) | 4.12 (1.05) | 0.72 (0.13) |
| protein no | 1 | p-EGF, p-IL1a, p-IL2, p-IL4, p-MCP1, p-MMPNG, p-NGAL | 1.64 (0.86) | 0.56 (0.77) | 1.36 (0.86) | 4.44 (0.77) | 0.72 (0.13) |
| protein no | 2 | p-dDimer, p-EGF, p-CRP, p-IL8, p-MMPNG, p-NSE, p-VEGF | 1.76 (0.88) | 0.84 (0.75) | 1.24 (0.88) | 4.16 (0.75) | 0.71 (0.17) |
| protein no | 3 | p-dDimer, p-EGF, p-IL1b, p-IL8, p-IL10, p-MMPNG, p-VEGF | 1.64 (0.76) | 0.68 (0.75) | 1.36 (0.76) | 4.32 (0.75) | 0.71 (0.14) |
| protein yes | 1 | p-IL1a, p-IL2, p-IL8, p-IL10, p-Ifng, p-MCP1, p-TM | 4.64 (0.64) | 1 (0.76) | 0.36 (0.64) | 1 (0.76) | 0.71 (0.19) |
| protein yes | 2 | p-IL1a, p-IL2, p-IL8, p-Ifng, p-MCP1, p-MMPNG, p-TM | 4.48 (0.65) | 1.04 (0.73) | 0.52 (0.65) | 0.96 (0.73) | 0.69 (0.21) |
| protein yes | 3 | p-EGF, p-CRP, p-IL1a, p-IL4, p-IL8, p-Ifng, p-TNFa | 4.56 (0.51) | 1.08 (0.57) | 0.44 (0.51) | 0.92 (0.57) | 0.69 (0.15) |
| age > 65 | 1 | p-CRP, p-IL1a, p-IL10, p-MMPNG, p-TM, p-TNFa, p-VEGF | 4.92 (0.28) | 1.68 (0.75) | 0.08 (0.28) | 1.32 (0.75) | 0.71 (0.13) |
| age > 65 | 2 | p-IL1a, p-IL6, p-IL10, p-MMPNG, p-TM, p-TNFa, p-VEGF | 4.64 (0.57) | 1.6 (0.76) | 0.36 (0.57) | 1.4 (0.76) | 0.7 (0.14) |
| age > 65 | 3 | p-CRP, p-IL1a, p-IL4, p-IL6, p-MMPNG, p-TM, p-TNFa | 4.72 (0.54) | 1.68 (0.85) | 0.28 (0.54) | 1.32 (0.85) | 0.69 (0.14) |
| alcohol yes | 1 | p-dDimer, p-IL1b, p-IL4, p-MMPNG, p-NGAL, p-NSE, p-VEGF | 2.92 (0.95) | 1.68 (1.03) | 1.08 (0.95) | 3.32 (1.03) | 0.7 (0.16) |
| alcohol yes | 2 | p-dDimer, p-IL1a, p-IL2, p-MMPNG, p-NSE, p-sTNFR, p-TNFa | 2.56 (0.77) | 1.44 (1.19) | 1.44 (0.77) | 3.56 (1.19) | 0.68 (0.12) |
| alcohol yes | 3 | p-dDimer, p-CRP, p-IL1a, p-IL4, p-IL10, p-NSE, p-sTNFR | 2.56 (0.92) | 1.48 (0.92) | 1.44 (0.92) | 3.52 (0.92) | 0.67 (0.15) |
| smoking yes | 1 | p-IL1a, p-IL1b, p-IL2, p-IL4, p-IL10, p-MMPNG, p-TNFa | 5.28 (1.02) | 2.04 (0.93) | 0.72 (1.02) | 1.96 (0.93) | 0.68 (0.16) |
| smoking yes | 2 | p-dDimer, p-IL1a, p-IL4, p-Ifng, p-MCP1, p-MMPNG, p-TM | 5.64 (0.64) | 2.32 (0.85) | 0.36 (0.64) | 1.68 (0.85) | 0.68 (0.1) |
| smoking yes | 3 | p-dDimer, p-EGF, p-IL1a, p-IL4, p-IL10, p-Ifng, p-MMPNG | 5.52 (0.59) | 2.32 (1.03) | 0.48 (0.59) | 1.68 (1.03) | 0.67 (0.14) |
| AH yes | 1 | p-dDimer, p-EGF, p-CRP, p-IL2, p-IL10, p-MMPNG, p-TM | 4.76 (0.52) | 1.36 (0.7) | 0.24 (0.52) | 0.64 (0.7) | 0.64 (0.17) |
| AH yes | 2 | p-CRP, p-IL1a, p-IL1b, p-IL4, p-IL6, p-Ifng, p-sTNFR | 4.8 (0.5) | 1.44 (0.51) | 0.2 (0.5) | 0.56 (0.51) | 0.62 (0.12) |
| AH yes | 3 | p-EGF, p-CRP, p-IL4, p-IL6, p-IL10, p-Ifng, p-MMPNG | 4.48 (0.71) | 1.32 (0.69) | 0.52 (0.71) | 0.68 (0.69) | 0.62 (0.14) |
| CI yes | 1 | p-IL1a, p-IL8, p-IL10, p-MCP1, p-MMPNG, p-NSE, p-TM | 4.68 (0.63) | 2.08 (0.7) | 0.32 (0.63) | 0.92 (0.7) | 0.62 (0.13) |
| CI yes | 2 | p-dDimer, p-IL2, p-IL6, p-IL8, p-MMPNG, p-TM, p-sTNFR | 4.68 (0.56) | 2.12 (0.78) | 0.32 (0.56) | 0.88 (0.78) | 0.61 (0.14) |
| CI yes | 3 | p-IL1a, p-IL2, p-IL6, p-IL8, p-MCP1, p-MMPNG, p-NSE | 4.6 (0.58) | 2.08 (0.76) | 0.4 (0.58) | 0.92 (0.76) | 0.61 (0.15) |

TABLE 13

Urine 7 biomarker classifiers

| Name | Num | Biomarker | AUC |
|---|---|---|---|
| Smoking no | 1 | u-EGF(up), u-CRP(up), u-IL8(down), u-NGAL(down), u-NSE(up), u-TM(up), u-HA(down) | 0.92 (0.1) |

TABLE 13-continued

Urine 7 biomarker classifiers

| Name | Num | Biomarker | AUC |
|---|---|---|---|
| Smoking no | 2 | u-BTA(down), u-EGF(up), u-IL8(down), u-MCP1(down), u-NGAL(down), u-NSE(up), u-sTNFR(up) | 0.89 (0.14) |
| Smoking no | 3 | u-BTA(down), u-IL4(down), u-MCP1(down), u-TM(up), u-sTNFR2(down), u-vWF(down), u-FAS(down) | 0.89 (0.12) |
| OCR yes | 1 | u-EGF(up), u-IL1a(down), u-IL8(down), u-MMP9NG(up), u-NSE(up), u-vWF(down), u-CK18(down) | 0.9 (0.1) |
| OCR yes | 2 | u-EGF(up), u-IL6(down), u-IL8(down), u-MMP9NG(up), u-NSE(up), u-VEGF(down), u-vWF(down) | 0.88 (0.13) |
| OCR yes | 3 | u-CRP(up), u-IL1a(down), n-IL6(down), u-IL8(down), u-MMP9NG(up), u-NSE(up), u-VEGF(down) | 0.87 (0.13) |
| age < 65 | 1 | u-EGF(up), u-CRP(up), u-IL1b(down), u-IL2(down), u-IL8(down), u-HA(down), u-CK18(down) | 0.89 (0.12) |
| age < 65 | 2 | u-EGF(up), u-IL1b(down), u-IL4(down), u-IL8(down), u-vWF(down), u-HA(down), u-CK18(down) | 0.88 (0.11) |
| age < 65 | 3 | u-EGF(up), u-IL1b(down), u-IL6(down), u-IL8(down), u-MMP9(down), u-HA(down), u-CK18(down) | 0.87 (0.13) |
| CI no | 1 | u-EGF(up), u-CRP(up), u-IL4(down), u-MCP1(up), u-VEGF(down), u-FAS(down), u-CK18(up) | 0.88 (0.15) |
| CI no | 2 | u-dDimer(down), u-EGF(up), u-CRP(up), u-IL4(down), u-IL6(down), u-sTNFR2(down), u-vWF(down) | 0.88 (0.14) |
| CI no | 3 | u-dDimer(down), u-EGF(up), u-CRP(up), u-IL4(down), u-IL6(down), u-sTNFR2(down), u-CK18(up) | 0.88 (0.21) |
| AC no | 1 | u-BTA(down), u-EGF(up), u-CRP(up), u-IL4(down), u-sTNFR(up), u-HA(down), u-CK18(up) | 0.86 (0.11) |
| AC no | 2 | u-EGF(up), u-IL1a(down), u-IL1b(down), u-IL4(down), u-sTNFR(up), u-VEGF(down), u-CK18(up) | 0.85 (0.14) |
| AC no | 3 | u-EGF(up), u-CRP(up), u-IL4(down), u-MMP9NG(up), u-NGAL(down), u-HA(down), u-CK18(up) | 0.85 (0.09) |
| Alcohol yes | 1 | u-EGF(up), u-IL1a(down), up-IL6(up), u-NGAL(down), u-sTNFR2(up), u-vWF(down), u-FAS(down) | 0.84 (0.13) |
| Alcohol yes | 2 | u-EGF(up), u-IL1a(down), u-IL2(down), u-IL6(down), u-NGAL(down), u-VEGF(down), u-vWF(down) | 0.84 (0.11) |
| Alcohol yes | 3 | u-EGF(up), u-IL1a(down), u-NGAL(down), u-NSE(up), u-sTNFR2(up), u-vWF(down), u-CK18(down) | 0.84 (0.12) |
| AC yes | 1 | u-BTA(down), u-CRP(up), u-IL1b(down), u-IL8(down), u-sTNFR2(down), u-vWF(down), u-FAS(down) | 0.83 (0.19) |
| AC yes | 2 | u-dDimer(down), u-IL4(up), u-IL6(down), u-MMP9(down), u-NSE(down), u-VFGF(down), u-CK18(up) | 0.83 (0.15) |
| AC yes | 3 | u-BTA(down), u-CRP(up), u-IL1a(down), u-IL2(down), u-sTNFR2(down), u-vWF(down), u-FAS(down) | 0.83 (0.18) |
| AH no | 1 | u-dDimer(down), u-CRP(up), u-IL2(down), u-NSE(up), u-VEGF(down), u-vWF(down), u-CK18(down) | 0.83 (0.12) |
| AH no | 2 | y-dDimer(down), u-CRP(up), u-IL2(down), u-NSE(up), u-TNFa(down), u-VEGF(down), u-HA(down) | 0.82 (0.14) |
| AH no | 3 | u-EGF(up), u-CRP(up), u-IL1a(down), u-IL1b(down), u-NGAL(down), u-VEGF(down), u-HA(down) | 0.81 (0.14) |
| CI yes | 1 | u-BTA(down), u-IL2(down), u-MMP9NG(down), u-NGAL(down), u-sTNFR(down), u-TNFa(up), u-VEGF(down) | 0.82 (0.14) |
| CI yes | 2 | u-BTA(down), u-IL2(down), u-MMP9NG(down), u-TM(down), u-sTNFR(down), u-vWF(down), u-FAS(down) | 0.79 (0.14) |
| CI yes | 3 | u-BTA(down), u-IL2(down), u-MMP9NG(down), u-sTNFR(down), u-VEGF(down), u-vWF(down), u-CK18(up) | 0.79 (0.13) |
| Protein no | 1 | u-dDimer(down), u-CRP(up), u-IL1a(down), u-IL4(down), u-MMP9MG(down), u-TM(up), u-CK18(up) | 0.82 (0.15) |
| Protein no | 2 | u-BTA(down), u-EGF(up), u-CRP(up), u-MMP9(down), u-NGAL(up), u-vWF(down), u-FAS(down) | 0.81 (0.15) |
| Protein no | 3 | u-BTA(down), u-CRP(up), u-NGAL(up), u-NSE(up), u-TM(up), u-TNFR2(down), u-vWF(down) | 0.81 (0.16) |
| Protein yes | 1 | u-EGF(down), u-IL1b(down), u-IL2(down), u-NSE(up), u-TM(down), u-VEGF(down), u-vWF(down) | 0.82 (0.16) |
| Protein yes | 2 | u-EGF(down), u-IL1b(down), u-MMP9(up), u-MMP9NG(up), u-TNFa(up), u-vWF(down), uHA(down) | 0.82 (0.17) |
| Protein yes | 3 | u-EGF(down), u-IL2(down), u-IL4(down), u-NGAL(down), u-NSE(up), u-TM(down), u-CK18(up) | 0.81 (0.19) |
| Alcohol no | 1 | u-IL1b(down), u-IL2(down), u-IL6(down), u-IL8(down), u-NGAL(down), u-NSE(up), u-CK18(up) | 0.81 (0.13) |
| Alcohol no | 2 | u-IL1a(down), u-IL2(down), u-IL6(down), u-IL8(down), u-NGAL(down), u-HA(down), u-CK18(up) | 0.81 (0.16) |
| Alcohol no | 3 | u-BTA(down), u-IL1a(down), u-IL2(down), u-IL8(down), u-NGAL(down), u-VEGF(down), u-CK18(up) | 0.81 (0.15) |
| AH yes | 1 | u-CRP(up), u-IL1b(down), u-IL6(down), u-IL8(down), u-MMP9(up), u-NGAL(up), u-vWF(down) | 0.81 (0.18) |
| AH yes | 2 | u-dDimer(down), u-IL8(down), u-MMP9(up), u-NSE(down), u-TM(up), u-sTNFR2(down), u-vWF(down) | 0.8 (0.18) |

TABLE 13-continued

Urine 7 biomarker classifiers

| Name | Num | Biomarker | AUC |
|---|---|---|---|
| AH yes | 3 | u-BTA(down), u-dDimer(down), u-EGF(down), u-IL4(down), u-NGAL(up), u-NSE(down), u-vWF(down) | 0.8 (0.14) |
| Age > 65 | 1 | u-dDimer(down), u-CRP(down), u-IL1a(down), u-IL2(down), u-NSE(down), u-vWF(down), u-HA(up) | 0.81 (0.19) |
| Age > 65 | 2 | u-BTA(down), u-IL1a(down), u-IL8(down), u-MMP9NG(up), u-vWF(down), u-HA(up), u-CK18(up) | 0.8 (0.18) |
| Age > 65 | 3 | u-Dimer(down), u-IL1a(down), u-MCP1(down), u-NSE(down), u-TNFa(down), u-vWF(down), u-HA(up) | 0.8 (0.18) |
| Smoking yes | 1 | u-EGF(up), u-IL1a(down), u-MMP9(up), u-MMP9NG(up), u-NSE(down), u-VEGF(down), u-vWF(down) | 0.8 (0.12) |
| Smoking yes | 2 | u-EGF(up), u-IL1b(down), u-NGAL(down), u-NSE(down), u-sTNFR(up), u-VEGF(down), u-vWF(down) | 0.8 (0.13) |
| Smoking yes | 3 | u-dDimer(down), u-EGF(up), u-IL1a(down), u-IL8(down), u-NSE(down), u-vWF(down), u-FAS(down) | 0.79 (0.12) |
| OCR no | 1 | u-BTA(down), u-dDimer(down), u-MMP9NG(up), u-TM(up), u-TNFa(down), u-vWF(down), u-HA(down) | 0.8 (0.13) |
| OCR no | 2 | u-IL6(-(down) u-NGAL(up), u-TNFR(down), u-TNFa(down), u-vWF(down), u-FAS(down), u-CK18(up) | 0.8 (0.13) |
| OCR no | 3 | u-BTA(down), u-IL1a(down), u-IL1b(down), u-IL6(down), u-NGAL(up), u-TNFa(down), u-CK18(up) | 0.79 (0.16) |

TABLE 14

Plasma biomarker classifiers

| name | num | Biomarker | AUC |
|---|---|---|---|
| smoking no | 1 | p-dDimer(down), p-EGF(down), p-IL1a(down), p-Ifng(down), p-MMPNG(down), p-TNFa(down), p-VEGF(up) | 0.8 (0.19) |
| smoking no | 2 | p-EGF(down), P-IL1a(down), p-IL2(down), p-MMPNG(down), p-NGAL(down), p-NSE(up), p-TM(down) | 0.79 (0.2) |
| smoking no | 3 | p-IL1a(down), p-Ifng(down), p-MMPNG(down), p-NGAL(down), p-NSE(up), p-TM(down), p-TNFa(down) | 0.78 (0.18) |
| OCR yes | 1 | p-IL1b(up), p-IL8(down), p-Ifng(down), p-MCP1(down), p-MMPNG(down), p-TM(down), p-sTNFR(up) | 0.79 (0.16) |
| OCR yes | 2 | p-IL1a(down), p-IL4(down), p-IL8(down), p-IL10(down), p-MCP1(down), p-TM(down), p-sTNFR(up) | 0.77 (0.18) |
| OCR yes | 3 | p-IL1a(down), p-IL1b(up), p-IL6(down), p-IL8(down), p-NGAL(down), p-NSE(down), p-VEGF(down) | 0.77 (0.13) |
| OCR no | 1 | p-IL4(up), p-IL6(down), p-IL10(down), p-MMPNG(down), p-NGAL(up), p-sTNFR(up), p-VEGF(up) | 0.78 (0.09) |
| OCR no | 2 | p-dDimer(down), p-CRP(up), p-IL1a(down), p-IL1b(down), p-IL2(down), p-IL4(up), p-MMPNG(down) | 0.78 (0.13) |
| OCR no | 3 | p-dDimer(down), p-CRP(up), p-IL1b(down), p-IL4(up), p-IL6(down), p-IL10(down), p-MMPNG(down) | 0.78 (0.13) |
| CI no | 1 | p-dDimer(down), p-IL1a(up), p-IL8(up), p-MMPNG(down), p-TM(down), p-TNFa(down), p-VEGF(up) | 0.76 (0.16) |
| CI no | 2 | p-dDimer(down), p-CRP(down), p-IL2(down), p-IL6(down), p-IL8(up), p-MMPNG(down), p-TNFa(down) | 0.76 (0.22) |
| CI no | 3 | p-dDimer(down), p-IL1a(down), p-IL1b(down), p-IL8(up), p-MMPNG(down), p-TM(down), p-VEGF(up) | 0.76 (0.19) |
| AC yes | 1 | p-dDimer(up), p-EGF(up), p-IL6(down), p-IL10(down), p-Ifng(down), p-MCP1(down), p-TNFa(down) | 0.74 (0.19) |
| AC yes | 2 | p-dDimer(up), p-IL10(down), p-Ifng(down), p-MCP1(down), p-NGAL(up), p-sTNFR(down), p-VEGF(up) | 0.73 (0.2) |
| AC yes | 3 | p-dDimer(up), p-IL6(down), p-IL8(down), p-IL10(down), p-NSE(up), p-TM(down), p-TNFa(down) | 0.72 (0.2) |
| age < 65 | 1 | p-CRP(up), p-IL4(up), P-IL6(down), p-IL8(down), p-IL10(down), p-MMPNG(down), p-TNFa(down) | 0.74 (0.19) |
| age < 65 | 2 | p-EGF(down), p-CRP(up), p-IL1b(down), p-IL8(down), p-Ifng(down), p-NGAL(down), p-sTNFR(up) | 0.74 (0.16) |
| age < 65 | 3 | p-dDimer(down), p-EGF(down), p-CRP(up), p-IL8(down), p-IL10(down), p-Ifng(down), p-MMPNG(down) | 0.73 (0.16) |
| alcohol no | 1 | p-IL1a(up), p-IL2(down), p-IL8(down), p-Ifng(down), p-MMPNG(down), p-sTNFR(up), p-TNFa(down) | 0.74 (0.16) |
| alcohol no | 2 | p-IL1a(up), p-IL2(down), p-IL6(down), p-IL10(down), p-MMPNG(down), p-TNFa(down), p-VEGF(down) | 0.73 (0.17) |
| alcohol no | 3 | p-IL1a(up), p-IL4(up), p-IL6(down), p-IL10(down), p-MMPNG(down), p-NGAL(down), p-VEGF(down) | 0.73 (0.19) |
| AH no | 1 | p-EGF(down), p-CRP(up), p-IL1a(down), p-IL8(down), p-MMPNG(down), p-TNFa(up), p-VEGF(up) | 0.74 (0.13) |
| AH no | 2 | p-EGF(down), p-CRP(up), p-IL1b(up), p-IL8(down), p-MMPNG(down), p-sTNFR(up), p-VEGF(up) | 0.73 (0.15) |

TABLE 14-continued

Plasma biomarker classifiers

| name | num | Biomarker | AUC |
|---|---|---|---|
| AH no | 3 | p-dDimer(down), p-EGF(down), p-IL1b(up), p-IL6(down), p-IL8(down), p-MMPNG(down), p-VEGF(up) | 0.72 (0.14) |
| AC no | 1 | p-IL1b(down), p-IL6(down), p-IL8(down), p-MMPNG(down), p-sTNFR(up), p-TNFa(down), p-VEGF(down) | 0.74 (0.11) |
| AC no | 2 | p-dDimer(down), p-IL1a(down), p-IL4(up), p-IL8(down), p-NGAL(down), p-TM(down), p-sTNFR(up) | 0.73 (0.12) |
| AC no | 3 | p-IL1a(down), p-IL1b(down), p-IL4(up), p-IL6(down), p-IL8(down), p-MMPNG(down), p-sTNFR(up) | 0.72 (0.13) |
| protein no | 1 | p-EGF(down), p-IL1a(down), p-IL2(down), p-IL4(up), p-MCP1(up), p-MMPNG(down), p-NGAL(down) | 0.72 (0.13) |
| protein no | 2 | p-dDimer(down), p-EGF(down), p-CRP(down), p-IL8(down), p-MMPNG(down), p-NSE(up), p-VEGF(down) | 0.71 (0.17) |
| protein no | 3 | p-dDimer(down), p-EGF(down), p-IL1b(down), p-IL8(up), p-IL10(down), p-MMPNG(down), p-VEGF(down) | 0.71 (0.14) |
| protein yes | 1 | p-IL1a(down), p-IL2(up), p-IL8(down), p-IL10(down), p-Ifng(down), p-MCP1(down), p-TM(down) | 0.71 (0.19) |
| protein yes | 2 | p-IL1a(down), p-IL2(up), p-IL8(down), p-Ifng(down), p-MCP1(down), p-MMPNG(down), p-TM(down) | 0.69 (0.21) |
| protein yes | 3 | p-EGF(up), p-CRP(up), p-IL1a(down), p-IL4(up), p-IL8(down), p-Ifng(down), p-TNFa(down) | 0.69 (0.13) |
| age > 65 | 1 | p-CRP(down), p-IL1a(up), p-IL10(down), p-MMPNG(down), p-TM(down), p-TNFa(up), p-VEGF(down) | 0.71 (0.13) |
| age > 65 | 2 | p-IL1a(up), p-IL6(down), p-IL10(down), p-MMPNG(down), p-TM(down), p-TNFa(up), p-VEGF(down) | 0.7 (0.14) |
| age > 65 | 3 | p-CRP(down), p-IL1a(up), p-IL4(up), p-IL6(down), p-MMPNG(down), p-TM(down), p-TNFa(up) | 0.69 (0.14) |
| alcohol yes | 1 | p-dDimer(down), p-IL1b(down), p-IL4(up), p-MMPNG(down), p-NGAL(down), p-NSE(up), p-VEGF(up) | 0.7 (0.16) |
| alcohol yes | 2 | p-dDimer(down), p-IL1a(up), p-IL2(down), p-MMPNG(down), p-NSE(up), p-sTNFA(up), p-TNFa(down) | 0.68 (0.12) |
| alcohol yes | 3 | p-dDimer(down), p-CRP(up), p-IL1a(up), p-IL4(up), p-IL10(down), p-NSE(up), p-sTNFR(up) | 0.67 (0.15) |
| smoking yes | 1 | p-IL1a(down), p-IL1b(up), p-IL2(up), p-IL4(up), p-IL10(down), p-MMPNG(down), p-TNFa(down) | 0.68 (0.16) |
| smoking yes | 2 | p-dDimer(down), p-IL1a(down), p-IL4(up), p-Ifng(up), p-MCP1(down), p-MMPNG(down), p-TM(down) | 0.68 (0.1) |
| smoking yes | 3 | p-dDimer(down), p-EGF(up), p-IL1a(down), p-IL4(up), p-IL10(down), p-Ifng(up), p-MMPNG(down) | 0.67 (0.14) |
| AH yes | 1 | p-dDimer(up), p-EGF(up), p-CRP(down), p-IL2(down), p-IL10(down), p-MMPNG(down), p-TM(down) | 0.64 (0.17) |
| AH yes | 2 | p-CRP(down), p-IL1a(down), p-IL1b(down), p-IL4(up), p-IL6(down), p-Ifng(down), p-sTNFR(up) | 0.62 (0.12) |
| AH yes | 3 | p-EGF(up), p-CRP(down), p-IL4(up), p-IL6(down), p-IL10(down), p-Ifng(down), p-MMPNG(down) | 0.62 (0.14) |
| CI yes | 1 | p-IL1a(down), p-IL8(down), p-IL10(down), p-MCP1(down), p-MMPNG(down), p-NSE(up), p-TM(down) | 0.62 (0.13) |
| CI yes | 2 | p-dDimer(down), p-IL2(down), p-IL6(up), p-IL8(down), p-MMPNG(down), p-TM(down), p-sTNFR(up) | 0.61 (0.14) |
| CI yes | 3 | p-IL1a(down), p-IL2(down), p-IL6(up), p-IL8(down), p-MCP1(down), p-MMPNG(down), pNSE(up) | 0.61 (0.15) |

TABLE 15

Serum 7 biomarker classifiers

| name | num | Biomarker | AUC |
|---|---|---|---|
| smoking no | 1 | s-CEA(up), s-EGF(down), s-CRP(down), s-IL4(up), s-IL8(down), s-NGAL(down), s-NSE(down) | 0.94 (0.13) |
| smoking no | 2 | s-CEA(up), s-IL6(down), s-IL8(down), s-Ifngg(down), s-NGAL(down), s-TM(down), s-VEGF(up) | 0.94 (0.1) |
| smoking no | 3 | s-CEA(up), s-FPSA(up), s-CRP(down), s-IL4(up), s-MMPNG(down), s-NGAL(down), s-TM(down) | 0.94 (0.12) |
| age < 65 | 1 | s-CEA(down), s-IL1a(up), s-IL2(down), s-IL4(up), s-IL8(down), s-Ifngg(down), s-MMPNG(down) | 0.87 (0.09) |
| age < 65 | 2 | s-CEA(down), s-EGF(down), s-FPSA(up), s-IL1a(up), s-IL4(up), s-IL8(down), s-VEGF(up) | 0.86 (0.12) |
| age < 65 | 3 | s-CEA(down), s-IL1a(up), s-IL3(down), s-IL8(down), s-Ifngg(down), s-MCP1(down), s-sTNFR(up) | 0.84 (0.17) |
| OCR no | 1 | s-CEA(down), s-dDimer(down), s-IL4(up) s-IL10(down), s-MCP1(up), s-MMPNG(down), s-NSE(up) | 0.83 (0.11) |

TABLE 15-continued

Serum 7 biomarker classifiers

| name | num | Biomarker | AUC |
|---|---|---|---|
| OCR no | 2 | s-CEA(down), s-dDimer(down), s-Ifngg(down), s-MCP1(up), s-MMPNG(down), s-TM(up), s-TPSA(up) | 0.84 (0.12) |
| OCR no | 3 | s-CEA(down), s-dDimer(down), s-EGF(up), s-IL6(down), s-IL10(down), s-MMPNG(down), s-TM(up) | 0.84 (0.12) |
| CI no | 1 | s-FPSA(up), s-IL2(down), s-IL4(up), s-IL6(down), s-MMPNG(down), s-NGAL(down), s-sTNFR(up) | 0.84 (0.18) |
| CI no CI | 2 | s-CEA(down), s-EGF(up), s-FPSA(up), s-CRP(down), s-IL4(up), s-IL6(down), s-MMPNG(down) | 0.84 (0.15) |
| no alcohol | 3 | s-dDimer(down), s-IL1b(down), s-IL4(up), s-IL8(down), s-MCP1(up), s-NGAL(down), s-TM(up) | 0.84 (0.14) |
| no alcohol | 1 | s-CEA(down), s-CRP(down), s-IL4(up), s-IL6(down), s-IL10(down), s-sTNFR(up), s-TPSA(up) | 0.84 (0.18) |
| no alcohol | 2 | s-CEA(down), s-dDimer(down), s-EGF(down), s-IL1a(up), s-IL10(down), s-NSE(down), s-sTNFR(up) | 0.83 (0.12) |
| no AC yes | 3 | s-CEA(down), s-dDimer(down), s-IL1a(up), s-IL1b(up), s-IL4(up), s-TM(down), s-sTNFR(up) | 0.83 (0.13) |
| AC yes | 1 | s-FPSA(up), s-IL1b(down), s-IL10(down), s-NGAL(down), s-TM(up), s-TNFa(down), s-VEGF(up) | 0.84 (0.13) |
| AC yes | 2 | s-CEA(down), s-IL1b(down), s-IL4(up), s-NGAL(down), s-TM(up), s-TPSA(up), s-VEGF(up) | 0.8 (0.12) |
| OCR yes | 3 | s-FPSA(up), s-IL1b(up), s-IL4(up), s-IL10(down), s-NGAL(down), s-TM(up), s-VEGF(up) | 0.8 (0.22) |
| OCR yes | 1 | s-FPSA(up), s-IL1b(up), s-IL2(up), s-IL4(up), s-IL8(down), s-MMPNG(down), s-NGAL(down) | 0.84 (0.13) |
| OCR yes | 2 | s-CEA(down), s-dDimer(down), s-IL8(down), s-IL10(up), s-Ifngg(up), s-NGAL(down), s-NSE(down) | 0.83 (0.16) |
| AC no | 3 | s-CEA(down), s-EGF(down), s-CRP(down), s-IL10(up), s-MCP1(down), s-NGAL(down), s-NSE(down) | 0.82 (0.15) |
| AC no | 1 | s-CEA(down), s-IL1a(up), s-IL4(up), s-IL6(down), s-IL8(down), s-TM(down), s-sTNFR(up) | 0.83 (0.11) |
| AC no | 2 | s-CEA(down), s-IL1a(up), s-IL1b(down), s-IL4(up), s-IL8(down), s-MMPNG(down), s-VEGF(down) | 0.82 (0.11) |
| alcohol yes | 3 | s-CEA(down), s-IL1a(up), s-IL4(up), s-IL10(down), s-MMPNG(down), s-TM(up), s-TNFa(down) | 0.82 (0.1) |
| alcohol yes | 1 | s-EGF(up), s-CRP(up), s-IL8(down), s-MCP1(down), s-MMPNG(down), s-NGAL(down), s-sTNFR(up) | 0.83 (0.12) |
| alcohol yes | 2 | s-CEA(down), s-EGF(up). s-CRP(up), s-IL1b(down), s-MMPNG(down), s-NGAL(down), s-TM(down) | 0.82 (0.11) |
| protein yes | 3 | s-CEA(down), s-dDimer(down), s-IL1a(up), s-IL2(up), s-IL4(up), s-IL10(down), s-NGAL(down) | 0.82 (0.11) |
| protein yes | 1 | s-CEA(down), s-IL1b(up), s-IL2(up), s-IL4(up), s-IL8(down), s-NSE(down), s-TNFa(down) | 0.82 (0.18) |
| protein yes | 2 | s-CEA(down), s-EGF(down), s-IL4(up), s-IL8(down), s-IL10(down), s-TPSA(up), s-VEGF(up) | 0.82 (0.17) |
| age > 65 | 3 | s-CEA(down), s-IL1b(up), s-IL2(up), s-IL4(up), s-IL10(down), s-MMPNG(down), s-TM(down) | 0.82 (0.17) |
| age > 65 | 1 | s-CEA(down), s-dDimer(down), s-FPSA(up), s-CRP(down), s-IL10(down), s-NGAL(down), s-TM(down) | 0.81 (0.15) |
| age > 65 | 2 | s-CEA(down), s-dDimer(down), s-CRP(down), s-NGAL(down), s-NSE(down), s-TM(down), s-TPSA(up) | 0.8 (0.13) |
| AH no | 3 | s-dDimer(down), s-IL1a(up), s-IL8(up), s-Ifngg(up), s-MMPNG(down), s-NGAL(down), s-TM(down) | 0.79 (0.12) |
| AH no | 1 | s-CEA(down), s-dDimer(down), s-EGF(down) s-IL4(up), s-IL8(down), s-IL10(up), s-NSE(down) | 0.8 (0.11) |
| AH no | 2 | s-CEA(down), s-dDimer(down), s-CRP(up), s-IL4(up), s-MCP1(down), s-MMPNG(down), s-TNFa(up) | 0.8 (0.13) |
| protein no | 3 | s-CEA(down), s-dDimer(down), s-CRP(up), s-IL4(up), s-IL6(down), s-TM(down), s-TNFa(up) | 0.8 (0.18) |
| protein no | 1 | s-FPSA(up), s-CRP(down), s-IL2(down), s-IL6(down), s-NGAL(down), s-TNFa(down), s-VEGF(down) | 0.8 (0.12) |
| protein no | 2 | s-CEA(down), s-FPSA(up), s-CRP(down), s-IL6(down), s-IL10(down), s-NGAL(down), s-VEGF(down) | 0.78 (0.13) |
| AH yes | 3 | s-dDimer(down), s-FPSA(up), s-IL1b(down), s-Ifngg(up), s-MMPNG(down), s-NGAL(down), s-TM(up) | 0.78 (0.14) |
| AH yes | 1 | s-CEA(down), s-IL1a(down), s-IL1b(down), s-IL10(down), s-NGAL(down), s-sTNFR(up), s-TNFa(down) | 0.76 (0.22) |
| AH yes | 2 | s-CEA(down), s-IL1a(down), s-NGAL(down), s-NSE(down), s-TM(down), s-TNFa(down), s-TPSA(up) | 0.75 (0.16) |
| smoking yes | 3 | s-CEA(down), s-IL1b(down), s-IL4(up), s-IL10(down), s-MMPNG(down), s-NGAL(down), s-TM(down) | 0.75 (0.3) |
| smoking yes | 1 | s-EGF(up), s-CRP(down), s-IL10(down), s-MMPNG(down), s-NGAL(down), s-TM(down), s-VEGF(down) | 0.74 (0.13) |

TABLE 15-continued

Serum 7 biomarker classifiers

| name | num | Biomarker | AUC |
|---|---|---|---|
| smoking yes | 2 | s-CEA(down), s-CRP(down), s-IL10(down), s-MMPNG(down), s-NGAL(down), s-TM(down) s-TNFa(down) | 0.72 (0.14) |
| CI yes | 3 | s-CEA(down), s-dDimer(down), s-IL2(up), s-IL8(down), s-IL10(down), s-Ifngg(up), s-NSE(down) | 0.71 (0.16) |
| CI yes | 1 | s-CEA(down), s-CRP(down), s-IL1b(down), s-IL2(up), s-TM(down), s-sTNFR(up), s-TPSA(down) | 0.74 (0.16) |
| CI yes | 2 | s-CRP(down), s-IL1b(down), s-IL2(up), s-IL6(up), s-MMPNG(down), s-NGAL(down), s-TNFa(up) | 0.74 (0.16) |
|  | 3 | s-CRP(down), s-IL1b(down), s-IL2(up), s-MMPNG(down), s-NGAL(down), s-NSE(down), s-TNFa(up) | 0.74 (0.14) |

TABLE 16

Urine 7 biomarker urothelial cancer (UC) classifiers. In parenthesis the pattern for up or down regulation of a biomarker in UC are shown.

| name | num | Biomarker | AUC |
|---|---|---|---|
| smoking no | 1 | u-EGF(down), u-CRP(down), u-IL8(up), u-NGAL(up), u-NSE(down), u-TM(down), u-HA(up) | 0.92 (0.1) |
| smoking no | 2 | u-BTA(up), u-EGF(down), u-IL8(up), u-MCP1(up), u-NGAL(up), u-NSE(down), u-sTNFR(down) | 0.89 (0.14) |
| smoking no | 3 | u-BTA(up), u-IL4(up), u-MCP1(up), u-TM(down), u-sTNFR2(up), u-vWF(up), u-FAS(up) | 0.89 (0.12) |
| OCR yes | 1 | u-EGF(down), u-IL1a(up), u-IL8(up), u-MMP9NG(down), u-NSE(down), u-vWF(up), u-CK18(up) | 0.9 (0.1) |
| OCR yes | 2 | u-EGF(down), u-IL6(up), u-IL8(up), u-MMP9NG(down), u-NSE(down), u-VEGF(up), u-vWF(up) | 0.88 (0.13) |
| OCR yes | 3 | u-CRP(down), u-IL1a(up), u-IL6(up), u-IL8(up), u-MMP9NG(down), u-NSE(down), u-VEGF(up) | 0.87 (0.13) |
| age < 65 | 1 | u-EGF(down), u-CRP(down), u-IL1b(up), u-IL2(up), u-IL3(up), u-HA(up), u-CK18(up) | 0.89 (0.12) |
| age < 65 | 2 | u-EGF(down), u-IL1b(up), u-IL4(up), u-IL8(up), u-vWF(up), u-HA(up), u-CK18(up) | 0.88 (0.11) |
| age < 65 | 3 | u-EGF(down), u-IL1b(up), u-IL6(up), u-IL8(up), u-MMP9(up), u-HA(up), u-CK18(up) | 0.87 (0.13) |
| CI no | 1 | u-EGF(down), u-CRP(down) u-IL4(up), u-MCP1(down), u-VEGF(up), u-FAS(up), u-CK18(down) | 0.88 (0.15) |
| CI no | 2 | u-dDimer(up), u-EGF(down), u-CRP(down), u-IL4(up), u-IL6(up), u-sTNFR2(up), u-vWF(up) | 0.88 (0.14) |
| CI no | 3 | u-dDimer(up), u-EGF(down), u-CRP(down), u-IL4(up), u-IL6(up), u-sTNFR2(up), u-CK18(down) | 0.88 (0.21) |
| AC no | 1 | u-BTA(up), u-EGF(down), u-CRP(down), u-IL4(up), u-sTNFR(down), u-HA(up), u-CK18(down) | 0.86 (0.14) |
| AC no | 2 | u-EGF(down), u-IL1a(up), u-IL1b(up), u-IL4(up), u-sTNFA(down), u-VEGF(up), u-CK18(down) | 0.85 (0.14) |
| AC no | 3 | u-EGF(down), u-CRP(down), u-IL4(up), u-MMP9NG(down), u-NGAL(up), u-HA(up), u-CK18(down) | 0.85 (0.09) |
| alcohol yes | 1 | u-EGF(down), u-IL1a(up), u-IL6(up), u-NGAL(up), u-sTNFR2(down), u-vWF(up), u-FAS(up) | 0.84 (0.13) |
| alcohol yes | 2 | u-EGF(down), u-IL1a(up), u-IL2(up), u-IL6(up), u-NGAL(up), u-VEGF(up), u-vWF(up) | 0.84 (0.11) |
| alcohol yes | 3 | u-EGF(down), u-IL1a(up), u-NGAL(up), u-NSE(down), u-sTNFR2(down), u-vWF(up), u-CK18(up) | 0.84 (0.12) |
| AC yes | 1 | u-BTA(up), u-CRP(down), u-IL1b(up), u-sTNFR2(up), u-vWF(up), u-FAS(up) | 0.83 (0.19) |
| AC yes | 2 | u-dDimer(up), u-IL4(down), u-IL69up), u-MMP9(up), u-NSE(up), u-VEGF(up), u-CK18(down) | 0.83 (0.15) |
| AC yes | 3 | u-BTA(up), u-CRP(down), u-IL1a(up), u-IL2(up), u-sTNFR2(up), u-vWF(up), u-FAS(up) | 0.83 (0.18) |
| AH no | 1 | u-dDimer(up), u-CRP(down), u-IL2(up), u-NSE(down) u-VEGF(up), u-vWF(up), u-CK18(up) | 0.83 (0.12) |
| AH no | 2 | u-dDimer(up), u-CRP(down), u-IL2(up), u-NSE(down), u-TNFa(up), u-VEGF(up), u-HA(up) | 0.82 (0.14) |
| AH no | 3 | u-EGF(down), u-CRP(down), u-IL1a(up), u-IL1b(up), u-NGAL(up), u-VEGF(up), u-HA(up) | 0.81 (0.14) |
| CI yes | 1 | u-BTA(up), u-IL2(up), u-MMP9NG(up), u-NGAL(up), u-sTNFR(up), u-TNFa(down), u-VEGF(up) | 0.82 (0.14) |
| CI yes | 2 | u-BTA(up), u-IL2(up), u-MMP9NG(up), u-TM(up), u-sTNFR(up), u-vWF(up), u-FAS(up) | 0.79 (0.14) |
| CI yes | 3 | u-BTA(up), u-IL2(up), u-MMP9NG(up), u-VEGF(up), u-vWF(up), u-CK18(down) | 0.79 (0.13) |

TABLE 16-continued

Urine 7 biomarker urothelial cancer (UC) classifiers. In parenthesis the pattern for up or down regulation of a biomarker in UC are shown.

| name | num | Biomarker | AUC |
|---|---|---|---|
| protein no | 1 | u-dDimer(up), u-CRP(down), u-IL1a(up), u-IL4(up), u-MMP9NG(up), u-TM(down), u-CK18(down) | 0.82 (0.15) |
| protein no | 2 | u-MTA(up), u-EGF(down), u-CRP(down), u-MMP9(up, u-NGAL(down), u-vWF(up), u-FAS(up) | 0.81 (0.15) |
| protein no | 3 | u-BTA(up), u-CRP(down), u-NGAL(down), u-NSE(down), u-TM(down), u-sTNFR2(up), u-vWF(up) | 0.81 (0.16) |
| protein yes | 1 | u-EGF(up), u-IL1b(up), u-IL2(up), u-NSE(down), u-TM(up), u-VEGF(up), u-vWF(up) | 0.82 (0.16) |
| protein yes | 2 | u-EGF(up), u-IL1b(up), u-MMP9(down), u-MMP9NG(down), u-TNFa(down), u-vWF(up), u-HA(up) | 0.82 (0.17) |
| protein yes | 3 | u-EGF(up), u-IL2(up), u-IL4(up), u-NGAL(up), u-NSE(down), u-TM(up), u-CK18(down) | 0.81 (0.19) |
| alcohol no | 1 | u-IL1b(up), u-IL2(up), u-IL6(up), u-IL8(up), u-NGAL(up), u-NSE(down), u-CK18(down) | 0.81 (0.13) |
| alcohol no | 2 | u-IL1a(up), u-IL2(up), u-IL6(up), u-IL8(up), u-NGAL(up), u-HA(up), u-CK18(down) | 0.81 (0.16) |
| alcohol no | 3 | u-BTA(up), u-IL1a(up), u-IL2(up), u-IL8(up), u-NGAL(up), u-VEGF(up), u-CK18(down) | 0.81 (0.15) |
| AH yes | 1 | u-CRP(down), u-IL1b(up), u-IL6(up), u-IL8(up), u-MMP9(down), u-NGAL(up), u-vWF(up) | 0.81 (0.18) |
| AH yes | 2 | u-dDimer(up), u-IL8(up), u-MMP9(down), u-NSE(up), u-TM(down), u-sTNFA2(up), u-vWF(up) | 0.8 (0.18) |
| AH yes | 3 | u-BTA(up), u-dDimer(up), u-EGF(up), u-IL4(up), u-NGAL(down), u-NSE(up), u-vWF(up) | 0.8 (0.14) |
| age > 65 | 1 | u-dDimer(up), u-CRP(up), u-IL1a(up), u-IL2(up), u-NSE(up), u-vWF(up), u-HA(down) | 0.81 (0.19) |
| age > 65 | 2 | u-BTA(up), u-IL1a(up), u-IL8(up), u-MMP9NG(down), u-vWF(up), u-HA(down), u-CK18(down) | 0.8 (0.18) |
| age > 65 | 3 | u-dDimer(up), u-IL1a(up), u-MCP1(up), u-NSE(up), u-TNFa(up), u-vWF(up), u-HA(down) | 0.8 (0.18) |
| smoking yes | 1 | u-EGF(down), u-IL1a(up), u-MMP9(down), u-MMP9NG(down), u-NSE(up), u-VEGF(up), u-vWF(up) | 0.8 (0.12) |
| smoking yes | 2 | u-EGF(down), u-IL1b(up), u-NGAL(up), u-sTNFR(down), u-VEGF(up), u-vWF(up) | 0.8 (0.13) |
| smoking yes | 3 | u-dDimer(up), u-EGF(down), u-IL1a(up), u-IL8(up), u-NSE(up), u-vWF(up), u-FAS(up) | 0.79 (0.12) |
| OCR no | 1 | u-BTA(up), u-dDimer(up), u-MMP9NG(down), u-TM(down), u-TNFa(up), u-vWF(up), u-HA(up) | 0.8 (0.13) |
| OCR no | 2 | u-IL6(up), u-NGAL(down), u-sTNFR(up), u-TNFa(up), u-vWF(up), u-FAS(up), u-CK18(down) | 0.8 (0.13) |
| OCR no | 3 | u-BTA(up), u-IL1a(up), u-IL1b(up), u-IL6(up), u-NGAL(down), u-TNFa(up), u-CK18(down) | 0.79 (0.16) |

TABLE 17

Serum 7 biomarker urothelial cancer (UC) classifiers. In parenthesis the pattern for up or down regulation of a biomarker in UC are shown.

| name | num | Biomarker | AUC |
|---|---|---|---|
| smoking no | 1 | s-CEA(down), s-EGF(up), s-CRP(up), s-IL4(down), s-IL8(up), s-NGAL(up), s-NSE(up) | 0.94 (0.13) |
| smoking no | 2 | s-CEA(down), s-IL6(up), s-IL8(up), s-Ifngg(up), s-NGAL(up), s-TM(up, s-VEGF(down) | 0.94 (0.1) |
| smoking no | 3 | s-CEA(down), s-FPSA(down), s-CRP(up), s-IL4(down), s-MMPNG(up), s-NGAL(up), s-TM(up) | 0.94 (0.12) |
| age < 65 | 1 | s-CEA(up), s-IL1a(down), s-IL2(up), s-IL4(down), s-IL8(up), s-Ifngg(up), s-MMPNG(up) | 0.87 (0.09) |
| age < 65 | 2 | s-CEA(up), s-EGF(up), s-FPSA(down), s-IL1a(down), s-IL4(down), s-IL8(up), s-VEGF(down) | 0.86 (0.12) |
| age < 65 | 3 | s-CEA(up), s-IL1a(down), s-IL2(up), s-IL8(up), s-Ifngg(up), s-MCP1(up), s-sTNFA(down) | 0.84 (0.17) |
| OCR no | 1 | s-CEA(up), s-dDimer(up), s-IL4(down), s-IL10(up), s-MCP1(down), s-MMPNG(up), s-NSE(down) | 0.85 (0.11) |
| OCR no | 2 | s-CEA(up), s-dDimer(up), s-Ifngg(up), s-MCP1(down), s-MMPNG(up), s-TM(down), s-TPSA(down) | 0.84 (0.12) |
| OCR no | 3 | s-CEA(up), s-dDimer(up), s-EGF(down), s-IL6(up), s-MMPNG(up), s-TM(down) | 0.84 (0.12) |
| CI no | 1 | s-FPSA(down), s-IL2(up), s-IL4(down), s-IL6(up), s-MMPNG(up), s-NGAL(up), s-sTNFR(down) | 0.84 (0.18) |
| CI no | 2 | s-CEA(up), s-EGF(down), s-FPSA(down), s-CRP(up), s-IL4(down), s-IL6(up), s-MMPNG(up) | 0.84 (0.15) |

TABLE 17-continued

Serum 7 biomarker urothelial cancer (UC) classifiers. In parenthesis the pattern for up
or down regulation of a biomarker in UC are shown.

| name | num | Biomarker | AUC |
| --- | --- | --- | --- |
| CI no | 3 | s-dDimer(up), s-IL1b(up), s-IL4(down), s-IL8(up), s-MCP1(down), s-NGAL(up), s-TM(down) | 0.84 (0.14) |
| alcohol no | 1 | s-CEA(up), s-CRP(up), s-IL4(down), s-IL6(up), s-IL10(up), s-sTNFR(down), s-TPSA(down) | 0.84 (0.18) |
| alcohol no | 2 | s-CEA(up), s-dDimer(up), s-EGF(up), s-IL1a(down), s-IL10(up), s-NSE(up), s-sTNFA(down) | 0.83 (0.12) |
| alcohol no | 3 | s-CEA(up), s-dDimer(up), s-IL1a(down), s-IL1b(down), s-IL4(down), s-TM(up) s-sTNFR(down) | 0.83 (0.13) |
| AC yes | 1 | s-FPSA(down), s-IL1b(up), s-IL10(up), s-NGAL(up), s-TM(down), s-TNFa(up), s-VEGF(down) | 0.84 (0.13) |
| AC yes | 2 | s-CEA(up), s-IL1b(up), s-IL4(down), s-NGAL(up), s-TM(down), s-TPSA(down), s-VEGF(down) | 0.8 (0.12) |
| AC yes | 3 | s-FPSA(down), s-IL1b(up), s-IL4(down), s-IL10(up), s-NGAL(up), s-TM(down), s-VEGF(down) | 0.8 (0.22) |
| OCR yes | 1 | s-FPSA(down), s-IL1b(down), s-IL2(down), s-IL4(down), s-IL8(up), s-MMPNG(up), s-NGAL(up) | 0.84 (0.13) |
| OCR yes | 2 | s-CEA(up), s-dDimer(up), s-IL8(up), s-IL10(down), s-Ifngg(down), s-NGAL(up), s-NSE(up) | 0.83 (0.16) |
| OCR yes | 3 | s-CEA(up), s-EGF(up), s-CRP(up), s-IL10(down), s-MCP1(up), s-NGAL(up), s-NSE(up) | 0.82 (0.15) |
| AC no | 1 | s-CEA(up), s-IL1a(down), s-IL4(down), s-IL6(up), s-IL8(up), s-TM(up), s-sTNFR(down) | 0.83 (0.11) |
| AC no | 2 | s-CEA(up), s-IL1a(down), s-IL1b(up), s-IL4(down), s-IL8(up), s-MMPNG(up), s-VEGF(up) | 0.82 (0.11) |
| AC no | 3 | s-CEA(up), s-IL1a(down), s-IL4(down), s-IL10(up), s-MMPNG(up), s-TM(up), s-TNFa(up) | 0.83 (0.1) |
| alcohol yes | 1 | s-EGF(down), s-CRP(down), s-IL8(up), s-MCP1(up), s-MMPNG(up), s-NGAL(up), s-sTNFR(down) | 0.83 (0.12) |
| alcohol yes | 2 | s-CEA(up), s-EGF(down), s-CRP(down), s-IL1b(up), s-MMPNG(up), s-NGAL(up), s-TM(up) | 0.82 (0.11) |
| alcohol yes | 3 | s-CEA(up), s-dDimer(up), s-IL1a(down), s-IL2(down), s-IL4(down), s-IL10(up), s-NGAL(up) | 0.82 (0.11) |
| protein yes | 1 | s-CEA(up), s-IL1b(down), s-IL2(down), s-IL4(down), s-IL8(up), s-NSE(up) s-TNFa(up) | 0.82 (0.18) |
| protein yes | 2 | s-CEA(up), s-EGF(up), s-IL4(down), s-IL8(up), s-IL10(up), s-TPSA(down), s-VEGF(down) | 0.82 (0.17) |
| protein yes | 3 | s-CEA(up), s-IL1b(down), s-IL2(down), s-IL4(down), s-IL10(up), s-MMPNG(up), s-TM(up) | 0.82 (0.17) |
| age > 65 | 1 | s-CEA(up), s-dDimer(up), s-FPSA(down), s-CRP(up), s-IL10(up), s-NGAL(up), s-TM(up) | 0.81 (0.15) |
| age > 65 | 2 | s-CEA(up), s-dDimer(up), s-CRP(up), s-NGAL(up), s-NSE(up), s-TM(up), s-TPSA(down) | 0.8 (0.13) |
| age > 65 | 3 | s-dDimer(up), s-IL1a(down), s-IL8(down), s-Ifngg(down), s-MMPNG(up), s-NGAL(up), s-TM(up) | 0.79 (0.12) |
| AH no | 1 | s-CEA(up), s-dDimer(up), s-EGF(up), s-IL4(down), s-IL8(up), s-IL10(down), s-NSE(up) | 0.8 (0.11) |
| AH no | 2 | s-CEA(up), s-dDimer(up), s-CRP(down), s-IL4(down), s MCP1(up), s-MMPNG(up), s-TNFa(down) | 0.8 (0.13) |
| AH no | 3 | s-CEA(up), s-dDimer(up), s-CRP(down), s-IL4(down), s-IL6(up), s-TM(up), s-TNFa(down) | 0.8 (0.18) |
| protein no | 1 | s-FPSA(down), s-CRP(up), s-IL2(up), s-IL6(up), s-NGAL(up), s-TNFa(up), s-VEGF(up) | 0.8 (0.12) |
| protein no | 2 | s-CEA(up), s-FPSA(down), s-CRP(up), s-IL5(up), s-IL10(up), s-NGAL(up), s-VEGF(up) | 0.78 (0.13) |
| protein no | 3 | s-dDimer(up), s-FPSA(down), s-IL1b(up), s-Ifngg(down), s-MMPNG(up), s-NGAL(up), s-TM(down) | 0.78 (0.14) |
| AH yes | 1 | s-CEA(up), s-IL1a(up), s-IL1b(up), s-IL10(up), s-NGAL(up), s-sTNFA(down), s-TNFa(up) | 0.76 (0.22) |
| AH yes | 2 | s-CEA(up), s-IL1a(up), s-NGAL(up), s-NSE(up), s-TM(up), s-TNFa(up), s-TPSA(down) | 0.75 (0.16) |
| AH yes | 3 | s-CEA(up), s-IL1b(up), s-IL4(down), s-IL10(up), s-MMPNG(up), s-NGAL(up), s-TM(up) | 0.75 (0.2) |
| smoking yes | 1 | s-EGF(down), s-CRP(up), s-IL10(up), s-MMPNG(up), NGAL(up), s-TM(up), s-VEGF(up) | 0.74 (0.13) |
| smoking yes | 2 | s-CEA(up), s-CRP(up), s-IL10(up), s-MMPNG(up), s-NGAL(up), s-TM(up), s-TNFa(up) | 0.72 (0.14) |
| smoking yes | 3 | s-CEA(up), s-dDimer(up), s-IL2(down), s-IL8(up), s-IL10(up), s-Ifngg(down), s-NSE(up) | 0.71 (0.16) |
| CI yes | 1 | s-CEA(up), s-CRP(up), s-IL1b(up), s-IL2(down), s-TM(up), s-sTNFR(down), s-TPSA(up) | 0.74 (0.16) |
| CI yes | 2 | s-CRP(up), s-IL1b(up), s-IL2(down), s-IL6(down), s-MMPNG(up), s-NGAL(up), s-TNFa(down) | 0.74 (0.16) |
| CI yes | 3 | s-CRP(up), s-IL1b(up), s-IL2(down), s-MPNG(up), s-NGAL(up), s-NSE(up), s-TNFa(down) | 0.74 (0.14) |

TABLE 18

Plasma 7 biomarker urothelial cancer (UC) classifiers. In parenthesis the pattern for up or down regulation of a biomarker in UC are shown.

| name | num | Biomarker | AUC |
|---|---|---|---|
| smoking no | 1 | p-dDimer(up), p-EGF(up), p-IL1a(up), p-Ifng(up), p-MMPNG(up), p-TNFa(up), p-VEGF(down) | 0.8 (0.19) |
| smoking no | 2 | p-EGF(up), p-IL1a(up), p-IL2(up), p-MMPNG(up), p-NGAL(up), p-NSE(down), p-TM(up) | 0.79 (0.2) |
| smoking no | 3 | p-IL1a(up), p-Ifng(up), p-MMPNG(up), p-NGAL(up), p-NSE(down), p-TM(up), p-TNFa(up) | 0.78 (0.18) |
| OCR yes | 1 | p-IL1b(down), p-IL8(up), p-Ifng(up), p-MCP1(up), p-MMPNG(up), p-TM(up), p-sTNFR(down) | 0.79 (0.16) |
| OCR yes | 2 | p-IL1a(up), p-IL4(up), p-IL8(up), p-IL10(up), p-MCP1(up), p-TM(up), p-sTNFR(down) | 0.77 (0.18) |
| OCR yes | 3 | p-IL1a(up), p-IL1b(down), p-IL6(up), p-IL8(up), p-NGAL(up), p-NSE(up), p-VEGF(up) | 0.77 (0.13) |
| OCR no | 1 | p-IL4(down), p-IL6(up), p-IL10(up), p-MMPNG(up), p-NGAL(down), p-sTNFR(down), p-VEGF(down) | 0.78 (0.09) |
| OCR no | 2 | p-dDimer(up), p-CRP(down), p-IL1a(up), p-IL1b(up), p-IL2(up), p-IL4(down), p-MMPNG(up) | 0.78 (0.13) |
| OCR no | 3 | p-dDimer(up), p-CRP(down), p-IL1b(up), p-IL4(down), p-IL6(up), p-IL10(up), p-MMPNG(up) | 0.78 (0.13) |
| CI no | 1 | p-dDimer(up), p-IL1a(down), p-IL8(down), p-MMPNG(up), p-TM(up), p-TNFa(up), p-VEGF(down) | 0.76 (0.16) |
| CI no | 2 | p-dDimer(up), p-CRP(up), p-IL2(up), p-IL6(up), p-IL8(down), p-MMPNG(up), p-TNFa(up) | 0.76 (0.22) |
| CI no | 3 | p-dDimer(up), p-IL1a(down), p-IL1b(up), p-IL8(down), p-MMPNG(up), p-TM(up), p-VEGF(down) | 0.76 (0.19) |
| AC yes | 1 | p-dDimer(down), p-EGF(down), p-IL6(up), p-IL10(up), p-Ifng(up), p-MCP1(up), p-TNFa(up) | 0.74 (0.19) |
| AC yes | 2 | p-dDimer(down), p-IL10(up), p-Ifng(up), p-MCP1(up), p-NGAL(down), p-sTNFR(up), p-VEGF(down) | 0.73 (0.2) |
| AC yes | 3 | p-dDImer(down), p-IL6(up), p-IL8(up), p-IL10(up), p-NSE(down), p-TM(up), p-TNFa(up) | 0.72 (0.2) |
| age < 65 | 1 | p-CRP(down), p-IL4(down), p-IL6(up), p-IL8(up), p-10(up), p-MMPNG(up), p-TNFa(up) | 0.74 (0.19) |
| age < 65 | 2 | p-EGF(up), p-CRP(down), p-IL1b(up), p-IL8(up), p-Ifng(up), p-NGAL(up), p-sTNFR(down) | 0.74 (0.16) |
| age < 65 | 3 | p-dDimer(up), p-EGF(up), p-CRP(down), p-IL8(up), p-IL10(up), p-Ifng(up), p-MMPNG(up) | 0.73 (0.16) |
| alcohol no | 1 | p-IL1a(down), p-IL2(up), p-IL8(up), p-Ifng(up), p-MMPNG(up), p-sTNFR(down), p-TNFa(up) | 0.74 (0.16) |
| alcohol no | 2 | p-IL1a(down), p-IL2(up), p-IL6(up), p-IL10(up), p-MMPNG(up), p-TNFa(up), p-VEGF(up) | 0.73 (0.17) |
| alcohol no | 3 | p-IL1a(down), p-IL4(down), p-IL6(up), p-IL10(up), p-MMPNG(up), p-NGAL(up), p-VEGF(up) | 0.73 (0.19) |
| AH no | 1 | p-EGF(up), p-CRP(down), p-IL1a(up), p-IL8(up), p-MMPNG(up), p-TNFa(down), p-VEGF(down) | 0.74 (0.13) |
| AH no | 2 | p-EGF(up), p-CRP(down), p-IL1b(down), p-IL8(up), p-MMPNG(up), p-sTNFR(down), p-VEGF(down) | 0.73 (0.15) |
| AH no | 3 | p-dDimer(up), p-EGF(up), p-IL1b(down), p-IL6(up), p-IL8(up), p-MMPNG(up), p-VEGF(down) | 0.73 (0.14) |
| AC no | 1 | p-IL1b(up), p-IL6(up), p-IL8(up), p-MMPNG(up), p-sTNFR(down), p-TNFa(up), p-VEGF(up) | 0.74 (0.11) |
| AC no | 2 | p-dDimer(up), p-IL1a(up), p-IL4(down), p-IL8(up), p-NGAL(up), p-TM(up), p-sTNFR(down) | 0.73 (0.12) |
| AC no | 3 | p-IL1a(up), p-IL1b(up), p-IL4(down), p-IL6(up), p-IL8(up), p-MMPNG(up), p-sTNFR(down) | 0.72 (0.13) |
| protein no | 1 | p-EGF(up), p-IL1a(up), p-IL2(up), p-IL4(down), p-MCP1(down), p-MMPNG(up), p-NGAL(up) | 0.73 (0.13) |
| protein no | 2 | p-dDimer(up), p-EGF(up), p-CRP(up), p-IL8(down), p-MMPNG(up), p-NSE(down), p-VEGF(up) | 0.71 (0.17) |
| protein no | 3 | p-dDimer(up), p-EGF(up), p-IL1b(up), p-IL8(down), p-IL10(up), p-MMPNG(up), p-VEGF(up) | 0.71 (0.14) |
| protein yes | 1 | p-IL1a(up), p-IL2(down), p-IL8(up), p-IL10(up), p-Ifng(up), p-MCP1(up), p-TM(up) | 0.71 (0.19) |
| protein yes | 2 | p-IL1a(up), p-IL2(down), p-IL8(up), p-Ifng(up), p-MCP1(up), p-MMPNG(up), p-TM(up) | 0.69 (0.21) |
| protein yes | 3 | p-EGF(down), p-CRP(down), p-IL1a(up), p-IL4(down), p-IL8(up), p-Ifng(up), p-TNFa(up) | 0.69 (0.15) |
| age > 65 | 1 | p-CRP(up), p-IL1a(down), p-IL10(up), p-MMPNG(up), p-TM(up), p-TNFa(down), p-VEGF(up) | 0.71 (0.13) |
| age > 65 | 2 | p-IL1a(down), p-IL6(up), p-IL10(up), p-MMPNG(up), p-TM(up), p-TNFa(down), p-VEGF(up) | 0.7 (0.14) |

TABLE 18-continued

Plasma 7 biomarker urothelial cancer (UC) classifiers. In parenthesis the pattern for up or down regulation of a biomarker in UC are shown.

| name | num | Biomarker | AUC |
|---|---|---|---|
| age > 65 | 3 | p-CRP(up), p-IL1a(down), p-IL4(down), p-IL6(up), p-MMPNG(up), p-TM(up), p-TNFa(down) | 0.69 (0.14) |
| alcohol yes | 1 | p-dDimer(up), p-IL1b(up), p-IL4(down), p-MMPNG(up), p-NGAL(up), p-NSE(down), p-VEGF(down) | 0.7 (0.16) |
| alcohol yes | 2 | p-dDimer(up), p-IL1a(down), p-IL2(up), p-MMPNG(up), p-NSE(down), p-sTNFR(down), p-TNFa(up) | 0.68 (0.12) |
| alcohol yes | 3 | p-dDimer(up), p-CRP(down), p-IL1a(down), p-IL4(down), p-IL10(up), p-NSE(down), p-sTNFR(down) | 0.67 (0.15) |
| smoking yes | 1 | p-IL1a(up), p-IL1b(down), p-IL2(down), p-IL4(down), p-IL10(up), p-MMPNG(up), p-TNFa(up) | 0.68 (0.16) |
| smoking yes | 2 | p-dDimer(up), p-IL1a(up), p-IL4(down), p-Ifng(down), p-MCP1(up), p-MMPNG(up), p-TM(up) | 0.68 (0.1) |
| smoking yes | 3 | p-dDimer(up), p-EGF(down), p-IL1a(up), p-IL4(down), p-IL10(up), p-Ifng(down), p-MMPNG(up) | 0.67 (0.14) |
| AH yes | 1 | p-dDimer(down), p-EGF(down), p-CRP(up), p-IL2(up), p-IL10(up), p-MMPNG(up), p-TM(up) | 0.64 (0.17) |
| AH yes | 2 | p-CRP(up), p-IL1a(up), p-IL1b(up), p-IL4(down), p-IL6(up), p-Ifng(up), p-sTNFR(down) | 0.62 (0.12) |
| AH yes | 3 | p-EGF(down), p-CRP(up), p-IL4(down), p-IL6(up), p-IL10(up), p-Ifng(up), p-MMPNG(up) | 0.62 (0.14) |
| CI yes | 1 | p-IL1a(up), p-IL8(up), p-IL10(up), p-MCP1(up), p-MMPNG(up), p-NSE(down), p-TM(up) | 0.62 (0.13) |
| CI yes | 2 | p-dDimer(up), p-IL2(up), p-IL6(down), p-IL8(up), p-MMPNG(up), p-TM(up), p-sTNFR(down) | 0.61 (0.14) |
| CI yes | 3 | p-IL1a(up), p-IL2(up), p-IL6(down), p-IL8(up), p-MCP1(up), p-MMPNG(up), p-NSE(down) | 0.61 (0.15) |

The invention is further described with reference to the following non-limiting embodiments:

Embodiment 1

A method of identifying a panel of biomarkers for diagnosis of serious disease, the method comprising:
(i) measuring the level of each biomarker in a biomarker panel in a sample obtained from each subject in a test population;
(ii) stratifying the test population into sub-populations defined by variables that individually divide the test population into groups containing at least 35% of the total test population; and
(iii) assessing combinations of biomarkers that allow accurate classification of disease in subjects in the sub-populations of the test population.

Embodiment 2

The method of embodiment 1, wherein the serious disease is urothelial cancer.

Embodiment 3

The method of embodiment 1 or embodiment 2, wherein the measured biomarkers are selected from the group consisting of Bladder Tumour Antigen (BTA), Carcino-embryonic antigen (CEA), Human cytokeratin 18 (CK18), C-reactive protein (CRP), Creatinine, d Dimer, Epidermal growth factor (EGF), FAS, Hyaluronidase (HA), IL1α, IL1β, IL2, IL4, IL6, IL8, IL10, Interferon gamma (IFNγ), Monocyte Chemoattractant Protein 1 (MCP1), matrix metalloproteinase 9 (MMP9), Neutrophil gelatinase-associated lipocalin (NGAL), MMP9NGAL complex, Neuron specific enolase (NSE), Free Prostate Specific Antigen (FPSA), Total Prostate Specific Antigen (TPSA), Thrombomodulin (TM), Tumour necrosis factor α (TNFα), sTNFR1, sTNFR2, Vascular endothelial growth factor (VEGF) and von Willebrand factor (vWF).

Embodiment 4

The method of any one of embodiments 1 to 3, wherein the variables are selected from the group consisting of history of smoking, age, gender, alcohol consumption, history of anti-cholesterol medication, history of anti-hypertensive medication, occupational exposure to hazardous chemicals, cytological detection of inflammatory cells and presence of measurable dipstick protein in urine.

Embodiment 5

The method of any one of embodiments 1 to 4, wherein the combinations of biomarkers are assessed by calculation of the Area Under the Curve measurement together with calculation of the standard deviation from repeated subsampling validation analyses.

Embodiment 6

A method of diagnosing urothelial cancer in a subject, comprising the steps of:
(i) assigning the subject to a sub-population according to one or more factors selected from smoking habits, age, gender, alcohol consumption, anti-cholesterol medication, anti-hypertensive medication, occupational risks, exposure to hazardous chemicals, cytological detection of inflammatory cells and measurable urinary dipstick protein;
(ii) measuring the level of each biomarker of a panel of biomarkers in one or more samples obtained from the subject; and (iii) correlating the measured levels of the panel of biomarkers with the likelihood of the subject having urothelial cancer such that the subject can be classified as having urothelial cancer or as being a control.

Embodiment 7

A method according to embodiment 6, wherein the subject is a patient presenting with haematuria.

Embodiment 8

A method according to any one of embodiments 6 or 7, wherein the urothelial cancer is urothelial carcinoma (UC).

Embodiment 9

The method according to any one of embodiments 6 to 8, wherein the one or more samples are selected from the group consisting of urine, blood, serum and plasma.

Embodiment 10

The method of embodiment 9, wherein the one or more samples include urine and wherein urinary biomarker levels are volume normalised.

Embodiment 11

The method of any one of embodiments 6 to 10, wherein the subject has a history of smoking.

Embodiment 12

The method of embodiment 11, wherein the panel of biomarkers is selected from the group consisting of:
(i) urinary EGF, urinary IL6, urinary VEGF and urinary CK18;
(ii) urinary EGF, serum IL8, urinary vWF and urinary FAS; and
(iii) urinary EGF, urinary IL1α, plasma MMP9NGAL and urinary vWF Embodiment 13

The method of embodiment 11, wherein the one or more sample is urine and the panel of biomarkers is selected from the group consisting of:
(i) EGF, IL1β, sTNFR, VEGF and CK18;
(ii) BTA, EGF, IL1β, vWF and FAS;
(iii) EGF, IL1β, IL8, TM, and vWF;
(iv) dDimer, EGF, IL1β, IL8, VEGF and vWF;
(v) EGF, IL1β, NSE, sTNFR2, VEGF and vWF;
(vi) EGF, IL2, TM, sTNFR2, VEGF and CK18;
(vii) EGF, IL1α, MMP9, MMP9NGAL, NSE, VEGF and vWF;
(viii) EGF, IL1β, NGAL, NSE, sTNFR1, VEGF and vWF; and
(ix) dDimer, EGF, IL1α, IL8, NSE, vWF and FAS.

Embodiment 14

The method of embodiment 11, wherein the one or more sample is serum and the panel of biomarkers is selected from the group consisting of:
(i) d-Dimer, EGF, IL1α, IL8 and NGAL;
(ii) IL1α, IL2, IL8, NGAL and sTNFR1;
(iii) IL1α, IL10, NGAL, NSE and TNFα;
(iv) d-Dimer, IL2, IL10, MMP9NGAL, NGAL and sTNFR1;
(v) EGF, FPSA, IL10, NGAL, TNFα and TPSA;
(vi) CEA, IL1α, IL4, IL8, IL10 and NGAL;
(vii) EGF, CRP, IL10, MMP9NGAL, NGAL, TM and VEGF;
(viii) CEA, CRP, IL10, MMP9NGAL, NGAL, TM and TNFα; and
(ix) CEA, d-Dimer, IL2, IL8, IL10, IFNγ and NSE.

Embodiment 15

The method of embodiment 11, wherein the one or more sample is plasma and the panel of biomarkers is selected from the group consisting of:
(i) IL4, IFNγ, MCP1, MMP9NGAL and TM;
(ii) IL1α, IL4, IFNγ, MCP1 and MMP9NGAL;
(iii) EGF, IL1α, IL4, MCP1, MMP9NGAL;
(iv) dDimer, IL1α, IL4, IL10, MMP9NGAL and sTNFR1;
(v) IL4, IL10, MMP9NGAL, TM, sTNFR1 and TNFα;
(vi) IL1β, IL4, IL8, MCP1, MMP9NGAL and TNFα;
(vii) IL1α, IL1β, IL2, IL4, IL10, MMP9NGAL and TNFα
(viii) d-Dimer, IL1α, IL4, IFNγ, MCP1, MMP9NGAL and TM; and
(ix) d-Dimer, EGF, IL1α, IL4, IL10, IFNγ, and MMP9NGAL.

Embodiment 16

The method of any one of embodiments 6 to 10, wherein the subject does not have a history of smoking.

Embodiment 17

The method of embodiment 16, wherein the panel of biomarkers is selected from the group consisting of:
(i) serum CEA, urinary EGF, plasma IL8 and urinary CK18;
(ii) serum CEA, plasma IL8, serum NGAL and serum TM; and
(iii) serum CEA, plasma IL8, serum NGAL and plasma NSE.

Embodiment 18

The method of embodiment 16, wherein the one or more sample is urine and the panel of biomarkers is selected from the group consisting of:
(i) BTA, MMP9NGAL, TM, sTNFR2 and VEGF;
(ii) BTA, IL4, MMP9, NSE and FAS;
(iii) BTA, MMP9NGAL, TNFα, sTNFR2 and VEGF;
(iv) BTA, MCP1, MMP9, sTNFR2, vWF and FAS;
(v) d-Dimer, IL6, IL8, NGAL, NSE and TNFα;
(vi) BTA, IL6, MCP1, TNFα, sTNFR2 and FAS;
(vii) EGF, CRP, IL8, NGAL, NSE, TM and HA;
(viii) BTA, EGF, IL8, MCP1, NGAL, NSE, sTNFR1; and
(ix) BTA, IL4, MCP1, TM, sTNFR2, vWF and FAS.

Embodiment 19

The method of embodiment 16, wherein the one or more sample is serum and the panel of biomarkers is selected from the group consisting of:
(i) CEA, EGF, IL4, NGAL and TNFα;
(ii) CEA, EGF, IL8, NGAL and TPSA;

(iii) CEA, IL8, MCP1, NGAL and TPSA;
(iv) CEA, IL6, IL8, MMP9NGAL, NGAL and VEGF;
(v) CEA, d-Dimer, CRP, MMP9NGAL, NGAL and NSE;
(vi) CEA, CRP, IL2, MMP9NGAL, NGAL and TM;
(vii) CEA, EGF, CRP, IL4, IL8, NGAL and NSE;
(viii) CEA, IL6, IL8, IFNγ, NGAL, TM and VEGF;
(ix) CEA, FPSA, CRP, IL4, MMP9NGAL, NGAL and TM.

Embodiment 20

The method of embodiment 16, wherein the one or more sample is plasma and the panel of biomarkers is selected from the group consisting of:
(i) IL1α, MMP9NGAL, NSE, sTNFR1 and VEGF;
(ii) IFNγ, MCP1, MMP9NGAL, NGAL and NSE;
(iii) IFNγ, MMP9NGAL, NGAL, NSE and TNFα;
(iv) IL6, IFNγ, MMP9NGAL, NGAL, NSE and TNFα;
(v) d-Dimer, IL1α, IL4, MMP9NGAL, NSE and VEGF;
(vi) d-Dimer, EGF, IL1α, IL8, MMP9NGAL and NSE;
(vii) d-Dimer, EGF, IL1α, IFNγ, MMP9NGAL, TNFα and VEGF;
(viii) EGF, IL1α, IL2, MMP9NGAL, NGAL, NSE and TM; and
(ix) IL1α, IFNγ, MMP9NGAL, NGAL, NSE, TM and TNFα.

Embodiment 21

The method of any one of embodiments 6 to 10, wherein the subject is aged 65 years or older.

Embodiment 22

The method of embodiment 21, wherein the panel of biomarkers is selected from the group consisting of:
(i) serum IL2, serum MMP9NGAL, serum NGAL and plasma sTNFR1;
(ii) urinary MMP9NGAL, serum NGAL, plasma NGAL and urinary vWF; and
(iii) serum CEA, serum d-Dimer, plasma d-Dimer and serum IFN-γ.

Embodiment 23

The method of embodiment 21, wherein the one or more sample is urine and the panel of biomarkers is selected from the group consisting of:
(i) BTA, IL1β, VEGF, vWF and HA;
(ii) d-Dimer, IL1α, NSE, vWF and HA;
(iii) BTA, d-Dimer, IL1β, vWF and HA;
(iv) BTA, IL1β, IL4, VEGF, vWF and HA;
(v) BTA, IL1β, IL8, sTNFR2, vWF and HA;
(vi) BTA, EGF, IL1α, NSE, vWF and HA;
(vii) d-Dimer, CRP, IL1α, IL2, NSE, vWF and HA;
(viii) BTA, IL1α, IL8, MMP9NGAL, vWF, HA and CK18; and
(ix) d-Dimer, IL1α, MCP1, NSE, TNFα, vWF and HA.

Embodiment 24

The method of embodiment 21, wherein the one or more sample is serum and the panel of biomarkers is selected from the group consisting of:
(i) CEA, d-Dimer, IL4, NGAL and TM;
(ii) IL1α, MMP9NGAL, NGAL, sTNFR1 and TNFα;
(iii) IL2, MMP9NGAL, NGAL, sTNFR1 and VEGF;
(iv) CEA, d-Dimer, IL1α, NGAL, NSE and TM;
(v) CEA, EGF, IL1α, MMP9NGAL, NGAL and TPSA;
(vi) CEA, d-Dimer, CRP, IL1β, NGAL and TM;
(vii) CEA, d-Dimer, FPSA, CRP, IL10, NGAL and TM;
(viii) CEA, d-Dimer, CRP, NGAL, NSE, TM and TPSA; and
(ix) d-Dimer, IL1α, IL8, IFNγ, MMP9NGAL, NGAL and TM.

Embodiment 25

The method of embodiment 21, wherein the one or more sample is plasma and the panel of biomarkers is selected from the group consisting of:
(i) CRP, IL1α, MMP9NGAL, TM and VEGF;
(ii) CRP, IL1α, IL1β, MMP9NGAL and NGAL;
(iii) CRP, IL1α, IL4, MMP9NGAL and TM;
(iv) CRP, IL1α, IL2, IL4, MMP9NGAL and TM;
(v) EGF, CRP, IL1α, IL1β, MMP9NGAL and VEGF;
(vi) EGF, IL1α, IL6, MMP9NGAL, TM and TNFα;
(vii) CRP, IL1α, IL10, MMP9NGAL, TM, TNFα and VEGF;
(viii) IL1α, IL6, IL10, MMP9NGAL, TM, TNFα and VEGF; and
(ix) CRP, IL1α, IL4, IL6, MMP9NGAL, TM and TNFα.

Embodiment 26

The method of any one of embodiments 6 to 10, wherein the subject is aged less than 65 years old.

Embodiment 27

The method of embodiment 26, wherein the panel of biomarkers is selected from the group consisting of:
(i) serum CEA, urinary EGF, serum IL1α and urinary VEGF;
(ii) serum CEA, urinary CRP, serum IL1α and urinary VEGF; and
(iii) serum CEA, serum-IL1α, plasma IFNγ and urinary VEGF.

Embodiment 28

The method of embodiment 26, wherein the one or more sample is urine and the panel of biomarkers is selected from the group consisting of:
(i) EGF, IL2, HA, FAS and CK18;
(ii) EGF, IL2, MMP9NGAL, HA and CK18;
(iii) EGF, vWF, HA, FAS and CK18;
(iv) EGF, IL2, IL8, MMP9, HA and CK18;
(v) BTA, EGF, IL1β, IL8, HA and CK18;
(vi) d-Dimer, EGF, NSE, vWF, HA and CK18;
(vii) EGF, CRP, IL1β, IL2, IL8, HA and CK18;
(viii) EGF, IL1β, IL4, IL8, vWF, HA and CK18; and
(ix) EGF, IL1β, IL6, IL8, MMP9, HA and CK18.

Embodiment 29

The method of embodiment 26, wherein the one or more sample is serum and the panel of biomarkers is selected from the group consisting of:
(i) CEA, IL1α, IL4, TM and TNFα;
(ii) CEA, IL1α, IL2, IL4 and IL8;
(iii) CEA, IL1α, IL1β, IL4 and VEGF;
(iv) CEA, IL1α, IL4, IL8, MMP9NGAL and sTNFR1;
(v) CEA, IL1α, IL2, IL4, NSE and sTNFR1;

(vi) CEA, EGF, IL1α, IL4, IL8 and TM;
(vii) CEA, IL1α, IL2, IL4, IL8, IFNγ and MMP9NGAL;
(viii) CEA, EGF, FPSA, IL1α, IL4, IL8 and VEGF; and
(ix) CEA, IL1α, IL2, IL8, IFNγ, MCP1 and sTNFR1.

Embodiment 30

The method of embodiment 26, wherein the one or more sample is plasma and the panel of biomarkers is selected from the group consisting of:
(i) d-Dimer, IL8, IL10, NSE and VEGF;
(ii) d-Dimer, IL8, MMP9NGAL, TNFα and VEGF;
(iii) EGF, IL8, IL10, MMP9NGAL and sTNFR1;
(iv) EGF, CRP, IL6, IL8, IL10 and sTNFR1;
(v) CRP, IL6, IL8, IL10, IFNγ and sTNFR1;
(vi) d-Dimer, IL4, IL8, MMP9NGAL, NGAL and TNFα;
(vii) CRP, IL4, IL6, IL8, IL10, MMP9NGAL and TNFα;
(viii) EGF, CRP, IL1β, IL8, IFNγ, NGAL and sTNFR1; and
(ix) d-Dimer, EGF, CRP, IL8, IL10, IFNγ and MMP9NGAL.

Embodiment 31

The method of any one of embodiments 6 to 10, wherein the subject has a history of anti-hypertensive medication.

Embodiment 32

The method of embodiment 31, wherein the panel of biomarkers is selected from the group consisting of:
(i) urinary EGF, urinary IL1α, serum IL10 and urinary vWF;
(ii) urinary EGF, plasma IL10, urinary VEGF and urinary vWF; and
(iii) serum sTNFR1, plasma sTNFR1, serum TNFα and urinary vWF.

Embodiment 33

The method of embodiment 31, wherein the one or more sample is urine and the panel of biomarkers is selected from the group consisting of:
(i) CRP, IL2, IL8, sTNFR2 and vWF;
(ii) EGF, IL8, NSE, TNFα and vWF;
(iii) BTA, EGF, IL4, vWF and HA;
(iv) BTA, EGF, IL1β, IL8, VEGF and vWF;
(v) d-Dimer, CRP, IL8, sTNFR2, vWF and CK18;
(vi) d-Dimer, EGF, IL2, VEGF, vWF and FAS;
(vii) CRP, IL1β, IL6, IL8, MMP9, NGAL and vWF;
(viii) d-Dimer, IL8, MMP9, NSE, TM, sTNFR2 and vWF; and
(ix) BTA, d-Dimer, EGF, IL4, NGAL, NSE and vWF.

Embodiment 34

The method of embodiment 31, wherein the one or more sample is serum and the panel of biomarkers is selected from the group consisting of:
(i) CEA, NGAL, NSE, TNFα and TPSA;
(ii) CEA, MMP9NGAL, NGAL, TM and TNFα;
(iii) CEA, IL1β, NGAL, sTNFR1 and TPSA;
(iv) CEA, IL1β, IL10, NGAL, TM and VEGF;
(v) CEA, d-Dimer, IL1β, MMP9NGAL, NGAL and TM;
(vi) CEA, EGF, IL1α, IL1β, NGAL and TNFα;
(vii) CEA, IL1α, IL1β, IL10, NGAL, sTNFR1 and TNFα;
(viii) CEA, IL1α, NGAL, NSE, TM, TNFα and TPSA; and
(ix) CEA, IL1β, IL4, IL10, MMP9NGAL, NGAL and TM.

Embodiment 35

The method of embodiment 31, wherein the one or more sample is plasma and the panel of biomarkers is selected from the group consisting of:
(i) IL1α, IL1β, IL4, IFNγ and VEGF;
(ii) EGF, CRP, IL2, IL4 and IL8;
(iii) EGF, CRP, IL2, IL10 and NGAL;
(iv) EGF, IL6, IL10, IFNγ, MCP1 and MMP9NGAL;
(v) d-Dimer, EGF, IL1β, IL4, IL6 and MCP1;
(vi) EGF, CRP, IL1β, IL2, MMP9NGAL and NGAL;
(vii) d-Dimer, EGF, CRP, IL2, IL10, MMP9NGAL and TM;
(viii) CRP, IL1α, IL1β, IL4, IL6, IFNγ and sTNFR1; and
(ix) EGF, CRP, IL4, IL6, IL10, IFNγ and MMP9NGAL.

Embodiment 36

The method of any one of embodiments 6 to 10, wherein the subject has no history of anti-hypertensive medication.

Embodiment 37

The method of embodiment 36, wherein the panel of biomarkers is selected from the group consisting of:
(i) serum CEA, urinary CRP, urinary NSE and serum TNFα;
(ii) serum CEA, urinary CRP, serum IL4 and urinary sTNFR1; and
(iii) urinary Creatinine, serum IL6, plasma MMP9NGAL and urinary VEGF.

Embodiment 38

The method of embodiment 36, wherein the one or more sample is urine and the panel of biomarkers is selected from the group consisting of:
(i) CRP, NGAL, VEGF, HA and CK18;
(ii) d-Dimer, TNFα, VEGF, HA and CK18;
(iii) MMP9, NSE, TM, VEGF and FAS;
(iv) EGF, NGAL, VEGF, vWF, HA and CK18;
(v) CRP, IL1β, IL6, sTNFR1, VEGF and vWF;
(vi) d-Dimer, EGF, IL4, VEGF, HA and CK18;
(vii) CRP, IL1β, IL6, IL8, MMP9, NGAL and vWF;
(viii) d-Dimer, IL8, MMP9, NSE, TM, sTNFR2 and vWF; and
(ix) BTA, d-Dimer, EGF, IL4, NGAL, NSE and vWF.

Embodiment 39

The method of embodiment 36, wherein the one or more sample is serum and the panel of biomarkers is selected from the group consisting of:
(i) CEA, d-Dimer, IL4, MMP9NGAL and sTNFR1;
(ii) CEA, EGF, IL10, MMP9NGAL and TNFα;
(iii) CEA, d-Dimer, CRP, IL4 and IL10;
(iv) CEA, d-Dimer, CRP, IL4, IL10 and TM;
(v) CEA, d-Dimer, CRP, IL4, IL6 and MMP9NGAL;
(vi) CEA, d-Dimer, IL2, IL4, IL8 and MMP9NGAL;
(vii) CEA, d-Dimer, EGF, IL4, IL8, IL10 and NSE;
(viii) CEA, d-Dimer, CRP, IL4, MCP1, MMP9NGAL and TNFα; and
(ix) CEA, d-Dimer, CRP, IL4, IL6, TM and TNFα.

Embodiment 40

The method of embodiment 36, wherein the one or more sample is plasma and the panel of biomarkers is selected from the group consisting of:

(i) EGF, IL1α, IL8, MMP9NGAL and VEGF;
(ii) IL1α, IL8, IFNγ, MMP9NGAL and VEGF;
(iii) CRP, IL1α, IL8, MMP9NGAL and NGAL;
(iv) EGF, CRP, IL1β, IL8, MMP9NGAL and VEGF;
(v) CRP, IL1α, IL6, IL8, IL10, MMP9NGAL;
(vi) EGF, IL1β, IL4, IL8, MMP9NGAL and VEGF;
(vii) EGF, CRP, IL1α, IL8, MMP9NGAL, TNFα and VEGF;
(viii) EGF, CRP, IL1β, IL8, MMP9NGAL, sTNFR1 and VEGF; and
(ix) d-Dimer, EGF, IL1β, IL6, IL8, MMP9NGAL and VEGF.

Embodiment 41

The method of any one of embodiments 6 to 10, wherein the subject has cytological detection of inflammatory cells.

Embodiment 42

The method of embodiment 41, wherein the panel of biomarkers is selected from the group consisting of:
(i) urinary BTA, serum CEA, plasma IL10 and urinary CK18;
(ii) urinary BTA, plasma IL6, serum NSE and plasma NSE; and
(iii) urinary dipstick protein, urinary BTA, plasma IL6 and serum NGAL.

Embodiment 43

The method of embodiment 41, wherein the one or more sample is urine and the panel of biomarkers is selected from the group consisting of:
(i) BTA, IL1α, NGAL, sTNFR1 and vWF;
(ii) BTA, IL8, MMP9NGAL, VEGF and CK18;
(iii) BTA, IL6, MMP9NGAL, NSE and CK18;
(iv) BTA, IL2, MMP9NGAL, sTNFR1, TNFα and VEGF;
(v) BTA, IL2, MMP9NGAL, NGAL, TNFα and CK18;
(vi) BTA, IL2, MMP9NGAL, NSE, VEGF and CK18;
(vii) BTA, IL2, MMP9NGAL, NGAL, sTNFR1, TNFα and VEGF;
(viii) BTA, IL2, MMP9NGAL, TM, sTNFR1, vWF and FAS; and
(ix) BTA, IL2, MMP9NGAL, sTNFR1, VEGF, vWF and CK18.

Embodiment 44

The method of embodiment 41, wherein the one or more sample is serum and the panel of biomarkers is selected from the group consisting of:
(i) CEA, IL1α, NGAL, NSE and TPSA;
(ii) IL1α, MMP9NGAL, NGAL, TPSA and VEGF;
(iii) CEA, IL1α, IL10, NGAL and VEGF;
(iv) CEA, IL10, MMP9NGAL, NGAL, TNFα and VEGF;
(v) IL1α, IL10, MMP9NGAL, NGAL, NSE and VEGF;
(vi) CRP, IL10, MMP9NGAL, NGAL, TPSA and VEGF;
(vii) CEA, CRP, IL1β, IL2, TM, sTNFR1 and TPSA;
(viii) CRP, IL1β, IL2, IL6, MMP9NGAL, NGAL and TNFα; and
(ix) CRP, IL1β, IL2, MMP9NGAL, NGAL, NSE and TNFα.

Embodiment 45

The method of embodiment 41, wherein the one or more sample is plasma and the panel of biomarkers is selected from the group consisting of:
(i) IL1α, IL6, IL8, MMP9NGAL and NSE;
(ii) IL6, IFNγ, MMP9NGAL, NSE and sTNFR1;
(iii) IL1α, IL1β, IL8, IL10 and MMP9NGAL;
(iv) IL6, IL8, IFNγ, MMP9NGAL, NGAL and NSE;
(v) IL1α, IL6, MMP9NGAL, NSE, TM and TNFα;
(vi) d-Dimer, IL4, IL8, IFNγ, MMP9NGAL and VEGF;
(vii) IL1α, IL8, IL10, MCP1, MMP9NGAL, NSE and TM;
(viii) d-Dimer, IL2, IL6, IL8, MMP9NGAL, TM and sTNFR1; and
(ix) IL1α, IL2, IL6, IL8, MCP1, MMP9NGAL and NSE.

Embodiment 46

The method of any one of embodiments 6 to 10, wherein the subject does not have cytological detection of inflammatory cells.

Embodiment 47

The method of embodiment 46, wherein the panel of biomarkers is selected from the group consisting of:
(i) serum CEA, plasma IL8, serum TNFα and urinary FAS;
(ii) urinary EGF, serum EGF, serum FPSA and serum IL4; and
(iii) urinary EGF, urinary CRP, urinary IL4 and urinary NSE.

Embodiment 48

The method of embodiment 46, wherein the one or more sample is urine and the panel of biomarkers is selected from the group consisting of:
(i) EGF, CRP, IL4, TM and vWF;
(ii) BTA, d-Dimer, EGF, CRP and IL4;
(iii) EGF, CRP, IL4, IL6 and vWF;
(iv) d-Dimer, EGF, CRP, IL4, sTNFR1 and vWF;
(v) d-Dimer, EGF, CRP, IL4, sTNFR1 and sTNFR2;
(vi) EGF, IL2, IL4, sTNFR2, VEGF and vWF;
(vii) EGF, CRP, IL4, MCP1, VEGF, FAS and CK18;
(viii) d-Dimer, EGF, CRP, IL4, IL6, sTNFR2 and vWF; and
(ix) d-Dimer, EGF, CRP, IL4, IL6, sTNFR2 and CK18.

Embodiment 49

The method of embodiment 46, wherein the one or more sample is serum and the panel of biomarkers is selected from the group consisting of:
(i) CEA, EGF, CRP, IL4 and IFNγ;
(ii) d-Dimer, FPSA, IL6, IFNγ and NGAL;
(iii) IL1α, IL4, MMP9NGAL, NGAL and TM;
(iv) IL4, MMP9NGAL, NGAL, NSE, sTNFR1 and TPSA;
(v) CEA, EGF, FPSA, IL4, NSE and sTNFR1;
(vi) CEA, EGF, FPSA, IL4, MCP1 and VEGF;
(vii) FPSA, IL2, IL4, IL6, MMP9NGAL, NGAL and sTNFR1;
(viii) CEA, EGF, FPSA, CRP, IL4, IL6 and MMP9NGAL; and
(ix) d-Dimer, IL1β, IL4, IL8, MCP1, NGAL and TM.

Embodiment 50

The method of embodiment 46, wherein the one or more sample is plasma and the panel of biomarkers is selected from the group consisting of:

(i) d-Dimer, IL1β, IL8, MMP9NGAL and TM;
(ii) d-Dimer, IL8, TM, TNFα and VEGF;
(iii) IL2, IL8, MMP9NGAL, TM and TNFα;
(iv) d-Dimer, IL8, MMP9NGAL, NSE, TM and TNFα;
(v) d-Dimer, IL2, IL8, MMP9NGAL, NSE and TNFα;
(vi) d-Dimer, IL8, IFNγ, MMP9NGAL, sTNFR1 and TNFα;
(vii) d-Dimer, IL1α, IL8, MMP9NGAL, TM, TNFα and VEGF;
(viii) d-Dimer, CRP, IL2, IL6, IL8, MMP9NGAL and TNFα; and
(ix) d-Dimer, IL1α, IL1β, IL8, MMP9NGAL, TM and VEGF.

Embodiment 51

The method of any one of embodiments 6 to 10, wherein the subject has a history of alcohol consumption.

Embodiment 52

The method of embodiment 51, wherein the panel of biomarkers is selected from the group consisting of:
(i) urinary EGF, urinary IL1β, serum MMP9NGAL and urinary vWF;
(ii) serum CEA, urinary EGF, urinary vWF and urinary CK18; and
(iii) serum CEA, urinary EGF, plasma NSE and urinary vWF.

Embodiment 53

The method of embodiment 51, wherein the one or more sample is urine and the panel of biomarkers is selected from the group consisting of:
(i) EGF, MMP9, sTNFR2, VEGF and vWF;
(ii) EGF, IL1α, IL4, vWF and FAS;
(iii) EGF, IL1α, MMP9, vWF and HA;
(iv) d-Dimer, EGF, CRP, IL1α, IL6 and vWF;
(v) EGF, CRP, IL1α, sTNFR, vWF and CK18;
(vi) BTA, EGF, CRP, IL1α, vWF and FAS;
(vii) EGF, IL1α, IL6, NGAL, sTNFR2, vWF and FAS;
(viii) EGF, IL1α, IL2, IL6, NGAL, VEGF and vWF; and
(ix) EGF, IL1α, NGAL, NSE, sTNFR2, vWF and CK18.

Embodiment 54

The method of embodiment 51, wherein the one or more sample is serum and the panel of biomarkers is selected from the group consisting of:
(i) CRP, IL1β, IL6, IL8 and NGAL;
(ii) d-Dimer, IL1β, IL4, IFNγ and NGAL;
(iii) CRP, IL1β, IL4, MCP1 and NGAL;
(iv) EGF, CRP, IL1α, IL1β, NGAL and TPSA;
(v) CEA, CRP, IL1β, IL2, NGAL and NSE;
(vi) CEA, d-Dimer, CRP, IL1α, IL6 and NGAL;
(vii) EGF, CRP, IL8, MCP1, MMP9NGAL, NGAL and sTNFR1;
(viii) CEA, EGF, CRP, IL1β, MMP9NGAL, NGAL and TM; and
(ix) CEA, d-Dimer, IL1α, IL2, IL4, IL10 and NGAL.

Embodiment 55

The method of embodiment 51, wherein the one or more sample is plasma and the panel of biomarkers is selected from the group consisting of:

(i) d-Dimer, IL4, MMP9NGAL, NSE and TM;
(ii) IL1β, IL4, MMP9NGAL, NSE and TNFα;
(iii) EGF, CRP, IL4, MMP9NGAL and sTNFR1;
(iv) IL1α, IL2, IL4, MMP9NGAL, NSE and TNFα;
(v) IL2, IL4, IL6, MMP9NGAL, NSE and TM;
(vi) CRP, IL1α, IL1β, IL4, MMP9NGAL and TNFα;
(vii) d-Dimer, IL1β, IL4, MMP9NGAL, NGAL, NSE and VEGF;
(viii) d-Dimer, IL1α, IL2, MMP9NGAL, NSE, sTNFR and TNFα; and
(ix) d-Dimer, CRP, IL1α, IL4, IL10, NSE and sTNFR.

Embodiment 56

The method of any one of embodiments 6 to 10, wherein the subject does not have a history of alcohol consumption.

Embodiment 57

The method of embodiment 56, wherein the panel of biomarkers is selected from the group consisting of:
(i) serum MMP9NGAL, serum sTNFR1, serum TNFα and urinary VEGF;
(ii) serum CEA, urinary EGF, serum IL10 and serum NGAL; and
(iii) urinary IL6, plasma MMP9NGAL, urinary VEGF and urinary CK18.

Embodiment 58

The method of embodiment 56, wherein the one or more sample is urine and the panel of biomarkers is selected from the group consisting of:
(i) IL2, IL8, NGAL, HA and CK18;
(ii) IL2, IL4, VEGF, HA and CK18;
(iii) IL1β, IL2, IL8, NGAL and CK18;
(iv) IL2, IL4, IL8, NGAL, HA and CK18;
(v) BTA, d-Dimer, IL2, IL8, MMP9NGAL and CK18;
(vi) IL2, IL4, IL8, sTNFR2, HA and CK18;
(vii) IL1β, IL2, IL6, IL8, NGAL, NSE and CK18;
(viii) IL1α, IL2, IL6, IL8, NGAL, HA and CK18; and
(ix) BTA, IL1α, IL2, IL8, NGAL, VEGF and CK18.

Embodiment 59

The method of embodiment 56, wherein the one or more sample is serum and the panel of biomarkers is selected from the group consisting of:
(i) CEA, IL1α, IL8, TM and sTNFR1;
(ii) CEA, IL1α, IL6, NGAL and TM;
(iii) CEA, IL1α, IL2, TM and sTNFR1;
(iv) CEA, IL2, IL8, NSE, TM and sTNFR1;
(v) CEA, IL10, MMP9NGAL, NSE, TM and sTNFR1;
(vi) CEA, CRP, IL2, IL10, NGAL and TM;
(vii) CEA, CRP, IL4, IL6, IL10, sTNFR1 and TPSA;
(viii) CEA, d-Dimer, EGF, IL1α, IL10, NSE and sTNFR1; and
(ix) CEA, d-Dimer, IL1α, IL1β, IL4, TM and sTNFR1.

Embodiment 60

The method of embodiment 56, wherein the one or more sample is plasma and the panel of biomarkers is selected from the group consisting of:
(i) IL1α, IFNγ, MMP9NGAL, sTNFR1 and TNFα;
(ii) EGF, IL4, MCP1, MMP9NGAL and sTNFR1;
(iii) IL1α, IL8, IL10, MMP9NGAL and VEGF;

(iv) IL1α, IL1β, IL10, IFNγ, MMP9NGAL and VEGF;
(v) EGF, CRP, IL1α, MMP9NGAL, TNFα and VEGF;
(vi) IL1α, IL6, IL8, IFNγ, MMP9NGAL and sTNFR1;
(vii) IL1α, IL2, IL8, IFNγ, MMP9NGAL, sTNFR1 and TNFα;
(viii) IL1α, IL2, IL6, IL10, MMP9NGAL, TNFα and VEGF; and
(ix) IL1α, IL4, IL6, IL10, MMP9NGAL, NGAL and VEGF.

Embodiment 61

The method of any one of embodiments 6 to 10, wherein the subject has a history of exposure to occupational risks or hazardous chemicals.

Embodiment 62

The method of embodiment 61, wherein the panel of biomarkers is selected from the group consisting of:
(i) serum CEA, urinary EGF, urinary VEGF and urinary vWF;
(ii) urinary EGF, serum IL8, urinary vWF and urinary HA; and
(iii) serum IL4, plasma IL8, serum MCP1 and urinary VEGF.

Embodiment 63

The method of embodiment 61, wherein the one or more sample is urine and the panel of biomarkers is selected from the group consisting of:
(i) BTA, IL2, IL4, MMP9NGAL and VEGF;
(ii) BTA, IL1α, IL8, NGAL and NSE;
(iii) BTA, CRP, IL4, NSE and CK18;
(iv) BTA, d-Dimer, CRP, IL4, sTNFR1 and vWF;
(v) IL4, IL8, NGAL, NSE, TM and sTNFR1;
(vi) CRP, IL2, IL8, MCP1, MMP9NGAL and TNFα;
(vii) EGF, IL1α, IL8, MMP9NGAL, NSE, vWF and CK18;
(viii) EGF, IL6, IL8, MMP9NGAL, NSE, VEGF and vWF; and
(ix) CRP, IL1α, IL6, IL8, MMP9NGAL, NSE and VEGF.

Embodiment 64

The method of embodiment 61, wherein the one or more sample is serum and the panel of biomarkers is selected from the group consisting of:
(i) IL2, IL10, NGAL, NSE and VEGF;
(ii) CEA, IL4, IL8, NGAL and TM;
(iii) CEA, CRP, NGAL, NSE and sTNFR1;
(iv) d-Dimer, CRP, IL6, IL8, NSE and sTNFR1;
(v) CEA, IL4, IL10, IFNγ, MCP1 and NGAL;
(vi) FPSA, IL4, IL8, MMP9NGAL, NSE and sTNFR1;
(vii) FPSA, IL1β, IL2, IL4, IL8, MMP9NGAL and NGAL;
(viii) CEA, d-Dimer, IL8, IL10, IFNγ, NGAL and NSE; and
(ix) CEA, EGF, CRP, IL10, MCP1, NGAL and NSE.

Embodiment 65

The method of embodiment 61, wherein the one or more sample is plasma and the panel of biomarkers is selected from the group consisting of:
(i) IL1α, IL6, MMP9NGAL, TM and sTNFR1;
(ii) IL1α, IL1β, IL6, IL8 and TNFα;
(iii) IL8, MMP9NGAL, NGAL, NSE and TNFα;
(iv) IL1β, IL2, IL8, MMP9NGAL, NGAL and NSE;
(v) IL1β, IL8, IL10, MCP1, NGAL and TM;
(vi) IL8, IFNγ, MMP9NGAL, TM, sTNFR1 and TNFα;
(vii) IL1β, IL8, IFNγ, MCP1, MMP9NGAL, TM and sTNFR1;
(viii) IL1α, IL4, IL8, IL10, MCP1, TM and sTNFR1; and
(ix) IL1α, IL1β, IL6, IL8, NGAL, NSE and VEGF.

Embodiment 66

The method of any one of embodiments 6 to 10, wherein the subject does not have a history of exposure to occupational risks or hazardous chemicals.

Embodiment 67

The method of embodiment 66, wherein the panel of biomarkers is selected from the group consisting of:
(i) serum CEA, serum d-Dimer, urinary EGF and serum IL1α;
(ii) serum CEA, serum d-Dimer, serum IL6 and serum MCP1; and
(iii) urinary BTA, serum CEA, urinary TNFα and urinary CK18.

Embodiment 68

The method of embodiment 66, wherein the one or more sample is urine and the panel of biomarkers is selected from the group consisting of:
(i) BTA, TM, TNFα, sTNFR2 and vWF;
(ii) BTA, TM, TNFα, vWF and FAS;
(iii) EGF, NSE, TNFα, vWF and HA;
(iv) IL6, MCP1, TNFα, vWF, FAS and CK18;
(v) BTA, d-Dimer, CRP, TNFα, vWF and HA;
(vi) BTA, IL1α, TNFα, vWF, HA and FAS;
(vii) BTA, d-Dimer, MMP9NGAL, TM, TNFα, vWF and HA;
(viii) IL6, NGAL, sTNFR, TNFα, vWF, FAS and CK18; and
(ix) BTA, IL1α, IL1β, IL6, NGAL, TNFα and CK18.

Embodiment 69

The method of embodiment 66, wherein the one or more sample is serum and the panel of biomarkers is selected from the group consisting of:
(i) CEA, d-Dimer, NSE, TM and TPSA;
(ii) CEA, EGF, IL10, MCP1 and sTNFR1;
(iii) CEA, d-Dimer, CRP, MCP1 and NGAL;
(iv) CEA, d-Dimer, EGF, IL8, IL10 and TM;
(v) CEA, d-Dimer, IL4, MCP1, MMP9NGAL and sTNFR1;
(vi) CEA, d-Dimer, EGF, IL6, NGAL and TM;
(vii) CEA, d-Dimer, IL4, IL10, MCP1, MMP9NGAL and NSE;
(viii) CEA, d-Dimer, IFNγ, MCP1, MMP9NGAL, TM and TPSA; and
(ix) CEA, d-Dimer, EGF, IL6, IL10, MMP9NGAL and TM.

Embodiment 70

The method of embodiment 66, wherein the one or more sample is plasma and the panel of biomarkers is selected from the group consisting of:
(i) IL4, IL6, IFNγ, MMP9NGAL and NGAL;
(ii) IL1β, IL4, IL10, MMP9NGAL and TM;

(iii) IL2, IL4, IL6, IFNγ and MMP9NGAL;
(iv) IL2, IL4, IL10, MMP9NGAL, TNFα and VEGF;
(v) CRP, IL4, IL10, MMP9NGAL, TNFα and VEGF;
(vi) IL1α, IL4, IL10, IFNγ, MMP9NGAL and NSE;
(vii) IL4, IL6, IL10, MMP9NGAL, NGAL, sTNFR1 and VEGF;
(viii) d-Dimer, CRP, IL1α, IL1β, IL2, IL4 and MMP9NGAL; and
(ix) d-Dimer, CRP, IL1β, IL4, IL6, IL10 and MMP9NGAL.

Embodiment 71

The method of any one of embodiments 6 to 10, wherein the subject has a history of anti-cholesterol medication.

Embodiment 72

The method of embodiment 71, wherein the panel of biomarkers is selected from the group consisting of:
(i) serum MCP1, plasma MCP1, serum NGAL and plasma NGAL;
(ii) urinary CRP, serum IL2, serum NGAL and plasma NGAL; and
(iii) urinary Creatinine, serum NGAL, plasma NGAL and plasma VEGF.

Embodiment 73

The method of embodiment 71, wherein the one or more sample is urine and the panel of biomarkers is selected from the group consisting of:
(i) CRP, MCP1, sTNFR2, vWF and FAS;
(ii) d-Dimer, IL6, MMP9NGAL, NSE and VEGF;
(iii) BTA, MCP1, sTNFR2, vWF and FAS;
(iv) d-Dimer, IL6, NGAL, NSE, VEGF and HA;
(v) IL1β, IL6, IL8, MMP9NGAL, NSE and VEGF;
(vi) BTA, d-Dimer, IL6, NGAL, NSE and VEGF;
(vii) BTA, CRP, IL1β, IL8, sTNFR2, vWF and FAS;
(viii) d-Dimer, IL4, IL6, MMP9, NSE, VEGF and CK18; and
(ix) BTA, CRP, IL1α, IL2, sTNFR2, vWF and FAS.

Embodiment 74

The method of embodiment 71, wherein the one or more sample is serum and the panel of biomarkers is selected from the group consisting of:
(i) IL6, IL8, NGAL, TPSA and VEGF;
(ii) FPSA, NGAL, TM, TNFα and VEGF;
(iii) IL1β, IL2, NGAL, TM and VEGF;
(iv) IL1α, MCP1, MMP9NGAL, NGAL, TM and TNFα;
(v) CEA, FPSA, IL8, NGAL, TM and VEGF;
(vi) FPSA, IL4, NGAL, NSE, TNFα and VEGF;
(vii) FPSA, IL1β, IL10, NGAL, TM, TNFα and VEGF;
(viii) CEA, IL1β, IL4, NGAL, TM, TPSA and VEGF; and
(ix) FPSA, IL1β, IL4, IL10, NGAL, TM and VEGF.

Embodiment 75

The method of embodiment 71, wherein the one or more sample is plasma and the panel of biomarkers is selected from the group consisting of:
(i) IL2, IFNγ, MCP1, MMP9NGAL and TM;
(ii) IL1α, IL1β, IL6, TNFα and VEGF;
(iii) IL4, IL6, IFNγ, MCP1 and TNFα;
(iv) d-Dimer, IL2, IL6, MMP9NGAL, TM and TNFα;
(v) IL2, IL10, IFNγ, MCP1, MMP9NGAL and TNFα;
(vi) IL6, MCP1, NGAL, NSE, TM and TNFα;
(vii) d-Dimer, EGF, IL6, IL10, IFNγ, MCP1 and TNFα;
(viii) d-Dimer, IL10, IFNγ, MCP1, NGAL, sTNFR and VEGF; and
(ix) d-Dimer, IL6, IL8, IL10, NSE, TM and TNFα.

Embodiment 76

The method of any one of embodiments 6 to 10, wherein the subject does not have a history of anti-cholesterol medication.

Embodiment 77

The method of embodiment 76, wherein the panel of biomarkers is selected from the group consisting of:
(i) serum CEA, urinary EGF, urinary HA and urinary CK18;
(ii) serum CEA, urinary EGF, urinary IL8 and urinary CK18; and
(iii) serum CEA, urinary EGF, plasma IL6 and urinary MMP9NGAL.

Embodiment 78

The method of embodiment 76, wherein the one or more sample is urine and the panel of biomarkers is selected from the group consisting of:
(i) BTA, CRP, IL2, IL4 and CK18;
(ii) EGF, IL1β, NGAL, VEGF and CK18;
(iii) BTA, IL4, IL8, HA and CK18;
(iv) EGF, CRP, IL4, VEGF, HA and CK18;
(v) EGF, IL4, IL6, IL8, vWF and CK18;
(vi) BTA, EGF, IL4, IL8, HA and CK18;
(vii) BTA, EGF, CRP, IL4, sTNFR1, HA and CK18;
(viii) EGF, IL1α, IL1β, IL4, sTNFR1, VEGF and CK18; and
(ix) EGF, CRP, IL4, MMP9NGAL, NGAL, HA and CK18.

Embodiment 79

The method of embodiment 76, wherein the one or more sample is serum and the panel of biomarkers is selected from the group consisting of:
(i) CEA, FPSA, IL10, IFNγ and NGAL;
(ii) CEA, IL1α, IL1β, MMP9NGAL and sTNFR1;
(iii) CEA, IL1α, MMP9NGAL, TM and TNFα;
(iv) CEA, IL1α, IL1β, IL6, NGAL and NSE;
(v) CEA, IL4, IL6, IL8, MMP9NGAL and TNFα;
(vi) CEA, d-Dimer, IL1α, IL4, IL6 and sTNFR1;
(vii) CEA, IL1α, IL4, IL6, IL8, TM and sTNFR1;
(viii) CEA, IL1α, IL1β, IL4, IL8, MMP9NGAL and VEGF; and
(ix) CEA, IL1α, IL4, IL10, MMP9NGAL, TM and TNFα.

Embodiment 80

The method of embodiment 76, wherein the one or more sample is plasma and the panel of biomarkers is selected from the group consisting of:
(i) IL1α, IL8, MMP9NGAL, NGAL and sTNFR1;
(ii) IL1α, IL1β, IL4, IFNγ and sTNFR1;
(iii) IL1α, IL1β, IL8, TM and sTNFR1;
(iv) d-Dimer, IL1α, IL4, IL10, MMP9NGAL and TNFα;

(v) CRP, IL8, IL10, MMP9NGAL, TM and sTNFR1;
(vi) d-Dimer, IL1α, IL1β, IL4, TM and sTNFR1;
(vii) IL1β, IL6, IL8, MMP9NGAL, sTNFR1, TNFα and VEGF;
(viii) d-Dimer, IL1α, IL4, IL8, NGAL, TM and sTNFR1; and
(ix) IL1α, IL1β, IL4, IL6, IL8, MMP9NGAL and sTNFR1.

Embodiment 81

The method of any one of embodiments 6 to 10, wherein the subject has proteinuria.

Embodiment 82

The method of embodiment 81, wherein the panel of biomarkers is selected from the group consisting of:
(i) serum CEA, plasma CRP, urinary IL8 and plasma TNFα;
(ii) urinary EGF, urinary IL1β, serum IL6 and urinary vWF; and
(iii) serum CEA, plasma SERUM-IL1α, urinary NSE and serum NSE.

Embodiment 83

The method of embodiment 81, wherein the one or more sample is urine and the panel of biomarkers is selected from the group consisting of:
(i) EGF, IL2, NSE, TM and CK18;
(ii) EGF, IL6, sTNFR1, HA and CK18;
(iii) EGF, NGAL, vWF, HA and CK18;
(iv) EGF, IL8, sTNFR2, VEGF, vWF and HA;
(v) EGF, IL1α, MMP9, NSE, vWF and HA;
(vi) EGF, CRP, IL2, IL4, TM and CK18;
(vii) EGF, IL1β, IL2, NSE, TM, VEGF and vWF;
(viii) EGF, IL1β, MMP9, MMP9NGAL, TNFα, vWF and HA; and
(ix) EGF, IL2, IL4, NGAL, NSE, TM and CK18.

Embodiment 84

The method of embodiment 81, wherein the one or more sample is serum and the panel of biomarkers is selected from the group consisting of:
(i) CEA, IL8, IL10, NSE and TNFα;
(ii) CEA, IL2, IL8, MMP9NGAL and NSE;
(iii) CEA, IL2, IL6, IL10 and NSE;
(iv) CEA, IL1β, IL2, IL8, IL10 and NSE;
(v) CEA, IL1β, IL2, IL8, NSE and TPSA;
(vi) CEA, CRP, IL10, MMP9NGAL, NGAL and VEGF;
(vii) CEA, IL1β, IL2, IL4, IL8, NSE and TNFα;
(viii) CEA, EGF, IL4, IL8, IL10, TPSA and VEGF; and
(ix) CEA, IL1β, IL2, IL4, IL10, MMP9NGAL and TM.

Embodiment 85

The method of embodiment 81, wherein the one or more sample is plasma and the panel of biomarkers is selected from the group consisting of:
(i) CRP, IL1α, IL8, IFNγ, TM;
(ii) CRP, IL1α, IL8, IFNγ, NGAL;
(iii) IL1α, IL2, IL8, MCP1, TM;
(iv) EGF, IL1α, IL4, IL8, IFNγ, TM;
(v) d-Dimer, IL1α, IL8, IFNγ, MCP1, TM;
(vi) IL1α, IL8, IFNγ, MCP1, TM, TNFα;
(vii) IL1α, IL2, IL8, IL10, IFNγ, MCP1, TM;
(viii) IL1α, IL2, IL8, IFNγ, MCP1, MMP9NGAL, TM; and
(ix) EGF, CRP, IL1α, IL4, IL8, IFNγ, TNFα.

Embodiment 86

The method of any one of embodiments 6 to 10, wherein the subject does not have proteinuria.

Embodiment 87

The method of embodiment 86, wherein the panel of biomarkers is selected from the group consisting of:
(i) urinary BTA, urinary NGAL, serum NGAL and urinary TNFα;
(ii) urinary d-Dimer, urinary CRP, urinary NGAL and serum TNFα; and
(iii) serum CEA, urinary CRP, plasma MMP9NGAL and urinary NGAL.

Embodiment 88

The method of embodiment 86, wherein the one or more sample is urine and the panel of biomarkers is selected from the group consisting of:
(i) d-Dimer, CRP, IL4, NGAL and sTNFR2;
(ii) CRP, MMP9NGAL, NGAL, sTNFR2 and VEGF;
(iii) BTA, CRP, IL4, NGAL and sTNFR2;
(iv) CRP, MCP1, MMP9, NGAL, sTNFR2 and VEGF;
(v) d-Dimer, CRP, IL2, IL4, NGAL and sTNFR;
(vi) BTA, CRP, IL2, NGAL, sTNFR2 and vWF;
(vii) d-Dimer, CRP, IL1α, IL4, MMP9NGAL, TM and CK18;
(viii) BTA, EGF, CRP, MMP9, NGAL, vWF and FAS; and
(ix) BTA, CRP, NGAL, NSE, TM, sTNFR2 and vWF.

Embodiment 89

The method of embodiment 86, wherein the one or more sample is serum and the panel of biomarkers is selected from the group consisting of:
(i) FPSA, IL1α, IL4, IFNγ and NGAL;
(ii) d-Dimer, IL2, IL4, NGAL and TM;
(iii) d-Dimer, IL6, NGAL, TM and sTNFR1;
(iv) d-Dimer, IL1β, IL8, NGAL, TM and TNFα;
(v) CEA, IL4, IL8, NGAL, TNFα and TPSA;
(vi) d-Dimer, FPSA, IL2, IL6, IL8 and NGAL;
(vii) FPSA, CRP, IL2, IL6, NGAL, TNFα and VEGF;
(viii) CEA, FPSA, CRP, IL6, IL10, NGAL and VEGF; and
(ix) d-Dimer, FPSA, IL1β, IFNγ, MMP9NGAL, NGAL and TM.

Embodiment 90

The method of embodiment 86, wherein the one or more sample is plasma and the panel of biomarkers is selected from the group consisting of:
(i) d-Dimer, IL4, MCP1, MMP9NGAL and TNFα;
(ii) EGF, IL1α, IL2, MMP9NGAL and NGAL;
(iii) d-Dimer, IL4, MCP1, MMP9NGAL and sTNFR1;
(iv) d-Dimer, IL1β, IL4, IL8, IL10 and MMP9NGAL;
(v) d-Dimer, EGF, IL8, IL10, MMP9NGAL and TM;
(vi) d-Dimer, EGF, IFNγ, MMP9NGAL, NSE and VEGF;

(vii) EGF, IL1α, IL2, IL4, MCP1, MMP9NGAL and NGAL;
(viii) d-Dimer, EGF, CRP, IL8, MMP9NGAL, NSE and VEGF; and
(ix) d-Dimer, EGF, IL1β, IL8, IL10, MMP9NGAL and VEGF.

Embodiment 91

A solid state device comprising a substrate comprising an antibody to one or more of the biomarkers selected from Bladder Tumour Antigen (BTA), Carcino-embryonic antigen (CEA), Human cytokeratin 18 (CK18), C-reactive protein (CRP), Creatinine, d Dimer, Epidermal growth factor (EGF), FAS, Hyaluronidase (HA), IL1α, IL1β, IL2, IL4, IL6, IL8, IL10, Interferon gamma (IFNγ), Monocyte Chemoattractant Protein 1 (MCP1), matrix metalloproteinase 9 (MMP9), Neutrophil gelatinase-associated lipocalin (NGAL), MMP9NGAL complex, Neuron specific enolase (NSE), Free Prostate Specific Antigen (FPSA), Total Prostate Specific Antigen (TPSA), Thrombomodulin (TM), Tumour necrosis factor α (TNFα), sTNFR1, sTNFR2, Vascular endothelial growth factor (VEGF) and von Willebrand factor (vWF).

Embodiment 92

A solid state device according to embodiment 91, wherein the antibody is a monoclonal antibody.

Embodiment 93

A solid state device according to embodiments 91 or 92, comprising antibodies that bind specifically to a panel of biomarkers selected from the group consisting of:
(i) urinary EGF, urinary IL6, urinary VEGF and urinary CK18;
(ii) urinary EGF, serum IL8, urinary vWF and urinary FAS;
(iii) urinary EGF, urinary IL1α, plasma MMP9NGAL and urinary vWF;
(iv) EGF, IL1β, sTNFR, VEGF and CK18;
(v) BTA, EGF, IL1β, vWF and FAS;
(vi) EGF, IL1β, IL8, TM, and vWF;
(vii) dDimer, EGF, IL1β, IL8, VEGF and vWF;
(viii) EGF, IL1β, NSE, sTNFR2, VEGF and vWF;
(ix) EGF, IL2, TM, sTNFR2, VEGF and CK18;
(x) EGF, IL1α, MMP9, MMP9NGAL, NSE, VEGF and vWF;
(xi) EGF, IL1β, NGAL, NSE, sTNFR1, VEGF and vWF;
(xii) d-Dimer, EGF, IL1α, IL8, NSE, vWF and FAS;
(xiii) d-Dimer, EGF, IL1α, IL8 and NGAL;
(xiv) IL1α, IL2, IL8, NGAL and sTNFR1;
(xv) IL1α, IL10, NGAL, NSE and TNFα;
(xvi) d-Dimer, IL2, IL10, MMP9NGAL, NGAL and sTNFR1;
(xvii) EGF, FPSA, IL10, NGAL, TNFα and TPSA;
(xviii) CEA, IL1α, IL4, IL8, IL10 and NGAL;
(xix) EGF, CRP, IL10, MMP9NGAL, NGAL, TM and VEGF;
(xx) CEA, CRP, IL10, MMP9NGAL, NGAL, TM and TNFα;
(xxi) CEA, d-Dimer, IL2, IL8, IL10, IFNγ and NSE;
(xxii) IL4, IFNγ, MCP1, MMP9NGAL and TM;
(xxiii) IL1α, IL4, IFNγ, MCP1 and MMP9NGAL;
(xxiv) EGF, IL1α, IL4, MCP1, MMP9NGAL;
(xxv) dDimer, IL1α, IL4, IL10, MMP9NGAL and sTNFR1;
(xxvi) IL4, IL10, MMP9NGAL, TM, sTNFR1 and TNFα;
(xxvii) IL1β, IL4, IL8, MCP1, MMP9NGAL and TNFα;
(xxviii) IL1α, IL1β, IL2, IL4, IL10, MMP9NGAL and TNFα
(xxix) d-Dimer, IL1α, IL4, IFNγ, MCP1, MMP9NGAL and TM; and
(xxx) d-Dimer, EGF, IL1α, IL4, IL10, IFNγ, and MMP9NGAL.

Embodiment 94

A solid state device according to embodiments 91 or 92, comprising antibodies that bind specifically to a panel of biomarkers selected from the group consisting of:
(i) serum CEA, urinary EGF, plasma IL8 and urinary CK18;
(ii) serum CEA, plasma IL8, serum NGAL and serum TM;
(iii) serum CEA, plasma IL8, serum NGAL and plasma NSE;
(iv) BTA, MMP9NGAL, TM, sTNFR2 and VEGF;
(v) BTA, IL4, MMP9, NSE and FAS;
(vi) BTA, MMP9NGAL, TNFα, sTNFR2 and VEGF;
(vii) BTA, MCP1, MMP9, sTNFR2, vWF and FAS;
(viii) d-Dimer, IL6, IL8, NGAL, NSE and TNFα;
(ix) BTA, IL6, MCP1, TNFα, sTNFR2 and FAS;
(x) EGF, CRP, IL8, NGAL, NSE, TM and HA;
(xi) BTA, EGF, IL8, MCP1, NGAL, NSE, sTNFR1;
(xii) BTA, IL4, MCP1, TM, sTNFR2, vWF and FAS;
(xiii) CEA, EGF, IL4, NGAL and TNFα;
(xiv) CEA, EGF, IL8, NGAL and TPSA;
(xv) CEA, IL8, MCP1, NGAL and TPSA;
(xvi) CEA, IL6, IL8, MMP9NGAL, NGAL and VEGF;
(xvii) CEA, d-Dimer, CRP, MMP9NGAL, NGAL and NSE;
(xviii) CEA, CRP, IL2, MMP9NGAL, NGAL and TM;
(xix) CEA, EGF, CRP, IL4, IL8, NGAL and NSE;
(xx) CEA, IL6, IL8, IFNγ, NGAL, TM and VEGF;
(xxi) CEA, FPSA, CRP, IL4, MMP9NGAL, NGAL and TM;
(xxii) IL1α, MMP9NGAL, NSE, sTNFR1 and VEGF;
(xxiii) IFNγ, MCP1, MMP9NGAL, NGAL and NSE;
(xxiv) IFNγ, MMP9NGAL, NGAL, NSE and TNFα;
(xxv) IL6, IFNγ, MMP9NGAL, NGAL, NSE and TNFα;
(xxvi) d-Dimer, IL1α, IL4, MMP9NGAL, NSE and VEGF;
(xxvii) d-Dimer, EGF, IL1α, IL8, MMP9NGAL and NSE;
(xxviii) d-Dimer, EGF, IL1α, IFNγ, MMP9NGAL, TNFα and VEGF;
(xxix) EGF, IL1α, IL2, MMP9NGAL, NGAL, NSE and TM; and
(xxx) IL1α, IFNγ, MMP9NGAL, NGAL, NSE, TM and TNFα.

Embodiment 95

A solid state device according to embodiments 91 or 92, comprising antibodies that bind specifically to a panel of biomarkers selected from the group consisting of:
(i) serum IL2, serum MMP9NGAL, serum NGAL and plasma sTNFR1;
(ii) urinary MMP9NGAL, serum NGAL, plasma NGAL and urinary vWF;
(iii) serum CEA, serum d-Dimer, plasma d-Dimer and serum IFNγ;

(iv) BTA, IL1β, VEGF, vWF and HA;
(v) d-Dimer, IL1α, NSE, vWF and HA;
(vi) BTA, d-Dimer, IL1β, vWF and HA;
(vii) BTA, IL1β, IL4, VEGF, vWF and HA;
(viii) BTA, IL1β, IL8, sTNFR2, vWF and HA;
(ix) BTA, EGF, IL1α, NSE, vWF and HA;
(x) d-Dimer, CRP, IL1α, IL2, NSE, vWF and HA;
(xi) BTA, IL1α, IL8, MMP9NGAL, vWF, HA and CK18;
(xii) d-Dimer, IL1α, MCP1, NSE, TNFα, vWF and HA;
(xiii) CEA, d-Dimer, IL4, NGAL and TM;
(xiv) IL1α, MMP9NGAL, NGAL, sTNFR1 and TNFα;
(xv) IL2, MMP9NGAL, NGAL, sTNFR1 and VEGF;
(xvi) CEA, d-Dimer, IL1α, NGAL, NSE and TM;
(xvii) CEA, EGF, IL1α, MMP9NGAL, NGAL and TPSA;
(xviii) CEA, d-Dimer, CRP, IL1β, NGAL and TM;
(xix) CEA, d-Dimer, FPSA, CRP, IL10, NGAL and TM;
(xx) CEA, d-Dimer, CRP, NGAL, NSE, TM and TPSA;
(xxi) d-Dimer, IL1α, IL8, IFNγ, MMP9NGAL, NGAL and TM;
(xxii) CRP, IL1α, MMP9NGAL, TM and VEGF;
(xxiii) CRP, IL1α, IL1β, MMP9NGAL and NGAL;
(xxiv) CRP, IL1α, IL4, MMP9NGAL and TM;
(xxv) CRP, IL1α, IL2, IL4, MMP9NGAL and TM;
(xxvi) EGF, CRP, IL1α, IL1β, MMP9NGAL and VEGF;
(xxvii) EGF, IL1α, IL6, MMP9NGAL, TM and TNFα;
(xxviii) CRP, IL1α, IL10, MMP9NGAL, TM, TNFα and VEGF;
(xxix) IL1α, IL6, IL10, MMP9NGAL, TM, TNFα and VEGF; and
(xxx) CRP, IL1α, IL4, IL6, MMP9NGAL, TM and TNFα.

Embodiment 96

A solid state device according to embodiments 91 or 92, comprising antibodies that bind specifically to a panel of biomarkers selected from the group consisting of:
(i) serum CEA, urinary EGF, serum IL1α and urinary VEGF;
(ii) serum CEA, urinary CRP, serum IL1α and urinary VEGF; and
(iii) serum CEA, serum-IL1α, plasma IFNγ and urinary VEGF.
(iv) EGF, IL2, HA, FAS and CK18;
(v) EGF, IL2, MMP9NGAL, HA and CK18;
(vi) EGF, vWF, HA, FAS and CK18;
(vii) EGF, IL2, IL8, MMP9, HA and CK18;
(viii) BTA, EGF, IL1β, IL8, HA and CK18;
(ix) d-Dimer, EGF, NSE, vWF, HA and CK18;
(x) EGF, CRP, IL1β, IL2, IL8, HA and CK18;
(xi) EGF, IL1β, IL4, IL8, vWF, HA and CK18;
(xii) EGF, IL1β, IL6, IL8, MMP9, HA and CK18;
(xiii) CEA, IL1α, IL4, TM and TNFα;
(xiv) CEA, IL1α, IL2, IL4 and IL8;
(xv) CEA, IL1α, IL1β, IL4 and VEGF;
(xvi) CEA, IL1α, IL4, IL8, MMP9NGAL and sTNFR1;
(xvii) CEA, IL1α, IL2, IL4, NSE and sTNFR1;
(xviii) CEA, EGF, IL1α, IL4, IL8 and TM;
(xix) CEA, IL1α, IL2, IL4, IL8, IFNγ and MMP9NGAL;
(xx) CEA, EGF, FPSA, IL1α, IL4, IL8 and VEGF;
(xxi) CEA, IL1α, IL2, IL8, IFNγ, MCP1 and sTNFR1;
(xxii) d-Dimer, IL8, IL10, NSE and VEGF;
(xxiii) d-Dimer, IL8, MMP9NGAL, TNFα and VEGF;
(xxiv) EGF, IL8, IL10, MMP9NGAL and sTNFR1;
(xxv) EGF, CRP, IL6, IL8, IL10 and sTNFR1;
(xxvi) CRP, IL6, IL8, IL10, IFNγ and sTNFR1;
(xxvii) d-Dimer, IL4, IL8, MMP9NGAL, NGAL and TNFα;
(xxviii) CRP, IL4, IL6, IL8, IL10, MMP9NGAL and TNFα;
(xxix) EGF, CRP, IL1β, IL8, IFNγ, NGAL and sTNFR1; and
(xxx) d-Dimer, EGF, CRP, IL8, IL10, IFNγ and MMP9NGAL.

Embodiment 97

A solid state device according to embodiments 91 or 92, comprising antibodies that bind specifically to a panel of biomarkers selected from the group consisting of:
(i) urinary EGF, urinary IL1α, serum IL10 and urinary vWF;
(ii) urinary EGF, plasma IL10, urinary VEGF and urinary vWF;
(iii) serum sTNFR1, plasma sTNFR1, serum TNFα and urinary vWF;
(iv) CRP, IL2, IL8, sTNFR2 and vWF;
(v) EGF, IL8, NSE, TNFα and vWF;
(vi) BTA, EGF, IL4, vWF and HA;
(vii) BTA, EGF, IL1β, IL8, VEGF and vWF;
(viii) d-Dimer, CRP, IL8, sTNFR2, vWF and CK18;
(ix) d-Dimer, EGF, IL2, VEGF, vWF and FAS;
(x) CRP, IL1β, IL6, IL8, MMP9, NGAL and vWF;
(xi) d-Dimer, IL8, MMP9, NSE, TM, sTNFR2 and vWF;
(xii) BTA, d-Dimer, EGF, IL4, NGAL, NSE and vWF;
(xiii) CEA, NGAL, NSE, TNFα and TPSA;
(xiv) CEA, MMP9NGAL, NGAL, TM and TNFα;
(xv) CEA, IL1β, NGAL, sTNFR1 and TPSA;
(xvi) CEA, IL1β, IL10, NGAL, TM and VEGF;
(xvii) CEA, d-Dimer, IL1β, MMP9NGAL, NGAL and TM;
(xviii) CEA, EGF, IL1α, IL1β, NGAL and TNFα;
(xix) CEA, IL1α, IL1β, IL10, NGAL, sTNFR1 and TNFα;
(xx) CEA, IL1α, NGAL, NSE, TM, TNFα and TPSA;
(xxi) CEA, IL1β, IL4, IL10, MMP9NGAL, NGAL and TM;
(xxii) IL1α, IL1β, IL4, IFNγ and VEGF;
(xxiii) EGF, CRP, IL2, IL4 and IL8;
(xxiv) EGF, CRP, IL2, IL10 and NGAL;
(xxv) EGF, IL6, IL10, IFNγ, MCP1 and MMP9NGAL;
(xxvi) d-Dimer, EGF, IL1β, IL4, IL6 and MCP1;
(xxvii) EGF, CRP, IL1β, IL2, MMP9NGAL and NGAL;
(xxviii) d-Dimer, EGF, CRP, IL2, IL10, MMP9NGAL and TM;
(xxix) CRP, IL1α, IL1β, IL4, IL6, IFNγ and sTNFR1; and
(xxx) EGF, CRP, IL4, IL6, IL10, IFNγ and MMP9NGAL.

Embodiment 98

A solid state device according to embodiments 91 or 92, comprising antibodies that bind specifically to a panel of biomarkers selected from the group consisting of:
(i) serum CEA, urinary CRP, urinary NSE and serum TNF;
(ii) serum CEA, urinary CRP, serum IL4 and urinary sTNFR1;
(iii) urinary Creatinine, serum IL6, plasma MMP9NGAL and urinary VEGF;
(iv) CRP, NGAL, VEGF, HA and CK18;
(v) d-Dimer, TNFα, VEGF, HA and CK18;
(vi) MMP9, NSE, TM, VEGF and FAS;
(vii) EGF, NGAL, VEGF, vWF, HA and CK18;

(viii) CRP, IL1β, IL6, sTNFR1, VEGF and vWF;
(ix) d-Dimer, EGF, IL4, VEGF, HA and CK18;
(x) CRP, IL1β, IL6, IL8, MMP9, NGAL and vWF;
(xi) d-Dimer, IL8, MMP9, NSE, TM, sTNFR2 and vWF;
(xii) BTA, d-Dimer, EGF, IL4, NGAL, NSE and vWF;
(xiii) CEA, d-Dimer, IL4, MMP9NGAL and sTNFR1;
(xiv) CEA, EGF, IL10, MMP9NGAL and TNFα;
(xv) CEA, d-Dimer, CRP, IL4 and IL10;
(xvi) CEA, d-Dimer, CRP, IL4, IL10 and TM;
(xvii) CEA, d-Dimer, CRP, IL4, IL6 and MMP9NGAL;
(xviii) CEA, d-Dimer, IL2, IL4, IL8 and MMP9NGAL;
(xix) CEA, d-Dimer, EGF, IL4, IL8, IL10 and NSE;
(xx) CEA, d-Dimer, CRP, IL4, MCP1, MMP9NGAL and TNFα;
(xxi) CEA, d-Dimer, CRP, IL4, IL6, TM and TNFα;
(xxii) EGF, IL1α, IL8, MMP9NGAL and VEGF;
(xxiii) IL1α, IL8, IFNγ, MMP9NGAL and VEGF;
(xxiv) CRP, IL1α, IL8, MMP9NGAL and NGAL;
(xxv) EGF, CRP, IL1β, IL8, MMP9NGAL and VEGF;
(xxvi) CRP, IL1α, IL6, IL8, IL10, MMP9NGAL;
(xxvii) EGF, IL1β, IL4, IL8, MMP9NGAL and VEGF;
(xxviii) EGF, CRP, IL1α, IL8, MMP9NGAL, TNFα and VEGF;
(xxix) EGF, CRP, IL1β, IL8, MMP9NGAL, sTNFR1 and VEGF; and
(xxx) d-Dimer, EGF, IL1β, IL6, IL8, MMP9NGAL and VEGF.

Embodiment 99

A solid state device according to embodiments 91 or 92, comprising antibodies that bind specifically to a panel of biomarkers selected from the group consisting of:
(i) urinary BTA, serum CEA, plasma IL10 and urinary CK18;
(ii) urinary BTA, plasma IL6, serum NSE and plasma NSE;
(iii) urinary dipstick protein, urinary BTA, plasma IL6 and serum NGAL;
(iv) BTA, IL1α, NGAL, sTNFR1 and vWF;
(v) BTA, IL8, MMP9NGAL, VEGF and CK18;
(vi) BTA, IL6, MMP9NGAL, NSE and CK18;
(vii) BTA, IL2, MMP9NGAL, sTNFR1, TNFα and VEGF;
(viii) BTA, IL2, MMP9NGAL, NGAL, TNFα and CK18;
(ix) BTA, IL2, MMP9NGAL, NSE, VEGF and CK18;
(x) BTA, IL2, MMP9NGAL, NGAL, sTNFR1, TNFα and VEGF;
(xi) BTA, IL2, MMP9NGAL, TM, sTNFR1, vWF and FAS;
(xii) BTA, IL2, MMP9NGAL, sTNFR1, VEGF, vWF and CK18;
(xiii) CEA, IL1α, NGAL, NSE and TPSA;
(xiv) IL1α, MMP9NGAL, NGAL, TPSA and VEGF;
(xv) CEA, IL1α, IL10, NGAL and VEGF;
(xvi) CEA, IL10, MMP9NGAL, NGAL, TNFα and VEGF;
(xvii) IL1α, IL10, MMP9NGAL, NGAL, NSE and VEGF;
(xviii) CRP, IL10, MMP9NGAL, NGAL, TPSA and VEGF;
(xix) CEA, CRP, IL1β, IL2, TM, sTNFR1 and TPSA;
(xx) CRP, IL1β, IL2, IL6, MMP9NGAL, NGAL and TNFα;
(xxi) CRP, IL1β, IL2, MMP9NGAL, NGAL, NSE and TNFα;
(xxii) IL1α, IL6, IL8, MMP9NGAL and NSE;
(xxiii) IL6, IFNγ, MMP9NGAL, NSE and sTNFR1;
(xxiv) IL1α, IL1β, IL8, IL10 and MMP9NGAL;
(xxv) IL6, IL8, IFNγ, MMP9NGAL, NGAL and NSE;
(xxvi) IL1α, IL6, MMP9NGAL, NSE, TM and TNFα;
(xxvii) d-Dimer, IL4, IL8, IFNγ, MMP9NGAL and VEGF;
(xxviii) IL1α, IL8, IL10, MCP1, MMP9NGAL, NSE and TM;
(xxix) d-Dimer, IL2, IL6, IL8, MMP9NGAL, TM and sTNFR1; and
(xxx) IL1α, IL2, IL6, IL8, MCP1, MMP9NGAL and NSE.

Embodiment 100

A solid state device according to embodiments 91 or 92, comprising antibodies that bind specifically to a panel of biomarkers selected from the group consisting of:
(i) serum CEA, plasma IL8, serum TNFα and urinary FAS;
(ii) urinary EGF, serum EGF, serum FPSA and serum IL4;
(iii) urinary EGF, urinary CRP, urinary IL4 and urinary NSE;
(iv) EGF, CRP, IL4, TM and vWF;
(v) BTA, d-Dimer, EGF, CRP and IL4;
(vi) EGF, CRP, IL4, IL6 and vWF;
(vii) d-Dimer, EGF, CRP, IL4, sTNFR1 and vWF;
(viii) d-Dimer, EGF, CRP, IL4, sTNFR1 and sTNFR2;
(ix) EGF, IL2, IL4, sTNFR2, VEGF and vWF;
(x) EGF, CRP, IL4, MCP1, VEGF, FAS and CK18;
(xi) d-Dimer, EGF, CRP, IL4, IL6, sTNFR2 and vWF;
(xii) d-Dimer, EGF, CRP, IL4, IL6, sTNFR2 and CK18;
(xiii) CEA, EGF, CRP, IL4 and IFNγ;
(xiv) d-Dimer, FPSA, IL6, IFNγ and NGAL;
(xv) IL1α, IL4, MMP9NGAL, NGAL and TM;
(xvi) IL4, MMP9NGAL, NGAL, NSE, sTNFR1 and TPSA;
(xvii) CEA, EGF, FPSA, IL4, NSE and sTNFR1;
(xviii) CEA, EGF, FPSA, IL4, MCP1 and VEGF;
(xix) FPSA, IL2, IL4, IL6, MMP9NGAL, NGAL and sTNFR1;
(xx) CEA, EGF, FPSA, CRP, IL4, IL6 and MMP9NGAL;
(xxi) d-Dimer, IL1β, IL4, IL8, MCP1, NGAL and TM;
(xxii) d-Dimer, IL1β, IL8, MMP9NGAL and TM;
(xxiii) d-Dimer, IL8, TM, TNFα and VEGF;
(xxiv) IL2, IL8, MMP9NGAL, TM and TNFα;
(xxv) d-Dimer, IL8, MMP9NGAL, NSE, TM and TNFα;
(xxvi) d-Dimer, IL2, IL8, MMP9NGAL, NSE and TNFα;
(xxvii) d-Dimer, IL8, IFNγ, MMP9NGAL, sTNFR1 and TNFα;
(xxviii) d-Dimer, IL1α, IL8, MMP9NGAL, TM, TNFα and VEGF;
(xxix) d-Dimer, CRP, IL2, IL6, IL8, MMP9NGAL and TNFα; and
(xxx) d-Dimer, IL1α, IL1β, IL8, MMP9NGAL, TM and VEGF.

Embodiment 101

A solid state device according to embodiments 91 or 92, comprising antibodies that bind specifically to a panel of biomarkers selected from the group consisting
(i) urinary EGF, urinary IL1β, plasma MMP9NGAL and urinary vWF;
(ii) serum CEA, urinary EGF, urinary vWF and urinary CK18;

(iii) serum CEA, urinary EGF, plasma NSE and urinary vWF;
(iv) EGF, MMP9, sTNFR2, VEGF and vWF;
(v) EGF, IL1α, IL4, vWF and FAS;
(vi) EGF, IL1α, MMP9, vWF and HA;
(vii) d-Dimer, EGF, CRP, IL1α, IL6 and vWF;
(viii) EGF, CRP, IL1α, sTNFR, vWF and CK18;
(ix) BTA, EGF, CRP, IL1α, vWF and FAS;
(x) EGF, IL1α, IL6, NGAL, sTNFR2, vWF and FAS;
(xi) EGF, IL1α, IL2, IL6, NGAL, VEGF and vWF;
(xii) EGF, IL1α, NGAL, NSE, sTNFR2, vWF and CK18;
(xiii) CRP, IL1β, IL6, IL8 and NGAL;
(xiv) d-Dimer, IL1β, IL4, IFNγ and NGAL;
(xv) CRP, IL1β, IL4, MCP1 and NGAL;
(xvi) EGF, CRP, IL1α, IL1β, NGAL and TPSA;
(xvii) CEA, CRP, IL1β, IL2, NGAL and NSE;
(xviii) CEA, d-Dimer, CRP, IL1α, IL6 and NGAL;
(xix) EGF, CRP, IL8, MCP1, MMP9NGAL, NGAL and sTNFR1;
(xx) CEA, EGF, CRP, IL1β, MMP9NGAL, NGAL and TM;
(xxi) CEA, d-Dimer, IL1α, IL2, IL4, IL10 and NGAL;
(xxii) d-Dimer, IL4, MMP9NGAL, NSE and TM;
(xxiii) IL1β, IL4, MMP9NGAL, NSE and TNFα;
(xxiv) EGF, CRP, IL4, MMP9NGAL and sTNFR1;
(xxv) IL1α, IL2, IL4, MMP9NGAL, NSE and TNFα;
(xxvi) IL2, IL4, IL6, MMP9NGAL, NSE and TM;
(xxvii) CRP, IL1α, IL1β, IL4, MMP9NGAL and TNFα;
(xxviii) d-Dimer, IL1β, IL4, MMP9NGAL, NGAL, NSE and VEGF;
(xxix) d-Dimer, IL1α, IL2, MMP9NGAL, NSE, sTNFR and TNFα; and
(xxx) d-Dimer, CRP, IL1α, IL4, IL10, NSE and sTNFR.

Embodiment 102

A solid state device according to embodiments 91 or 92, comprising antibodies that bind specifically to a panel of biomarkers selected from the group consisting of:
(i) serum MMP9NGAL, serum sTNFR1, serum TNFα and urinary VEGF;
(ii) serum CEA, urinary EGF, serum IL10 and serum NGAL;
(iii) urinary IL6, plasma MMP9NGAL, urinary VEGF and urinary CK18;
(iv) IL2, IL8, NGAL, HA and CK18;
(v) IL2, IL4, VEGF, HA and CK18;
(vi) IL1β, IL2, IL8, NGAL and CK18;
(vii) IL2, IL4, IL8, NGAL, HA and CK18;
(viii) BTA, d-Dimer, IL2, IL8, MMP9NGAL and CK18;
(ix) IL2, IL4, IL8, sTNFR2, HA and CK18;
(x) IL1β, IL2, IL6, IL8, NGAL, NSE and CK18;
(xi) IL1α, IL2, IL6, IL8, NGAL, HA and CK18;
(xii) BTA, IL1α, IL2, IL8, NGAL, VEGF and CK18;
(xiii) CEA, IL1α, IL8, TM and sTNFR1;
(xiv) CEA, IL1α, IL6, NGAL and TM;
(xv) CEA, IL1α, IL2, TM and sTNFR1;
(xvi) CEA, IL2, IL8, NSE, TM and sTNFR1;
(xvii) CEA, IL10, MMP9NGAL, NSE, TM and sTNFR1;
(xviii) CEA, CRP, IL2, IL10, NGAL and TM;
(xix) CEA, CRP, IL4, IL6, IL10, sTNFR1 and TPSA;
(xx) CEA, d-Dimer, EGF, IL1α, IL10, NSE and sTNFR1;
(xxi) CEA, d-Dimer, IL1α, IL1β, IL4, TM and sTNFR1;
(xxii) IL1α, IFNγ, MMP9NGAL, sTNFR1 and TNFα;
(xxiii) EGF, IL4, MCP1, MMP9NGAL and sTNFR1;
(xxiv) IL1α, IL8, IL10, MMP9NGAL and VEGF;
(xxv) IL1α, IL1β, IL10, IFNγ, MMP9NGAL and VEGF;
(xxvi) EGF, CRP, IL1α, MMP9NGAL, TNFα and VEGF;
(xxvii) IL1α, IL6, IL8, IFNγ, MMP9NGAL and sTNFR1;
(xxviii) IL1α, IL2, IL8, IFNγ, MMP9NGAL, sTNFR1 and TNFα;
(xxix) IL1α, IL2, IL6, IL10, MMP9NGAL, TNFα and VEGF; and
(xxx) IL1α, IL4, IL6, IL10, MMP9NGAL, NGAL and VEGF.

Embodiment 103

A solid state device according to embodiments 91 or 92, comprising antibodies that bind specifically to a panel of biomarkers selected from the group consisting of:
(i) serum CEA, urinary EGF, urinary VEGF and urinary vWF;
(ii) urinary EGF, serum IL8, urinary vWF and urinary HA;
(iii) serum IL4, plasma IL8, serum MCP1 and urinary VEGF;
(iv) BTA, IL2, IL4, MMP9NGAL and VEGF;
(v) BTA, IL1α, IL8, NGAL and NSE;
(vi) BTA, CRP, IL4, NSE and CK18;
(vii) BTA, d-Dimer, CRP, IL4, sTNFR1 and vWF;
(viii) IL4, IL8, NGAL, NSE, TM and sTNFR1;
(ix) CRP, IL2, IL8, MCP1, MMP9NGAL and TNFα;
(x) EGF, IL1α, IL8, MMP9NGAL, NSE, vWF and CK18;
(xi) EGF, IL6, IL8, MMP9NGAL, NSE, VEGF and vWF;
(xii) CRP, IL1α, IL6, IL8, MMP9NGAL, NSE and VEGF;
(xiii) IL2, IL10, NGAL, NSE and VEGF;
(xiv) CEA, IL4, IL8, NGAL and TM;
(xv) CEA, CRP, NGAL, NSE and sTNFR1;
(xvi) d-Dimer, CRP, IL6, IL8, NSE and sTNFR1;
(xvii) CEA, IL4, IL10, IFNγ, MCP1 and NGAL;
(xviii) FPSA, IL4, IL8, MMP9NGAL, NSE and sTNFR1;
(xix) FPSA, IL1β, IL2, IL4, IL8, MMP9NGAL and NGAL;
(xx) CEA, d-Dimer, IL8, IL10, IFNγ, NGAL and NSE;
(xxi) CEA, EGF, CRP, IL10, MCP1, NGAL and NSE;
(xxii) IL1α, IL6, MMP9NGAL, TM and sTNFR1;
(xxiii) IL1α, IL1β, IL6, IL8 and TNFα;
(xxiv) IL8, MMP9NGAL, NGAL, NSE and TNFα;
(xxv) IL1β, IL2, IL8, MMP9NGAL, NGAL and NSE;
(xxvi) IL1β, IL8, IL10, MCP1, NGAL and TM;
(xxvii) IL8, IFNγ, MMP9NGAL, TM, sTNFR1 and TNFα;
(xxviii) IL1β, IL8, IFNγ, MCP1, MMP9NGAL, TM and sTNFR1;
(xxix) IL1α, IL4, IL8, IL10, MCP1, TM and sTNFR1; and
(xxx) IL1α, IL1β, IL6, IL8, NGAL, NSE and VEGF.

Embodiment 104

A solid state device according to embodiments 91 or 92, comprising antibodies that bind specifically to a panel of biomarkers selected from the group consisting of:
(i) serum CEA, serum d-Dimer, urinary EGF and serum IL1α;
(ii) serum CEA, serum d-Dimer, serum IL6 and serum MCP1;
(iii) urinary BTA, serum CEA, urinary TNFα and urinary CK18;
(iv) BTA, TM, TNFα, sTNFR2 and vWF;
(v) BTA, TM, TNFα, vWF and FAS;
(vi) EGF, NSE, TNFα, vWF and HA;

(vii) IL6, MCP1, TNFα, vWF, FAS and CK18;
(viii) BTA, d-Dimer, CRP, TNFα, vWF and HA;
(ix) BTA, IL1α, TNFα, vWF, HA and FAS;
(x) BTA, d-Dimer, MMP9NGAL, TM, TNFα, vWF and HA;
(xi) IL6, NGAL, sTNFR, TNFα, vWF, FAS and CK18;
(xii) BTA, IL1α, IL1β, IL6, NGAL, TNFα and CK18;
(xiii) CEA, d-Dimer, NSE, TM and TPSA;
(xiv) CEA, EGF, IL10, MCP1 and sTNFR1;
(xv) CEA, d-Dimer, CRP, MCP1 and NGAL;
(xvi) CEA, d-Dimer, EGF, IL8, IL10 and TM;
(xvii) CEA, d-Dimer, IL4, MCP1, MMP9NGAL and sTNFR1;
(xviii) CEA, d-Dimer, EGF, IL6, NGAL and TM;
(xix) CEA, d-Dimer, IL4, IL10, MCP1, MMP9NGAL and NSE;
(xx) CEA, d-Dimer, IFNγ, MCP1, MMP9NGAL, TM and TPSA;
(xxi) CEA, d-Dimer, EGF, IL6, IL10, MMP9NGAL and TM;
(xxii) IL4, IL6, IFNγ, MMP9NGAL and NGAL;
(xxiii) IA1β, IL4, IL10, MMP9NGAL and TM;
(xxiv) IL2, IL4, IL6, IFNγ and MMP9NGAL;
(xxv) IL2, IL4, IL10, MMP9NGAL, TNFα and VEGF;
(xxvi) CRP, IL4, IL10, MMP9NGAL, TNFα and VEGF;
(xxvii) IL1α, IL4, IL10, IFNγ, MMP9NGAL and NSE;
(xxviii) IL4, IL6, IL10, MMP9NGAL, NGAL, sTNFR1 and VEGF;
(xxix) d-Dimer, CRP, IL1α, IL1β, IL2, IL4 and MMP9NGAL; and
(xxx) d-Dimer, CRP, IL1β, IL4, IL6, IL10 and MMP9NGAL.

Embodiment 105

A solid state device according to embodiments 91 or 92, comprising antibodies that bind specifically to a panel of biomarkers selected from the group consisting of:
(i) serum MCP1, plasma MCP1, serum NGAL and plasma NGAL;
(ii) urinary CRP, serum IL2, serum NGAL and plasma NGAL;
(iii) urinary Creatinine, serum NGAL, plasma NGAL and plasma VEGF;
(iv) CRP, MCP1, sTNFR2, vWF and FAS;
(v) d-Dimer, IL6, MMP9NGAL, NSE and VEGF;
(vi) BTA, MCP1, sTNFR2, vWF and FAS;
(vii) d-Dimer, IL6, NGAL, NSE, VEGF and HA;
(viii) IL1β, IL6, IL8, MMP9NGAL, NSE and VEGF;
(ix) BTA, d-Dimer, IL6, NGAL, NSE and VEGF;
(x) BTA, CRP, IL1β, IL8, sTNFR2, vWF and FAS;
(xi) d-Dimer, IL4, IL6, MMP9, NSE, VEGF and CK18;
(xii) BTA, CRP, IL1α, IL2, sTNFR2, vWF and FAS;
(xiii) IL6, IL8, NGAL, TPSA and VEGF;
(xiv) FPSA, NGAL, TM, TNFα and VEGF;
(xv) IL1β, IL2, NGAL, TM and VEGF;
(xvi) IL1α, MCP1, MMP9NGAL, NGAL, TM and TNFα;
(xvii) CEA, FPSA, IL8, NGAL, TM and VEGF;
(xviii) FPSA, IL4, NGAL, NSE, TNFα and VEGF;
(xix) FPSA, IL1β, IL10, NGAL, TM, TNFα and VEGF;
(xx) CEA, IL1β, IL4, NGAL, TM, TPSA and VEGF;
(xxi) FPSA, IL1β, IL4, IL10, NGAL, TM and VEGF;
(xxii) IL2, IFNγ, MCP1, MMP9NGAL and TM;
(xxiii) IL1α, IL1β, IL6, TNFα and VEGF;
(xxiv) IL4, IL6, IFNγ, MCP1 and TNFα;
(xxv) d-Dimer, IL2, IL6, MMP9NGAL, TM and TNFα;
(xxvi) IL2, IL10, IFNγ, MCP1, MMP9NGAL and TNFα;
(xxvii) IL6, MCP1, NGAL, NSE, TM and TNFα;
(xxviii) d-Dimer, EGF, IL6, IL10, IFNγ, MCP1 and TNFα;
(xxix) d-Dimer, IL10, IFNγ, MCP1, NGAL, sTNFR and VEGF; and
(xxx) d-Dimer, IL6, IL8, IL10, NSE, TM and TNFα.

Embodiment 106

A solid state device according to embodiments 91 or 92, comprising antibodies that bind specifically to a panel of biomarkers selected from the group consisting of:
(i) serum CEA, urinary EGF, urinary HA and urinary CK18;
(ii) serum CEA, urinary EGF, urinary IL8 and urinary CK18;
(iii) serum CEA, urinary EGF, plasma IL6 and urinary MMP9NGAL;
(iv) BTA, CRP, IL2, IL4 and CK18;
(v) EGF, IL1β, NGAL, VEGF and CK18;
(vi) BTA, IL4, IL8, HA and CK18;
(vii) EGF, CRP, IL4, VEGF, HA and CK18;
(viii) EGF, IL4, IL6, IL8, vWF and CK18;
(ix) BTA, EGF, IL4, IL8, HA and CK18;
(x) BTA, EGF, CRP, IL4, sTNFR1, HA and CK18;
(xi) EGF, IL1α, IL1β, IL4, sTNFR1, VEGF and CK18;
(xii) EGF, CRP, IL4, MMP9NGAL, NGAL, HA and CK18;
(xiii) CEA, FPSA, IL10, IFNγ and NGAL;
(xiv) CEA, IL1α, IL1β, MMP9NGAL and sTNFR1;
(xv) CEA, IL1α, MMP9NGAL, TM and TNFα;
(xvi) CEA, IL1α, IL1β, IL6, NGAL and NSE;
(xvii) CEA, IL4, IL6, IL8, MMP9NGAL and TNFα;
(xviii) CEA, d-Dimer, IL1α, IL4, IL6 and sTNFR1;
(xix) CEA, IL1α, IL4, IL6, IL8, TM and sTNFR1;
(xx) CEA, IL1α, IL1β, IL4, IL8, MMP9NGAL and VEGF;
(xxi) CEA, IL1α, IL4, IL10, MMP9NGAL, TM and TNFα;
(xxii) IL1α, IL8, MMP9NGAL, NGAL and sTNFR1;
(xxiii) IL1α, IL1β, IL4, IFNγ and psTNFR1;
(xxiv) IL1α, IL1β, IL8, TM and psTNFR1;
(xxv) d-Dimer, IL1α, IL4, IL10, MMP9NGAL and TNFα;
(xxvi) CRP, IL8, IL10, MMP9NGAL, TM and sTNFR1;
(xxvii) d-Dimer, IL1α, IL1β, IL4, TM and sTNFR1;
(xxviii) IL1β, IL6, IL8, MMP9NGAL, sTNFR1, TNFα and VEGF;
(xxix) d-Dimer, IL1α, IL4, IL8, NGAL, TM and sTNFR1; and
(xxx) IL1α, IL1β, IL4, IL6, IL8, MMP9NGAL and sTNFR1.

Embodiment 107

A solid state device according to embodiments 91 or 92, comprising antibodies that bind specifically to a panel of biomarkers selected from the group consisting of:
(i) serum CEA, plasma CRP, urinary IL8 and plasma TNF;
(ii) urinary EGF, urinary IL1β, serum IL6 and urinary vWF;
(iii) serum CEA, plasma IL1α, urinary NSE and serum NSE;
(iv) EGF, IL2, NSE, TM and CK18;
(v) EGF, IL6, sTNFR1, HA and CK18;

(vi) EGF, NGAL, vWF, HA and CK18;
(vii) EGF, IL8, sTNFR2, VEGF, uvWF and HA;
(viii) EGF, IL1α, MMP9, NSE, uvWF and HA;
(ix) EGF, CRP, IL2, IL4, TM and CK18;
(x) EGF, IL1β, IL2, NSE, TM, VEGF and vWF;
(xi) EGF, IL1β, MMP9, MMP9NGAL, TNFα, vWF and HA;
(xii) EGF, IL2, IL4, NGAL, NSE, TM and CK18;
(xiii) CEA, IL8, IL10, NSE and TNFα;
(xiv) CEA, IL2, IL8, MMP9NGAL and NSE;
(xv) CEA, IL2, IL6, IL10 and NSE;
(xvi) CEA, IL1β, IL2, IL8, IL10 and NSE;
(xvii) CEA, IL1β, IL2, IL8, NSE and TPSA;
(xviii) CEA, CRP, IL10, MMP9NGAL, NGAL and VEGF;
(xix) CEA, IL1β, IL2, IL4, IL8, NSE and TNFα;
(xx) CEA, EGF, IL4, IL8, IL10, TPSA and VEGF;
(xxi) CEA, IL1β, IL2, IL4, IL10, MMP9NGAL and TM;
(xxii) CRP, IL1α, IL8, IFNγ, TM;
(xxiii) CRP, IL1α, IL8, IFNγ, NGAL;
(xxiv) IL1α, IL2, IL8, MCP1, TM;
(xxv) EGF, IL1α, IL4, IL8, IFNγ, TM;
(xxvi) d-Dimer, IL1α, IL8, IFNγ, MCP1, TM;
(xxvii) IL1α, IL8, IFNγ, MCP1, TM, TNFα;
(xxviii) IL1α, IL2, IL8, IL10, IFNγ, MCP1, TM;
(xxix) IL1α, IL2, IL8, IFNγ, MCP1, MMP9NGAL, TM; and
(xxx) EGF, CRP, IL1α, IL4, IL8, IFNγ, TNFα.

Embodiment 108

A solid state device according to embodiments 91 or 92, comprising antibodies that bind specifically to a panel of biomarkers selected from the group consisting of:
(i) urinary BTA, urinary NGAL, serum NGAL and urinary TNF;
(ii) urinary d-Dimer, urinary CRP, urinary NGAL and serum TNF;
(iii) serum CEA, urinary CRP, plasma MMP9NGAL and urinary NGAL;
(iv) d-Dimer, CRP, IL4, NGAL and sTNFR2;
(v) CRP, MMP9NGAL, NGAL, sTNFR2 and VEGF;
(vi) BTA, CRP, IL4, NGAL and sTNFR2;
(vii) CRP, MCP1, MMP9, NGAL, sTNFR2 and VEGF;
(viii) d-Dimer, CRP, IL2, IL4, NGAL and sTNFR;
(ix) BTA, CRP, IL2, NGAL, sTNFR2 and vWF;
(x) d-Dimer, CRP, IL1α, IL4, MMP9NGAL, TM and CK18;
(xi) BTA, EGF, CRP, MMP9, NGAL, vWF and FAS;
(xii) BTA, CRP, NGAL, NSE, TM, sTNFR2 and vWF;
(xiii) FPSA, IL1α, IL4, IFNγ and NGAL;
(xiv) d-Dimer, IL2, IL4, NGAL and TM;
(xv) d-Dimer, IL6, NGAL, TM and sTNFR1;
(xvi) d-Dimer, IL1β, IL8, NGAL, TM and TNFα;
(xvii) CEA, IL4, IL8, NGAL, TNFα and TPSA;
(xviii) d-Dimer, FPSA, IL2, IL6, IL8 and NGAL;
(xix) FPSA, CRP, IL2, IL6, NGAL, TNFα and VEGF;
(xx) CEA, FPSA, CRP, IL6, IL10, NGAL and VEGF;
(xxi) d-Dimer, FPSA, IL1β, IFNγ, MMP9NGAL, NGAL and TM;
(xxii) d-Dimer, IL4, MCP1, MMP9NGAL and TNFα;
(xxiii) EGF, IL1α, IL2, MMP9NGAL and NGAL;
(xxiv) d-Dimer, IL4, MCP1, MMP9NGAL and sTNFR1;
(xxv) d-Dimer, IL1β, IL4, IL8, IL10 and MMP9NGAL;
(xxvi) d-Dimer, EGF, IL8, IL10, MMP9NGAL and TM;
(xxvii) d-Dimer, EGF, IFNγ, MMP9NGAL, NSE and VEGF;
(xxviii) EGF, IL1α, IL2, IL4, MCP1, MMP9NGAL and NGAL;
(xxix) d-Dimer, EGF, CRP, IL8, MMP9NGAL, NSE and VEGF; and
(xxx) d-Dimer, EGF, IL1β, IL8, IL10, MMP9NGAL and VEGF.

Embodiment 109

Use of a solid substrate according to embodiment 93 to identify a subject having urothelial cancer, wherein the subject has a history of smoking.

Embodiment 110

Use of a solid substrate according to embodiment 94 to identify a subject having urothelial cancer, wherein the subject does not have a history of smoking.

Embodiment 111

Use of a solid substrate according to embodiment 95 to identify a subject having urothelial cancer, wherein the subject is 65 years of age or older.

Embodiment 112

Use of a solid substrate according to embodiment 96 to identify a subject having urothelial cancer, wherein the subject is less than 65 years of age.

Embodiment 113

Use of a solid substrate according to embodiment 97 to identify a subject having urothelial cancer, wherein the subject has a history of anti-hypertensive medication.

Embodiment 114

Use of a solid substrate according to embodiment 98 to identify a subject having urothelial cancer, wherein the subject does not have a history of anti-hypertensive medication.

Embodiment 115

Use of a solid substrate according to embodiment 99 to identify a subject having urothelial cancer, wherein the subject has cytological detection of inflammatory cells.

Embodiment 116

Use of a solid substrate according to embodiment 100 to identify a subject having urothelial cancer, wherein the subject does not have cytological detection of inflammatory cells.

Embodiment 117

Use of a solid substrate according to embodiment 101 to identify a subject having urothelial cancer, wherein the subject has a history of alcohol consumption.

Embodiment 118

Use of a solid substrate according to embodiment 102 to identify a subject having urothelial cancer, wherein the subject does not have a history of alcohol consumption.

Embodiment 119

Use of a solid substrate according to embodiment 103 to identify a subject having urothelial cancer, wherein the subject has a history of exposure to occupational risk or hazardous chemicals.

Embodiment 120

Use of a solid substrate according to embodiment 104 to identify a subject having urothelial cancer, wherein the subject does not have a history of exposure to occupational risk or hazardous chemicals.

Embodiment 121

Use of a solid substrate according to embodiment 105 to identify a subject having urothelial cancer, wherein the subject has a history of anti-cholesterol medication.

Embodiment 122

Use of a solid substrate according to embodiment 106 to identify a subject having urothelial cancer, wherein the subject does not have a history of anti-cholesterol medication.

Embodiment 123

Use of a solid substrate according to embodiment 107 to identify a subject having urothelial cancer, wherein the subject has proteinuria.

Embodiment 124

Use of a solid substrate according to embodiment 108 to identify a subject having urothelial cancer, wherein the subject does not have proteinuria.

Embodiment 125

Use according to any of embodiments 109 to 124 wherein the subject is patient a presenting with haematuria.

Embodiment 126

Use according to any of embodiments 109 to 124, wherein the urothelial cancer is urothelial carcinoma (UC).

REFERENCES

1. Margulis V, Sagalowsky A I. Assessment of hematuria. Med Clin North Am 2011; 95:153-159.
2. Abogunrin F, O'Kane H F, Ruddock M W, Stevenson M, Reid C N, O'Sullivan J M, et al. The impact of biomarkers in multivariate algorithms for bladder cancer diagnosis in patients with hematuria. Cancer 2012; 118:2641-2650.
3. Bellmunt J, Orsola A, Wiegel T, Guix M, De Santis M and Kataja V, et al. Bladder cancer: ESMO Clinical Practice Guidelines for diagnosis, treatment and follow-up. Amn Oncol 2011; 22 Suppl 6:vi45-9.
4. Edwards T J, Dickinson A J, Natale S, Gosling J, McGrath J S. A prospective analysis of the diagnostic yield resulting from the attendance of 4020 patients at a protocol-driven haematuria clinic. BJU Int 2006; 97:301-5.
5. Khadra M H, Pickard R S, Charlton M, Powell P H, Neal D E. A prospective analysis of 1,930 patients with hematuria to evaluate current diagnostic practice. J Urol 2000; 163:524-527.
6. Fradet Y, Lockhard C. Performance characteristics of a new monoclonal antibody test for bladder cancer: ImmunoCyt trade mark. Can J Urol 1997; 4:400-405.
7. Malkowicz S B. The application of human complement factor H-related protein (BTA TRAK) in monitoring patients with bladder cancer. Urol Clin North Am 2000; 27:63-73.
8. Moonen P M, Kiemeney L A, Witjes J A. Urinary NMP22 BladderChek test in the diagnosis of superficial bladder cancer. Eur Urol 2005; 48:951-956.
9. Leyh H, Marberger M, Conort P, Sternberg C, Pansadoro V, Pagano F, et al. Comparison of the BTA stat test with voided urine cytology and bladder wash cytology in the diagnosis and monitoring of bladder cancer. Eur Urol 1999; 35:52-6
10. Johnston B, Morales A, Emerson L, Lundie M. Rapid detection of bladder cancer: a comparative study of point of care tests. J Urol 1997; 158: 2098-2101.
11. Lotan Y, Elias K, Svatek R S, Bagrodia A, Nuss G, and Moran B, et al. Bladder cancer screening in a high risk asymptomatic population using a point of care urine based protein tumor marker. J Urol 2009; 182:52-58.
12. Bravaccini S, Casadio V, Gunelli R, Bucchi L, Zoli W, Amadori D, et al. Combining cytology, TRAP assay, and FISH analysis for the detection of bladder cancer in symptomatic patients. Ann Oncol 2011; 22:2294-2298.
13. Burger M, Catto J W, Dalbagni G, Grossman H B, Herr H, Karakiewicz P, et al. Epidemiology and risk factors of urothelial bladder cancer. Eur Urol 2013; 63:234-241.
14. Fitzgerald S P, Lamont J V, McConnell R I, Benchikh el O. Development of a high-throughput automated analyzer using biochip array technology. Clin Chem 2005; 51:1165-1176.
15. Dobson A J. An Introduction to Generalized Linear Models, Second Edition. In: Chatfield C, Lindsay J, Tanner M, Zidek I, editors. Texts in Statistical Science. Chapman and Hall/CRC, 2008. p. 115-134.
16. Fawcett T. An introduction to ROC analysis. Pattern Recog Lett 2006; 27:861-874.
17. Breiman L, Olfert S M, Felknor S A, Delclos G L. Random Forests; Mach Learning 2001; 45:5-32.
18. Benjamini Y, Hochberg Y. Controlling the false discovery rate: a practical and powerful approach to multiple testing. Journal of the Royal Statistical Society, Series B (Methodological) 1995; 57:125-133.
19. Lindén M, Segersten U, Runeson M, Wester K, Busch C, Pettersson U, et al. Tumour expression of bladder cancer-associated urinary proteins. BJU Int 2013; 112:407-415.
20. Schlomer B J, Ho R, Sagalowsky A, Ashfaq R, Lotan Y. Prospective validation of the clinical usefulness of reflex fluorescence in situ hybridization assay in patients with atypical cytology for the detection of urothelial carcinoma of the bladder. J Urol 2010; 183:62-67.
21. Rantalainen M, Holmes C C. Accounting for control mislabeling in case-control biomarker studies. J Proteome Res 2011; 10:5562-5567.

The invention claimed is:
1. A method, comprising:
measuring the level of each biomarker of a panel of protein biomarkers in a urine sample obtained from a subject having a history of smoking, wherein the panel of biomarkers consists of:

urinary epidermal growth factor (EGF), urinary IL6, urinary vascular endothelial growth factor (VEGF) and urinary cytokeratin 18 (CK18).

2. A method according to claim 1, wherein the subject is a patient presenting with haematuria.

3. The method according to claim 1, wherein the urine and urinary biomarker levels are volume normalized.

* * * * *